(12) United States Patent
Coffin

(10) Patent No.: US 10,167,482 B2
(45) Date of Patent: Jan. 1, 2019

(54) GENES AND USES FOR PLANT ENHANCEMENT

(71) Applicant: Monsanto Technology LLC, St. Louis, MO (US)

(72) Inventor: Marie Coffin, Cary, NC (US)

(73) Assignee: Monsanto Technology LLC, St. Louis, MO (US)

(*) Notice: Subject to any disclaimer, the term of this patent is extended or adjusted under 35 U.S.C. 154(b) by 266 days.

(21) Appl. No.: 14/757,273

(22) Filed: Dec. 10, 2015

(65) Prior Publication Data

US 2016/0244777 A1    Aug. 25, 2016

Related U.S. Application Data

(63) Continuation of application No. 13/385,376, filed on Feb. 16, 2012, which is a continuation of application No. 12/157,153, filed on Jun. 5, 2008.

(60) Provisional application No. 60/933,428, filed on Jun. 6, 2007.

(51) Int. Cl.
    *C12N 15/82*    (2006.01)
    *C12Q 1/6895*   (2018.01)

(52) U.S. Cl.
    CPC ..... *C12N 15/8261* (2013.01); *C12N 15/8247* (2013.01); *C12N 15/8251* (2013.01); *C12N 15/8262* (2013.01); *C12N 15/8267* (2013.01); *C12N 15/8271* (2013.01); *C12N 15/8273* (2013.01); *C12N 15/8274* (2013.01); *C12N 15/8275* (2013.01); *C12Q 1/6895* (2013.01); *Y02A 40/146* (2018.01)

(58) Field of Classification Search
    None
    See application file for complete search history.

(56) References Cited

U.S. PATENT DOCUMENTS

| | | |
|---|---|---|
| 6,096,953 A | 8/2000 | Hoffbeck |
| 2003/0140380 A1 | 7/2003 | Henkes et al. |
| 2003/0233067 A1 | 12/2003 | Yongwei et al. |
| 2003/0233675 A1 | 12/2003 | Cao et al. |
| 2004/0123343 A1 | 6/2004 | La Rosa et al. |
| 2004/0216190 A1 | 10/2004 | Kovalic |
| 2006/0048240 A1 | 3/2006 | Alexandrov et al. |
| 2006/0150283 A1 | 7/2006 | Alexandrov et al. |
| 2011/0214199 A1 | 9/2011 | Coffin |
| 2013/0305398 A1 | 11/2013 | Coffin |

FOREIGN PATENT DOCUMENTS

| | | |
|---|---|---|
| WO | WO-2006076423 A2 | 7/2006 |
| WO | WO-2007044043 A2 | 4/2007 |
| WO | WO-2008153927 A2 | 12/2008 |
| WO | WO-2008153927 A3 | 12/2008 |
| WO | WO-2009091518 A2 | 7/2009 |
| WO | WO-2009134339 A2 | 11/2009 |

OTHER PUBLICATIONS

Weigel et al 2000 (Plant Physiology 122: p. 1003-1013).*
Theologis et al 2000 (Nature 408: p. 816-820).*
"European Application Serial No. 14181041.6, Communication Pursuant to Article 94(3) EPC dated Feb. 13, 2017", 3 pgs.
"European Application Serial No. 14181041.6, Office Action dated Mar. 2, 2015", 2 pgs.
"European Application Serial No. 14181041.6, Response filed Aug. 25, 2015 to Office Action dated Mar. 2, 2015", 10 pgs.
"U.S. Appl. No. 12/157,153, Non Final Office Action dated Oct. 17, 2011", 17 pgs.
"U.S. Appl. No. 12/157,153, Response filed Aug. 22, 2011 to Restriction Requirement dated Jun. 21, 2011", 11 pgs.
"U.S. Appl. No. 12/157,153, Restriction Requirement dated Jun. 21, 2011", 11 pgs.
"U.S. Appl. No. 13/385,376, Final Office Action dated Sep. 10, 2015", 17 pgs.
"U.S. Appl. No. 13/385,376, Non Final Office Action dated Feb. 27, 2015", 18 pgs.
"U.S. Appl. No. 13/385,376, Preliminary Amendment filed Feb. 16, 2012", 7 pgs.
"U.S. Appl. No. 13/385,376, Response filed Feb. 13, 2015 to Restriction Requirement dated Dec. 16, 2014", 8 pgs.
"U.S. Appl. No. 13/385,376, Response filed Jun. 26, 2015 to Non Final Office Action dated Feb. 27, 2015", 8 pgs.
"U.S. Appl. No. 13/385,376, Restriction Requirement dated Dec. 16, 2014", 6 pgs.
"European Application Application Serial No. 08768181.3, Communication dated Sep. 9, 2010", 1 pg.
"European Application Application Serial No. 08768181.3, Response filed Mar. 16, 2011 to Communication dated Sep. 9, 2010", 8 pgs.
"European Application Serial No. 08768181.3, Communication dated Jan. 19, 2010", 2 pgs.
"European Application Serial No. 08768181.3, Communication noting loss of rights dated Sep. 11, 2012", 1 pg.
"European Application Serial No. 08768181.3, Extended European Search Report dated Aug. 23, 2010", 6 pgs.
"European Application Serial No. 08768181.3, Office Action dated Jan. 26, 2012", 4 pgs.
"European Application Serial No. 08768181.3, Response filed Feb. 16, 2010 to Communication dated Jan. 19, 2010", 10 pgs.
"European Application Serial No. 12179231, Communication noting of loss of rights dated Aug. 19, 2013", 1 pg.

(Continued)

*Primary Examiner* — Matthew R Keogh
(74) *Attorney, Agent, or Firm* — Schwegman Lundberg & Woessner, P.A.

(57) ABSTRACT

Transgenic seed for crops with enhanced agronomic traits are provided by trait-improving recombinant DNA in the nucleus of cells of the seed where plants grown from such transgenic seed exhibit one or more enhanced traits as compared to a control plant. Of particular interest are transgenic plants that have increased yield. The present invention also provides recombinant DNA molecules for expression of a protein, and recombinant DNA molecules for suppression of a protein.

13 Claims, 7 Drawing Sheets

Specification includes a Sequence Listing.

(56) References Cited

OTHER PUBLICATIONS

"European Application Serial No. 12179231, European Search Report dated Dec. 10, 2012", 6 pgs.
"European Application Serial No. 12179231, Invitation to Remedy Deficiencies dated Aug. 16, 2012", 1 pg.
"European Application Serial No. 12179231, Reply filed Oct. 19, 2012 to Invitation to Remedy Deficiencies dated Aug. 16, 2012", 4 pgs.
"European Application Serial No. 13174081.3, European Search Report dated Jan. 17, 2014", 6 pgs.
"European Application Serial No. 13174081.3, Invitation to Remedy Deficiencies dated Jul. 17, 2013", 1 pg.
"European Application Serial No. 13174081.3, Reply filed Sep. 25, 2013 to Invitation to Remedy Deficiencies dated Jul. 17, 2013", 5 pgs.
"European Application Serial No. 14181041.6, Extended European Search Report dated Jan. 26, 2015", 7 pgs.
"International Application Serial No. PCT/US2008/007105, International Preliminary Report on Patentability dated Dec. 17, 2009", 10 pgs.
"International Application Serial No. PCT/US2008/007105, International Search Report dated Jan. 30, 2009", 5 pgs.
"International Application Serial No. PCT/US2008/007105, International Written Opinion dated Jan. 30, 2009", 6 pgs.
"RNA Recognition Motif-Containing Protein (*Arabidopsis thaliana*) (AEE75400)", http://www.ncbi.nlm.nih.gov (submitted Feb. 18, 2011), (Feb. 18, 2011), 2 pgs.
"RNA Recognition Motif-Containing Protein (*Arabidopsis thaliana*) (NP_187983)", http://www.ncbi.nlm.nih.gov (submitted Feb. 18, 2011), (Feb. 18, 2011), 2 pgs.
"RNA Recognition Motif-Containing Protein (B3H4P0_ARATH)", http://www.uniprot.org (last modified Jul. 22, 2008), (Jul. 22, 2008), 2 pgs.
"RNA-Binding Protein, Putative (IPI00523019.1)", http://www.ebi.ac.uk (created Jan. 5, 2005), (Jan. 5, 2005), 1 pg.
"Subname: Full=Transducin/WD40 domaining-containing protein; Subname: Full-WD40-repeat protein", Retrieved from EBI Accession No. UNIPROT:Q9LFE2 [online]. [retrieved on Nov. 26, 2012]. Retrieved from the Internet: <URL: http://www.uniprot.org/uniprot/Q9LFE2.txt>, 2 pgs.
Bork, P., et al., "Go hunting in sequence databases but watch out for the traps", TIG, vol. 12, No. 10, (1996), 425-427.
Clinton, R, et al., "Alternative oxidases in *Arabidopsis*: A comparative analysis of differential expression in the gene family provides new insights into function of non-phosphorylating bypasses", Biochim Biophys Acta., 1757(7), (Jul. 2006), 730-741.
De Angeli, et al., "", Nature 442:24, (2006), 939-942.
Doerks, Tobias, et al., "Protein Annotation: detective work for function prediction", Trends in Genetics, vol. 14, No. 6, (1998), 248-250.
Frame, et al., "", Plant Physiology 129, (2002), 13-22.
Geelen, et al., "", Genbank Accession # AF044313, (1998).
Geelen, et al., "", The Plant Journal 21:3, (2000), 259-267.
Guo, H. H., et al., "Protein tolerance to random amino acid change", Proc. Natl. Acad. Sci. USA, 101, (2004), 9205-9210.
Hechenberger, "A family of putative chloride channels from *Arabidopsis* and functional complementation of a yeast strain with a CLC gene disruption", Journal of Biological Chemistry, vol. 271, No. 52 (Dec. 1, 1996), 33632-33638.
Keskin, O., et al., "A new, structurally nonredundant, diverse data set of protein-protein interfaces and its implications", Protein Science, 13, (2004), 1043-1055.
Lorkovic, Z. J., et al., "Genome analysis: RNA recognition motif (RRM) and K homology (KH) domain RNA-binding proteins from the flowering plant *Arabidopsis thaliana*", Nucleic Acids Research, 30, (2002), 623-635.
Mitchell, R A, et al., "A novel bioinformatics approach identifies candidate genes for the synthesis and feruloylation of arabinoxylan", Plant Physiol., 144(1), (May 2007), 43-53.
Mitchell, Rowan A, et al., "A Novel Bioinformatics Approach Identifies Candidate Genes for the Synthesis and Feruloylation of Arabinoxylan", Plant Physiology, 144(1), (2007), 43-53.
Ngo, J. Thomas, et al., "In the Protein Folding Problem and Tertiary Structure Prediction", Merz, et al., (ed.), Birkhauser, Boston, MA, (1994), 492-495.
Nishimura, A., et al., "Over-expression of tobacco knotted1-type class1 homeobox genes alters various leaf morphology", Plant Cell Physiol., 41(5), (2000), 583-590.
Saisho, D, et al., "Characterization of the gene family for alternative oxidase from *Arabidopsis thaiana*", Plant Mol Biol., 35(5), (Nov. 1997), 585-96.
Salanoubat, et al., "NCBI", GenBank Accession No. NP_187983, (Aug. 13, 2001), 1-2.
Sivasankar, et al., "", Plant Physiology 114, (1997), 583-589.
Smith, Temple F, et al., "The Challenges of Genome Sequence Annotation or "The Devil is in the Details"", Nature Biotechnology, 15(12), (Nov. 1997), 1222-1223.
Sonnhammer, E. L, et al., "Pfam: a comprehensive database of protein domain families based on seed alignments.", Proteins, 28(3), (Jul. 1997), 405-420.
Thornton, J. M., et al., "From structure to function: Approaches and limitations", Nature Structural Biology—Structural Genomics Supplement, (Nov. 2000), 991-994.
Wells, J. A., "Additivity of Mutational Effects in Proteins", Biochemistry, 29(37), (1990), 8509-8517.
Zhou, et al., "", Biotechnology Letters 31, (2009), 1811-1815.
"European Application Serial No. 14181041.6, Communication Pursuant to Article 94(3) EPC dated Oct. 2, 2017", 4 pgs.
"European Application Serial No. 14181041.6, Response filed Jun. 23, 2017 to Communication Pursuant to Article 94(3) EPC dated Feb. 13, 2017", 14 pgs.
"European Application Serial No. 14181041.6, Response filed Feb. 7, 2018 to Communication Pursuant to Article 94(3) EPC dated Oct. 2, 2017", 18 pgs.

\* cited by examiner

SEQ ID NO

```
4038        ------------------------------------------------------------
3777        ------------------------------------------------------------
27198       ------------------------------------------------------------
7302        ------------------------------------------------------------
44992       ------------------------------------------------------------
66893       ------------------------------------------------------------
768         ------------------------------------------------------------
15584       ------------------------------------------------------------
42579       ------------------------------------------------------------
45333       MSYSNSNPENYSAATSSPELKLYQAFIFSVPICFTFIILFLFYLIYLRRSSSDLSSLGMR
19299       ------------------------------------------------------------
21692       ------------------------------------------------------------
57173       ------------------------------------------------------------
57659       ------------------------------------------------------------
4374        -------------------------MARNPTRTVYIGNLDEKVTERILYEILIQPGR
55005       ------------------------------------------------------------
42612       ------------------------------------------------------------
67783       ------------------------------------------------------------
consensus ------------------------------------------------------------
            ------------------------------------------------------------
            ------------------------------------------------------------
            ------------------------------------------------------------
            ------------------------------------------------------------
            ------------------------------------------------------------
            ------------------------------------------------------------
            ------------------------------------------------------------
            ------------------------------------------------------------
            ------------------------------------------------------------
            TTFIPGNSLSTIELGLSKELREMLPIVVFKESFTVMDSQCSVCLGDYQPNDKLQQIPVCK
            ------------------------------------------------------------
            ------------------------------------------------------------
            ------------------------------------------------------------
            ------------------------------------------------------------
            VVDLCIPRDKETSCPKGYAFAEYETEEIAQYAVQLFSGLVRLYGKTLKFAISGQDKPSSN
            ------------------------------------------------------------
            ------------------------------------------------------------
            ------------------------------------------------------------

---------------MNQDLAKVQTEEDDFLIEISGEAPLTYSTLEGCVPPTFRSMTVGPI
            ------------------------------------------------------------
            ------------------------------------------------------------
            ------------------------------------------------------------
            -------------------------------MSTVPREFAGLDPRSADFHPALTRCPV
            ------------------------------------------------------------
            ------------------------------------------------------------
            ------------------------------------------------------------
            ------------------------------------------------------------
            HTFHMDCIDLWLTSHTTCPLCRLALIPSRSRQSQDDPVPSLVSPDEEVSSQPESEPVNHR
            ------------------------------------------------------------
```

FIG. 4A

```
------------------------------------------------------------------
------------------------------------------------------------------
------------------------------------------------------------------
GNNPVMPKLNPVPLPKQPQFVHHSDMHVLHTPADPMHYQLDPCIATEGSAMVWRLCFECC
------------------------------------------------------------------
------------------------------------------------------------------
------------------------------------------------------------------
------------------------------------------------------------------

YQVFDMGGNAVSVQRHGNFASVGILTLVSTRAK---PLEVEIAKE---------------
-MVFDMGGNAVSVQRHGNFASVGILTLVSTRAK---PLEVEIAKE---------------
----------MNSRRS------RSVKLVSTRAK---PLEVEIAKE---------------
----------MNSRRS------RSVKLVSARANGDGALEVDVPEEEG--------------
TCGFCCAGRLIRRAPWMNSRRSRSVKLVSARANGDGALEVDVPEEEG--------------
-----------------------------------MGLIKN-------------------
-----------------------------------MGLIKN-------------------
-----------------------------------MGLIKN-------------------
----------------------------------MG-SIQN------------------
VVSTQPESEPVNHSGVSSQPESQPVVNHRGVSSQPESQPVN-HINDGHEQQCDQDVEGFK
-----------------------------------MGS---------------------
-------------------------------------------------------------
----------------------------------MDSIQN-------------------
-------------------------MKMESPGVQPAAAGEEEGGG--------------
WPWSSEATNVVSVLLGTKEGNLPREEAMKMESPGVQPAAAGEEEGGG--------------
-------------------------MEVEADGIQEATAGAGDGGGX--------------
-------------------------MEVEADGIQEATAGAGDGGG---------------
----------xxxxxx------xxxxxxxxxxxxxxxxxxxxxxx---------------

-----------DERMSSSADNTVYCCIAKGR----KIIYCYNSKDGDPHME---TTAALC
-----------DERMSSSADNTVYCCIAKGR----KIIYCYNSKDGDPHME---TTAALC
-----------DERMSSSADNTVYCCIAKGR----KIIYCYNSKDGDPHME---TTAALC
-----------DERMSSSADNTVYCCIAKGR----KIIYCYNSKDGDPHME---TTAALC
-----------DARMSSSAANXVYWCIGRGR----SVIYRYSSKGGDPQAE---ATAALC
-------------------TVHYCCVSRDN----QILYSYNGG--DQTNE---SLAALC
-------------------TVHYCCVSRDN----QILYSYNGG--DQTNE---SLAALC
-------------------TVHYCCVSRDN----QILYAYNGG--DQSNE---SLAGLC
-------------------TVHYCCVSRDN----QIMYAYNNAGDHRNNE---SLAALC
EMEEDERNNIGTSSACCSCRTVHYCCVSRDN----QIMYAYNNAGDHRNNE---SLAALC
-------------------TVHYCCVSRGN----QILYGYNNGGDHHRNE---SLAALC
-----------------------WCVSRGT----HILYGYNCGRHPPRNE---SLSALC
-------------------KVYYCCVSKGN----NVLYVYGGG--DQEVE---KVAALC
-------------------GVFFCVAVTSRGRTDRLSYFQAEGDGDDAEEVARATAALC
-------------------GVFFCVAVTSRGRTDRLSYFQAEGDGDDAEEVARATAALC
-------------------GTHVFFCVAATSRGNKNSISYFHTNAVGEDAES-ALALAALC
-------------------VDDVFFCVAATSRGNKNSISYFHTNAGGEDAES-ALALAALC
----------xxxxxxxxxxxxxyccxxxxx----xixYxyxxxxxxxxxe---xxaaLC LENAPLYHRHYIHTAG-SRSYGYLMADG-HTFFAIIDPSVGNVGALQFLERVREVFRTVN
LENAPSYHRHYIHTAG-SRSYGYLMADG-HTFFAIIDPSVGNVGALQFLERVREVFRTVN
LENAPSYHRHYIHTAG-SRSYGYLMADG-HTFFAIIDPSVGNVGALQFLERVREVFRTVN
LENAPSYHRHYIHTAG-SRSYGYLMADG-HTFFAIIDPSVGNVGALQFLERVREVFRTVN
LDRSPPHHRHYVHTSG-RRSYGYLTADG-HTFFAIIDPSVGSAGALQFLERVRDAFRSSA
LEKSPPFHTWYFETIG-KRRFGFLIGDG-FVYFAIVDEVLKRSSVLKFLEHLRDEFKKAA
LEKSPPFHTWYFETIG-KRRFGFLIGDG-FVYFAIVDEVLKRSSVLKFLEHLRDEFKKAA
LEKTPPFHAWYFESIG-KRRFGFLTGDG-FVYFAIVDEVLGKVSVLKFLEHLR-------
```

FIG. 4B

```
LEKTPPFHKWYFETRG-KKTFGFLMKDD-FVYFAIVDDVFKKSSVLDFLEKLRDELKEAN
LEKTPPFHKWYFETRG-KKTFGFLMKDD-FVYFAIVDDVFKKSSVLDFLEKLRDELKEAN
LEKTPPFHKWYFETIS-KWTFGFLIEEDGLVYFAIVDEVFKRSSVLXFLENLRDELKKAA
LKNTPPFHVWYFEPIC-KRTFGFLIEKDALVYLPFVDEVFERSRVLEFLETLRDELENAH
LERAPPFHRWYFETIG-KRTFGFFMEDG-YVYFTIVDKGLGNPVVLQFLEHVRDEFKKLA
LDHAPEHHHWHHHTVVGRRTFAFLAGDDGRTYFAVADPTPGSAETVRFLQRVRDAFGSCG
LDHAPEHHHWHHHTVVGRRTFAFLAGDDGRTYFAVADPTPGSAETVRFLQRVRDAFGSCG
LDHAPDHHRWHHHTVAGAKTFAFLSADDGRTYFAAADPSPGAAEVVRFLERVRDACD---
LDHAPDHDRWHHHTVARTKTFTFLSADDGRTYFAAADPSPGAAEVVRFLERVRDACD---
LxxxPxxhxwyxxtxx-xrxfgflxxdxxxxyfaixDxxxxxxxxlxFLexxRdxxxxxx RSG------------FHDSLVPAVQRLVASLEKMPRATFD-----------LEESVEKG
RSG------------FHDSLVPAVQRLVASLEKMPHATFD-----------LEESVEKG
RSG------------FHDSLVPAVQRLVASLEKMPHATFD-----------LEESVEKG
RSG------------FHDSLVPAVQRLVASLEKMPHATFD-----------LEESVEKG
GVGGR----------QPHESLVPAVQRLVASLEKMPHAAFV-----------LDG-AGAG
RENSRGSFTAMIGSINVEDQLVPVVTRLIASLERVAESSS------------NNELKSSN
RENSRGSFTAMIGSINVEDQLVPVVTRLIASLERVAESSS------------NNELKSSN
------------------------------------------------------------
KKNSRGSFSGSISFSNVQDQIV---RRLIASLE-FDHTCL------------PLSSPSID
KKNSRGSFSGSISFSNVQDQIV---RRLIASLE-FDHTCL------------PLSSPSID
EKNSRGSFS---------------------------------------------------
ENISRGLFSGSIFFNCVQDPLV---RTLISSLERVAESTN-----------PLTCLPI-
RKGSRGILP-NMNSIYIQEKLVPVIRGLITSLESVSHGSSNWRDETSLSFQVDLSPSPSN
GGGGGGATRRR---NQRDDAVDAVVWQFVRALR-ASAGRGT---------------AAL
GGGGGGATRRR---NQRDDAVDAVVWQFVRALR-ASAGRGT---------------AAL
------AAPRK---RLRDEAVAPVARQFARTLRAAAAGPSS---------------GAE
------AAPRK---RLRDEAVAPVARQFARTLRAAAAGPSS---------------GAE
xxxxxxxxxxxxxxxxxxxxxxxxxxxxxxxxlxxxxxxxxx-----------xxxxxxx EPSDSSSCTSSKVPLLGRSGSRKDKKKAKEKAASAA------VCEDEQHGTR----GVRI
EPSDSSSCTSSKVPLLGRSGSRKDKKKAKEKAASAA------VCEDEQHGTR----GVRI
EPSDSSSCTSSKVPLLGRSGSRKDKKKAKEKAASAA------VCEDEQHGTR----GVRI
EPSDSSSCTSSKVPLLGRSGSRKDKKKAKEKAASAAG-----LXEDEQHGTR----GVRX
AGDGDGCTSSSKAPLLGKSGSRKEKRRSRDKLSSSAAGAGAGGCEDEHHGTR----AVRI
LGEQSEGSNSTKAPLLGRL-SKQEKKKGKDHV-----IELEEHRKSNDRGN---------
LGEQSEGSNSTKAPLLGRL-SKQEKKKGKDHV-----IELEEHRKSNDRGN---------
------------------------------------------------------------
GAEQSYASNS-KAPLLGRS-NKQDKKKGRDHAHSLRGIEIEEHRKSNDRGN---------
GAEQSYASNS-KAPLLGRS-NKQDKKKGRDHAHSLRGIEIEEHRKSNDRGN---------
------------------------------------------------------------
LNGQIEGASSTKAPLLGKS-NKPDKKKVKDHVIAMRDVELEEHQKSTDRGARVDSCNLDG
FPGDDSRGGGDASSADGDKDDEEEEDDR--------------------------------
FPGDDSRGGGDASSADGDKDDEEEEDDR--------------------------------
LPEASLQAKEPSTPLAPVCEKDEEERQR--------------------------------
LPEASLQAKEPSTPLAPVCEKDEEERQR--------------------------------
xxxxxxxxxxxxxplxgxxxxxxxxxxxxxxxxxx-xxxxxxxxxxxxx----xxxx DVPP-EQVGGMSLERSASQSRLRRQHSSRSLWVRHVK---------------IIIVV
DVPP-EEVGGMSLERSASQSRLRRQHSSRSLWVRHVK---------------IIIVV
DVPP-EEVGGMSLERSASQSRLRRQHSSRSLWVRHVK---------------IIIVV
DVPP-EEVGGMSLERSASQSRLRRQHSSRSLWVRHVK---------------IIIVV
DVMPAEDVGGMSLERSGSQSRLRRQQSSRSLWMRHVK---------------VIVAV
```

FIG. 4C

```
ITDDSAGAGTSLEKECVSSSGRSVTQSFEWKWRRPINRLRETNLPKEKNQQNQNKATVSL
ITDDSAGAGTSLEKECVSSSGRSVTQSFEWKWRRLV------------------QIVLAI
------------------------------------------------------------
VTECSN-ASSESATYVPRRGRSGGSQSIERKWRRQV------------------KIVLAI
VTECSN-ASSESATYVPRRGRSGGSQSIERKWRRQV------------------KIVLAI
------------------------------------------------------------
VSQGGAGASVSLQKDMGSMRMRSAPQNIRKKWWRQVR-----------------IVLAI
--------GGE---AMAVAADGARRRT-RRSWWRYSK-----------------VVIGV
--------GGE---AMAVAADGARRRT-RRSWWRYSK-----------------VVIGV
--------AGERRRAFLQPEESASALPGWRPWWRHAS-----------------VVIVV
--------AGERRRAFLQPEESASALPGWRPWWRHAS-----------------VVIVV
xxxxxxxxxxxxxxxxxxxxxxxxxxxxxwxIxxx-------------------xxxxx DAIICIL--------------------LFAAWLAVCKGFQCVSS----------------
DAIICIL--------------------LFAAWLAVCKGFQCVSS----------------
DAIICIL--------------------LFAAWLAVCKGFQCVSS----------------
DAIICIL--------------------LFAAWLAVCKGFQCVSS----------------
DAVVCLV--------------------LLAAWLAVCKGFQCVSG----------------
SLSLSLTSSPPFSPLKPDQKPSFIRALLGQQMFTSGNVTARVFERQIRTPPPGASVNRAR
DAAICLT--------------------LFGIWLAICR----------------GIECTRS-
------------------------------------------------------------
DIAICLT--------------------LLGVWLAICHGIECTRS----------------
DIAICLT--------------------LLGVWLAICHGIECTRS----------------
------------------------------------------------------------
DAAVCIL--------------------LFIIWLVICHGISCIR-----------------
ELVLFLV--------------------LFVVWMIVCKGFNCVQR----------------
ELVLFLV--------------------LFVVWMIVCKGFNCVQR----------------
DVVLCLV--------------------LFAVWMGVCKGFGCLR-----------------
DVVLCLV--------------------LFAVWMGVCKGF--------------------
xxxxxxx--------------------lxxxwxxxcxgxxxxxx----------------

------------------------------------------------------------
------------------------------------------------------------
------------------------------------------------------------
------------------------------------------------------------
HFYENLVPSYTLYDVESPDHCFRKFTEDGLFLISFSRNHQELIVYRPSWLTYSTTDDSTT
------------------------------------------------------------
```

FIG. 4D

GENES AND USES FOR PLANT ENHANCEMENT

RELATED APPLICATIONS

This application is a continuation of U.S. patent application Ser. No. 13/385,375, filed on Feb. 16, 2012, which application is a continuation of U.S. patent application of U.S. patent application Ser. No. 12/157,153, filed on Jun. 5, 2008, which application the benefits of priority to U.S. Provisional Application Ser. No. 60/933,428, filed Jun. 6, 2007, the contents of which are incorporated herein by reference in their entireties.

INCORPORATION OF SEQUENCE LISTING

Two copies of the sequence listing (Copy 1 and Copy 2) and a computer readable form (CRF) of the sequence listing, all on CD-Rs, each containing the file named "38-21(54866)A_seqListing.txt", which is 239,913,045 bytes (measured in MS-WINDOWS) and was created on Jun. 5, 2008, are incorporated herein by reference in their entirety.

INCOPORATION OF TABLES

Two copies of Table 16 on CD-ROMs, each containing the file named "38-21(54866)A_table16.txt", which is 646,705 bytes when measured in MS-WINDOWS ® operating system, was created on Jun. 5, 2008, and comprises 150 pages when viewed in MS Word ® program, are incorporated herein by reference in their entirety.

FIELD OF THE INVENTION

Disclosed herein are recombinant DNA useful for providing enhanced traits to transgenic plants, seeds, pollen, plant cells and plant nuclei of such transgenic plants, methods of making and using such recombinant DNA, plants, seeds, pollen, plant cells and plant nuclei. Also disclosed are methods of producing hybrid seed comprising such recombinant DNA.

SUMMARY OF THE INVENTION

This invention provides recombinant DNA constructs comprising polynucleotides characterized by SEQ ID NO: 1-759 and the cognate amino acid sequences of SEQ ID NO: 760-1518. The recombinant DNA is useful for providing enhanced traits when stably integrated into the chromosomes and expressed in the nuclei of transgenic plants cells. In some aspects the recombinant DNA encodes a protein; in other aspects the recombinant DNA is transcribed to RNA that suppresses the expression of a native gene.

Such recombinant DNA in a plant cell nucleus of this invention is provided in as a construct comprising a promoter that is functional in plant cells and that is operably linked to DNA that encodes a protein or to DNA that results in gene suppression. Such DNA in the construct is sometimes defined by protein domains of an encoded protein targeted for production or suppression., e.g. a "Pfam domain module." (as defined herein below) from the group of Pfam domain modules identified in Table 17. Alternatively, e.g. where a Pfam domain module is not available, such DNA in the construct is defined a consensus amino acid sequence of an encoded protein that is targeted for production e.g. a protein having amino acid sequence with at least 90% identity to a consensus amino acid sequence in the group of SEQ ID NO: 67782 through SEQ ID NO: 67894. In a particular aspect of the invention the recombinant DNA is characterized by its cognate amino acid sequence that has at least 70% identity to any of SEQ ID NO: 760-1518.

This invention also provides transgenic plant cell nuclei comprising the recombinant DNA of the invention, transgenic plant cells comprising such nuclei, transgenic plants comprising a plurality of such transgenic plant cells, and transgenic seeds and transgenic pollen of such plants. Such transgenic plants are selected from a population of transgenic plants regenerated from plant cells transformed with recombinant DNA by screening transgenic plants for an enhanced trait as compared to control plants. The enhanced trait is one or more of enhanced water use efficiency, enhanced cold tolerance, increased yield, enhanced nitrogen use efficiency, enhanced heat tolerance, enhanced shade tolerance, enhanced high salinity tolerance, enhanced seed protein and enhanced seed oil. Such recombinant DNA in a plant cell nucleus of this invention is provided in as a construct comprising a promoter that is functional in plant cells and that is operably linked to DNA that encodes a protein or to DNA that results in gene suppression. Such DNA in the construct is sometimes defined by protein domains of an encoded protein targeted for production or suppression., e.g. a "Pfam domain module" (as defined herein below) from the group of Pfam domain modules identified in Table 17. Alternatively, e.g. where a Pfam domain module is not available, such DNA in the construct is defined a consensus amino acid sequence of an encoded protein that is targeted for production e.g. a protein having amino acid sequence with at least 90% identity to a consensus amino acid sequence in the group of SEQ ID NO: 67782 through SEQ ID NO: 67894.

In another aspect of the invention the plant cell nuclei, cells, plants, seeds, and pollen further comprise DNA expressing a protein that provides tolerance from exposure to an herbicide applied at levels that are lethal to a wild type plant cell.

This invention also provides methods for manufacturing non-natural, transgenic seed that can be used to produce a crop of transgenic plants with an enhanced trait resulting from expression of stably-integrated, recombinant DNA in the nucleus of the plant cells. More specifically the method comprises (a) screening a population of plants for an enhanced trait and recombinant DNA, where individual plants in the population can exhibit the trait at a level less

---

LENGTHY TABLES

The patent contains a lengthy table section. A copy of the table is available in electronic form from the USPTO web site (http://seqdata.uspto.gov/?pageRequest=docDetail&DocID=US10167482B2). An electronic copy of the table will also be available from the USPTO upon request and payment of the fee set forth in 37 CFR 1.19(b)(3).

than, essentially the same as or greater than the level that the trait is exhibited in control plants which do not express the recombinant DNA; (b) selecting from the population one or more plants that exhibit the trait at a level greater than the level that said trait is exhibited in control plants and (c) collecting seed from a selected plant. Such method further comprises steps (a) verifying that the recombinant DNA is stably integrated in said selected plants; and (b) analyzing tissue of a selected plant to determine the production of a protein having the function of a protein encoded by a recombinant DNA with a sequence of one of SEQ ID NO: 1-759; In one aspect of the invention the plants in the population further comprise DNA expressing a protein that provides tolerance to exposure to an herbicide applied at levels that are lethal to wild type plant cells and where the selecting is effected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, canola, alfalfa, wheat or rice seed selected as having one of the enhanced traits described above.

Another aspect of the invention provides a method of producing hybrid corn seed comprising acquiring hybrid corn seed from a herbicide tolerant corn plant which also has a nucleus of this invention with stably-integrated, recombinant DNA The method further comprises producing corn plants from said hybrid corn seed, where a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Still other aspects of this invention relate to transgenic plants with enhanced water use efficiency or enhanced nitrogen use efficiency. For instance, this invention provides methods of growing a corn, cotton, soybean, or canola crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton, soybean or canola crop without added nitrogen fertilizer comprising planting seed having plant cells of the invention which are selected for enhanced nitrogen use efficiency.

In another aspect of the invention transgenic plants comprise recombinant DNA constructs which affect the expression of two or more proteins disclosed herein.

BRIEF DESCRIPTION OF THE DRAWINGS

FIGS. 4A-4D illustrates a consensus amino acid sequence of SEQ ID NO: 768 and its homologs.

DETAILED DESCRIPTION OF THE INVENTION

Figure 1:
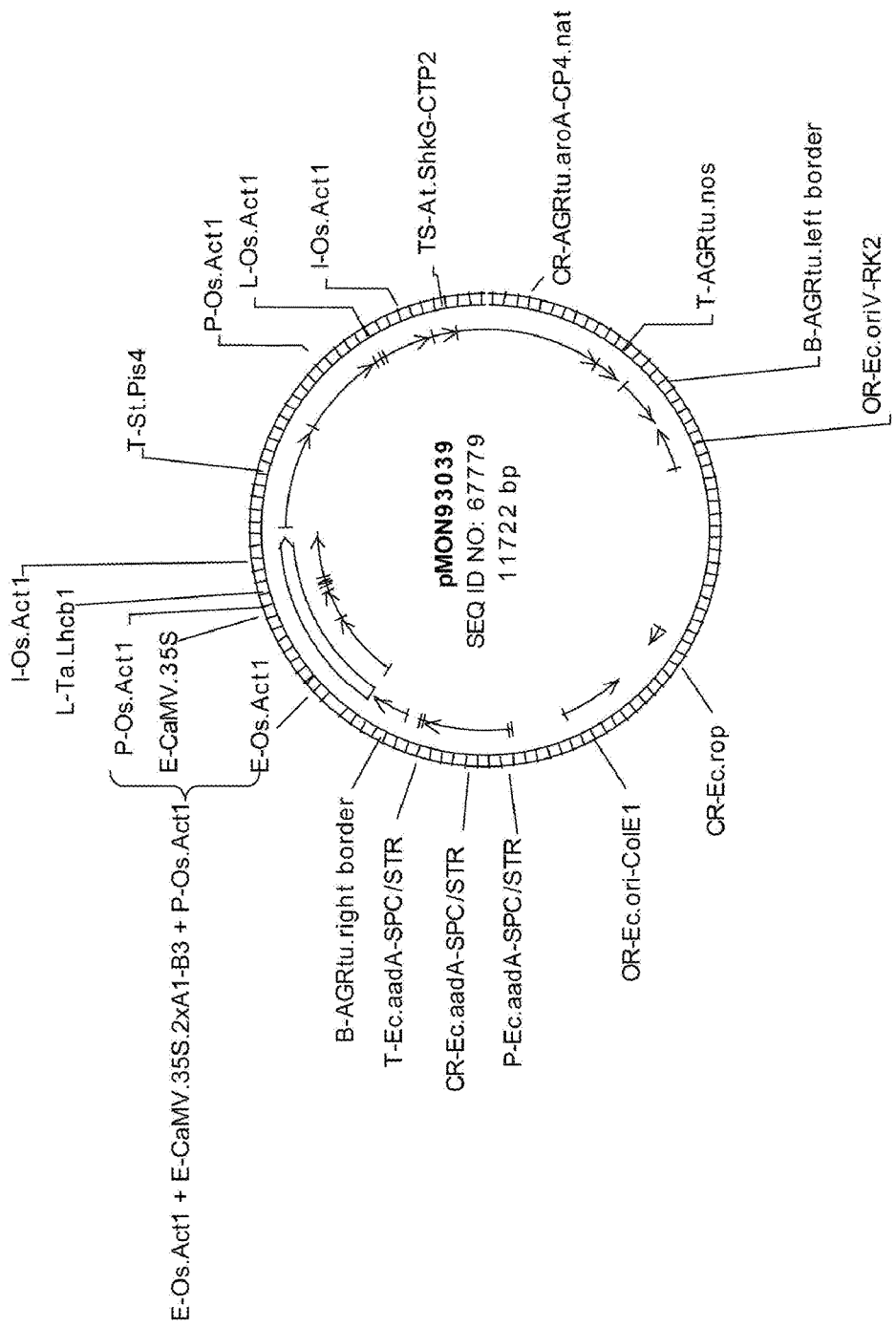
FIGS. 1, 2 and 3 illustrate plasmid maps.

In the attached sequence listing:
SEQ ID NO: 1-759 are nucleotide sequences of the protein coding strand of DNA" used in the recombinant DNA for imparting an enhanced trait in plant cells;

SEQ ID NO: 760-1518 are amino acid sequences of the cognate protein of the nucleotide sequences of SEQ ID NO: 1-759;

SEQ ID NO: 1519- 67778 are amino acid sequences of homologous proteins; SEQ ID NO: 67779 is a nucleotide sequence of a plasmid base vector useful for corn transformation; and SEQ ID NO: 67780 is a DNA sequence of a plasmid base vector useful for soybean transformation.

SEQ ID NO: 67781 is a DNA sequence of a plasmid base vector useful for cotton transformation.

SEQ ID NO: 67782-67894 are consensus sequences.

Table 1 lists the protein SEQ ID NOs and their corresponding consensus SEQ ID NOs.

TABLE 1

| Gene ID | SEQ ID NO | Consensus SEQ ID NO |
|---|---|---|
| CGPG1083 | 767 | 67782 |
| CGPG1088 | 768 | 67783 |
| CGPG1092 | 769 | 67784 |
| CGPG1108 | 770 | 67785 |
| CGPG1140 | 772 | 67786 |
| CGPG1143 | 773 | 67787 |
| CGPG1170 | 775 | 67788 |
| CGPG1192 | 778 | 67789 |
| CGPG1311 | 786 | 67790 |
| CGPG1391 | 792 | 67791 |
| CGPG1633 | 809 | 67792 |
| CGPG1715 | 814 | 67793 |
| CGPG1895 | 822 | 67794 |
| CGPG2035 | 836 | 67795 |
| CGPG2068 | 840 | 67796 |
| CGPG2118 | 844 | 67797 |
| CGPG2191 | 848 | 67798 |
| CGPG2313 | 855 | 67799 |
| CGPG2426 | 864 | 67800 |
| CGPG2437 | 866 | 67801 |
| CGPG2452 | 867 | 67802 |
| CGPG2855 | 882 | 67803 |
| CGPG3004 | 887 | 67804 |
| CGPG3084 | 892 | 67805 |
| CGPG3269 | 905 | 67806 |
| CGPG3270 | 906 | 67807 |
| CGPG3410 | 913 | 67808 |
| CGPG3605 | 922 | 67809 |
| CGPG3612 | 923 | 67810 |
| CGPG3616 | 924 | 67811 |
| CGPG3631 | 925 | 67812 |
| CGPG375 | 933 | 67813 |
| CGPG3931 | 940 | 67814 |
| CGPG3975 | 944 | 67815 |
| CGPG4346 | 974 | 67816 |
| CGPG4383 | 977 | 67817 |
| CGPG4437 | 983 | 67818 |
| CGPG4660 | 995 | 67819 |
| CGPG4772 | 1007 | 67820 |
| CGPG5196 | 1043 | 67821 |
| CGPG5212 | 1046 | 67822 |
| CGPG5304 | 1057 | 67823 |
| CGPG5510 | 1072 | 67824 |
| CGPG5732 | 1100 | 67825 |
| CGPG5889 | 1116 | 67826 |
| CGPG5921 | 1120 | 67827 |
| CGPG5925 | 1121 | 67828 |
| CGPG5926 | 1122 | 67829 |
| CGPG6049 | 1135 | 67830 |
| CGPG6120 | 1142 | 67831 |
| CGPG6201 | 1151 | 67832 |
| CGPG6311 | 1169 | 67833 |
| CGPG6353 | 1176 | 67834 |
| CGPG6636 | 1214 | 67835 |
| CGPG691 | 1235 | 67836 |
| CGPG6930 | 1238 | 67837 |
| / | / | / |
| CGPG6934 | 1239 | 67838 |
| CGPG7056 | 1249 | 67839 |

TABLE 1-continued

| Gene ID | SEQ ID NO | Consensus SEQ ID NO |
|---|---|---|
| CGPG7071 | 1250 | 67840 |
| CGPG7243 | 1270 | 67841 |
| CGPG7258 | 1271 | 67842 |
| CGPG7324 | 1277 | 67843 |
| CGPG7338 | 1279 | 67844 |
| CGPG7352 | 1282 | 67845 |
| CGPG7362 | 1285 | 67846 |
| CGPG7430 | 1295 | 67847 |
| CGPG7438 | 1296 | 67848 |
| CGPG7450 | 1299 | 67849 |
| CGPG7452 | 1300 | 67850 |
| CGPG7480 | 1302 | 67851 |
| CGPG7510 | 1308 | 67852 |
| CGPG7517 | 1310 | 67853 |
| CGPG7523 | 1311 | 67854 |
| CGPG7532 | 1314 | 67855 |
| CGPG7548 | 1316 | 67856 |
| CGPG7599 | 1320 | 67857 |
| CGPG7616 | 1324 | 67858 |
| CGPG7793 | 1333 | 67859 |
| CGPG7816 | 1338 | 67860 |
| CGPG7826 | 1339 | 67861 |
| CGPG7861 | 1340 | 67862 |
| CGPG8054 | 1362 | 67863 |
| CGPG8059 | 1363 | 67864 |
| CGPG8084 | 1367 | 67865 |
| CGPG8093 | 1368 | 67866 |
| CGPG8097 | 1371 | 67867 |
| CGPG8112 | 1372 | 67868 |
| CGPG8120 | 1373 | 67869 |
| CGPG8157 | 1376 | 67870 |
| CGPG8158 | 1377 | 67871 |
| CGPG8212 | 1382 | 67872 |
| CGPG8375 | 1403 | 67873 |
| CGPG8383 | 1405 | 67874 |
| CGPG8544 | 1422 | 67875 |
| CGPG8546 | 1423 | 67876 |
| CGPG8549 | 1424 | 67877 |
| CGPG8588 | 1429 | 67878 |
| CGPG8597 | 1430 | 67879 |
| CGPG8629 | 1433 | 67880 |
| CGPG8636 | 1437 | 67881 |
| CGPG8646 | 1440 | 67882 |
| CGPG8677 | 1442 | 67883 |
| CGPG8716 | 1446 | 67884 |
| CGPG8754 | 1447 | 67885 |
| CGPG9001 | 1471 | 67886 |
| CGPG9069 | 1476 | 67887 |
| CGPG9097 | 1480 | 67888 |
| CGPG9106 | 1481 | 67889 |
| CGPG9143 | 1487 | 67890 |
| CGPG9188 | 1498 | 67891 |
| CGPG9248 | 1505 | 67892 |
| CGPG9285 | 1509 | 67893 |
| CGPG9315 | 1513 | 67894 |

The nuclei of this invention are identified by screening transgenic plants for one or more traits including enhanced drought stress tolerance, enhanced heat stress tolerance, enhanced cold stress tolerance, enhanced high salinity stress tolerance, enhanced low nitrogen availability stress tolerance, enhanced shade stress tolerance, enhanced plant growth and development at the stages of seed imbibition through early vegetative phase, and enhanced plant growth and development at the stages of leaf development, flower production and seed maturity.

As used herein a "plant cell" means a plant cell that is transformed with stably-integrated, non-natural, recombinant DNA, e.g. by Agrobacterium-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and to artificially-created variants. Degeneracy of the genetic code provides the possibility to substitute at least one base of the protein encoding sequence of a gene with a different base without causing the amino acid sequence of the polypeptide produced from the gene to be changed. Hence, a polynucleotide useful in the present invention may have any base sequence that has been changed from SEQ ID NO: 1 through SEQ ID NO: 803 through substitution in accordance with degeneracy of the genetic code. Homologs are proteins that, when optimally aligned, have at least 60% identity, more preferably about 70% or higher, more preferably at least 80% and even more preferably at least 90% identity over the full length of a protein identified as being associated with imparting an enhanced trait when expressed in plant cells. Homologs include proteins with an amino acid sequence that has at least 90% identity to a consensus amino acid sequence of proteins and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein a "control plant" means a plant that does not contain the recombinant DNA that expressed a protein that imparts an enhanced trait. A control plant is to identify and select a transgenic plant that has an enhance trait. A suitable control plant can be a non-transgenic plant of the parental line used to generate a transgenic plant, i.e. devoid of recombinant DNA. A suitable control plant may in some cases be a progeny of a hemizygous transgenic plant line that is does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil.

In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tonnes per acre, tons per acre, kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alterations in the ratios of seed components.

"*Arabidopsis*" means plants of *Arabidopsis thaliana*.

"Pfam" database is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by candidate DNA against the Hidden Markov Models which characterizes the Pfam domains using HMMER software which is publicly available from the Pfam Consortium. Candidate proteins meeting the same Pfam domain module are in the protein family and have cognate DNA that is useful in constructing recombinant DNA for the use in the plant cells of this invention. Hidden Markov Model databases for use with HMMER software in identifying DNA expressing protein with a common Pfam domain module for recombinant DNA in the plant cells of this invention are also publicly available from the Pfam Consortium.

Version 19.0 of the HMMER software and Pfam databases were used to identify known domains in the proteins corresponding to amino acid sequence of SEQ ID NO: 760 through SEQ ID NO: 1518. All DNA encoding proteins that have scores higher than the gathering cutoff disclosed in Table 19 by Pfam analysis disclosed herein can be used in recombinant DNA of the plant cells of this invention, e.g. for selecting transgenic plants having enhanced agronomic traits. The relevant Pfam modules for use in this invention, as more specifically disclosed below, are Saccharop_dh, Isoamylase_N::Alpha-amylase, RRM_1, Pribosyltran, Skp1_POZ::Skp1, PTR2, PSI_PsaH, OTU, Aldedh, p450, AP2, CBS, TPT, zf-UBR, zf-C3HC4, ADH_N::ADH_zinc_N, Pre-SET::SET, OstA, Myb_DNA-binding, Cpn60_TCP1, SKI, Cyt-b5::FA_desaturase, Pkinase, KT112, SNARE, NLE::WD40::WD40::WD40::WD40, zf-C3HC4, Complex1_30 kDa::Complex1_49 kDa, iPGM_N::Metalloenzyme, adh_short, IQ::IQ, Glutaredoxin, LRRNT_2::LRR_1::LRR_1::Pkinase, Pkinase, Pribosyltran, DUF623, AWPM-19, Glucokinase, Pkinase_Tyr, Ribosomal_S8, F-box::Sel1::Sel1::zf-MYND, DUF313, WRKY, Aa_trans, Aminotran_1_2, Cystatin, PFK, PGAM, F-box, Ras, WD40::WD40::WD40::WD40, C2, Gal-bind_lectin::Galactosyl_T, Pyr_redox_2::Pyr_redox_dim, Ank::Ank::Pkinase_Tyr, Aminotran_1_2, AMP-binding, Aminotran_3, PEARL1-4, RRM_1, LRRNT_2::LRR_1::LRR_1::LRR_1::LRR_1::Pkinase, SNARE_assoc, FKBP_C, ELFV_dehydrog_N::ELFV_dehydrog, Sugar_tr, SPT2, DUF23, Dehydrin, Prefoldin, WD40::WD40::WD40::WD40::WD40::WD40::WD40, IQ::IQ, zf-Tim10_DDP, PPR::PPR::PPR::PPR::PPR::PPR::PPR, F-box::FBA_3, SH3_1, RNA_poll_A14, GAF::HisKA, Pkinase::efhand::efhand, Y_phosphatase2, 60KD_IMP, ADH_zinc_N, Glutaminase, p450, p450, Transket_pyr::Transketolase_C, B3_4::B5, Zip, DUF791::MFS_1, AA_permease, Pkinase, SAC3_GANP, DUF862, Pkinase, CS, TFIIS, Ribosomal_L19, Sugar_tr, NIF, SRF-TF::K-box, MSP, PGAM, Aha1_N::AHSA1, p450, F-box::FBA_1, Amino_oxidase, Tryp_alpha_amyl, Sugar_tr, zf-CW::MBD, Cytochrom_C, Tryp_alpha_amyl, Tcp11, Cys_Met_Meta_PP, UQ_con, zf-CCHC, Pyr_redox_2, efhand::efhand::efhand, Maf, MATH::BTB, LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase, Glyco_hydro_17, IQ, V-SNARE, Pkinase, Thioredoxin, AA_permease, Metallothio_PEC, HLH, p450, Pyr_redox_2::efhand, PP2C, GILT, F-box::Kelch_1::Kelch_1, AlaDh_PNT_N::AlaDh_PNT_C::Saccharop_dh_N::Saccharop_dh, WD40::WD40, Molybdop_Fe4S4::Molybdopterin::Molydop_binding, Aldedh, efhand, ETC_C1_NDUFA4, PG1, Transthyretin, GRP, Spot11E, Dirigent, NUDIX, p450, Actin, Uricase::Uricase, Xan_ur_permease, NTP_transferase::Hexapep::Hexapep, zf-C3HC4, PPDK_N::PEP-utilizers::PEP-utilizers_C, Ribosomal_L37, Globin, Peptidase_M22, NADPH_Ox::Ferric_reduct::FAD_binding_8::NAD_binding_6, Glutaminase, XG_FTase, Enolase_N::Enolase_C, F-box::FBA_1, SOR_SNZ::ThiG, ABC_tran::ABC2_membrane::PDR_assoc::ABC_tran::ABC2_membrane, HMA::HMA, GATase::GMP_synt_C, Pkinase, CN_hydrolase::NAD_synthase, Usp::Pkinase, GRAM, Pkinase, DUF6::DUF6, Sugar_tr, Iso_dh, Tim17, Band_7, Polyketide_cyc, Cyclin_N::Cyclin_C, DUF26::DUF26::Pkinase, PPR::PPR::PPR::PPR::PPR::PPR::PPR::PPR, Amidohydro_2, 2OG-FeII_Oxy, PfkB, GILT, DUF246, Response_reg, TB2_DP1_HVA22, PP2C, ArfGap, TFIIF_alpha, ABC1, Methyltransf_12, Aldedh, TB2_DP1_HVA22, DUF6::TPT, Gp_dh_N::Gp_dh_C, efhand, SRF-TF, IQ::IQ, Lectin_legB::Pkinase, Self-incomp_S1, Hin1, Aminotran_1_2, Copine, ADH_N::ADH_zinc_N, Sugar_tr, DUF860, Pkinase, Sugar_tr, Nol1_Nop2_Fmu, zf-MYND::UCH, Aldedh, F-box::Kelch_1::Kelch_1, TOM20_plant, Sugar_tr, DHDPS, CPDase, Aldedh, Invertase_neut, Metallophos, PBP, Reticulon, Histone, DUF260, Phi_1, p450, Lectin_legB::Pkinase, Abhydrolase_1, AMP-binding, DAGK_cat, Pkinase::NAF, IQ::IQ, DnaJ::DnaJ_CXXCXGXG::DnaJ_C, RRM_1, RRM_1, Citrate_synt, Glutaminase, DUF6::DUF6, PRACH::PRA-PH, Aldedh, adh_short, Pkinase, Cyclin_N::Cyclin_C, CCT, AP2, Cullin, Lung_7-TM_R, DUF1677, Rib_5-P_isom_A, TPK_catalytic::TPK_B1_binding, Sugar_tr, DUF926, AstE_AspA, Cyt-b5, HEAT::Arm::HEAT::Arm, Arf, SRF-TF, Aldedh, Glyco_transf_8, F-box::LRR_2::FBD, p450, DUF833, IQ::IQ, Aldedh, P13_P14_kinase, p450, RNA_pol_1_A49, Abhydrolase_1, TFIIS_C, HMG-CoA_red, HEAT::HEAT::HEAT::HEAT::HEAT::HEAT::HEAT::HEAT::HEAT::HEAT::HEAT::HEAT, MMR_HSR1, Ank::Ank::Ank, CorA, DUF827, Cyclin, Glyco_transf_8, DUF623, zf-C3HC4, AA_permease, RRM_1::zf-CCHC, Ras, DEAD::Helicase_C::DSHCT, PAS_2::GAF::Phytochrome::HisKA::HATPase_c, Tetraspannin, NIR_SIR_ferr::NIR_SIR::NIR_SIR_ferr::NIR_SIR, ELFV_dehydrog_N::ELFV_dehydrog, F-box::Kelch_1::Kelch_1, Aldedh, RRM_1::RRM_1, RRM_1, PPR::PPR::PPR::PPR::PPR::PPR, DUF617, HD::ReIA_SpoT, Diphthamide_syn, Gp_dh_N::Gp_dh_C, ThiC, CRAL_TRIO_N::CRAL_TRIO, FTHFS, MIP, Fibrillarin, Pkinase, Pkinase, GTP_EFTU::GTP_EFTU_D2::EFG_C, PPR::PPR::PPR::PPR::PPR::PPR, PTR2, FAD_binding_4, ScpA_ScpB, NDUF_B7, TPT, DEA D::Helicase_C, DnaJ, TPT, cobW, HIT, DHquinase_1::Shikimate_dh_N::Shikimate_DH, IQ::IQ, Aldedh, DUF231, PG1, zf-C3HC4, CorA, Transketolase_N::Transket_pyr:Transketolase_C, Dehydrin, RRM_1, Sterol_desat, eIF2A, ArfGap::C2, NTP_transferase, DAG, Sugar_tr, DUF21::CBS, Pkinase::NAF, Sulfotransfer_1, p450, PGM_PMM_I::PGM_PMM_II::PGM_PMM_III::PGM_PMM_IV, CPSase_L_chain::CPSase_L_D2::CPSase_L_D3::CPSase_L_chain::CPSase_L_D2::MGS, Pro_CA, DUF617, Voltage_CLC::CBS, F-box, Histone, 14-3-3, UBX, polyprenyl_synt, Rho_GDI, TPR_2, Aldedh, LRR_I::LRR_I::LRR_I::Pkinase, DUF239, Pkinase, Glycolytic, adh_short, DUF1001, PTR2, ATP_synt_H, p450, Mito_carr:Mito_cam:Mito_carr, Gar1, Gln-synt_N::Gln-synt_C, PseudoU_synth_1::PseudoU_synth_1, DUF1635, Pkinase, Pro_dh, DUF506, Acyltransferase, DJ-1_Pfp1::DJ-1_Pfp1, PAP2, IQ, Isy1, Glutaredoxin, Molybdop_Fe4S4::Molybdopterin::Molydop_binding:Fer2_BFD, DUF778, Cyclin_N, zf-C3HC4, DUF300, DUF1639, Peptidasc_C26, P21-Arc, Mo25, Pkinasc, Ras, DUF788, iPGM_N::Metalloenzyme, adh_short, Pyr_redox, Gln-synt_N::Gln-synt_C, FA_desaturase, zf-MYND::UCH, Skp1_POZ::Skp1, Cornichon, 1GPD, Orn_Arg_deC_N::Orn_DAP_Arg_deC, DUF260, Gln-synt_N::Gln-synt_C, RRM_1, 2OG-Fell_Oxy, SNARE, RRM_1, DUF212, F-box, Phytochelatin::DUF1984, SRF-TF, TIM, MSF1, Ribonuc_L-PSP, p450, Transaldolase, Snf7, p450, FA_desaturase, F-box, efhand_like::PI-PLC-X::PI-PLC-Y::C2, Trehalose_PPase, Aminotran_4, Thioredoxin, Chitin_bind_1::Barwin, TLD, GATase_2::Asn_synthase, Pkinase, Pyridoxal_deC, Biotin_lipoyl::E3_binding::2-oxoacid_dh, H_PPase, DUF914, WD40::WD40::WD40, SIR2, Pkinase::efhand::efhand::efhand::efhand, LSM, PetM, DUF23, DUF862, tRNA-synt_1g, Radical_SAM, LRR_1::LRR_1::LRR_1::LRR_1::LRR_1::LRR_1::LRR_1::LRR_1::Pkinase, DUF1644, Mov34, NOI, DUF6::TPT, Transket_pyr:Transketolase_C, F-box::LRR_2, zf-C3HC4, Phosphoesterase, SET, adh_short, Exo_endo_phos, Pkinase, Stig1, TFIIS_M::SPOC, Gln-synt_N::Gln-synt_C, B56, Aminotran_1_2, Aldose_epim, DUF1645, iPGM_N::Metalloenzyme, LRRNT_2::LRR_1::LRR_1::LRR_1::LRR_1::LRR_1::Pkinase, DUF538, Not3::NOT2_3_5, YjeF_N::Carb_kinase, DUF538, F-box, Cyclin_N::Cyclin_C, Aldedh, F-box, Pyr_redox_2, ELFV_dehydrog_N::ELEV_dehydrog, BCNT, Mago-bind, RRM_1, DUF783, Aminotran_3, ADH_N::ADH_zinc_N, Pkinase_Tyr, Ribosomal_S8, Pkinase, LRR_1, UDPGT, Peptidase_C54, mTERF, Skp1_POZ::Skp1, WD40::WD40::WD40::WD40, MtN3_slv::MtN3_slv, LRRNT_2::LRR_1::LRR_1::LRR_1::LRR_1::Pkinase, Aminotran_1_2, adh_short, PP2C, Senescence, Response_reg, DEAD::Helicase_C, Pkinase, zf-LSD1::zf-LSD1::zf-LSD1, PB1::Pkinase_Tyr, BTB::NPH3, PBD, Exo_endo_phos, Fer4::Fer4, WD40::WD40::WD40::WD40::PWP2, LysM, NTP_transferase, Tim17, Aa_trans, Ras, 1PK, F-box::LRR_2, FBPase, PP2C, Aldedh, Ank::Ank::Ank::Pkinase, Brix, PTR2, 2OG-Fell_Oxy, MCM, NTP_transferase::Hexapep::Hexapep::Hexapep::Hexapep, SapB_1::SaPB_2::SapB_1::SapB_2, Aldedh, DUF581, AAA, Cyclin_N, ARM_1, IQ::IQ, Pkinase, ubiquitin::UBA::XPC-binding::UBA, Pkinase, TIM, Abhydrolase_1, CBS, Pkinase, Pyr_redox_2::Pyr_redox_dim, NicO, CCT, zf-PARP::zf-PARP::PADR1::BRCT::WGR::PARP_reg::PARP, Spermine_synth, NDK, E1_dh, LRR_1::LRR_1::LRR_1::LRR_1::LRR_1::LRR_1::LRR_1::LRR_1, MATH::MATH, Cyclin_N::Cyclin_C, ADH_N::ADH_zinc_N, RRM_I, DUF393, LRR_1::LRR_1::LRR_1::LRR_1::LRR_1::LRR_1::LRR_1::LRR_1::LRR_1::LRR_1::LRR_1::LRR_1::LRR_1, AAA, zf-C3HC4::YDG_SRA, RWD, GHMP_kinases_N::GHMP_kinases_C, DZC, Glutaredoxin, DEAD::Helicase_C, Sterol_desat, DUF212, Pkinase, DREPP, PTR2, MGDG_synth::Glyco_tran_28_C, ACT::ACT, OTU, Pkinase, Glyco_hydro_1, Nuc_sug_transp, WD40::WD40::WD40::WD40::WD40::WD40::WD40::WD40::WD40::WD40::WD40::Utp13, Nramp, MFS_1, Metallophos, DUF1005, CTP_transf_1, RNA_pol_A_bac, DUF383::DUF384, DUF676, SAC3_GANP, ADH_N::ADH_zinc_N, PLAT::Lipoxygenase, SIS::CBS, Pkinase, Bystin, Response_reg, Phi_1, MFS_1, Pkinase, Pkinase, Gln-synt_N::Gln-synt_C, NUDIX, NIR_SIR_ferr::NIR_SIR::NIR_SIR_ferr::NIR_SIR, UFD1, DUF581, p450, WD40::WD40::WD40::WD40, p450, Gp_dh_N::Gp_dh_C, Abhydrolase_3, TP_methylase, Pkinase, LRR_1::LRR_1::LRR_1::LRR_1::LRR_1::LRR_1::LRR_1, GATase::GMP_synt_C, PfkB, RRM_1, malic::Malic_M, DUF525, FBPase, DUF59, Pro_isomerase, Arm::Arm, Pkinase_Tyr, Pkinase::NAF, BNR::BNR::BNR, DUF1350, CAF1, TMEM14, MATH, DUF1000, PC_rep::PC_rep::PC_rep::PC_rep::PC_rep::PC_rep, Pkinase, FHA::PP2C, Pkinase, Di19, WD40::WD40, 200-Fell_Oxy, Pkinase, adh_short, Aldedh, DUF793, DUF1749, AAA, PGK, Aminotran_3, Str_synth, e1F-1a, Hydrolase, Sugar_tr, DUF640, PCI, Sina, PBP, AOX, OPT, Pkinase_Tyr, Rib_5-P_isom_A, DUF740, PP2C, Pkinase, and Cyclin_N::Cyclin_C.

Recombinant DNA Constructs

The invention uses recombinant DNA for imparting one or more enhanced traits to transgenic plant when incorporated into the nucleus of the plant cells. DNA constructs comprising one or more polynucleotides disclosed herein are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876, which discloses a rice actin promoter, U.S. Pat. No. 7,151,204, which discloses a maize chloroplast aldolase promoter and a maize aldolase (FDA) promoter, and U.S. Patent Application Publication 2003/0131377 A1, which discloses a maize nicotianamine synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters of interest for such uses include those from genes such as *Arabidopsis thaliana* ribulose-1,5-bisphosphate carboxylase (Rubisco) small subunit (Fischhoff et al. (1992) *Plant Mol Biol.* 20:81-93), aldolase and pyruvate orthophosphate dikinase (PPDK) (Taniguchi et al. (2000) *Plant Cell Physiol.* 41(1): 42-48).

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5.593,874) and the maize shrunken 1 gene.

In other aspects of the invention, sufficient expression in plant seed tissues is desired to affect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol Biol.* 31(6)1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1, 6-biphosphatase gene, a rice glutelin gene, a rice lactate dehydrogenase gene and a rice beta-tubulin gene, all of which arc disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. No. 5,188,642 and U.S. Pat. No. 5,728,925, incorporated herein by reference. For description of the transit peptide region of an *Arabidopsis* EPSPS gene useful in the present invention, see Klee, H. J. et al (*MGG* (1987) 210:437-442).

Gene suppression includes any of the well-known methods for suppressing transcription of a gene or the accumulation of the mRNA corresponding to that gene thereby preventing translation of the transcript into protein. Post-transcriptional gene suppression is mediated by transcription of RNA that forms double-stranded RNA (dsRNA) having homology to a gene targeted for suppression. Suppression can also be achieved by insertion mutations created by transposable elements may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance. traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 also for imparting glyphosate tolerance; dicamba monooxygenase disclosed in U.S. Patent Application publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtl) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for impartinig pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260, all of said U.S. Patents and Patent Application Publications are incorporated herein by reference. Molecules and methods for imparting insect/nematode/virus resistance are disclosed in U.S. Pat. Nos. 5,250,515; 5,880, 275; 6,506,599; 5,986,175 and U.S. Patent Application Publication 2003/0150017 A1, all of which are incorporated herein by reference.

Table 2 provides a list of genes that provided recombinant DNA that was expressed in a model plant and identified from screening as imparting an enhanced trait. When the stated orientation is "sense", the expression of the gene or a homolog in a crop plant provides the means to identify transgenic events that provide an enhanced trait in the crop plant. When the stated orientation is "antisense", the suppression of the native homolog in a crop plant provides the means to identify transgenic events that provide an enhanced trait in the crop plant. In some cases the expression/suppression in the model plant exhibited an enhanced trait that corresponds to an enhanced agronomic trait, e.g. cold stress tolerance, water deficit stress tolerance, low nitrogen stress tolerance and the like. In other cases the expression/suppression in the model plant exhibited an enhanced trait that is a surrogate to an enhanced agronomic trait, e.g. salinity stress tolerance being a surrogate to drought tolerance or improvement in plant growth and development being a surrogate to enhanced yield. Even when expression of a transgene or suppression of a native gene imparts an enhanced trait in a model plant, not every crop plant expressing the same transgene or suppressing the same native gene will necessarily demonstrate an indicated enhanced agronomic trait. For instance, it is well known that multiple transgenic events are required to identify a transgenic plant that can exhibit an enhanced agronomic trait. However, by with routine experimentation a transgenic plant cell nuclei, cell, plant or seed of this invention can be identified by making a reasonable number of transgenic events and engaging in screening process identified in this specification and illustrated in the examples. An understanding of Table 2 is facilitated by the following description of the headings:

"NUC SEQ ID NO" refers to a SEQ ID NO. for particular DNA sequence in the Sequence Listing.

"PEP SEQ ID NO" refers to a SEQ ID NO. in the Sequence Listing for the amino acid sequence of a protein cognate to a particular DNA "construct_id" refers to an arbitrary number used to identify a particular recombinant DNA construct comprising the particular DNA.

"Gene ID" refers to an arbitrary name used to identify the particular DNA.

"orientation" refers to the orientation of the particular DNA in a recombinant DNA construct relative to the promoter.

TABLE 2

| NUC Seq ID | PEP Seq ID | Gene ID | Construct ID | Orientation |
|---|---|---|---|---|
| 1 | 760 | CGPG1022 | 12792 | ANTI-SENSE |
| 2 | 761 | CGPG1035 | 13673 | ANTI-SENSE |
| 3 | 762 | CGPG1043 | 12020 | SENSE |
| 4 | 763 | CGPG105 | 10174 | ANTI-SENSE |
| 5 | 764 | CGPG1060 | 11827 | ANTI-SENSE |
| 6 | 765 | CGPG1069 | 12435 | SENSE |
| 7 | 766 | CGPG108 | 12015 | SENSE |
| 8 | 767 | CGPG1083 | 11836 | ANTI-SENSE |
| 9 | 768 | CGPG1088 | 12141 | ANTI-SENSE |
| 10 | 769 | CGPG1092 | 12040 | SENSE |
| 11 | 770 | CGPG1108 | 12437 | SENSE |
| 12 | 771 | CGPG1136 | 12156 | ANTI-SENSE |
| 13 | 772 | CGPG1140 | 11853 | ANTI-SENSE |
| 14 | 773 | CGPG1143 | 12224 | SENSE |
| 15 | 774 | CGPG1145 | 11856 | ANTI-SENSE |
| 16 | 775 | CGPG1170 | 12065 | SENSE |
| 17 | 776 | CGPG1173 | 12419 | ANTI-SENSE |
| 18 | 777 | CGPG1176 | 12208 | SENSE |
| 19 | 778 | CGPG1192 | 14803 | SENSE |
| 20 | 779 | CGPG122 | 10176 | ANTI-SENSE |
| 21 | 780 | CGPG126 | 18011 | SENSE |
| 22 | 781 | CGPG1262 | 12714 | ANTI-SENSE |
| 23 | 782 | CGPG128 | 10507 | ANTI-SENSE |
| 24 | 783 | CGPG1280 | 15039 | SENSE |
| 25 | 784 | CGPG1291 | 12733 | ANTI-SENSE |
| 26 | 785 | CGPG1295 | 13237 | SENSE |
| 27 | 786 | CGPG1311 | 13504 | SENSE |
| 28 | 787 | CGPG1315 | 12932 | SENSE |
| 29 | 788 | CGPG1335 | 75935 | SENSE |
| 30 | 789 | CGPG1344 | 73333 | SENSE |
| 31 | 790 | CGPG1352 | 75993 | SENSE |
| 32 | 791 | CGPG1364 | 19401 | SENSE |
| 33 | 792 | CGPG1391 | 12766 | ANTI-SENSE |

TABLE 2-continued

| NUC Seq ID | PEP Seq ID | Gene ID | Construct ID | Orientation |
|---|---|---|---|---|
| 34 | 793 | CGPG1396 | 76025 | SENSE |
| 35 | 794 | CGPG1398 | 13708 | ANTI-SENSE |
| 36 | 795 | CGPG1399 | 13305 | ANTI-SENSE |
| 37 | 796 | CGPG1429 | 15806 | SENSE |
| 38 | 797 | CGPG1430 | 14712 | SENSE |
| 39 | 798 | CGPG1445 | 76013 | SENSE |
| 40 | 799 | CGPG146 | 10192 | ANTI-SENSE |
| 41 | 800 | CGPG1492 | 74775 | SENSE |
| 42 | 801 | CGPG1528 | 13841 | ANTI-SENSE |
| 43 | 802 | CGPG1530 | 15805 | SENSE |
| 44 | 803 | CGPG1535 | 14253 | ANTI-SENSE |
| 45 | 804 | CGPG1546 | 13650 | ANTI-SENSE |
| 46 | 805 | CGPG1567 | 13855 | ANTI-SENSE |
| 47 | 806 | CGPG1568 | 76049 | SENSE |
| 48 | 807 | CGPG1575 | 14271 | ANTI-SENSE |
| 49 | 808 | CGPG1619 | 73927 | SENSE |
| 50 | 809 | CGPG1633 | 13657 | ANTI-SENSE |
| 51 | 810 | CGPG1641 | 13938 | ANTI-SENSE |
| 51 | 810 | CGPG1641 | 14730 | SENSE |
| 52 | 811 | CGPG1651 | 73948 | SENSE |
| 53 | 812 | CGPG1656 | 18116 | ANTI-SENSE |
| 54 | 813 | CGPG1668 | 14341 | ANTI-SENSE |
| 55 | 814 | CGPG1715 | 13960 | ANTI-SENSE |
| 55 | 814 | CGPG1715 | 74391 | SENSE |
| 56 | 815 | CGPG1740 | 75957 | SENSE |
| 57 | 816 | CGPG177 | 70240 | SENSE |
| 58 | 817 | CGPG1785 | 70748 | ANTI-SENSE |
| 59 | 818 | CGPG182 | 70807 | SENSE |
| 60 | 819 | CGPG1837 | 73986 | SENSE |
| 61 | 820 | CGPG1873 | 77005 | SENSE |
| 62 | 821 | CGPG1891 | 70410 | ANTI-SENSE |
| 63 | 822 | CGPG1895 | 14827 | ANTI-SENSE |
| 64 | 823 | CGPG1899 | 19122 | SENSE |
| 65 | 824 | CGPG1913 | 16446 | SENSE |
| 66 | 825 | CGPG1918 | 15143 | SENSE |
| 67 | 826 | CGPG1919 | 70401 | SENSE |
| 68 | 827 | CGPG1922 | 16182 | SENSE |
| 69 | 828 | CGPG1929 | 15126 | SENSE |
| 70 | 829 | CGPG1938 | 15628 | ANTI-SENSE |
| 71 | 830 | CGPG1956 | 78355 | SENSE |
| 72 | 831 | CGPG1964 | 70560 | SENSE |
| 73 | 832 | CGPG1973 | 19133 | SENSE |
| 74 | 833 | CGPG1977 | 73602 | SENSE |
| 75 | 834 | CGPG1996 | 71702 | SENSE |
| 76 | 835 | CGPG2005 | 14909 | ANTI-SENSE |
| 77 | 836 | CGPG2035 | 14927 | ANTI-SENSE |
| 78 | 837 | CGPG2044 | 75945 | SENSE |
| 79 | 838 | CGPG2059 | 16553 | ANTI-SENSE |
| 80 | 839 | CGPG2065 | 75221 | SENSE |
| 81 | 840 | CGPG2068 | 70746 | ANTI-SENSE |
| 82 | 841 | CGPG2072 | 70403 | SENSE |
| 83 | 842 | CGPG2074 | 15966 | ANTI-SENSE |
| 84 | 843 | CGPG2116 | 76076 | SENSE |
| 85 | 844 | CGPG2118 | 17014 | SENSE |
| 86 | 845 | CGPG2142 | 16007 | ANTI-SENSE |
| 87 | 846 | CGPG2148 | 16208 | SENSE |
| 88 | 847 | CGPG2190 | 17310 | SENSE |
| 89 | 848 | CGPG2191 | 15716 | ANTI-SENSE |
| 90 | 849 | CGPG221 | 15627 | SENSE |
| 91 | 850 | CGPG2213 | 15409 | ANTI-SENSE |
| 91 | 850 | CGPG2213 | 17201 | SENSE |
| 92 | 851 | CGPG2247 | 15903 | ANTI-SENSE |
| 93 | 852 | CGPG228 | 10332 | ANTI-SENSE |
| 94 | 853 | CGPG2301 | 73968 | SENSE |
| 95 | 854 | CGPG2304 | 17003 | SENSE |
| 96 | 855 | CGPG2313 | 73847 | SENSE |
| 97 | 856 | CGPG2348 | 76041 | SENSE |
| 98 | 857 | CGPG2349 | 74567 | SENSE |
| 99 | 858 | CGPG2354 | 15809 | ANTI-SENSE |
| 100 | 859 | CGPG2369 | 70110 | SENSE |
| 101 | 860 | CGPG2382 | 70123 | SENSE |
| 102 | 861 | CGPG2392 | 74702 | SENSE |
| 103 | 862 | CGPG2397 | 75936 | SENSE |
| 104 | 863 | CGPG240 | 10462 | ANTI-SENSE |
| 105 | 864 | CGPG2426 | 17402 | SENSE |
| 106 | 865 | CGPG2433 | 73707 | SENSE |
| 107 | 866 | CGPG2437 | 17129 | ANTI-SENSE |

TABLE 2-continued

| NUC Seq ID | PEP Seq ID | Gene ID | Construct ID | Orientation |
|---|---|---|---|---|
| 108 | 867 | CGPG2452 | 72665 | SENSE |
| 109 | 868 | CGPG2464 | 18206 | SENSE |
| 110 | 869 | CGPG2472 | 17151 | ANTI-SENSE |
| 111 | 870 | CGPG2480 | 17813 | SENSE |
| 112 | 871 | CGPG253 | 70845 | SENSE |
| 113 | 872 | CGPG2538 | 16607 | SENSE |
| 114 | 873 | CGPG2567 | 72675 | SENSE |
| 115 | 874 | CGPG2571 | 72677 | SENSE |
| 116 | 875 | CGPG258 | 74534 | SENSE |
| 117 | 876 | CGPG268 | 74535 | SENSE |
| 118 | 877 | CGPG274 | 10204 | ANTI-SENSE |
| 119 | 878 | CGPG275 | 10472 | SENSE |
| 120 | 879 | CGPG277 | 10431 | ANTI-SENSE |
| 121 | 880 | CGPG2785 | 72906 | SENSE |
| 122 | 881 | CGPG2832 | 78362 | SENSE |
| 123 | 882 | CGPG2855 | 17930 | SENSE |
| 124 | 883 | CGPG2865 | 18442 | SENSE |
| 125 | 884 | CGPG2874 | 73207 | SENSE |
| 126 | 885 | CGPG2914 | 19166 | SENSE |
| 127 | 886 | CGPG295 | 10469 | SENSE |
| 128 | 887 | CGPG3004 | 18415 | SENSE |
| 129 | 888 | CGPG3009 | 18418 | SENSE |
| 130 | 889 | CGPG3030 | 19532 | SENSE |
| 131 | 890 | CGPG3048 | 18423 | SENSE |
| 132 | 891 | CGPG3056 | 77909 | SENSE |
| 133 | 892 | CGPG3084 | 19656 | SENSE |
| 134 | 893 | CGPG309 | 10217 | ANTI-SENSE |
| 135 | 894 | CGPG3094 | 18874 | SENSE |
| 136 | 895 | CGPG3095 | 18875 | SENSE |
| 137 | 896 | CGPG3137 | 19256 | SENSE |
| 138 | 897 | CGPG3156 | 19537 | SENSE |
| 139 | 898 | CGPG3157 | 74201 | SENSE |
| 140 | 899 | CGPG3205 | 74233 | SENSE |
| 141 | 900 | CGPG3236 | 18644 | SENSE |
| 142 | 901 | CGPG3248 | 18827 | SENSE |
| 143 | 902 | CGPG3255 | 18220 | SENSE |
| 144 | 903 | CGPG3258 | 18830 | SENSE |
| 145 | 904 | CGPG3261 | 19205 | SENSE |
| 146 | 905 | CGPG3269 | 18226 | SENSE |
| 147 | 906 | CGPG3270 | 18227 | SENSE |
| 148 | 907 | CGPG3283 | 18239 | SENSE |
| 149 | 908 | CGPG3302 | 70415 | SENSE |
| 150 | 909 | CGPG3334 | 18329 | SENSE |
| 151 | 910 | CGPG3361 | 72606 | SENSE |
| 152 | 911 | CGPG337 | 10230 | ANTI-SENSE |
| 153 | 912 | CGPG3400 | 19608 | SENSE |
| 154 | 913 | CGPG3410 | 18271 | SENSE |
| 155 | 914 | CGPG3424 | 18347 | SENSE |
| 156 | 915 | CGPG3428 | 18403 | SENSE |
| 157 | 916 | CGPG3465 | 74206 | SENSE |
| 158 | 917 | CGPG347 | 10234 | ANTI-SENSE |
| 159 | 918 | CGPG351 | 71115 | SENSE |
| 160 | 919 | CGPG3567 | 18406 | SENSE |
| 161 | 920 | CGPG3575 | 19619 | SENSE |
| 162 | 921 | CGPG3579 | 19623 | SENSE |
| 163 | 922 | CGPG3605 | 18381 | SENSE |
| 164 | 923 | CGPG3612 | 18408 | SENSE |
| 165 | 924 | CGPG3616 | 18720 | SENSE |
| 166 | 925 | CGPG3631 | 77537 | SENSE |
| 167 | 926 | CGPG365 | 70833 | SENSE |
| 168 | 927 | CGPG3665 | 19328 | SENSE |
| 169 | 928 | CGPG3684 | 19312 | SENSE |
| 170 | 929 | CGPG3690 | 70538 | SENSE |
| 171 | 930 | CGPG3717 | 70440 | SENSE |
| 172 | 931 | CGPG372 | 11319 | ANTI-SENSE |
| 173 | 932 | CGPG3724 | 70443 | SENSE |
| 174 | 933 | CGPG375 | 72357 | SENSE |
| 175 | 934 | CGPG3781 | 70466 | SENSE |
| 176 | 935 | CGPG380 | 70241 | SENSE |
| 177 | 936 | CGPG3821 | 70476 | SENSE |
| 178 | 937 | CGPG3824 | 70477 | SENSE |
| 179 | 938 | CGPG3901 | 19713 | SENSE |
| 180 | 939 | CGPG391 | 12601 | SENSE |
| 181 | 940 | CGPG3931 | 19747 | SENSE |
| 182 | 941 | CGPG394 | 11117 | ANTI-SENSE |
| 183 | 942 | CGPG3964 | 70965 | SENSE |
| 184 | 943 | CGPG397 | 10366 | ANTI-SENSE |
| 184 | 943 | CGPG397 | 13404 | SENSE |
| 185 | 944 | CGPG3975 | 70935 | SENSE |
| 186 | 945 | CGPG3983 | 77717 | SENSE |
| 187 | 946 | CGPG3986 | 19966 | SENSE |
| 188 | 947 | CGPG3991 | 70909 | SENSE |
| 189 | 948 | CGPG4050 | 19906 | SENSE |
| 190 | 949 | CGPG4070 | 70974 | SENSE |
| 191 | 950 | CGPG4071 | 19802 | SENSE |
| 192 | 951 | CGPG4099 | 19746 | SENSE |
| 193 | 952 | CGPG4138 | 70902 | SENSE |
| 194 | 953 | CGPG4152 | 19933 | SENSE |
| 195 | 954 | CGPG4153 | 19927 | SENSE |
| 196 | 955 | CGPG4164 | 70976 | SENSE |
| 197 | 956 | CGPG4169 | 71440 | SENSE |
| 198 | 957 | CGPG421 | 10413 | ANTI-SENSE |
| 199 | 958 | CGPG422 | 11119 | ANTI-SENSE |
| 200 | 959 | CGPG4223 | 78659 | SENSE |
| 201 | 960 | CGPG4240 | 78665 | SENSE |
| 202 | 961 | CGPG4242 | 78969 | SENSE |
| 203 | 962 | CGPG4248 | 78970 | SENSE |
| 204 | 963 | CGPG425 | 71250 | SENSE |
| 205 | 964 | CGPG4265 | 78972 | SENSE |
| 206 | 965 | CGPG4283 | 78677 | SENSE |
| 207 | 966 | CGPG4297 | 70632 | SENSE |
| 208 | 967 | CGPG43 | 75205 | SENSE |
| 209 | 968 | CGPG430 | 10359 | ANTI-SENSE |
| 209 | 968 | CGPG430 | 11408 | SENSE |
| 210 | 969 | CGPG4305 | 73616 | SENSE |
| 211 | 970 | CGPG4307 | 78358 | SENSE |
| 212 | 971 | CGPG4315 | 71839 | SENSE |
| 213 | 972 | CGPG4320 | 78417 | SENSE |
| 214 | 973 | CGPG4344 | 71952 | SENSE |
| 215 | 974 | CGPG4346 | 78717 | SENSE |
| 216 | 975 | CGPG4349 | 75040 | SENSE |
| 217 | 976 | CGPG4365 | 71843 | SENSE |
| 218 | 977 | CGPG4383 | 70666 | SENSE |
| 219 | 978 | CGPG4389 | 71846 | SENSE |
| 220 | 979 | CGPG4404 | 71314 | SENSE |
| 221 | 980 | CGPG4405 | 76410 | SENSE |
| 222 | 981 | CGPG4419 | 71322 | SENSE |
| 223 | 982 | CGPG4432 | 73214 | SENSE |
| 224 | 983 | CGPG4437 | 71963 | SENSE |
| 225 | 984 | CGPG4443 | 71326 | SENSE |
| 226 | 985 | CGPG445 | 70834 | SENSE |
| 227 | 986 | CGPG4453 | 73215 | SENSE |
| 228 | 987 | CGPG4481 | 71334 | SENSE |
| 229 | 988 | CGPG4490 | 71335 | SENSE |
| 230 | 989 | CGPG4498 | 71347 | SENSE |
| 231 | 990 | CGPG4506 | 71820 | SENSE |
| 232 | 991 | CGPG4553 | 70764 | SENSE |
| 233 | 992 | CGPG4583 | 70680 | SENSE |
| 234 | 993 | CGPG4643 | 72375 | SENSE |
| 235 | 994 | CGPG4650 | 72469 | SENSE |
| 236 | 995 | CGPG4660 | 73951 | SENSE |
| 237 | 996 | CGPG468 | 11003 | ANTI-SENSE |
| 238 | 997 | CGPG4684 | 71613 | SENSE |
| 239 | 998 | CGPG4689 | 78203 | SENSE |
| 240 | 999 | CGPG4691 | 71638 | SENSE |
| 241 | 1000 | CGPG4702 | 71631 | SENSE |
| 242 | 1001 | CGPG4703 | 72368 | SENSE |
| 243 | 1002 | CGPG4710 | 78202 | SENSE |
| 244 | 1003 | CGPG4713 | 78207 | SENSE |
| 245 | 1004 | CGPG4730 | 75209 | SENSE |
| 246 | 1005 | CGPG4747 | 72457 | SENSE |
| 247 | 1006 | CGPG4755 | 73639 | SENSE |
| 248 | 1007 | CGPG4772 | 72526 | SENSE |
| 249 | 1008 | CGPG4779 | 72531 | SENSE |
| 250 | 1009 | CGPG4848 | 73336 | SENSE |
| 251 | 1010 | CGPG4879 | 73722 | SENSE |
| 252 | 1011 | CGPG4882 | 72650 | SENSE |
| 253 | 1012 | CGPG4892 | 73686 | SENSE |
| 254 | 1013 | CGPG4903 | 78353 | SENSE |
| 255 | 1014 | CGPG4925 | 73726 | SENSE |
| 258 | 1015 | CGPG4937 | 74715 | SENSE |
| 257 | 1016 | CGPG4949 | 73230 | SENSE |
| 258 | 1017 | CGPG4971 | 72663 | SENSE |
| 259 | 1018 | CGPG499 | 70822 | SENSE |

TABLE 2-continued

| NUC Seq ID | PEP Seq ID | Gene ID | Construct ID | Orientation |
|---|---|---|---|---|
| 260 | 1019 | CGPG5004 | 72827 | SENSE |
| 261 | 1020 | CGPG5028 | 78339 | SENSE |
| 262 | 1021 | CGPG5032 | 73309 | SENSE |
| 263 | 1022 | CGPG5038 | 78725 | SENSE |
| 264 | 1023 | CGPG5045 | 74222 | SENSE |
| 265 | 1024 | CGPG5048 | 78341 | SENSE |
| 266 | 1025 | CGPG5051 | 78342 | SENSE |
| 267 | 1026 | CGPG5061 | 78349 | SENSE |
| 268 | 1027 | CGPG5062 | 73683 | SENSE |
| 269 | 1028 | CGPG5069 | 73280 | SENSE |
| 270 | 1029 | CGPG5070 | 73281 | SENSE |
| 271 | 1030 | CGPG5097 | 73313 | SENSE |
| 272 | 1031 | CGPG510 | 12772 | ANTI-SENSE |
| 273 | 1032 | CGPG5100 | 73314 | SENSE |
| 274 | 1033 | CGPG5117 | 73861 | SENSE |
| 275 | 1034 | CGPG5151 | 73676 | SENSE |
| 276 | 1035 | CGPG5155 | 74212 | SENSE |
| 277 | 1036 | CGPG5159 | 74218 | SENSE |
| 278 | 1037 | CGPG516 | 71218 | SENSE |
| 279 | 1038 | CGPG5161 | 73731 | SENSE |
| 280 | 1039 | CGPG5186 | 73251 | SENSE |
| 281 | 1040 | CGPG519 | 12773 | ANTI-SENSE |
| 282 | 1041 | CGPG5190 | 73254 | SENSE |
| 283 | 1042 | CGPG5191 | 73255 | SENSE |
| 284 | 1043 | CGPG5196 | 73257 | SENSE |
| 285 | 1044 | CGPG521 | 11049 | SENSE |
| 286 | 1045 | CGPG5211 | 74231 | SENSE |
| 287 | 1046 | CGPG5212 | 73266 | SENSE |
| 288 | 1047 | CGPG5213 | 75823 | SENSE |
| 289 | 1048 | CGPG522 | 11353 | SENSE |
| 290 | 1049 | CGPG5223 | 72025 | SENSE |
| 291 | 1050 | CGPG5224 | 72037 | SENSE |
| 292 | 1051 | CGPG5225 | 72049 | SENSE |
| 293 | 1052 | CGPG5254 | 78213 | SENSE |
| 294 | 1053 | CGPG5257 | 72007 | SENSE |
| 295 | 1054 | CGPG5262 | 72067 | SENSE |
| 296 | 1055 | CGPG5265 | 72008 | SENSE |
| 297 | 1056 | CGPG5262 | 72022 | SENSE |
| 298 | 1057 | CGPG5304 | 72096 | SENSE |
| 299 | 1058 | CGPG532 | 10811 | ANTI-SENSE |
| 300 | 1059 | CGPG5336 | 72138 | SENSE |
| 301 | 1060 | CGPG5350 | 74261 | SENSE |
| 302 | 1061 | CGPG5355 | 74264 | SENSE |
| 303 | 1062 | CGPG5376 | 74271 | SENSE |
| 304 | 1063 | CGPG5377 | 74272 | SENSE |
| 305 | 1064 | CGPG5382 | 78442 | SENSE |
| 306 | 1065 | CGPG5385 | 76709 | SENSE |
| 307 | 1066 | CGPG539 | 75002 | SENSE |
| 308 | 1067 | CGPG5437 | 78361 | SENSE |
| 309 | 1068 | CGPG5450 | 74238 | SENSE |
| 310 | 1069 | CGPG5473 | 78434 | SENSE |
| 311 | 1070 | CGPG55 | 73932 | SENSE |
| 312 | 1071 | CGPG5505 | 72713 | SENSE |
| 313 | 1072 | CGPG5510 | 72773 | SENSE |
| 314 | 1073 | CGPG5514 | 72678 | SENSE |
| 315 | 1074 | CGPG5541 | 72765 | SENSE |
| 316 | 1075 | CGPG5546 | 72730 | SENSE |
| 317 | 1076 | CGPG5552 | 72707 | SENSE |
| 318 | 1077 | CGPG5556 | 72755 | SENSE |
| 319 | 1078 | CGPG557 | 10610 | ANTI-SENSE |
| 320 | 1079 | CGPG5576 | 73953 | SENSE |
| 321 | 1080 | CGPG5596 | 73173 | SENSE |
| 322 | 1081 | CGPG5605 | 73979 | SENSE |
| 323 | 1082 | CGPG5606 | 73966 | SENSE |
| 324 | 1083 | CGPG561 | 12776 | ANTI-SENSE |
| 325 | 1084 | CGPG5618 | 72960 | SENSE |
| 326 | 1085 | CGPG5642 | 73021 | SENSE |
| 327 | 1086 | CGPG5644 | 73163 | SENSE |
| 328 | 1087 | CGPG5647 | 73187 | SENSE |
| 329 | 1088 | CGPG5655 | 73188 | SENSE |
| 330 | 1089 | CGPG5660 | 73153 | SENSE |
| 331 | 1090 | CGPG5662 | 73983 | SENSE |
| 332 | 1091 | CGPG568 | 11516 | ANTI-SENSE |
| 333 | 1092 | CGPG5686 | 73179 | SENSE |
| 334 | 1093 | CGPG5702 | 73009 | SENSE |
| 335 | 1094 | CGPG5712 | 73109 | SENSE |
| 336 | 1095 | CGPG5713 | 73121 | SENSE |
| 337 | 1096 | CGPG5715 | 73157 | SENSE |
| 338 | 1097 | CGPG5723 | 73158 | SENSE |
| 339 | 1098 | CGPG5729 | 73088 | SENSE |
| 340 | 1099 | CGPG5730 | 73135 | SENSE |
| 341 | 1100 | CGPG5732 | 73005 | SENSE |
| 342 | 1101 | CGPG5741 | 73171 | SENSE |
| 343 | 1102 | CGPG5752 | 73042 | SENSE |
| 344 | 1103 | CGPG5771 | 73067 | SENSE |
| 345 | 1104 | CGPG5778 | 73148 | SENSE |
| 346 | 1105 | CGPG5782 | 72933 | SENSE |
| 347 | 1106 | CGPG5785 | 77723 | SENSE |
| 348 | 1107 | CGPG5797 | 73048 | SENSE |
| 349 | 1108 | CGPG580 | 10616 | ANTI-SENSE |
| 350 | 1109 | CGPG5805 | 72923 | SENSE |
| 351 | 1110 | CGPG5810 | 78501 | SENSE |
| 352 | 1111 | CGPG5822 | 78371 | SENSE |
| 353 | 1112 | CGPG5837 | 74332 | SENSE |
| 354 | 1113 | CGPG5855 | 74738 | SENSE |
| 355 | 1114 | CGPG5868 | 75225 | SENSE |
| 356 | 1115 | CGPG587 | 11149 | SENSE |
| 357 | 1116 | CGPG5889 | 74739 | SENSE |
| 358 | 1117 | CGPG5893 | 74748 | SENSE |
| 359 | 1118 | CGPG5909 | 78113 | SENSE |
| 360 | 1119 | CGPG5914 | 75233 | SENSE |
| 361 | 1120 | CGPG5921 | 77311 | SENSE |
| 362 | 1121 | CGPG5925 | 77008 | SENSE |
| 363 | 1122 | CGPG5926 | 77321 | SENSE |
| 364 | 1123 | CGPG5930 | 76214 | SENSE |
| 365 | 1124 | CGPG5945 | 75238 | SENSE |
| 366 | 1125 | CGPG5958 | 76118 | SENSE |
| 367 | 1126 | CGPG5977 | 75243 | SENSE |
| 368 | 1127 | CGPG598 | 72602 | SENSE |
| 369 | 1128 | CGPG5986 | 75810 | SENSE |
| 370 | 1129 | CGPG5994 | 75094 | SENSE |
| 371 | 1130 | CGPG5996 | 75818 | SENSE |
| 372 | 1131 | CGPG6021 | 75248 | SENSE |
| 373 | 1132 | CGPG6027 | 74605 | SENSE |
| 374 | 1133 | CGPG6035 | 75252 | SENSE |
| 375 | 1134 | CGPG604 | 10620 | ANTI-SENSE |
| 376 | 1135 | CGPG6049 | 74611 | SENSE |
| 377 | 1136 | CGPG606 | 11152 | SENSE |
| 378 | 1137 | CGPG6069 | 76610 | SENSE |
| 379 | 1138 | CGPG608 | 70243 | SENSE |
| 380 | 1139 | CGPG6080 | 74371 | SENSE |
| 381 | 1140 | CGPG6082 | 74373 | SENSE |
| 382 | 1141 | CGPG6089 | 74615 | SENSE |
| 383 | 1142 | CGPG6120 | 74620 | SENSE |
| 384 | 1143 | CGPG6128 | 74626 | SENSE |
| 385 | 1144 | CGPG614 | 10622 | ANTI-SENSE |
| 386 | 1145 | CGPG6149 | 74636 | SENSE |
| 387 | 1146 | CGPG6172 | 74656 | SENSE |
| 388 | 1147 | CGPG6174 | 74658 | SENSE |
| 389 | 1148 | CGPG6176 | 74659 | SENSE |
| 390 | 1149 | CGPG6197 | 74673 | SENSE |
| 391 | 1150 | CGPG620 | 13518 | ANTI-SENSE |
| 391 | 1150 | CGPG620 | 70824 | SENSE |
| 392 | 1151 | CGPG6201 | 75267 | SENSE |
| 393 | 1152 | CGPG6204 | 75283 | SENSE |
| 394 | 1153 | CGPG621 | 13805 | SENSE |
| 395 | 1154 | CGPG6210 | 76221 | SENSE |
| 396 | 1155 | CGPG6211 | 76226 | SENSE |
| 397 | 1156 | CGPG6214 | 76222 | SENSE |
| 398 | 1157 | CGPG6215 | 76611 | SENSE |
| 399 | 1158 | CGPG6222 | 76228 | SENSE |
| 400 | 1159 | CGPG6229 | 76435 | SENSE |
| 401 | 1160 | CGPG6233 | 76436 | SENSE |
| 402 | 1161 | CGPG6237 | 78743 | SENSE |
| 403 | 1162 | CGPG6243 | 75814 | SENSE |
| 404 | 1163 | CGPG6248 | 77016 | SENSE |
| 405 | 1164 | CGPG6252 | 78734 | SENSE |
| 406 | 1165 | CGPG6267 | 75274 | SENSE |
| 407 | 1166 | CGPG6272 | 76233 | SENSE |
| 408 | 1167 | CGPG6294 | 74674 | SENSE |
| 409 | 1168 | CGPG63 | 70225 | SENSE |
| 410 | 1169 | CGPG6311 | 75291 | SENSE |
| 411 | 1170 | CGPG6317 | 75292 | SENSE |
| 412 | 1171 | CGPG6328 | 78607 | SENSE |

TABLE 2-continued

| NUC Seq ID | PEP Seq ID | Gene ID | Construct ID | Orientation |
|---|---|---|---|---|
| 413 | 1172 | CGPG6334 | 78367 | SENSE |
| 414 | 1173 | CGPG6336 | 76528 | SENSE |
| 415 | 1174 | CGPG6349 | 77319 | SENSE |
| 416 | 1175 | CGPG6352 | 74677 | SENSE |
| 417 | 1176 | CGPG6353 | 78109 | SENSE |
| 418 | 1177 | CGPG6364 | 77725 | SENSE |
| 419 | 1178 | CGPG6366 | 73437 | SENSE |
| 420 | 1179 | CGPG6375 | 73450 | SENSE |
| 421 | 1180 | CGPG6388 | 73416 | SENSE |
| 422 | 1181 | CGPG6391 | 73452 | SENSE |
| 423 | 1182 | CGPG6399 | 73453 | SENSE |
| 424 | 1183 | CGPG6407 | 73454 | SENSE |
| 425 | 1184 | CGPG6418 | 73491 | SENSE |
| 426 | 1185 | CGPG6430 | 73445 | SENSE |
| 427 | 1186 | CGPG6432 | 73469 | SENSE |
| 428 | 1187 | CGPG6437 | 73434 | SENSE |
| 429 | 1188 | CGPG6445 | 73471 | SENSE |
| 430 | 1189 | CGPG6450 | 73436 | SENSE |
| 431 | 1190 | CGPG6458 | 73525 | SENSE |
| 432 | 1191 | CGPG6465 | 73514 | SENSE |
| 433 | 1192 | CGPG6476 | 73551 | SENSE |
| 434 | 1193 | CGPG6505 | 73519 | SENSE |
| 435 | 1194 | CGPG6507 | 73543 | SENSE |
| 436 | 1195 | CGPG6509 | 73567 | SENSE |
| 437 | 1196 | CGPG6510 | 73579 | SENSE |
| 438 | 1197 | CGPG6515 | 73556 | SENSE |
| 439 | 1198 | CGPG6520 | 73545 | SENSE |
| 440 | 1199 | CGPG6531 | 73511 | SENSE |
| 441 | 1200 | CGPG6553 | 74138 | SENSE |
| 442 | 1201 | CGPG6557 | 74186 | SENSE |
| 443 | 1202 | CGPG6563 | 74163 | SENSE |
| 444 | 1203 | CGPG6564 | 74175 | SENSE |
| 445 | 1204 | CGPG6572 | 74176 | SENSE |
| 446 | 1205 | CGPG6577 | 74141 | SENSE |
| 447 | 1206 | CGPG6588 | 74178 | SENSE |
| 448 | 1207 | CGPG6596 | 74179 | SENSE |
| 449 | 1208 | CGPG6614 | 74110 | SENSE |
| 450 | 1209 | CGPG6619 | 74170 | SENSE |
| 451 | 1210 | CGPG6623 | 74123 | SENSE |
| 452 | 1211 | CGPG6626 | 74159 | SENSE |
| 453 | 1212 | CGPG663 | 10633 | ANTI-SENSE |
| 454 | 1213 | CGPG6635 | 74172 | SENSE |
| 455 | 1214 | CGPG6636 | 74184 | SENSE |
| 456 | 1215 | CGPG6641 | 74582 | SENSE |
| 457 | 1216 | CGPG6642 | 74584 | SENSE |
| 458 | 1217 | CGPG6645 | 74687 | SENSE |
| 459 | 1218 | CGPG6660 | 74461 | SENSE |
| 460 | 1219 | CGPG6671 | 74403 | SENSE |
| 461 | 1220 | CGPG6697 | 74430 | SENSE |
| 462 | 1221 | CGPG6706 | 74443 | SENSE |
| 463 | 1222 | CGPG6723 | 74457 | SENSE |
| 464 | 1223 | CGPG6729 | 74434 | SENSE |
| 465 | 1224 | CGPG6738 | 74447 | SENSE |
| 466 | 1225 | CGPG6742 | 74495 | SENSE |
| 467 | 1226 | CGPG6752 | 74513 | SENSE |
| 468 | 1227 | CGPG6760 | 74514 | SENSE |
| 469 | 1228 | CGPG6768 | 74515 | SENSE |
| 470 | 1229 | CGPG6779 | 74552 | SENSE |
| 471 | 1230 | CGPG6785 | 74529 | SENSE |
| 472 | 1231 | CGPG6800 | 74519 | SENSE |
| 473 | 1232 | CGPG686 | 10638 | ANTI-SENSE |
| 474 | 1233 | CGPG6898 | 76547 | SENSE |
| 475 | 1234 | CGPG6900 | 76548 | SENSE |
| 476 | 1235 | CGPG691 | 14703 | SENSE |
| 477 | 1236 | CGPG6920 | 75856 | SENSE |
| 478 | 1237 | CGPG6921 | 76642 | SENSE |
| 479 | 1238 | CGPG6930 | 77522 | SENSE |
| 480 | 1239 | CGPG6934 | 77516 | SENSE |
| 481 | 1240 | CGPG6945 | 75864 | SENSE |
| 482 | 1241 | CGPG6946 | 76275 | SENSE |
| 483 | 1242 | CGPG6948 | 76276 | SENSE |
| 484 | 1243 | CGPG6974 | 75869 | SENSE |
| 485 | 1244 | CGPG6976 | 76558 | SENSE |
| 486 | 1245 | CGPG6996 | 75876 | SENSE |
| 487 | 1246 | CGPG7002 | 75878 | SENSE |
| 488 | 1247 | CGPG7013 | 75881 | SENSE |
| 489 | 1248 | CGPG7021 | 77525 | SENSE |
| 490 | 1249 | CGPG7056 | 76454 | SENSE |
| 491 | 1250 | CGPG7071 | 75895 | SENSE |
| 492 | 1251 | CGPG7075 | 78377 | SENSE |
| 493 | 1252 | CGPG7080 | 75896 | SENSE |
| 494 | 1253 | CGPG7094 | 77527 | SENSE |
| 495 | 1254 | CGPG7095 | 78984 | SENSE |
| 496 | 1255 | CGPG7104 | 77528 | SENSE |
| 497 | 1256 | CGPG7118 | 76752 | SENSE |
| 498 | 1257 | CGPG7122 | 78106 | SENSE |
| 499 | 1258 | CGPG713 | 11720 | ANTI-SENSE |
| 500 | 1259 | CGPG7130 | 78740 | SENSE |
| 501 | 1260 | CGPG7145 | 76157 | SENSE |
| 502 | 1261 | CGPG7166 | 77530 | SENSE |
| 503 | 1262 | CGPG7179 | 76755 | SENSE |
| 504 | 1263 | CGPG7184 | 76166 | SENSE |
| 505 | 1264 | CGPG7185 | 76756 | SENSE |
| 506 | 1265 | CGPG7192 | 78990 | SENSE |
| 507 | 1266 | CGPG7199 | 78460 | SENSE |
| 508 | 1267 | CGPG72 | 11022 | ANTI-SENSE |
| 509 | 1268 | CGPG7231 | 77533 | SENSE |
| 510 | 1269 | CGPG7241 | 76572 | SENSE |
| 511 | 1270 | CGPG7243 | 76186 | SENSE |
| 512 | 1271 | CGPG7258 | 76190 | SENSE |
| 513 | 1272 | CGPG7265 | 77071 | SENSE |
| 514 | 1273 | CGPG7274 | 76194 | SENSE |
| 515 | 1274 | CGPG7291 | 78112 | SENSE |
| 516 | 1275 | CGPG7303 | 74802 | SENSE |
| 517 | 1276 | CGPG7315 | 74851 | SENSE |
| 518 | 1277 | CGPG7324 | 74864 | SENSE |
| 519 | 1278 | CGPG7327 | 74805 | SENSE |
| 520 | 1279 | CGPG7338 | 74842 | SENSE |
| 521 | 1280 | CGPG7347 | 78231 | SENSE |
| 522 | 1281 | CGPG7348 | 74867 | SENSE |
| 523 | 1282 | CGPG7352 | 74820 | SENSE |
| 524 | 1283 | CGPG7356 | 74868 | SENSE |
| 525 | 1284 | CGPG7359 | 74809 | SENSE |
| 526 | 1285 | CGPG7362 | 74845 | SENSE |
| 527 | 1286 | CGPG7372 | 74870 | SENSE |
| 528 | 1287 | CGPG7379 | 74859 | SENSE |
| 529 | 1288 | CGPG7398 | 74985 | SENSE |
| 530 | 1289 | CGPG7403 | 74950 | SENSE |
| 531 | 1290 | CGPG7404 | 74962 | SENSE |
| 532 | 1291 | CGPG7410 | 74939 | SENSE |
| 533 | 1292 | CGPG7417 | 74928 | SENSE |
| 534 | 1293 | CGPG7423 | 74905 | SENSE |
| 535 | 1294 | CGPG7424 | 74917 | SENSE |
| 536 | 1295 | CGPG7430 | 74989 | SENSE |
| 537 | 1296 | CGPG7438 | 74990 | SENSE |
| 538 | 1297 | CGPG7443 | 74955 | SENSE |
| 539 | 1298 | CGPG7449 | 74932 | SENSE |
| 540 | 1299 | CGPG7450 | 74944 | SENSE |
| 541 | 1300 | CGPG7452 | 74968 | SENSE |
| 542 | 1301 | CGPG7459 | 74957 | SENSE |
| 543 | 1302 | CGPG7480 | 75374 | SENSE |
| 544 | 1303 | CGPG7481 | 75386 | SENSE |
| 545 | 1304 | CGPG7483 | 77807 | SENSE |
| 546 | 1305 | CGPG7497 | 75388 | SENSE |
| 547 | 1306 | CGPG7503 | 75365 | SENSE |
| 548 | 1307 | CGPG7504 | 75377 | SENSE |
| 549 | 1308 | CGPG7510 | 75354 | SENSE |
| 550 | 1309 | CGPG7516 | 75331 | SENSE |
| 551 | 1310 | CGPG7517 | 75343 | SENSE |
| 552 | 1311 | CGPG7523 | 77809 | SENSE |
| 553 | 1312 | CGPG7524 | 75332 | SENSE |
| 554 | 1313 | CGPG7525 | 75344 | SENSE |
| 555 | 1314 | CGPG7532 | 75333 | SENSE |
| 556 | 1315 | CGPG7537 | 75393 | SENSE |
| 557 | 1316 | CGPG7548 | 75335 | SENSE |
| 558 | 1317 | CGPG7575 | 75462 | SENSE |
| 559 | 1318 | CGPG7577 | 75486 | SENSE |
| 560 | 1319 | CGPG7590 | 75452 | SENSE |
| 561 | 1320 | CGPG7599 | 75465 | SENSE |
| 562 | 1321 | CGPG7601 | 75489 | SENSE |
| 563 | 1322 | CGPG7605 | 75442 | SENSE |
| 564 | 1323 | CGPG7607 | 75466 | SENSE |
| 565 | 1324 | CGPG7616 | 75479 | SENSE |
| 566 | 1325 | CGPG7632 | 75481 | SENSE |

TABLE 2-continued

| NUC Seq ID | PEP Seq ID | Gene ID | Construct ID | Orientation |
|---|---|---|---|---|
| 567 | 1326 | CGPG7673 | 78233 | SENSE |
| 568 | 1327 | CGPG7683 | 75539 | SENSE |
| 569 | 1328 | CGPG773 | 11919 | ANTI-SENSE |
| 570 | 1329 | CGPG7776 | 75603 | SENSE |
| 571 | 1330 | CGPG7781 | 75663 | SENSE |
| 572 | 1331 | CGPG7785 | 75616 | SENSE |
| 573 | 1332 | CGPG7787 | 75640 | SENSE |
| 574 | 1333 | CGPG7793 | 75617 | SENSE |
| 575 | 1334 | CGPG7796 | 75653 | SENSE |
| 576 | 1335 | CGPG7797 | 75665 | SENSE |
| 577 | 1336 | CGPG7801 | 75618 | SENSE |
| 578 | 1337 | CGPG7813 | 78238 | SENSE |
| 579 | 1338 | CGPG7816 | 75608 | SENSE |
| 580 | 1339 | CGPG7826 | 75633 | SENSE |
| 581 | 1340 | CGPG7861 | 75761 | SENSE |
| 582 | 1341 | CGPG7863 | 75785 | SENSE |
| 583 | 1342 | CGPG7868 | 75750 | SENSE |
| 584 | 1343 | CGPG7881 | 75716 | SENSE |
| 585 | 1344 | CGPG7887 | 78129 | SENSE |
| 586 | 1345 | CGPG7899 | 77539 | SENSE |
| 587 | 1346 | CGPG7901 | 77540 | SENSE |
| 588 | 1347 | CGPG7909 | 77542 | SENSE |
| 589 | 1348 | CGPG7911 | 77543 | SENSE |
| 590 | 1349 | CGPG7919 | 77545 | SENSE |
| 591 | 1350 | CGPG7935 | 77550 | SENSE |
| 592 | 1351 | CGPG7940 | 77552 | SENSE |
| 593 | 1352 | CGPG7959 | 77556 | SENSE |
| 594 | 1353 | CGPG7967 | 77559 | SENSE |
| 595 | 1354 | CGPG7975 | 77957 | SENSE |
| 596 | 1355 | CGPG7996 | 77565 | SENSE |
| 597 | 1356 | CGPG8006 | 78508 | SENSE |
| 598 | 1357 | CGPG801 | 11748 | ANTI-SENSE |
| 599 | 1358 | CGPG8023 | 77920 | SENSE |
| 600 | 1359 | CGPG8025 | 77573 | SENSE |
| 601 | 1360 | CGPG8038 | 77961 | SENSE |
| 602 | 1361 | CGPG8053 | 77922 | SENSE |
| 603 | 1362 | CGPG8054 | 77337 | SENSE |
| 604 | 1363 | CGPG8059 | 77924 | SENSE |
| 605 | 1364 | CGPG8070 | 77926 | SENSE |
| 606 | 1365 | CGPG8073 | 77964 | SENSE |
| 607 | 1366 | CGPG8076 | 77346 | SENSE |
| 608 | 1367 | CGPG8084 | 77350 | SENSE |
| 609 | 1368 | CGPG8093 | 77929 | SENSE |
| 610 | 1369 | CGPG8095 | 77586 | SENSE |
| 611 | 1370 | CGPG8096 | 78510 | SENSE |
| 612 | 1371 | CGPG8097 | 77930 | SENSE |
| 613 | 1372 | CGPG8112 | 77590 | SENSE |
| 614 | 1373 | CGPG8120 | 77592 | SENSE |
| 615 | 1374 | CGPG8129 | 77361 | SENSE |
| 616 | 1375 | CGPG8140 | 77934 | SENSE |
| 617 | 1376 | CGPG8157 | 77367 | SENSE |
| 618 | 1377 | CGPG8158 | 78121 | SENSE |
| 619 | 1378 | CGPG8165 | 77370 | SENSE |
| 620 | 1379 | CGPG8169 | 78117 | SENSE |
| 621 | 1380 | CGPG8203 | 77950 | SENSE |
| 622 | 1381 | CGPG8205 | 78905 | SENSE |
| 623 | 1382 | CGPG8212 | 75913 | SENSE |
| 624 | 1383 | CGPG8213 | 75925 | SENSE |
| 625 | 1384 | CGPG8225 | 75974 | SENSE |
| 626 | 1385 | CGPG8227 | 75903 | SENSE |
| 627 | 1386 | CGPG8235 | 75904 | SENSE |
| 628 | 1387 | CGPG8236 | 75916 | SENSE |
| 629 | 1388 | CGPG8244 | 75917 | SENSE |
| 630 | 1389 | CGPG8254 | 75942 | SENSE |
| 631 | 1390 | CGPG8255 | 75954 | SENSE |
| 632 | 1391 | CGPG8262 | 75943 | SENSE |
| 633 | 1392 | CGPG8264 | 75967 | SENSE |
| 634 | 1393 | CGPG8269 | 75932 | SENSE |
| 635 | 1394 | CGPG8271 | 75956 | SENSE |
| 636 | 1395 | CGPG8305 | 78135 | SENSE |
| 637 | 1396 | CGPG8320 | 78612 | SENSE |
| 638 | 1397 | CGPG8326 | 77969 | SENSE |
| 639 | 1398 | CGPG8344 | 78136 | SENSE |
| 640 | 1399 | CGPG8347 | 77627 | SENSE |
| 641 | 1400 | CGPG8359 | 78142 | SENSE |
| 642 | 1401 | CGPG8370 | 77973 | SENSE |
| 643 | 1402 | CGPG8371 | 78141 | SENSE |
| 644 | 1403 | CGPG8375 | 78963 | SENSE |
| 645 | 1404 | CGPG8378 | 78153 | SENSE |
| 646 | 1405 | CGPG8383 | 78156 | SENSE |
| 647 | 1406 | CGPG841 | 11807 | ANTI-SENSE |
| 648 | 1407 | CGPG8436 | 78528 | SENSE |
| 649 | 1408 | CGPG8438 | 78530 | SENSE |
| 650 | 1409 | CGPG8450 | 78618 | SENSE |
| 651 | 1410 | CGPG8451 | 78919 | SENSE |
| 652 | 1411 | CGPG8459 | 77974 | SENSE |
| 653 | 1412 | CGPG8461 | 77630 | SENSE |
| 654 | 1413 | CGPG8463 | 78921 | SENSE |
| 655 | 1414 | CGPG8471 | 78620 | SENSE |
| 656 | 1415 | CGPG8474 | 77975 | SENSE |
| 657 | 1416 | CGPG8475 | 78536 | SENSE |
| 658 | 1417 | CGPG8476 | 78537 | SENSE |
| 659 | 1418 | CGPG8490 | 78540 | SENSE |
| 660 | 1419 | CGPG8510 | 77993 | SENSE |
| 661 | 1420 | CGPG8530 | 78924 | SENSE |
| 662 | 1421 | CGPG8533 | 78009 | SENSE |
| 663 | 1422 | CGPG8544 | 78014 | SENSE |
| 664 | 1423 | CGPG8546 | 78015 | SENSE |
| 665 | 1424 | CGPG8549 | 78018 | SENSE |
| 666 | 1425 | CGPG8555 | 78021 | SENSE |
| 667 | 1426 | CGPG8561 | 78158 | SENSE |
| 668 | 1427 | CGPG8569 | 78026 | SENSE |
| 669 | 1428 | CGPG8573 | 78028 | SENSE |
| 670 | 1429 | CGPG8588 | 78032 | SENSE |
| 671 | 1430 | CGPG8597 | 78388 | SENSE |
| 672 | 1431 | CGPG8607 | 78044 | SENSE |
| 673 | 1432 | CGPG8611 | 78047 | SENSE |
| 674 | 1433 | CGPG8629 | 78055 | SENSE |
| 675 | 1434 | CGPG8632 | 78057 | SENSE |
| 876 | 1435 | CGPG8634 | 78059 | SENSE |
| 677 | 1435 | CGPG8635 | 78553 | SENSE |
| 678 | 1437 | CGPG8636 | 78163 | SENSE |
| 679 | 1438 | CGPG8640 | 78060 | SENSE |
| 880 | 1439 | CGPG8642 | 78062 | SENSE |
| 681 | 1440 | CGPG8646 | 78065 | SENSE |
| 682 | 1441 | CGPG8666 | 78590 | SENSE |
| 683 | 1442 | CGPG8677 | 78177 | SENSE |
| 684 | 1443 | CGPG8688 | 78952 | SENSE |
| 685 | 1444 | CGPG8689 | 78559 | SENSE |
| 686 | 1445 | CGPG8704 | 78169 | SENSE |
| 687 | 1446 | CGPG8716 | 78178 | SENSE |
| 688 | 1447 | CGPG8754 | 78932 | SENSE |
| 689 | 1448 | CGPG8769 | 78185 | SENSE |
| 690 | 1449 | CGPG8774 | 78186 | SENSE |
| 691 | 1450 | CGPG8778 | 78572 | SENSE |
| 692 | 1451 | CGPG8784 | 78631 | SENSE |
| 693 | 1452 | CGPG879 | 12425 | ANTI-SENSE |
| 694 | 1453 | CGPG8797 | 78938 | SENSE |
| 695 | 1454 | CGPG8810 | 78961 | SENSE |
| 696 | 1455 | CGPG8827 | 78584 | SENSE |
| 697 | 1456 | CGPG8853 | 78589 | SENSE |
| 698 | 1457 | CGPG8873 | 78252 | SENSE |
| 699 | 1458 | CGPG8877 | 76314 | SENSE |
| 700 | 1459 | CGPG8878 | 76326 | SENSE |
| 701 | 1460 | CGPG8881 | 76362 | SENSE |
| 702 | 1461 | CGPG8895 | 76340 | SENSE |
| 703 | 1462 | CGPG8906 | 76377 | SENSE |
| 704 | 1463 | CGPG8917 | 76319 | SENSE |
| 705 | 1464 | CGPG8919 | 76343 | SENSE |
| 706 | 1465 | CGPG8925 | 76320 | SENSE |
| 707 | 1466 | CGPG8930 | 76380 | SENSE |
| 708 | 1467 | CGPG8937 | 77831 | SENSE |
| 709 | 1468 | CGPG8942 | 76334 | SENSE |
| 710 | 1469 | CGPG8946 | 76382 | SENSE |
| 711 | 1470 | CGPG8990 | 76838 | SENSE |
| 712 | 1471 | CGPG9001 | 77841 | SENSE |
| 713 | 1472 | CGPG9008 | 77838 | SENSE |
| 714 | 1473 | CGPG9016 | 76865 | SENSE |
| 715 | 1474 | CGPG9036 | 77834 | SENSE |
| 716 | 1475 | CGPG9060 | 76823 | SENSE |
| 717 | 1476 | CGPG9069 | 76836 | SENSE |
| 718 | 1477 | CGPG908 | 14133 | ANTI-SENSE |
| 719 | 1478 | CGPG9093 | 76927 | SENSE |
| 720 | 1479 | CGPG9096 | 76963 | SENSE |

TABLE 2-continued

| NUC Seq ID | PEP Seq ID | Gene ID | Construct ID | Orientation |
|---|---|---|---|---|
| 721 | 1480 | CGPG9097 | 76975 | SENSE |
| 722 | 1481 | CGPG9106 | 76988 | SENSE |
| 723 | 1482 | CGPG9111 | 76953 | SENSE |
| 724 | 1483 | CGPG9112 | 76965 | SENSE |
| 725 | 1484 | CGPG9123 | 77161 | SENSE |
| 726 | 1485 | CGPG9124 | 77852 | SENSE |
| 727 | 1486 | CGPG9138 | 77151 | SENSE |
| 728 | 1487 | CGPG9143 | 77116 | SENSE |
| 729 | 1488 | CGPG9150 | 77105 | SENSE |
| 730 | 1489 | CGPG9152 | 77129 | SENSE |
| 731 | 1490 | CGPG9162 | 77154 | SENSE |
| 732 | 1491 | CGPG9165 | 77190 | SENSE |
| 733 | 1492 | CGPG9166 | 77107 | SENSE |
| 734 | 1493 | CGPG9171 | 77167 | SENSE |
| 735 | 1494 | CGPG9177 | 77144 | SENSE |
| 736 | 1495 | CGPG9178 | 77156 | SENSE |
| 737 | 1496 | CGPG9179 | 77168 | SENSE |
| 738 | 1497 | CGPG9181 | 77192 | SENSE |
| 739 | 1498 | CGPG9188 | 77181 | SENSE |
| 740 | 1499 | CGPG9189 | 77193 | SENSE |
| 741 | 1500 | CGPG9201 | 77147 | SENSE |
| 742 | 1501 | CGPG9222 | 77853 | SENSE |
| 743 | 1502 | CGPG9234 | 77854 | SENSE |
| 744 | 1503 | CGPG9237 | 77287 | SENSE |
| 745 | 1504 | CGPG9244 | 77276 | SENSE |
| 746 | 1505 | CGPG9248 | 77229 | SENSE |
| 747 | 1506 | CGPG9249 | 77241 | SENSE |
| 748 | 1507 | CGPG9251 | 77265 | SENSE |
| 749 | 1508 | CGPG9280 | 77233 | SENSE |
| 750 | 1509 | CGPG9285 | 77293 | SENSE |
| 751 | 1510 | CGPG9302 | 77473 | SENSE |
| 752 | 1511 | CGPG931 | 76402 | SENSE |
| 753 | 1512 | CGPG9313 | 77428 | SENSE |
| 754 | 1513 | CGPG9315 | 77429 | SENSE |
| 755 | 1514 | CGPG9327 | 78277 | SENSE |
| 756 | 1515 | CGPG933 | 11935 | ANTI-SENSE |
| 757 | 1516 | CGPG9334 | 78259 | SENSE |
| 758 | 1517 | CGPG967 | 12276 | ANTI-SENSE |
| 759 | 1518 | CGPG988 | 12365 | SENSE |

Recombinant DNA

DNA for use in the present invention to improve traits in plants have a nucleotide sequence of SEQ ID NO: 1 through SEQ ID NO: 759, as well as the homologs of such DNA molecules. A subset of the DNA for gene suppression aspects of the invention includes fragments of the disclosed full polynucleotides consisting of oligonucleotides of 21 or more consecutive nucleotides. Oligonucleotides the larger molecules having a sequence selected from the group consisting of SEQ ID NO: 1 through SEQ ID NO: 759 are useful as probes and primers for detection of the polynucleotides used in the invention. Also useful in this invention are variants of the DNA. Such variants may be naturally occurring, including DNA from homologous genes from the same or a different species, or may be non-natural variants, for example DNA synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, a DNA useful in the present invention may have any base sequence that has been changed from the sequences provided herein by substitution in accordance with degeneracy of the genetic code.

Homologs of the genes providing DNA demonstrated as useful in improving traits in model plants disclosed herein will generally have significant identity with the DNA disclosed herein. DNA is substantially identical to a reference DNA if, when the sequences of the polynucleotides are optimally aligned there is about 60% nucleotide equivalence; more preferably 70%; more preferably 80% equivalence; more preferably 85% equivalence; more preferably 90%; more preferably 95%; and/or more preferably 98% or 99% equivalence over a comparison window. A comparison window is preferably at least 50-100 nucleotides, and more preferably is the entire length of the polynucleotide provided herein. Optimal alignment of sequences for aligning a comparison window may be conducted by algorithms; preferably by computerized implementations of these algorithms (for example, the Wisconsin Genetics Software Package Release 7.0-10.0, Genetics Computer Group, 575 Science Dr., Madison, Wis.). The reference polynucleotide may be a full-length molecule or a portion of a longer molecule. Preferentially, the window of comparison for determining polynucleotide identity of protein encoding sequences is the entire coding region.

Proteins useful for imparting enhanced traits are entire proteins or at least a sufficient portion of the entire protein to impart the relevant biological activity of the protein. Proteins useful for generation of transgenic plants having enhanced straits include the proteins with an amino acid sequence provided herein as SEQ ID NO: 760 through SEQ ID NO: 1518, as well as homologs of such proteins.

Homologs of the proteins useful in the invention are identified by comparison of the amino acid sequence of the protein to amino acid sequences of proteins from the same or different plant sources, e.g., manually or by using known homology-based search algorithms Such as those commonly known and referred to as BLAST, FASTA, and Smith-Waterman. As used herein, a homolog is a protein from the same or a different organism that performs the same biological function as the polypeptide to which it is compared. An orthologous relation between two organisms is not necessarily manifest as a one-to-one correspondence between two genes, because a gene can be duplicated or deleted after organism phylogenetic separation, such as speciation. For a given protein, there may be no ortholog or more than one ortholog. Other complicating factors include alternatively spliced transcripts from the same gene, limited gene identification, redundant copies of the same gene with different sequence lengths or corrected sequence. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal BLAST search is used in the present invention to filter hit sequences with significant E-values for ortholog identification. The reciprocal BLAST entails search of the significant hits against a database of amino acid sequences from the base organism that are similar to the sequence of the query protein. A hit is a likely ortholog, when the reciprocal BLAST's best hit is the query protein itself or a protein encoded by a duplicated gene after speciation. Thus, homolog is used herein to describe proteins that are assumed to have functional similarity by inference from sequence base similarity. The relationship of homologs with amino acid sequences of SEQ ID NO: 1519 to SEQ ID NO: 67778 to the proteins with amino acid sequences of SEQ ID NO: to 760 to SEQ ID NO: 1518 are found in the listing of Table 16.

Other functional homolog proteins differ in one or more amino acids from those of a trait-improving protein disclosed herein as the result of one or more of the well-known conservative amino acid substitutions, e.g., valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises proteins that differ in one or more amino acids from those of a described protein sequence as the result of deletion or insertion of one or more amino acids in a native sequence.

Homologs of the trait-improving proteins provided herein will generally demonstrate significant sequence identity. Of particular interest are proteins having at least 50% sequence identity, more preferably at least about 70% sequence identity or higher, e.g., at least about 80% sequence identity with an amino acid sequence of SEQ ID NO: 760 through SEQ ID NO: 1518. Of course useful proteins also include those with higher identity, e.g., 90% to 99% identity. Identity of protein homologs is determined by optimally aligning the amino acid sequence of a putative protein homolog with a defined amino acid sequence and by calculating the percentage of identical and conservatively substituted amino acids over the window of comparison. The window of comparison for determining identity can be the entire amino acid sequence disclosed herein, e.g., the full sequence of any of SEQ ID NO: 760 through SEQ ID NO: 1518.

Genes that are homologous to each other can be grouped into families and included in multiple sequence alignments. Then a consensus sequence for each group can be derived. This analysis enables the derivation of conserved and class- (family) specific residues or motifs that are functionally important. These conserved residues and motifs can be further validated with 3D protein structure if available. The consensus sequence can be used to define the full scope of the invention, e.g., to identify proteins with a homolog relationship. Thus, the present invention contemplates that protein homologs include proteins with an amino acid sequence that has at least 90% identity to such a consensus amino acid sequence sequences.

Gene Stacking

The present invention also contemplates that the trait-improving recombinant DNA provided herein can be used in combination with other recombinant DNA to create plants with multiple desired traits or a further enhanced trait. The combinations generated can include multiple copies of any one or more of the recombinant DNA constructs. These stacked combinations can be created by any method, including but not limited to cross breeding of transgenic plants, or multiple genetic transformation.

Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 6,384,301 (soybean), U.S. Pat. No. 7,026,528 (wheat) and U.S. Pat. No. 6,329,57.1 (rice), all of which are incorporated herein by reference. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the trangenci nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (npt11), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550;318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from transgenic plant cells having a transgenic nucleus of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Discovery of Trait-improving Recombinant DNA

To identify nuclei with recombinant DNA that confer enhanced traits to plants, Arabidopsis thaliana was transformed with a candidate recombinant DNA construct and screened for an enhanced trait.

Arabidopsis thaliana is used a model for genetics and metabolism in plants. Arabidopsis has a small genome, and well-documented studies are available. It is easy to grow in large numbers and mutants defining important genetically controlled mechanisms are either available, or can readily be obtained. Various methods to introduce and express isolated homologous genes are available (see Koncz, e.g., Methods in Arabidopsis Research e.g., (1992), World Scientific, New Jersey, N.J., in "Preface").

A two-step screening process was employed which comprised two passes of trait characterization to ensure that the trait modification was dependent on expression of the recombinant DNA, but not due to the chromosomal location of the integration of the transgene. Twelve independent transgenic lines for each recombinant DNA construct were established and assayed for the transgene expression levels. Five transgenic lines with high transgene expression levels were used in the first pass screen to evaluate the transgene's function in T2 transgenic plants. Subsequently, three transgenic events, which had been shown to have one or more enhanced traits, were further evaluated in the second pass screen to confirm the transgene's ability to impart an enhanced trait. The following Table 3 summarizes the enhanced traits that have been confirmed as provided by a recombinant DNA construct.

In particular, Table 3 reports:

"PEP SEQ ID" which is the amino acid sequence of the protein cognate to the DNA in the recombinant DNA construct corresponding to a protein sequence of a SEQ ID NO. in the Sequence Listing.

"construct_id" is an arbitrary name for the recombinant DNA describe more particularly in Table 1.

"annotation" refers to a description of the top hit protein obtained from an amino acid sequence query of each PEP SEQ ID NO to GenBank database of the National Center for Biotechnology Information (ncbi). More particularly, "gi" is the GenBank ID number for the top BLAST hit.

"description" refers to the description of the top BLAST hit.

"e-value" provides the expectation value for the BLAST hit.

"% id" refers to the percentage of identically matched amino acid residues along the length of the portion of the sequences which is aligned by BLAST between the sequence of interest provided herein and the hit sequence in GenBank.

"traits" identify by two letter codes the confirmed enhancement in a transgenic plant provided by the recombinant DNA. The codes for enhanced traits are:

"CK" which indicates cold tolerance enhancement identified under a cold shock tolerance screen;

"CS" which indicates cold tolerance enhancement identified by a cold germination tolerance screen; "DS" which indicates drought tolerance enhancement identified by a soil drought stress tolerance screen;

"PEG" which indicates osmotic stress tolerance enhancement identified by a PEG induced osmotic stress tolerance screen;

"HS" which indicates heat stress tolerance enhancement identified by a heat stress tolerance screen;

"SS" which indicates high salinity stress tolerance enhancement identified by a salt stress tolerance screen;

"LN" which indicates nitrogen use efficiency enhancement identified by a limited nitrogen tolerance screen;

"LL" which indicates attenuated shade avoidance response identified by a shade tolerance screen under a low light condition;

"PP" which indicates enhanced growth and development at early stages identified by an early plant growth and development screen;

"SP" which indicates enhanced growth and development at late stages identified by a late plant growth and development screen provided herein.

TABLE 3

| PEP Seq ID No. | Construct ID | Annotation | | | Trait | |
|---|---|---|---|---|---|---|
| | | E-value | % id | Description | | |
| 760 | 12792 | 1.00E−107 | 73 | ref|NP_198588.2|nucleic acid binding [*Arabidopsis thaliana*] | DS | |
| 761 | 13673 | 0 | 94 | ref|NP_850412.1|peptidase [*Arabidopsis thaliana*] | SS | |
| 762 | 12020 | 6.00E−50 | 100 | gb|AAF70854.1|AC003113_21F24O1.1 [*Arabidopsis thaliana*] | SP | |
| 763 | 10174 | 1.00E−111 | 90 | ref|NP_567720.1|DREB1A (DEHYDRATION RESPONSE ELEMENT B1A); DNA binding/transcription factor/ transcriptional activator [*Arabidopsis thaliana*] | HS | PEG |
| 764 | 11827 | 2.00E−83 | 89 | ref|NP_565558.1|unknown protein [*Arabidopsis thaliana*] | LN | |
| 765 | 12435 | 3.00E−53 | 100 | ref|NP_565280.1|NADH dehydrogenase (ubiquinone)/NADH dehydrogenase [*Arabidopsis thaliana*] | LN | |
| 766 | 12015 | 0 | 94 | ref|NP_197429.1|KAPP; protein phosphatase type 2C [*Arabidopsis thaliana*] | LN | |
| 767 | 11836 | 1.00E−146 | 97 | ref|NP_566060.1|unknown protein [*Arabidopsis thaliana*] | LN | |
| 768 | 12141 | 1.00E−134 | 94 | ref|NP_192755.1|unknown protein [*Arabidopsis thaliana*] | LN | |
| 769 | 12040 | 5.00E−97 | 91 | ref|NP_567673.1|unknown protein [*Arabidopsis thaliana*] | DS | |
| 770 | 12437 | 7.00E−35 | 85 | ref|NP_190335.1|unknown protein [*Arabidopsis thaliana*] | LN | |
| 771 | 12156 | 6.00E−55 | 100 | ref|NP_179093.1|RNA binding/nucleic acid binding [*Arabidopsis thaliana*] | DS | |
| 772 | 11853 | 1.00E−81 | 94 | ref|NP_565677.1|unknown protein [*Arabidopsis thaliana*] gb|AAC79591.1| | SS | |
| 773 | 12224 | 1.00E−145 | 82 | ref|NP_565860.1|unknown protein [*Arabidopsis thaliana*] gb|AAC98059.1| | LL | |
| 774 | 11856 | 1.00E−103 | 100 | ref|NP_565273.1|hydrolase [*Arabidopsis thaliana*] | LN | |
| 775 | 12065 | 9.00E−20 | 78 | ref|NP_179185.1|unknown protein [*Arabidopsis thaliana*] | LN | |
| 776 | 12419 | 1.00E−148 | 100 | ref|NP_186847.1|oxidoreductase [*Arabidopsis thaliana*] | LN | |
| 777 | 12208 | 0 | 100 | ref|NP_565169.1|unknown protein [*Arabidopsis thaliana*] | LN | |
| 778 | 14803 | 2.00E−82 | 79 | ref|NP_187893.1|unknown protein [*Arabidopsis thaliana*] | HS | |
| 779 | 10176 | 0 | 100 | ref|NP_178313.1|ATPTR2-B (NITRATE TRANSPORTER 1); transporter [*Arabidopsis thaliana*] | LN | |
| 780 | 18011 | 1.00E−109 | 82 | ref|NP_172517.1|ARR4 (RESPONSE REGULATOR 4); transcription regulator/two-component response regulator [*Arabidopsis thaliana*] | CS | |
| 781 | 12714 | 5.00E−53 | 100 | ref|NP_566217.1|RNA binding/rRNA binding [*Arabidopsis thaliana*] | CK | |
| 782 | 10507 | 9.00E−99 | 100 | ref|NP_201097.1|ARR6 (RESPONSE REGULATOR 6); transcription regulator/two-component response regulator [*Arabidopsis thaliana*] | LN | |
| 783 | 15039 | 0 | 99 | dbj|BAF02191.1|hypothetical protein [*Arabidopsis thaliana*] | LN | |
| 784 | 12733 | 1.00E−137 | 94 | ref|NP_194298.1|unknown protein [*Arabidopsis thaliana*] | DS | |
| 785 | 13237 | 1.00E−52 | 100 | ref|NP_180192.1|unknown protein [*Arabidopsis thaliana*] | LN | |
| 786 | 13504 | 1.00E−137 | 100 | ref|NP_177643.1|unknown protein [*Arabidopsis thaliana*] | DS | |
| 787 | 12932 | 1.00E−174 | 94 | ref|NP_564618.1|unknown protein [*Arabidopsis thaliana*] | SP | |
| 788 | 75935 | 0 | 93 | ref|NP_565242.1|protein binding [*Arabidopsis thaliana*] | CS | |
| 789 | 73333 | 0 | 95 | ref|NP_198718.1|ATP binding/kinase/protein kinase/protein serine/threonine kinase/protein-tyrosine kinase [*Arabidopsis thaliana*] | SS | |
| 790 | 75993 | 0 | 93 | ref|NP_171661.1|ATP binding/kinase/protein kinase/protein serine/threonine kinase/protein-tyrosine kinase [*Arabidopsis thaliana*] | LL | |
| 791 | 19401 | 0 | 94 | ref|NP_195275.1|ATP binding/kinase/protein kinase/protein serine/threonine kinase/protein-tyrosine kinase [*Arabidopsis thaliana*] | LN | |
| 792 | 12766 | 5.00E−74 | 100 | ref|NP_565233.1|unknown protein [*Arabidopsis thaliana*] | SS | |
| 793 | 76025 | 0 | 95 | ref|NP_179580.1|malic enzyme/oxidoreductase, acting on NADH or NADPH, NAD or NADP as acceptor [*Arabidopsis thaliana*] | PEG | |
| 794 | 13708 | 0 | 100 | ref|NP_181187.1|fructose-bisphosphate aldolase [*Arabidopsis thaliana*] | LN | |
| 795 | 13305 | 0 | 94 | ref|NP_180287.1|PAP1 (PURPLE ACID PHOSPHATASE 1); hydrolase/protein serine/threonine phosphatase [*Arabidopsis thaliana*] | LN | |
| 796 | 15806 | 0 | 97 | ref|NP_174089.1|APL2 [*Arabidopsis thaliana*] | SS | |
| 797 | 14712 | 0 | 92 | ref|NP_171617.1|PDH-E1 ALPHA (PYRUVATE DEHYDROGENASE E1 ALPHA); oxidoreductase, acting on the aldehyde or oxo group of donors, disulfide as acceptor/pyruvate dehydrogenase (acetyl-transferring) [*Arabidopsis thaliana*] | LN | |
| 798 | 76013 | 0 | 92 | ref|NP_194141.2|ATP binding/kinase/protein kinase/protein serine/threonine kinase/protein-tyrosine kinase [*Arabidopsis thaliana*] | DS | |

TABLE 3-continued

| PEP Seq ID No. | Construct ID | Annotation | | | Trait | | | | |
|---|---|---|---|---|---|---|---|---|---|
| | | E-value | % id | Description | | | | | |
| 799 | 10192 | 0 | 99 | ref|NP_180997.1|CYP710A1; heme binding/iron ion binding/ monooxygenase/oxygen binding [*Arabidopsis thaliana*] | CS | PP | SS | | |
| 800 | 74775 | 0 | 96 | ref|NP_175812.1|ALDH7B4; aldehyde dehydrogenase/ oxidoreductase [*Arabidopsis thaliana*] | DS | | | | |
| 801 | 13841 | 2.00E-33 | 100 | ref|NP_194401.1|hydrogen-transporting ATP synthase, rotational mechanism/hydrogen-transporting ATPase, rotational mechanism [*Arabidopsis thaliana*] | LN | | | | |
| 802 | 15805 | 0 | 100 | ref|NP_567620.1|ZAC; ARF GTPase activator [*Arabidopsis thaliana*] | LN | | | | |
| 803 | 14253 | 1.00E-167 | 87 | ref|NP_195499.1|unknown protein [*Arabidopsis thaliana*] | LN | | | | |
| 804 | 13650 | 1.00E-151 | 91 | ref|NP_196069.1|phosphatidate cytidylyltransferase [*Arabidopsis thaliana*] | LN | | | | |
| 805 | 13855 | 1.00E-94 | 86 | ref|NP_567531.1|structural constituent of ribosome [*Arabidopsis thaliana*] | LN | | | | |
| 806 | 76049 | 0 | 99 | ref|NP_182198.2|unknown protein [*Arabidopsis thaliana*] | DS | HS | | | |
| 807 | 14271 | 0 | 82 | ref|NP_181342.1|unknown protein [*Arabidopsis thaliana*] | DS | | | | |
| 808 | 73927 | 0 | 100 | ref|NP_189059.1|FAD binding/disulfide oxidoreductase/ glutathione-disulfide reductase/oxidoreductase [*Arabidopsis thaliana*] | CS | | | | |
| 809 | 13657 | 6.00E-76 | 72 | ref|NP_565661.2|HDT4 [*Arabidopsis thaliana*] | LN | | | | |
| 810 | 13938 | 2.00E-90 | 77 | gb|AAL67123.1|AT3g06760/F3E22_10 [*Arabidopsis thaliana*] | SP | | | | |
| 810 | 14730 | 2.00E-90 | 77 | gb|AAL67123.1|AT3g06760/F3E22_10 [*Arabidopsis thaliana*] | SP | | | | |
| 811 | 73948 | 0 | 97 | ref|NP_176185.1|ATP binding/ATP-dependent helicase/ helicase/nucleic acid binding [*Arabidopsis thaliana*] | CS | | | | |
| 812 | 18116 | 0 | 100 | ref|NP_182144.1|oxidoreductase [*Arabidopsis thaliana*] | CS | | | | |
| 813 | 14341 | 0 | 100 | ref|NP_176646.1|unknown protein [*Arabidopsis thaliana*] | SS | | | | |
| 814 | 13960 | 1.00E-179 | 100 | ref|NP_565875.1|unknown protein [*Arabidopsis thaliana*] | SP | | | | |
| 814 | 74391 | 1.00E-179 | 100 | ref|NP_565875.1|unknown protein [*Arabidopsis thaliana*] | SP | | | | |
| 815 | 75957 | 0 | 95 | gb|ABK28258.1|unknown [*Arabidopsis thaliana*] | LL | | | | |
| 816 | 70240 | 0 | 100 | ref|NP_172751.1|AN11; nucleotide binding [*Arabidopsis thaliana*] | CS | | | | |
| 817 | 70748 | 0 | 97 | ref|NP_173077.1|ATP binding/protein kinase/protein serine/threonine kinase/protein-tyrosine kinase [*Arabidopsis thaliana*] | CK | | | | |
| 818 | 70807 | 0 | 93 | ref|NP_188160.2|protein binding [*Arabidopsis thaliana*] | CS | | | | |
| 819 | 73986 | 0 | 87 | ref|NP_974833.1|unknown protein [*Arabidopsis thaliana*] | DS | | | | |
| 820 | 77005 | 0 | 97 | ref|NP_566580.1|CIPK1 (CBL-INTERACTING PROTEIN KINASE 1); ATP binding/kinase/protein kinase/protein serine/threonine kinase/protein-tyrosine kinase [*Arabidopsis thaliana*] | CS | | | | |
| 821 | 70410 | 5.00E-34 | 86 | ref|NP_850158.1|CLE5 (CLAVATA3/ESR-RELATED 5); receptor binding [*Arabidopsis thaliana*] | SP | | | | |
| 822 | 14827 | 1.00E-153 | 88 | ref|NP_564658.2|unknown protein [*Arabidopsis thaliana*] | DS | | | | |
| 823 | 19122 | 0 | 93 | ref|NP_566009.1|unknown protein [*Arabidopsis thaliana*] | LL | | | | |
| 824 | 16446 | 0 | 94 | ref|NP_566277.2|unknown protein [*Arabidopsis thaliana*] | SP | | | | |
| 825 | 15143 | 6.00E-84 | 100 | ref|NP_194152.1|SLY1 (SLEEPY1) [*Arabidopsis thaliana*] | LN | | | | |
| 826 | 70401 | 0 | 93 | sp|Q9SMZ3|FBX13_ARATHF-box only protein 13 emb|CAB36790.1| putative protein [*Arabidopsis thaliana*] | PEG | | | | |
| 827 | 16182 | 0 | 100 | emb|CAB44691.1|putative protein [*Arabidopsis thaliana*] | DS | | | | |
| 828 | 15126 | 1.00E-138 | 95 | ref|NP_198741.1|unknown protein [*Arabidopsis thaliana*] | CS | | | | |
| 829 | 15628 | 0 | 100 | ref|NP_567421.1|unknown protein [*Arabidopsis thaliana*] | CS | | | | |
| 830 | 78355 | 0 | 90 | gb|AAD10665.1|hypothetical protein [*Arabidopsis thaliana*] | SS | | | | |
| 831 | 70560 | 0 | 100 | gb|AAB81879.1|putative zinc finger protein [*Arabidopsis thaliana*] | CS | | | | |
| 832 | 19133 | 0 | 97 | ref|NP_194117.3|protein binding/ubiquitin-protein ligase/zinc ion binding [*Arabidopsis thaliana*] | DS | | | | |
| 833 | 73602 | 0 | 74 | gb|AAR28013.1|mutant TFIIF-alpha [*Arabidopsis thaliana*] | CS | | | | |
| 834 | 71702 | 1.00E-169 | 100 | pir||T49271CELL DIVISION CONTROL PROTEIN 2 HOMOLOG A - *Arabidopsis thaliana* | LL | | | | |
| 835 | 14909 | 0 | 98 | gb|AAC39477.1|respiratory burst oxidase protein C [*Arabidopsis thaliana*] | CS | PP | HS | SS | PEG |
| 836 | 14927 | 1.00E-88 | 65 | ref|NP_568285.1|unknown protein [*Arabidopsis thaliana*] | LN | | | | |
| 837 | 75945 | 0 | 94 | ref|NP_563899.1|NRT1.1; transporter [*Arabidopsis thaliana*] | SP | | | | |
| 838 | 16553 | 0 | 100 | ref|NP_567083.1|nucleotide-sugar transporter/sugar porter [*Arabidopsis thaliana*] | SS | | | | |
| 839 | 75221 | 0 | 87 | ref|NP_195567.2|unknown protein [*Arabidopsis thaliana*] | CS | HS | | | |
| 840 | 70746 | 5.00E-60 | 79 | gb|AAM64668.1|unknown [*Arabidopsis thaliana*] | PEG | | | | |
| 841 | 70403 | 1.00E-137 | 85 | gb|AAK26011.1|AF360301_1unknown protein [*Arabidopsis thaliana*] | PP | | | | |
| 842 | 15966 | 2.00E-73 | 71 | ref|NP_568974.1|ATFP3; metal ion binding [*Arabidopsis thaliana*] | CK | | | | |
| 843 | 76076 | 4.00E-34 | 100 | ref|NP_179357.1|unknown protein [*Arabidopsis thaliana*] | PP | | | | |
| 844 | 17014 | 2.00E-57 | 76 | ref|NP_564008.1|unknown protein [*Arabidopsis thaliana*] | SS | PEG | | | |
| 845 | 16007 | 0 | 100 | ref|NP_564729.1|ZW9 [*Arabidopsis thaliana*] | DS | | | | |
| 846 | 16208 | 1.00E-06 | 100 | gb|AAF79580.1|AC022464_38F22G5.2 [*Arabidopsis thaliana*] | CS | | | | |
| 847 | 17310 | 0 | 96 | ref|NP_188117.1|catalytic [*Arabidopsis thaliana*] | HS | | | | |
| 848 | 15716 | 1.00E-164 | 96 | ref|NP_563630.1|8PS1 (BYPASS 1) [*Arabidopsis thaliana*] | LN | | | | |
| 849 | 15627 | 0 | 89 | ref|NP_565533.1|heat shock protein binding/unfolded protein binding [*Arabidopsis thaliana*] | SS | | | | |

TABLE 3-continued

| PEP Seq ID No. | Construct ID | E-value | % id | Description | Trait | |
|---|---|---|---|---|---|---|
| 850 | 15409 | 0 | 95 | ref|NP_188010.1|unknown protein [*Arabidopsis thaliana*] | CK | PEG |
| 850 | 17201 | 0 | 95 | ref|NP_188010.1|unknown protein [*Arabidopsis thaliana*] | PEG | |
| 851 | 15903 | 0 | 86 | ref|NP_199280.1|unknown protein [*Arabidopsis thaliana*] | CK | |
| 852 | 10332 | 0 | 96 | ref|NP_188080.1|CYP72A8; heme binding/iron ion binding/ monooxygenase/oxygen binding [*Arabidopsis thaliana*] | SP | |
| 853 | 73968 | 0 | 90 | ref|NP_565477.1|unknown protein [*Arabidopsis thaliana*] | LN | |
| 854 | 17003 | 1.00E−171 | 95 | ref|NP_174746.1|PHI-1 (PHOSPHATE-INDUCED 1) [*Arabidopsis thaliana*] | DS | SS |
| 855 | 73847 | 0 | 97 | ref|NP_849912.1|ATP binding/kinase [*Arabidopsis thaliana*] | LN | |
| 856 | 76041 | 0 | 97 | ref|NP_566284.1|transferase, transferring glycosyl groups/ transferase, transferring hexosyl groups [*Arabidopsis thaliana*] | CS | LL |
| 857 | 74567 | 0 | 75 | ref|NP_566917.1|calmodulin binding [*Arabidopsis thaliana*] ref|NP_974405.1|calmodulin binding [*Arabidopsis thaliana*] | CS | LL |
| 858 | 15809 | 0 | 97 | ref|NP_568150.1|unknown protein [*Arabidopsis thaliana*] | PP | |
| 859 | 70110 | 0 | 92 | ref|NP_014814.1|Lcb4p [*Saccharomyces cerevisiae*] | LN | |
| 860 | 70123 | 1.00E−180 | 100 | ref|NP_014392.1|Lst8p [*Saccharomyces cerevisiae*] | CK | SS |
| 861 | 74702 | 0 | 87 | ref|NP_850390.1|unknown protein [*Arabidopsis thaliana*] | SP | |
| 862 | 75936 | 0 | 95 | ref|NP_187671.1|CAT7 (CATIONIC AMINO ACID TRANSPORTER 7); cationic amino acid transporter [*Arabidopsis thaliana*] | CS | |
| 863 | 10462 | 1.00E−136 | 100 | ref|NP_565895.1|catalytic/hydrolase [*Arabidopsis thaliana*] | DS | |
| 864 | 17402 | 1.00E−60 | 100 | ref|NP_190775.1|unknown protein [*Arabidopsis thaliana*] | CS | |
| 865 | 73707 | 0 | 94 | ref|NP_564272.1|unknown protein [*Arabidopsis thaliana*] | CS | |
| 866 | 17129 | 3.00E−61 | 100 | ref|NP_564630.1|unknown protein [*Arabidopsis thaliana*] | LN | |
| 867 | 72665 | 3.00E−54 | 89 | ref|NP_564090.1|unknown protein [*Arabidopsis thaliana*] | LL | |
| 868 | 18206 | 0 | 100 | ref|NP_564983.1|transferase, transferring glycosyl groups/ transferase, transferring hexosyl groups [*Arabidopsis thaliana*] | LN | |
| 869 | 17151 | 1.00E−155 | 100 | ref|NP_171882.1|ATPHB2 (PROHIBITIN 2) [*Arabidopsis thaliana*] | LN | |
| 870 | 17813 | 5.00E−98 | 100 | ref|NP_199762.1|protein binding [*Arabidopsis thaliana*] | SS | |
| 871 | 70845 | 0 | 100 | ref|NP_173920.1|RCN1 (ROOTS CURL IN NPA); protein phosphatase type 2A regulator [*Arabidopsis thaliana*] | CS | |
| 872 | 16607 | 1.00E−171 | 95 | ref|NP_355455.1|hypothetical protein AGR_C_4560 [*Agrobacterium tumefaciens* str. C58] | SP | |
| 873 | 72675 | 1.00E−179 | 78 | ref|NP_200091.1|protein binding/ubiquitin-protein ligase/zinc ion binding [*Arabidopsis thaliana*] | LL | LN |
| 874 | 72677 | 0 | 86 | sp|Q5EAE9|ATL5C_ARATH RING-H2 finger protein ATL5C precursor dbj|BAB09675.1| unnamed protein product [*Arabidopsis thaliana*] | LL | |
| 875 | 74534 | 0 | 95 | ref|NP_196233.1|CYC1BAT; cyclin-dependent protein kinase regulator [*Arabidopsis thaliana*] | PP | |
| 876 | 74535 | 0 | 85 | ref|NP_564978.1|NTL1; calcium ion binding/transporter [*Arabidopsis thaliana*] | CS | |
| 877 | 10204 | 0 | 89 | ref|NP_179544.1|nucleotide binding [*Arabidopsis thaliana*] | PP | LL |
| 878 | 10472 | 1.00E−157 | 100 | ref|NP_565480.1|catalytic/protein phosphatase type 2C [*Arabidopsis thaliana*] | LN | |
| 879 | 10431 | 1.00E−118 | 88 | ref|NP_850625.1|imidazoleglycerol-phosphate dehydratase [*Arabidopsis thaliana*] | LN | |
| 880 | 72906 | 0 | 92 | ref|NP_200387.1|DNA binding [*Arabidopsis thaliana*] | PP | |
| 881 | 78362 | 0 | 95 | ref|NP_176118.2|DNA binding/transcription factor [*Arabidopsis thaliana*] | CS | |
| 882 | 17930 | 1.00E−11 | 60 | ref|NP_173425.2|unknown protein [*Arabidopsis thaliana*] | SS | |
| 883 | 18442 | 0 | 92 | ref|NP_198690.1|transcription factor [*Arabidopsis thaliana*] | SS | |
| 884 | 73207 | 0 | 94 | ref|NP_173148.2|dimethylallyltranstransferase [*Arabidopsis thaliana*] | CS | |
| 885 | 19166 | 4.00E−99 | 91 | emb|CAB45503.1|hypothetical protein [*Arabidopsis thaliana*] | DS | |
| 886 | 10469 | 1.00E−137 | 95 | ref|NP_191762.1|ROC4; peptidyl-prolyl cis-trans isomerase [*Arabidopsis thaliana*] | LN | |
| 887 | 18415 | 1.00E−111 | 71 | emb|CAB85519.1|putative protein [*Arabidopsis thaliana*] | CS | |
| 888 | 18418 | 1.00E−113 | 100 | ref|NP_200034.1|ATGB1 [*Arabidopsis thaliana*] | CK | SS |
| 889 | 19532 | 1.00E−179 | 100 | ref|NP_190986.1|CDC2B (CDC2-LIKE GENE); kinase [*Arabidopsis thaliana*] | CS | |
| 890 | 18423 | 1.00E−151 | 100 | ref|NP_180496.1|SAG13; oxidoreductase [*Arabidopsis thaliana*] | LN | |
| 891 | 77909 | 0 | 92 | ref|NP_191785.1|catalytic/protein phosphatase type 2C | CK | DS |
| 892 | 19656 | 4.00E−48 | 77 | ref|NP_200260.1|PBP1 (PINOID-BINDING PROTEIN 1); calcium ion binding [*Arabidopsis thaliana*] | CS | SS |
| 893 | 10217 | 1.00E−135 | 94 | ref|NP_199674.1|cyclin-dependent protein kinase [*Arabidopsis thaliana*] | LN | |
| 894 | 18874 | 2.00E−81 | 100 | ref|NP_176511.1|unknown protein [*Arabidopsis thaliana*] | SS | |
| 895 | 18875 | 0 | 96 | ref|NP_198127.1|unknown protein [*Arabidopsis thaliana*] | SS | |
| 896 | 19256 | 0 | 96 | ref|NP_568785.1|SPDS3 (SPERMIDINE SYNTHASE 3) [*Arabidopsis thaliana*] | DS | |
| 897 | 19537 | 0 | 100 | ref|NP_568931.1|ATP binding/ATP-dependent helicase/ helicase/nucleic acid binding [*Arabidopsis thaliana*] | LL | |
| 898 | 74201 | 0 | 90 | ref|NP_567067.1|ATP binding/ATP-dependent helicase/ helicase/nucleic acid binding [*Arabidopsis thaliana*] | LN | |

TABLE 3-continued

| PEP Seq ID No. | Construct ID | Annotation E-value | % id | Description | Trait | |
|---|---|---|---|---|---|---|
| 899 | 74233 | 0 | 97 | ref|NP_199051.1|unknown protein [*Arabidopsis thaliana*] | SS | |
| 900 | 18644 | 7.00E−62 | 100 | ref|NP_172620.1|electron transporter/thiol-disulfide exchange intermediate [*Arabidopsis thaliana*] | DS | |
| 901 | 18827 | 0 | 91 | ref|NP_565206.1|ubiquitin-protein ligase/zinc ion binding [*Arabidopsis thaliana*] | CS | |
| 902 | 18220 | 0 | 100 | ref|NP_177629.1|nucleotidyltransferase [*Arabidopsis thaliana*] | SP | |
| 903 | 18830 | 0 | 96 | ref|NP_188813.1|UDP-glycosyltransferase/transferase, transferring glycosyl groups [*Arabidopsis thaliana*] | PEG | |
| 904 | 19205 | 1.00E−161 | 84 | gb|ABF55664.2|double MYC-lagged mitogen activated protein kinase kinase 4 [synthetic construct] | LN | |
| 905 | 18226 | 7.00E−99 | 92 | ref|NP_197890.1|unknown protein [*Arabidopsis thaliana*] | CS | |
| 906 | 18227 | 1.00E−62 | 73 | ref|NP_564432.3|OHP2 (ONE-HELIX PROTEIN 2) [*Arabidopsis thaliana*] | LN | |
| 907 | 18239 | 0 | 100 | ref|NP_193460.1|unknown protein [*Arabidopsis thaliana*] | SP | |
| 908 | 70415 | 1.00E−136 | 96 | ref|NP_849930.1|AGL3 (AGAMOUS-LIKE 3); DNA binding/transcription factor [*Arabidopsis thaliana*] | CK | |
| 909 | 18329 | 7.00E−06 | 70 | ref|NP_178619.1|unknown protein [*Arabidopsis thaliana*] | LN | |
| 910 | 72606 | 1.00E−166 | 79 | ref|NP_566784.1|unknown protein [*Arabidopsis thaliana*] | CS | |
| 911 | 10230 | 0 | 96 | ref|NP_172406.1|transferase, transferring glycosyl groups/transferase, transferring hexosyl groups [*Arabidopsis thaliana*] | LN | |
| 912 | 19608 | 0 | 82 | ref|NP_201045.1|calmodulin binding [*Arabidopsis thaliana*] | CS | |
| 913 | 18271 | 3.00E−97 | 82 | gb|AAA21820.1|alpha-subunit; putative | LN | |
| 914 | 18347 | 2.00E−65 | 100 | ref|NP_566786.1|DNA binding/transcription factor [*Arabidopsis thaliana*] | SP | |
| 915 | 18403 | 0 | 89 | ref|NP_187364.1|unknown protein [*Arabidopsis thaliana*] | CK | |
| 916 | 74206 | 0 | 91 | ref|NP_201348.1|cysteine-type endopeptidase/ubiquitin thiolesterase [*Arabidopsis thaliana*] | CS | |
| 917 | 10234 | 2.00E−60 | 72 | ref|NP_193759.1|unknown protein [*Arabidopsis thaliana*] | LN | |
| 918 | 71115 | 1.00E−167 | 87 | ref|NP_189058.1|PMP (PUTATIVE TYPE 1 MEMBRANE PROTEIN) [*Arabidopsis thaliana*] | DS | |
| 919 | 18406 | 8.00E−79 | 100 | ref|NP_564160.1|unknown protein [*Arabidopsis thaliana*] | SS | |
| 920 | 19619 | 2.00E−87 | 83 | ref|NP_563890.1|unknown protein [*Arabidopsis thaliana*] | HS | |
| 921 | 19623 | 1.00E−125 | 100 | ref|NP_563994.1|SYP51 (SYNTAXIN OF PLANTS 51) [*Arabidopsis thaliana*] | DS | |
| 922 | 18381 | 9.00E−96 | 84 | ref|NP_564601.1|unknown protein [*Arabidopsis thaliana*] | SS | |
| 923 | 18408 | 8.00E−69 | 91 | ref|NP_564808.1|unknown protein [*Arabidopsis thaliana*] | DS | |
| 924 | 18720 | 1.00E−175 | 89 | ref|NP_564840.1|unknown protein [*Arabidopsis thaliana*] | CK | |
| 925 | 77537 | 1.00E−122 | 81 | ref|NP_565125.1|unknown protein [*Arabidopsis thaliana*] | CS | |
| 926 | 70833 | 0 | 90 | ref|NP_566212.2|ATBPM4; protein binding [*Arabidopsis thaliana*] | LL | |
| 927 | 19328 | 0 | 93 | ref|NP_638257.1|hypothetical protein XCC2909 [*Xanthomonas campestris* pv. *campestris* str. ATCC 33913] | DS | |
| 928 | 19312 | 0 | 100 | ref|NP_013243.1|Proline oxidase, nuclear-encoded mitochondrial protein involved in utilization of proline as sole nitrogen source; PUT1 transcription is induced by Put3p in the presence of proline and the absence of a preferred nitrogen source [*Saccharomyces cerevisiae*] | SS | |
| 929 | 70538 | 1.00E−146 | 93 | ref|NP_199892.1|unknown protein [*Arabidopsis thaliana*] | SS | |
| 930 | 70440 | 0 | 88 | ref|NP_195953.1|cysteine-type peptidase [*Arabidopsis thaliana*] | CK | LN |
| 931 | 11319 | 0 | 97 | ref|NP_177797.2|unknown protein [*Arabidopsis thaliana*] | LN | |
| 932 | 70443 | 1.00E−151 | 81 | ref|NP_173841.1|unknown protein [*Arabidopsis thaliana*] | CS | |
| 933 | 72357 | 1.00E−141 | 100 | ref|NP_190300.1|ubiquitin-protein ligase/zinc ion binding [*Arabidopsis thaliana*] | PP | |
| 934 | 70466 | 1.00E−172 | 94 | ref|NP_196084.1|DNA binding/transcription factor [*Arabidopsis thaliana*] | LL | |
| 935 | 70241 | 5.00E−39 | 100 | gb|EAZ44836.1|hypothetical protein OsJ_028319 [*Oryza sativa* (japonica cultivar-group)] | SP | |
| 936 | 70476 | 1.00E−153 | 95 | ref|NP_176240.1|unknown protein [*Arabidopsis thaliana*] | LN | |
| 937 | 70477 | 1.00E−150 | 100 | ref|NP_564877.1|WRKY67; transcription factor [*Arabidopsis thaliana*] | SS | |
| 938 | 19713 | 0 | 100 | ref|NP_637886.1|oxidoreductase [*Xanthomonas campestris* pv. *campestris* str. ATCC 33913] | PP | |
| 939 | 12601 | 3.00E−70 | 100 | ref|NP_195713.1|DNA binding [*Arabidopsis thaliana*] ref|NP_001050276.1| Os03g0390600 [*Oryza sativa* (japonica cultivar-group)] gb|AAB36494.1| histone H3.2 [*Medicago sativa*] | CK | |
| 940 | 19747 | 0 | 69 | emb|CAB54847.1|hydroperoxide lyase [*Medicago sativa*] | CS | |
| 941 | 11117 | 1.00E−174 | 91 | ref|NP_973592.1|ATPUP2 [*Arabidopsis thaliana*] | LN | |
| 942 | 70965 | 3.00E−95 | 46 | gb|EAY82507.1|hypothetical protein OsI_036466 [*Oryza sativa* (indica cultivar-group)] | CS | |
| 943 | 10366 | 1.00E−153 | 92 | ref|NP_181358.1|unknown protein [*Arabidopsis thaliana*] | CK | |
| 943 | 13404 | 1.00E−153 | 92 | ref|NP_181358.1|unknown protein [*Arabidopsis thaliana*] | LN | |
| 944 | 70935 | 0 | 77 | gb|ABE91638.1|hypothetical protein MtrDRAFT_AC142394g9v2 [*Medicago truncatula*] | CS | |
| 945 | 77717 | 1.00E−136 | 69 | ref|NP_565111.1|unknown protein [*Arabidopsis thaliana*] | CS | |
| 946 | 19966 | 1.00E−163 | 80 | gb|AAF27919.1|AF220203_1Ttg1-like protein [*Malus x domestica*] | SS | |

TABLE 3-continued

| PEP Seq ID No. | Construct ID | Annotation E-value | % id | Description | Trait | |
|---|---|---|---|---|---|---|
| 947 | 70909 | 1.00E−116 | 74 | ref|NP_192696.3|unknown protein [*Arabidopsis thaliana*] | SP | |
| 948 | 19906 | 0 | 79 | gb|AAD11430.1|protein phosphatase 2C homolog [*Mesembryanthemum crystallinum*] | CK | |
| 949 | 70974 | 0 | 72 | gb|ABN09819.1|Not CCR4-Not complex component, N-terminal; tRNA-binding arm [*Medicago truncatula*] | SP | |
| 950 | 19802 | 0 | 90 | gb|AAK11734.1|serine/threonine/tyrosine kinase [*Arachis hypogaea*] | CS | |
| 951 | 19746 | 1.00E−127 | 92 | sp|Q96450|1433A_SOYBN14-3.3-like protein A (SGF14A) gb|AAB09580.1|SGF14A [*Glycine max*] | CS | |
| 952 | 70902 | 1.00E−135 | 81 | gb|ABE77803.1|oxidoreductase; short chain dehydrogenase/reductase family, putative [*Medicago truncatula*] | PEG | |
| 953 | 19933 | 2.00E−92 | 68 | gb|ABE81369.1|RNA-binding region RNP-1 |RNA recognition motif) [*Medicago truncatula*] | SP | |
| 954 | 19927 | 0 | 76 | gb|ABE88827.1|Hydroxymethylglutaryl-coenzyme A reductase, putative [*Medicago truncatula*] | CS | SS |
| 955 | 70976 | 1.00E−164 | 79 | ref|NP_194914.1|catalytic/protein phosphatase type 2C [*Arabidopsis thaliana*] | PEG | |
| 956 | 71440 | 0 | 60 | ref|NP_196473.1|nucleotide binding [*Arabidopsis thaliana*] | CS | |
| 957 | 10413 | 0 | 93 | ref|NP_197748.1|CDPK9 (CALCIUM-DEPENDENT PROTEIN KINASE 9); ATP binding/calcium ion binding/calcium- and calmodulin-dependent protein kinase/kinase/protein kinase/ protein serine/threonine kinase/protein-tyrosine kinase [*Arabidopsis thaliana*] | LN | |
| 958 | 11119 | 1.00E−172 | 89 | ref|NP_196779.1|CPK17; ATP binding/calcium ion binding/ calcium- and calmodulin-dependent protein kinase/kinase/ protein kinase/protein serine/threonine kinase/protein-tyrosine kinase [*Arabidopsis thaliana*] | LN | |
| 959 | 78659 | 1.00E−164 | 90 | ref|NP_175249.1|DNA binding/transcription factor [*Arabidopsis thaliana*] | LN | |
| 960 | 78665 | 0 | 100 | ref|NP_567343.1|ubiquitin-protein ligase [*Arabidopsis thaliana*] | DS | |
| 961 | 78969 | 0 | 100 | ref|NP_194509.1|catalytic/protein phosphatase type 2C [*Arabidopsis thaliana*] | LN | |
| 962 | 78970 | 7.00E−86 | 100 | ref|NP_564143.1|calcium ion binding [*Arabidopsis thaliana*] | HS | |
| 963 | 71250 | 1.00E−160 | 100 | ref|NP_567676.1|ATP binding/protein kinase/protein serine/threonine kinase/protein-tyrosine kinase/signal transducer [*Arabidopsis thaliana*] | SS | LN |
| 964 | 78972 | 0 | 94 | ref|NP_176647.1|catalytic [*Arabidopsis thaliana*] | LN | |
| 965 | 78677 | 2.00E−25 | 43 | gb|AAG40050.2|AF324699_1At1g76180 [*Arabidopsis thaliana*] | SS | |
| 966 | 70632 | 3.00E−85 | 100 | ref|NP_187663.1|AHB2 [*Arabidopsis thaliana*] | DS | |
| 967 | 75205 | 0 | 92 | ref|NP_196484.1|AAP2 (AMINO ACID PERMEASE 2); amino acid permease [*Arabidopsis thaliana*] | SS | |
| 968 | 10359 | 1.00E−156 | 100 | gb|AAR10436.1|YDA [*Arabidopsis thaliana*] | DS | |
| 968 | 11408 | 1.00E−156 | 100 | gb|AAR10436.1|YDA [*Arabidopsis thaliana*] | LL | |
| 969 | 73616 | 1.00E−163 | 100 | ref|NP_199265.1|ribose-5-phosphate isomerase [*Arabidopsis thaliana*] | LN | |
| 970 | 78358 | 0 | 100 | ref|NP_188056.1|diaminopimelate decarboxylase [*Arabidopsis thaliana*] | LL | |
| 971 | 71839 | 0 | 96 | ref|NP_200945.1|unknown protein [*Arabidopsis thaliana*] | LN | PEG |
| 972 | 78417 | 0 | 91 | ref|NP_191221.1|unknown protein [*Arabidopsis thaliana*] | LN | |
| 973 | 71952 | 1.00E−169 | 100 | ref|NP_197477.1|binding/oxidative phosphorylation uncoupler [*Arabidopsis thaliana*] | LL | |
| 974 | 78717 | 0 | 85 | ref|NP_566301.1|unknown protein [*Arabidopsis thaliana*] | LN | PEG |
| 975 | 75040 | 0 | 92 | ref|NP_566410.1|unknown protein [*Arabidopsis thaliana*] | LL | |
| 976 | 71843 | 1.00E−134 | 94 | ref|NP_194519.1|unknown protein [*Arabidopsis thaliana*] | LN | |
| 977 | 70666 | 3.00E−79 | 91 | ref|NP_565742.1|unknown protein [*Arabidopsis thaliana*] | LN | |
| 978 | 71846 | 0 | 100 | ref|NP_177890.1|1-aminocyclopropane-1-carboxylate synthase/ transaminase/transferase, transferring nitrogenous groups [*Arabidopsis thaliana*] | SP | |
| 979 | 71314 | 0 | 96 | ref|NP_172774.1|CYP86C4; heme binding/iron ion binding/ monooxygenase/oxygen binding [*Arabidopsis thaliana*] | SP | |
| 980 | 76410 | 0 | 99 | ref|NP_188081.1|CYP72A9; heme binding/iron ion binding/ monooxygenase/oxygen binding [*Arabidopsis thaliana*] | LL | LN |
| 981 | 71322 | 0 | 93 | ref|NP_680111.1|CYP71A21; heme binding/iron ion binding/ monooxygenase/oxygen binding [*Arabidopsis thaliana*] | LN | |
| 982 | 73214 | 0 | 97 | ref|NP_196559.1|CYP78A7; heme binding/iron ion binding/ monooxygenase/oxygen binding [*Arabidopsis thaliana*] | DS | |
| 983 | 71963 | 0 | 97 | ref|NP_199079.1|AOS (ALLENE OXIDE SYNTHASE); hydro- lyase/oxygen binding [*Arabidopsis thaliana*] | SP | PP |
| 984 | 71326 | 0 | 83 | pir||T00605probable cytochrome P450 At2g02580 [imported] - *Arabidopsis thaliana* | LN | |
| 985 | 70834 | 0 | 95 | ref|NP_175900.1|LOX1; lipoxygenase [*Arabidopsis thaliana*] | CS | |
| 986 | 73215 | 0 | 97 | gb|AAF97287.1|AC010164_9Putative cytochrome P450 [*Arabidopsis thaliana*] | CS | |
| 987 | 71334 | 0 | 97 | ref|NP_193568.2|hydrolase, hydrolyzing O-glycosyl compounds [*Arabidopsis thaliana*] | SP | LN |

TABLE 3-continued

| PEP Seq ID No. | Construct ID | E-value | % id | Description | Trait | |
|---|---|---|---|---|---|---|
| 988 | 71335 | 0 | 96 | ref|NP_173573.1|catalytic [*Arabidopsis thaliana*] | LN | |
| 989 | 71347 | 0 | 100 | ref|NP_568479.1|TGG2 (GLUCOSIDE GLUCOHYDROLASE 2); hydrolase, hydrolyzing O-glycosyl compounds [*Arabidopsis thaliana*] | CK | |
| 990 | 71820 | 3.00E−55 | 75 | emb|CAC03600.1|splicing factor SC35 [*Arabidopsis thaliana*] | LL | |
| 991 | 70764 | 1.00E−164 | 94 | ref|NP_172084.2|unknown protein [*Arabidopsis thaliana*] | LL | |
| 992 | 70680 | 8.00E−79 | 100 | ref|NP_567038.1|protein kinase C binding/zinc ion binding [*Arabidopsis thaliana*] | LL | |
| 993 | 72375 | 0 | 73 | gb|ABE85332.1|Protein kinase [*Medicago truncatula*] | SP | |
| 994 | 72469 | 0 | 90 | dbj|BAD95891.1|Ser/Thr protein kinase [*Lotus japonicus*] | CK | |
| 995 | 73951 | 0 | 81 | gb|AAR15466.1|WD-repeat protein [*Capsella rubella*] | CS | |
| 996 | 11003 | 1.00E−118 | 94 | ref|NP_178022.1|NADH dehydrogenase (ubiquinone)/electron transporter/iron ion binding [*Arabidopsis thaliana*] | LN | |
| 997 | 71613 | 1.00E−110 | 85 | ref|NP_199556.1|AtTIP2; 3; water channel [*Arabidopsis thaliana*] | LL | |
| 998 | 78203 | 0 | 93 | gb|AAF27063.1|AC008262_12F4N2.23 [*Arabidopsis thaliana*] | CS | |
| 999 | 71638 | 0 | 90 | ref|NP_174210.1|ATS9 (19S PROTEOSOME SUBUNIT 9) [*Arabidopsis thaliana*] | CS | |
| 1000 | 71631 | 0 | 96 | ref|NP_564785.1|antiporter/glucose-6-phosphate transporter [*Arabidopsis thaliana*] | LL | |
| 1001 | 72368 | 0 | 98 | ref|NP_187640.1|organic anion transporter [*Arabidopsis thaliana*] | SP | |
| 1002 | 78202 | 0 | 98 | ref|NP_564338.1|CARB (CARBAMOYL PHOSPHATE SYNTHETASE B); ATP binding/carbamoyl-phosphate synthase/ligase [*Arabidopsis thaliana*] | CK | |
| 1003 | 78207 | 0 | 96 | ref|NP_030560.1|unknown protein [*Arabidopsis thaliana*] | CS | HS |
| 1004 | 75209 | 0 | 92 | ref|NP_187286.1|EMB3004; 3-dehydroquinate dehydratase/shikimate 5-dehydrogenase [*Arabidopsis thaliana*] | LN | |
| 1005 | 72457 | 7.00E−86 | 100 | ref|NP_568956.1|ubiquitin conjugating enzyme/ubiquitin-like activating enzyme [*Arabidopsis thaliana*] | CS | |
| 1006 | 73639 | 0 | 98 | ref|NP_197589.1|ATP binding/protein binding [*Arabidopsis thaliana*] | CS | |
| 1007 | 72526 | 1.00E−55 | 81 | ref|NP_567335.1|unknown protein [*Arabidopsis thaliana*] | CK | |
| 1008 | 72531 | 0 | 100 | ref|NP_194003.1|O-sialoglycoprotein endopeptidase [*Arabidopsis thaliana*] | CS | |
| 1009 | 73336 | 1.00E−167 | 100 | ref|NP_201090.1|catalytic [*Arabidopsis thaliana*] | LL | |
| 1010 | 73722 | 0 | 94 | ref|NP_191029.1|sugar binding [*Arabidopsis thaliana*] | CS | |
| 1011 | 72650 | 1.00E−168 | 85 | ref|NP_568218.1|unknown protein [*Arabidopsis thaliana*] | DS | |
| 1012 | 73686 | 5.00E−67 | 100 | ref|NP_189296.1|unknown protein [*Arabidopsis thaliana*] | CK | LL |
| 1013 | 78353 | 1.00E−14 | 86 | sp|Q9SLB6|LBD17_ARATHLOB domain-containing protein 17 gb|AAD23726.1| hypothelical protein [*Arabidopsis thaliana*] | LL | LN |
| 1014 | 73726 | 0 | 100 | ref|NP_179795.1|nucleotide binding [*Arabidopsis thaliana*] | LN | |
| 1015 | 74715 | 0 | 97 | ref|NP_197059.1|nucleotide binding [*Arabidopsis thaliana*] | CS | |
| 1016 | 73230 | 0 | 96 | ref|NP_191164.1|ATP binding/kinase/protein kinase/protein serine/threonine kinase/protein-tyrosine kinase [*Arabidopsis thaliana*] | CS | |
| 1017 | 72663 | 2.00E−97 | 100 | ref|NP_565393.1|ATP binding/kinase/shikimate kinase [*Arabidopsis thaliana*] | LN | |
| 1018 | 70822 | 0 | 94 | ref|NP_198905.1|ATCLC-A (CHLORIDE CHANNEL A); anion channel/voltage-gated chloride channel [*Arabidopsis thaliana*] | HS | |
| 1019 | 72827 | 1.00E−164 | 95 | ref|NP_173856.1|oxidoreductase [*Arabidopsis thaliana*] | LN | |
| 1020 | 78339 | 0 | 96 | ref|NP_197098.1|oxidoreductase [*Arabidopsis thaliana*] | LL | |
| 1021 | 73309 | 1.00E−171 | 100 | dbj|BAA96982.1|11-beta-hydroxysteroid dehydrogenase-like [*Arabidopsis thaliana*] | LL | |
| 1022 | 78725 | 0 | 94 | ref|NP_192359.1|kinase [*Arabidopsis thaliana*] | LN | |
| 1023 | 74222 | 0 | 93 | ref|NP_174039.1|ATP binding/kinase/protein serine/threonine kinase [*Arabidopsis thaliana*] | LL | LN |
| 1024 | 78341 | 0 | 93 | ref|NP_176603.1|ATP binding/kinase/protein serine/threonine kinase [*Arabidopsis thaliana*] | LN | PEG |
| 1025 | 78342 | 1.00E−178 | 93 | ref|NP_188875.1|AOX1B; alternative oxidase [*Arabidopsis thaliana*] | LL | LN |
| 1026 | 78349 | 2.00E−55 | 100 | ref|NP_568772.3|FIB1 (FIBRILLARIN 1) [*Arabidopsis thaliana*] | CS | |
| 1027 | 73683 | 7.00E−90 | 100 | ref|NP_564105.1|ASK4; ubiquitin-protein ligase [*Arabidopsis thaliana*] | DS | |
| 1028 | 73280 | 7.00E−86 | 94 | ref|NP_565297.1|ASK16 (*ARABIDOPSIS* SKP1-LIKE 16); ubiquitin-protein ligase [*Arabidopsis thaliana*] | SP | |
| 1029 | 73281 | 3.00E−77 | 96 | ref|NP_565467.1|MEO (MEIDOS); ubiquitin-protein ligase [*Arabidopsis thaliana*] | LN | |
| 1030 | 73313 | 0 | 95 | ref|NP_172572.1|kinase [*Arabidopsis thaliana*] | CS | |
| 1031 | 12772 | 1.00E−117 | 94 | ref|NP_176435.1|Rho GDP-dissociation inhibitor [*Arabidopsis thaliana*] | SS | |
| 1032 | 73314 | 0 | 89 | ref|NP_186833.1|ATP binding/kinase/protein kinase/protein serine/threonine kinase/protein-tyrosine kinase [*Arabidopsis thaliana*] | DS | |
| 1033 | 73861 | 0 | 97 | ref|NP_195565.2|ATPLC1; phospholipase C [*Arabidopsis thaliana*] | PEG | |
| 1034 | 73676 | 1.00E−164 | 100 | ref|NP_201532.2|CYP81G1; heme binding/iron ion binding/monooxygenase/oxygen binding [*Arabidopsis thaliana*] | PEG | |

TABLE 3-continued

| PEP Seq ID No. | Construct ID | Annotation | | | Trait | |
|---|---|---|---|---|---|---|
| | | E-value | % id | Description | | |
| 1035 | 74212 | 0 | 100 | ref|NP_176086.1|heme binding/iron ion binding/ monooxygenase/oxygen binding [Arabidopsis thaliana] | LL | |
| 1036 | 74218 | 0 | 98 | gb|AAG60111.1|AC073178_22cytochrome P450 putative [Arabidopsis thaliana] | CK | DS |
| 1037 | 71218 | 0 | 91 | ref|NP_188021.1|RSH2 (RELA-SPOT HOMOLOG); catalytic [Arabidopsis thaliana] | PP | |
| 1038 | 73731 | 0 | 94 | ref|NP_179782.1|CYP96A5; heme binding/iron ion binding/ monooxygenase/oxygen binding [Arabidopsis thaliana] | CS | |
| 1039 | 73251 | 1.00E-98 | 100 | ref|NP_186922.1|electron transporter/thiol-disulfide exchange intermediate [Arabidopsis thaliana] | CS | |
| 1040 | 12773 | 0 | 100 | ref|NP_565903.1|catalytic/hydrolase [Arabidopsis thaliana] | PEG | |
| 1041 | 73254 | 8.00E-50 | 80 | ref|NP_566150.1|unknown protein [Arabidopsis thaliana] | CS | |
| 1042 | 73255 | 1.00E-169 | 100 | ref|NP_850995.1|unknown protein [Arabidopsis thaliana] | SP | |
| 1043 | 73257 | 6.00E-39 | 85 | gb|AAF01528.1|AC009991_24hypothetical protein [Arabidopsis thaliana] | LN | |
| 1044 | 11049 | 0 | 100 | ref|NP_181474.2|catalytic/hydrolase [Arabidopsis thaliana] | LN | |
| 1045 | 74231 | 0 | 84 | ref|NP_190740.1|unknown protein [Arabidopsis thaliana] | CS | |
| 1046 | 73266 | 2.00E-89 | 79 | ref|NP_190816.1|unknown protein [Arabidopsis thaliana] | PP | |
| 1047 | 75823 | 1.00E-101 | 70 | ref|NP_566967.1|unknown protein [Arabidopsis thaliana] | LL | |
| 1048 | 11353 | 1.00E-155 | 85 | ref|NP_565721.1|ADS2; iron ion binding/oxidoreductase/ stearoyl-CoA 9-desaturase [Arabidopsis thaliana] | LN | |
| 1049 | 72025 | 0 | 95 | ref|NP_199995.1|PGM (PHOSPHOGLUCOMUTASE) [Arabidopsis thaliana] | CS | |
| 1050 | 72037 | 0 | 91 | ref|NP_179336.1|protein binding [Arabidopsis thaliana] | SS | |
| 1051 | 72049 | 0 | 100 | emb|CAA16713.1|cytochrome P450 [Arabidopsis thaliana] | SP | |
| 1052 | 78213 | 1.00E-151 | 93 | ref|NP_181836.1|AT-P4H-1; oxidoreductase, acting on paired donors, with incorporation or reduction of molecular oxygen, 2-oxoglutarate as one donor, and incorporation of one atom each of oxygen into both donors/procollagen-proline 4-dioxygenase [Arabidopsis thaliana] | CS | |
| 1053 | 72007 | 0 | 100 | ref|NP_011943.1|Mitochondrially localized type 2C protein phosphatase; expression induced by growth on ethanol and by sustained osmotic stress; possible role in carbon source utilization in low oxygen environments (Saccharomyces cerevisiae) | CK | |
| 1054 | 72067 | 1.00E-171 | 83 | ref|NP_011043.1|Sho1p (Saccharomyces cerevisiae) | DS | |
| 1055 | 72008 | 4.00E-71 | 100 | sp|P40001|YEA8_YEASTHypothetical 14.0 kDa protein in GCN4-WBP1 intergenic region gb|AAB64485.1| Yel008wp [Saccharomyces cerevisiae] | LL | |
| 1056 | 72022 | 1.00E-127 | 72 | ref|NP_564894.1|unknown protein [Arabidopsis thaliana] | CK | |
| 1057 | 72096 | 3.00E-64 | 66 | ref|NP_001051798.1|Os03g0831900 [Oryza sativa (japonica cultivar-group)] | CS | |
| 1058 | 10811 | 0 | 96 | ref|NP_175947.1|BCDH BETA1 (BRANCHED-CHAIN ALPHA-KETO ACID DECARBOXYLASE E1 BETA SUBUNIT); 3-methyl-2-oxobutanoate dehydrogenase (2-methylpropanoyl-transferring) [Arabidopsis thaliana] | LN | |
| 1059 | 72138 | 4.00E-89 | 65 | ref|NP_180496.1|SAG13; oxidoreductase [Arabidopsis thaliana] | CK | |
| 1060 | 74261 | 0 | 98 | ref|NP_566923.1|branched-chain-amino-acid transaminase/ catalytic [Arabidopsis thaliana] | LL | |
| 1061 | 74264 | 1.00E-122 | 100 | ref|NP_196452.1|unknown protein [Arabidopsis thaliana] | CS | |
| 1062 | 74271 | 0 | 93 | ref|NP_195096.2|unknown protein [Arabidopsis thaliana] | CS | |
| 1063 | 74272 | 1.00E-112 | 90 | ref|NP_195409.1|unknown protein [Arabidopsis thaliana] | SS | |
| 1064 | 78442 | 0 | 91 | ref|NP_189231.1|protein phosphatase type 2A regulator [Arabidopsis thaliana] | LL | |
| 1065 | 76709 | 0 | 96 | ref|NP_174119.1|carboxy-lyase [Arabidopsis thaliana] | CK | |
| 1066 | 75002 | 0 | 94 | ref|NP_566016.1|ATCS; citrate (SI)-synthase [Arabidopsis thaliana] | CS | PP |
| 1067 | 78361 | 0 | 82 | gb|AAL09767.1|AT5g03040/F15A17_70 [Arabidopsis thaliana] | SS | |
| 1068 | 74238 | 0 | 92 | ref|NP_850730.1|dihydrodipicolinate synthase [Arabidopsis thaliana] | SS | |
| 1069 | 78434 | 0 | 100 | ref|NP_180966.1|permease [Arabidopsis thaliana] | DS | |
| 1070 | 73932 | 0 | 85 | ref|NP_173508.1|carbohydrate transporter/nucleoside transporter/sugar porter [Arabidopsis thaliana] | SS | |
| 1071 | 72713 | 0 | 97 | ref|NP_567914.1|LKR [Arabidopsis thaliana] ref|NP_849486.1| LKR [Arabidopsis thaliana] | SS | |
| 1072 | 72773 | 1.00E-149 | 93 | ref|NP_013180.1|Inhibitor of Cdc28-Clb kinase complexes that controls G1/S phase transition, preventing premature S phase and ensuring genomic integrity; phosphorylation targets Sic1p for SCF(CDC4)-dependent turnover; functional homolog of mammalian Kip1 [Saccharomyces cerevisiae] | PP | |
| 1073 | 72678 | 0 | 91 | ref|NP_015445.1|B-type cyclin involved in DNA replication during S phase; activates Cdc28p to promote initiation of DNA synthesis; functions in formation of mitotic spindles along with Clb3p and Clb4p; most abundant during late G1 phase [Saccharomyces cerevisiae] | PEG | |

TABLE 3-continued

| PEP Seq ID No. | Construct ID | Annotation | | | Trait | | |
|---|---|---|---|---|---|---|---|
| | | E-value | % id | Description | | | |
| 1074 | 72765 | 0 | 88 | ref|NP_009934.1|Sat4p [*Saccharomyces cerevisiae*] | PP | PEG | |
| 1075 | 72730 | 1.00E−146 | 92 | ref|NP_012214.1|Pcl7p [*Saccharomyces cerevisiae*] | CS | | |
| 1076 | 72707 | 5.00E−66 | 90 | ref|NP_011461.1|Erv14p [*Saccharomyces cerevisiae*] | CK | | |
| 1077 | 72755 | 1.00E−134 | 89 | ref|NP_116710.1|Rpn12p [*Saccharomyces cerevisiae*] | PP | PEG | |
| 1078 | 10610 | 1.00E−110 | 89 | ref|NP_187123.1|PR4 (PATHOGENESIS-RELATED 4) [*Arabidopsis thaliana*] | LN | | |
| 1079 | 73953 | 0 | 92 | ref|NP_850165.1|DNA binding/NAD+ ADP-ribosyltransferase [*Arabidopsis thaliana*] | LL | | |
| 1080 | 73173 | 1.00E−113 | 91 | ref|NP_191263.1|ARR9 (RESPONSE REACTOR 4); transcription regulator [*Arabidopsis thaliana*] | HS | | |
| 1081 | 73979 | 0 | 96 | sp|O49289|RH29_ARATHPutative DEAD-box ATP-dependent RNA helicase 29 gb|AAC00620.1| Similar ATP-dependent RNA Helicase [*Arabidopsis thaliana*] | SS | PEG | |
| 1082 | 73966 | 0 | 94 | ref|NP_194578.1|HAESA (RECEPTOR-LIKE PROTEIN KINASE 5); ATP binding/kinase/protein serine/threonine kinase [*Arabidopsis thaliana*] | LN | | |
| 1083 | 12776 | 0 | 100 | ref|NP_178421.1|FT1 (FUCOSYLTRANSFERASE 1); fucosyltransferase/transferase, transferring glycosyl groups [*Arabidopsis thaliana*] | PP | | |
| 1084 | 72960 | 0 | 87 | ref|NP_190906.1|carbohydrate binding/kinase) *Arabidopsis thaliana*] | PEG | | |
| 1085 | 73021 | 0 | 100 | ref|NP_243103.1|NADP-dependent glyceraldehyde-3-phosphate dehydrogenase [*Bacillus halodurans* C-125] | CS | PP | PEG |
| 1086 | 73163 | 0 | 99 | ref|NP_243584.1|glutamate dehydrogenase [*Bacillus halodurans* C-125] | CS | SS | |
| 1087 | 73187 | 0 | 93 | ref|NP_244808.1|1-pyrroline-5-carboxylate dehydrogenase [*Bacillus halodurans* C-125] | CK | | |
| 1088 | 73188 | 1.00E−173 | 100 | ref|NP_389366.1|glutaminase [*Bacillus subtilis* subsp. *subtilis* str. 168] | PEG | | |
| 1089 | 73153 | 1.00E−159 | 92 | ref|NP_415018.1|predicted glutaminase [*Escherichia coli* K12] | CK | | |
| 1090 | 73983 | 0 | 99 | ref|ZP_00107721.1|COG0160: 4-aminobutyrate aminotransferase and related aminotransferases [*Nostoc punctiforme* PCC 73102] | CK | | |
| 1091 | 11516 | 0 | 98 | ref|NP_564571.1|THFS (10-FORMYLTETRAHYDROFOLATE SYNTHETASE); ATP binding/formate-tetrahydrofolate ligase [*Arabidopsis thaliana*] | LN | | |
| 1092 | 73179 | 0 | 97 | ref|NP_387399.1|beta alanine-pyruvate transaminase [*Sinorhizobium meliloti* 1021] | LL | | |
| 1093 | 73009 | 0 | 87 | ref|NP_927600.1|glutamine synthetase [*Photorhabdus luminescens* subsp. *laumondii* TTO1] | SS | | |
| 1094 | 73109 | 4.00E−95 | 100 | ref|NP_840275.1|adenine phosphoribosyltransferase [*Nitrosomonas europaea* ATCC 19718] | PEG | | |
| 1095 | 73121 | 1.00E−117 | 94 | ref|ZP_00109456.1|COG0120: Ribose 5-phosphate isomerase [*Nostoc punctiforme* PCC 73102] | PEG | | |
| 1096 | 73157 | 1.00E−98 | 100 | ref|NP_791813.1|adenine phosphoribosyltransferase [*Pseudomonas syringae* pv. tomato str. DC3000] | CS | | |
| 1097 | 73158 | 5.00E−71 | 93 | ref|NP_928672.1|nucleoside diphosphate kinase [*Photorhabdus luminescens* subsp. *laumondii* TTO1] | SS | | |
| 1098 | 73088 | 0 | 100 | ref|NP_013311.1|B-type cyclin involved in cell cycle progression; activates Cdc28p to promote the G2/M transition; may be involved in DNA replication and spindle assembly; accumulates during S phase and G2, then targeted for ubiquitin-mediated degradation [*Saccharomyces cerevisiae*] | DS | | |
| 1099 | 73135 | 0 | 91 | ref|NP_011846.1|Putative protein of unknown function; green fluorescent protein (GFP)-fusion protein co-localizes with clathrin-coated vesicles [*Saccharomyces cerevisiae*] | PP | | |
| 1100 | 73005 | 2.00E−63 | 90 | ref|NP_014508.1|Hrt1p [*Saccharomyces cerevisiae*) | CS | | |
| 1101 | 73171 | 0 | 87 | ref|NP_015262.1|Constituent of the mitochondrial inner membrane presequence translocase (TIM23 complex); may promote binding of incoming precursor proteins to the intermembrane space domain of Tom22p during translocation [*Saccharomyces cerevisiae*] | CK | | |
| 1102 | 73042 | 0 | 88 | ref|NP_014450.1|Pop2p [*Saccharomyces cerevisiae*) | SS | | |
| 1103 | 73067 | 0 | 100 | ref|NP_010301.1|Probable membrane protein with three predicted transmembrane domains; homologous to Ybr042cp, similar to *C. elegans* F55A11.5 and maize 1-acyl-glycerol-3-phosphate acyltransferase; null exhibits no apparent phenotype [*Saccharomyces cerevisiae*] | CS | | |
| 1104 | 73148 | 0 | 100 | emb|CAA56013.1|A-509 protein [*Saccharomyces cerevisiae*) | CS | | |
| 1105 | 72933 | 0 | 94 | ref|NP_010632.1|Hxt3p [*Saccharomyces cerevisiae*] | LN | | |
| 1106 | 77723 | 0 | 90 | ref|NP_012321.1|Hxt8p [*Saccharomyces cerevisiae*] | CK | CS | |
| 1107 | 73048 | 0 | 93 | ref|NP_010331.1|Amino acid permease involved in the uptake of cysteine, leucine, isoleucine and valine [*Saccharomyces cerevisiae*] | CS | | |
| 1108 | 10616 | 0 | 100 | ref|NP_194906.1|MGD1 (MONOGALACTOSYLDIACYLGLYCEROL SYNTHASE 1); 1,2-diacylglycerol 3-beta-galactosyltransferase [*Arabidopsis thaliana*] | LN | | |

TABLE 3-continued

| PEP Seq ID No. | Construct ID | E-value | % id | Annotation Description | Trait | | |
|---|---|---|---|---|---|---|---|
| 1109 | 72923 | 0 | 98 | ref|NP_116600.1|Agp3p [*Saccharomyces cerevisiae*] | SP | | |
| 1110 | 78501 | 0 | 100 | gb|AAD32292.1|putative protein kinase [*Arabidopsis thaliana*] | SP | | |
| 1111 | 78371 | 0 | 94 | gb|AAF27112.1|AC011809_21Putative protein kinase [*Arabidopsis thaliana*] | LL | | |
| 1112 | 74332 | 1.00E−174 | 95 | ref|NP_178581.1|ATP binding/kinase/protein kinase/protein serine/threonine kinase/protein-tyrosine kinase [*Arabidopsis thaliana*] | LL | | |
| 1113 | 74738 | 0 | 94 | ref|NP_850311.1|ATP binding/kinase/protein kinase/protein serine/threonine kinase/protein-tyrosine kinase [*Arabidopsis thaliana*] | SS | LN | |
| 1114 | 75225 | 0 | 100 | ref|NP_849998.1|ATP binding/kinase/protein kinase/protein serine/threonine kinase/protein-tyrosine kinase [*Arabidopsis thaliana*] | CS | | |
| 1115 | 11149 | 1.00E−110 | 91 | ref|NP_568067.1|FK506 binding/peptidyl-prolyl cis-trans isomerase [*Arabidopsis thaliana*] | DS | | |
| 1116 | 74739 | 0 | 87 | ref|NP_564844.1|ATP binding/protein kinase [*Arabidopsis thaliana*] | CS | | |
| 1117 | 74748 | 1.00E−172 | 92 | ref|NP_179308.1[ATP binding/kinase/protein kinase/protein serine/threonine kinase/protein-tyrosine kinase [*Arabidopsis thaliana*] | LL | | |
| 1118 | 78113 | 0 | 100 | ref|NP_198610.1|oxidoreductase/zinc ion binding [*Arabidopsis thaliana*] | PEG | | |
| 1119 | 75233 | 0 | 96 | ref|NP_851257.1|oxidoreductase/zinc ion binding [*Arabidopsis thaliana*] | CS | | |
| 1120 | 77311 | 0 | 83 | ref|NP_850553.1|ATP binding/nucleoside-triphosphatase/ nucleotide binding [*Arabidopsis thaliana*] | LN | | |
| 1121 | 77008 | 0 | 89 | ref|NP_177460.2|ATP binding/ATP-dependent peptidase/ nucleoside-triphosphatase/nucleotide binding/serine-type endopeptidase [*Arabidopsis thaliana*] | CS | | |
| 1122 | 77321 | 0 | 98 | ref|NP_565299.1|ATP binding/ATP-dependent helicase/DNA binding/nucleoside-triphosphatase/nucleotide binding [*Arabidopsis thaliana*] | CS | | |
| 1123 | 76214 | 0 | 100 | ref|NP_564533.1|unknown protein [*Arabidopsis thaliana*] | DS | | |
| 1124 | 75238 | 0 | 96 | ref|NP_566361.1|disulfide oxidoreductase/oxidoreductase [*Arabidopsis thaliana*] | PEG | | |
| 1125 | 76118 | 0 | 92 | ref|NP_568125.1|disulfide oxidoreductase/oxidoreductase [*Arabidopsis thaliana*] | PP | HS | |
| 1126 | 75243 | 0 | 91 | ref|NP_567074.2|ATP binding/kinase/protein kinase/protein serine/threonine kinase/protein-tyrosine kinase [*Arabidopsis thaliana*] | CS | | |
| 1127 | 72602 | 0 | 91 | ref|NP_178198.1|NRAMP1; manganese ion transporter/metal ion transporter [*Arabidopsis thaliana*] | LN | | |
| 1128 | 75810 | 0 | 100 | gb|ABG54332.1|double HA-tagged mitogen activated protein kinase 5 [synthetic construct] | SS | | |
| 1129 | 75094 | 0 | 89 | ref|NP_199951.1|unknown protein [*Arabidopsis thaliana*] | CS | | |
| 1130 | 75818 | 1.00E−150 | 91 | ref|NP_566411.2|unknown protein [*Arabidopsis thaliana*] | CS | | |
| 1131 | 75248 | 0 | 88 | ref|NP_568685.1|RNA binding/nucleic acid binding [*Arabidopsis thaliana*] | LL | | |
| 1132 | 74605 | 6.00E−60 | 86 | ref|NP_200911.1|RNA binding/nucleic acid binding [*Arabidopsis thaliana*] | LL | | |
| 1133 | 75252 | 0 | 97 | ref|NP_567801.1|NADH dehydrogenase/disulfide oxidoreductase [*Arabidopsis thaliana*] | LL | | |
| 1134 | 10620 | 2.00E−56 | 77 | ref|NP_175633.1|unknown protein [*Arabidopsis thaliana*] | LN | | |
| 1135 | 74611 | 4.00E−57 | 63 | ref|NP_683304.1|unknown protein [*Arabidopsis thaliana*] | LL | LN | |
| 1136 | 11152 | 0 | 91 | ref|NP_199220.1|CAD1 (CADMIUM SENSITIVE 1) [*Arabidopsis thaliana*] | LL | | |
| 1137 | 76610 | 0 | 100 | ref|NP_176261.1|ATRPAC43: DNA binding/DNA-directed RNA polymerase [*Arabidopsis thaliana*] | CS | | |
| 1138 | 70243 | 1.00E−107 | 100 | ref|NP_177128.1|ATHVA22C [*Arabidopsis thaliana*] | SS | | |
| 1139 | 74371 | 1.00E−170 | 100 | ref|NP_177541.1|strictosidine synthase [*Arabidopsis thaliana*] | LN | | |
| 1140 | 74373 | 1.00E−100 | 93 | ref|NP_177712.1|ATROP4 (RHO-LIKE GTP BINDING PROTEIN 4); GTP binding [*Arabidopsis thaliana*] | CS | SS | LN |
| 1141 | 74615 | 1.00E−177 | 87 | ref|NP_565394.1|nickel ion transporter [*Arabidopsis thaliana*] | SS | | |
| 1142 | 74620 | 6.00E−77 | 100 | ref|NP_188045.1|unknown protein [*Arabidopsis thaliana*] | LN | | |
| 1143 | 74626 | 5.00E−93 | 88 | ref|NP_566635.1|unknown protein [*Arabidopsis thaliana*] | LL | | |
| 1144 | 10622 | 1.00E−147 | 100 | ref|NP_001031481.1|UREG; metal ion binding/nickel ion binding/ nucleotide binding [*Arabidopsis thaliana*] | LN | | |
| 1145 | 74636 | 2.00E−89 | 94 | gb|AAO19647.1|CAXIP1 protein [*Arabidopsis thaliana*] | LL | | |
| 1146 | 74656 | 1.00E−107 | 93 | ref|NP_195699.1|GTP binding [*Arabidopsis thaliana*] | CS | | |
| 1147 | 74658 | 1.00E−115 | 100 | ref|NP_195709.1|ATGB3 (GTP-BINDING PROTEIN 3); GTP binding [*Arabidopsis thaliana*] | HS | | |
| 1148 | 74659 | 4.00E−99 | 88 | ref|NP_568121.1|ATRAB ALPHA; GTP binding [*Arabidopsis thaliana*] | CS | | |
| 1149 | 74673 | 0 | 92 | gb|AAL24269.1|AT5g51550/K17N15_10 [*Arabidopsis thaliana*] | SS | | |
| 1150 | 13518 | 0 | 94 | ref|NP_191100.1|ATP binding/methionine-tRNA ligase/tRNA ligase [*Arabidopsis thaliana*] | DS | | |

TABLE 3-continued

| PEP Seq ID No. | Construct ID | Annotation | | | Trait | |
|---|---|---|---|---|---|---|
| | | E-value | % id | Description | | |
| 1150 | 70824 | 0 | 94 | ref|NP_191100.1|ATP binding/methionine-tRNA ligase/tRNA ligase [*Arabidopsis thaliana*] | CK | |
| 1151 | 75267 | 0 | 90 | ref|NP_200758.1|unknown protein [*Arabidopsis thaliana*] | LL | |
| 1152 | 75283 | 0 | 93 | ref|NP_201300.1|unknown protein [*Arabidopsis thaliana*] | LN | |
| 1153 | 13805 | 0 | 94 | ref|NP_186764.1|PTB (POLYPYRIMIDINE TRACT-BINDING); RNA binding/nucleic acid binding [*Arabidopsis thaliana*] | LN | |
| 1154 | 76221 | 0 | 97 | ref|NP_187191.2|carbohydrate transporter/sugar porter [*Arabidopsis thaliana*] | SP | PP |
| 1155 | 76226 | 0 | 93 | ref|NP_187247.1|carbohydrate transporter/sugar porter [*Arabidopsis thaliana*] | DS | |
| 1156 | 76222 | 0 | 95 | ref|NP_188627.1|STP4 (SUGAR TRANSPORTER); carbohydrate transporter/sugar porter [*Arabidopsis thaliana*] | LL | |
| 1157 | 76611 | 0 | 97 | ref|NP_190157.2|transporter [*Arabidopsis thaliana*] | LL | |
| 1158 | 76228 | 0 | 92 | ref|NP_197718.1|carbohydrate transporter/sugar porter [*Arabidopsis thaliana*] | LL | |
| 1159 | 76435 | 0 | 93 | ref|NP_175449.1|carbohydrate transporter/sugar porter [*Arabidopsis thaliana*] | LL | |
| 1160 | 76436 | 0 | 91 | ref|NP_178054.1|carbohydrate transporter/sugar porter [*Arabidopsis thaliana*] | DS | |
| 1161 | 78743 | 0 | 90 | ref|NP_179438.1|carbohydrate transporter/sugar porter [*Arabidopsis thaliana*] | LN | |
| 1162 | 75814 | 0 | 91 | ref|NP_201166.1|HEN3 (HUA ENHANCER 3); ATP binding/kinase/kinase/protein serine/threonine kinase/protein-tyrosine kinase [*Arabidopsis thaliana*] | CS | PP |
| 1163 | 77016 | 0 | 93 | ref|NP_195802.1|ATSR1 (SERINE/THREONINE PROTEIN KINASE 1); ATP binding/kinase/protein kinase/protein serine/threonine kinase/protein-tyrosine kinase [*Arabidopsis thaliana*] | CS | |
| 1164 | 78734 | 0 | 98 | ref|NP_199394.1|CIPK20 (CBL-INTERACTING PROTEIN KINASE 20); kinase [*Arabidopsis thaliana*] | PEG | |
| 1165 | 75274 | 0 | 100 | ref|NP_200709.2|ATP binding/protein kinase/protein serine/threonine kinase/protein-tyrosine kinase [*Arabidopsis thaliana*] | CS | |
| 1166 | 76233 | 0 | 89 | ref|NP_197154.2|ATP binding/kinase/protein kinase/protein serine/threonine kinase/protein-tyrosine kinase [*Arabidopsis thaliana*] | SP | |
| 1167 | 74674 | 0 | 100 | ref|NP_191331.2|ATP binding/kinase/protein kinase/protein serine/threonine kinase/protein-tyrosine kinase [*Arabidopsis thaliana*] | PEG | |
| 1168 | 70225 | 0 | 94 | ref|NP_187668.1|CYP77A6; heme binding/iron ion binding/monooxygenase/oxygen binding [*Arabidopsis thaliana*] | CS | |
| 1169 | 75291 | 0 | 98 | ref|NP_201303.1|unknown protein [*Arabidopsis thaliana*] dbj|BAA97310.1| unnamed protein product [*Arabidopsis thaliana*] | CS | |
| 1170 | 75292 | 0 | 91 | gb|AAL57662.1|At1g72120/F28P5_2 [*Arabidopsis thaliana*] | SS | |
| 1171 | 78607 | 0 | 96 | gb|AAC39370.1|trehalose-6-phosphate phosphatase [*Arabidopsis thaliana*] | LN | |
| 1172 | 78367 | 1.00E−172 | 100 | ref|NP_186907.1|STE1 (STEROL 1); C-5 sterol desaturase [*Arabidopsis thaliana*] | CK | DS |
| 1173 | 76528 | 1.00E−165 | 93 | gb|AAM64961.1|putative C-4 sterol methyl oxidase [*Arabidopsis thaliana*] | DS | LL |
| 1174 | 77319 | 0 | 77 | ref|NP_568416.1|protein binding [*Arabidopsis thaliana*] | CS | |
| 1175 | 74677 | 2.00E−73 | 87 | gb|AAM67086.1|unknown [*Arabidopsis thaliana*] | SS | |
| 1176 | 78109 | 1.00E−149 | 87 | ref|NP_182332.1|PAC (PALE CRESS) [*Arabidopsis thaliana*] | CS | |
| 1177 | 77725 | 0 | 100 | ref|NP_391274.1|glyceraldehyde-3-phosphate dehydrogenase [*Bacillus subtilis* subsp. *subtilis* str. 168] | HS | |
| 1178 | 73437 | 0 | 99 | ref|YP_517842.1|glyceraldehyde 3-phosphate dehydrogenase [*Desulfitobacterium hafniense* Y51] | SS | |
| 1179 | 73450 | 0 | 100 | ref|YP_350062.1|hypothetical protein Pfl_4334 [*Pseudomonas fluorescens* PfO-1] | CS | |
| 1180 | 73416 | 0 | 100 | ref|NP_443010.1|glucose-1-phosphate adenylyltransferase [*Synechocystis* sp. PCC 6803] | HS | |
| 1181 | 73452 | 0 | 97 | ref|NP_388496.1|sorbitol dehydrogenase [*Bacillus subtilis* subsp. *subtilis* str. 168] | SS | LN |
| 1182 | 73453 | 0 | 95 | ref|NP_414890.1|alcohol dehydrogenase class III/glutathione-dependent formaldehyde dehydrogenase [*Escherichia coli* K12] | CK | |
| 1183 | 73454 | 0 | 95 | ref|ZP_00110545.1|COG0837: Glucokinase [*Nostoc punctiforme* PCC 73102] | PP | SS |
| 1184 | 73491 | 0 | 91 | ref|NP_791383.1|alcohol dehydrogenase, class III [*Pseudomonas syringae* pv. tomato str. DC3000] | CS | |
| 1185 | 73445 | 1.00E−176 | 83 | ref|ZP_00709024.1|COG0473: Isocitrate/isopropylmalate dehydrogenase [*Escherichia coli* B171] | SP | |
| 1186 | 73469 | 1.00E−131 | 65 | ref|YP_958498.1|Alcohol dehydrogenase GroES domain protein [*Marinobacter aquaeolei* VT8] | CS | |

TABLE 3-continued

| PEP Seq ID No. | Construct ID | E-value | % id | Annotation Description | Trait | | |
|---|---|---|---|---|---|---|---|
| 1187 | 73434 | 0 | 94 | ref|NP_012342.1|Putative protein of unknown function, predicted to encode a triose phosphate transporter subfamily member based on phylogenetic analysis; similar to YOR307C/SLY41; deletion mutant has a respiratory growth defect [*Saccharomyces cerevisiae*] | CS | | |
| 1188 | 73471 | 0 | 93 | ref|NP_391658.1|pyrroline-5 carboxylate dehydrogenase [*Bacillus subtilis* subsp. *subtilis* str. 168] | CS | | |
| 1189 | 73436 | 0 | 91 | ref|YP_355035.1|Aldehyde dehydrogenase family protein [*Rhodobacter sphaeroides* 2.4.1] | SP | SS | |
| 1190 | 73525 | 0 | 95 | ref|NP_790108.1|succinate-semialdehyde dehydrogenase [*Pseudomonas syringae* pv. tomato str. DC3000] | PP | | |
| 1191 | 73514 | 1.00E-174 | 100 | ref|NP_242723.1|fructokinase [*Bacillus halodurans* C-125] dbj|BAB05576.1|fructokinase [*Bacillus halodurans* C-125] | SP | | |
| 1192 | 73551 | 1.00E-171 | 95 | ref|YP_690914.1|6-phosphofructokinase I [*Shigella flexneri* 5 str. 8401] | LL | | |
| 1193 | 73519 | 0 | 95 | ref|NP_414696.1|glutamate-1-semialdehyde aminotransferase [*Escherichia coli* K12] | CS | | |
| 1194 | 73543 | 0 | 99 | ref|NP_389628.1|glutamine synthetase [*Bacillus subtilis* subsp. *subtilis* str. 168] | CS | | |
| 1195 | 73567 | 1.00E-159 | 92 | ref|NP_415018.1|predicted glutaminase [*Escherichia coli* K12] | CS | DS | |
| 1196 | 73579 | 0 | 96 | ref|NP_792487.1|succinate-semialdehyde dehydrogenase [*Pseudomonas syringae* pv. tomato str. DC3000] | PP | | |
| 1197 | 73556 | 0 | 97 | ref|NP_790150.1|succinate-semialdehyde dehydrogenase [*Pseudomonas syringae* pv. tomato str. DC3000] | SP | | |
| 1198 | 73545 | 0 | 99 | ref|NP_792858.1|aldehyde dehydrogenase family protein [*Pseudomonas syringae* pv. tomato str. DC3000] | PEG | | |
| 1199 | 73511 | 1.00E-161 | 66 | ref|YP_546017.1|Phosphopyruvate hydratase [*Methylobacillus flagellatus* KT] | LL | | |
| 1200 | 74138 | 0 | 97 | ref|NP_415933.1|aldehyde dehydrogenase A, NAD-linked [*Escherichia coli* K12] | PEG | | |
| 1201 | 74186 | 0 | 100 | ref|NP_416275.1|glutamate dehydrogenase [*Escherichia coli* K12] | CS | | |
| 1202 | 74163 | 0 | 95 | ref|NP_391649.1|hypothetical protein BSU37690 [*Bacillus subtilis* subsp. *subtilis* str. 168] | PP | | |
| 1203 | 74175 | 0 | 96 | ref|NP_244424.1|phosphoglyceromutase [*Bacillus halodurans* C-125] | LN | | |
| 1204 | 74176 | 0 | 99 | ref|YP_517842.1|glyceraldehyde 3-phosphate dehydrogenase [*Desulfitobacterium hafniense* Y51] | LN | | |
| 1205 | 74141 | 0 | 99 | ref|YP_543116.1|2,3-bisphosphoglycerate-independent phosphoglycerate mutase [*Escherichia coli* UTI89] | LN | | |
| 1206 | 74178 | 0 | 98 | ref|NP_387154.1|dihydrolipoamide dehydrogenase [*Sinorhizobium meliloti* 1021] | LN | | |
| 1207 | 74179 | 0 | 83 | ref|NP_441936.1|dihydrolipoamide acetyltransferase [*Synechocystis* sp. PCC 6803] | CS | | |
| 1208 | 74110 | 0 | 92 | ref|NP_930835.1|pyruvate dehydrogenase E1 component [*Photorhabdus luminescens* subsp. *laumondii* TT01] | SP | | |
| 1209 | 74170 | 0 | 98 | ref|ZP_00106110.1|COG0021: Transketolase [*Nostoc punctiforme* PCC 73102] | CS | | |
| 1210 | 74123 | 1.00E-174 | 100 | ref|NP_014585.1|Gpm3p [*Saccharomyces cerevisiae*] | LL | | |
| 1211 | 74159 | 1.00E-71 | 88 | ref|NP_440036.1|hypothetical protein slr0250 [*Synechocystis* sp. PCC 6803] | PP | | |
| 1212 | 10633 | 1.00E-150 | 81 | ref|NP_850491.1|CA1 (CARBONIC ANHYDRASE 1); carbonate dehydratase/zinc ion binding [*Arabidopsis thaliana*] | LN | | |
| 1213 | 74172 | 2.00E-62 | 99 | ref|NP_440674.1|cytochrome c553 [*Synechocystis* sp. PCC 6803] | SS | | |
| 1214 | 74184 | 7.00E-47 | 98 | ref|NP_440475.1|hypothetical protein ssr1698 [*Synechocystis* sp. PCC 6803] | CS | PP | SS |
| 1215 | 74582 | 1.00E-164 | 99 | ref|NP_440558.1|aspartoacylase [*Synechocystis* sp. PCC 6803] | CS | | |
| 1216 | 74584 | 0 | 99 | ref|NP_009780.1|E1 beta subunit of the pyruvate dehydrogenase (PDH) complex, which is an evolutionarily-conserved multi-protein complex found in mitochondria [*Saccharomyces cerevisiae*] | CS | | |
| 1217 | 74687 | 1.00E-142 | 99 | ref|NP_385544.1|PROBABLE TRIOSEPHOSPHATE ISOMERASE PROTEIN [*Sinorhizobium meliloti* 1021] | LL | | |
| 1218 | 74461 | 3.00E-70 | 99 | ref|NP_638210.1|hypothetical protein XCC2862 [*Xanthomonas campestris* pv. *campestris* str. ATCC 33913] | SS | | |
| 1219 | 74403 | 0 | 98 | ref|NP_356568.1|glucose-1-phosphate adenylyltransferase [*Agrobacterium tumefaciens* str. C58] | LL | | |
| 1220 | 74430 | 1.00E-178 | 99 | ref|NP_289016.1|transaldolase [*Escherichia coli* O157:H7 EDL933] | SS | | |
| 1221 | 74443 | 0 | 97 | ref|NP_391271.1|phosphoglyceromutase [*Bacillus subtilis* subsp. *subtilis* str. 168] | LL | | |
| 1222 | 74457 | 0 | 100 | ref|YP_350062.1|hypothetical protein Pfl_4334 [*Pseudomonas fluorescens* PfO-1] | LL | | |
| 1223 | 74434 | 0 | 99 | ref|NP_790208.1|glutamine synthetase, type I [*Pseudomonas syringae* pv. tomato str. DC3000] | CS | | |
| 1224 | 74447 | 0 | 91 | ref|NP_385430.1|PUTATIVE AMINOTRANSFERASE PROTEIN [*Sinorhizobium meliloti* 1021] | LN | | |

TABLE 3-continued

| PEP Seq ID No. | Construct ID | E-value | % id | Description | Trait | |
|---|---|---|---|---|---|---|
| 1225 | 74495 | 0 | 94 | ref\|NP_386611.1\|PUTATIVE ALDEHYDE DEHYDROGENASE PROTEIN [*Sinorhizobium meliloti* 1021] | PEG | |
| 1226 | 74513 | 1.00E−115 | 87 | ref\|YP_052359.1\|triosephosphate isomerase [*Erwinia carotovora* subsp. *atroseptica* SCRI1043] | LL | |
| 1227 | 74514 | 0 | 100 | ref\|NP_242374.1\|asparagine synthetase [*Bacillus halodurans* C-125] | PEG | |
| 1228 | 74515 | 0 | 98 | ref\|YP_350541.1\|glucose-6-phosphate isomerase [*Pseudomonas fluorescens* PfO-1] | CS | LL |
| 1229 | 74552 | 0 | 98 | ref\|NP_390871.1\|pullulanase [*Bacillus subtilis* subsp. *subtilis* str. 168] | PEG | |
| 1230 | 74529 | 0 | 96 | ref\|NP_418330.1\|formate dehydrogenase-O, large subunit [*Escherichia coli* K12] | CS | |
| 1231 | 74519 | 0 | 86 | ret\|NP_931552. 1\|glucose-6-phosphate isomerase [*Photorhabdus luminescens* subsp. *laumondii* TT01] | CS | |
| 1232 | 10638 | 1.00E−70 | 58 | ref\|NP_189273.1\|ARRZ-1A; RNA binding/nucleotide binding [*Arabidopsis thaliana*] | LN | |
| 1233 | 76547 | 5.00E−89 | 89 | ref\|NP_190024.1\|unknown protein [*Arabidopsis thaliana*] | PP | |
| 1234 | 76548 | 0 | 94 | ref\|NP_190153.1\|ATP binding/kinase/protein kinase/protein serine/threonine kinase/protein-tyrosine kinase [*Arabidopsis thaliana*] | SS | |
| 1235 | 14703 | 1.00E−56 | 87 | gb\|ABK28584.1\|unknown [*Arabidopsis thaliana*] | LN | |
| 1236 | 75856 | 8.00E−18 | 42 | ref\|NP_190667.2\|unknown protein [*Arabidopsis thaliana*] | CS | |
| 1237 | 76642 | 0 | 92 | ref\|NP_563988.1\|metal ion transporter [*Arabidopsis thaliana*] | LL | |
| 1238 | 77522 | 0 | 83 | ref\|NP_190912.1\|unknown protein [*Arabidopsis thaliana*] | CK | |
| 1239 | 77516 | 0 | 90 | ref\|NP_191095.1\|unknown protein [*Arabidopsis thaliana*] | CS | |
| 1240 | 75864 | 3.00E−63 | 100 | ref\|NP_191376.1\|ATBS14A; protein transporter [*Arabidopsis thaliana*] | LL | |
| 1241 | 76275 | 1.00E−157 | 84 | ref\|NP_191386.1\|unknown protein [*Arabidopsis thaliana*] | CS | |
| 1242 | 76276 | 0 | 100 | ref\|NP_191408.1\|phosphoric ester hydrolase [*Arabidopsis thaliana*] | SP | |
| 1243 | 75869 | 1.00E−85 | 100 | ref\|NP_192145.1\|unknown protein [*Arabidopsis thaliana*] | DS | |
| 1244 | 76558 | 2.00E−77 | 73 | ref\|NP_192181.2\|unknown protein [*Arabidopsis thaliana*] | PP | |
| 1245 | 75876 | 1.00E−101 | 100 | pdb\|1FSI\|AChain A, Crystal Structure Of Cyclic Nucleotide Phosphodiesterase Of Appr>p From *Arabidopsis Thaliana* | HS | |
| 1246 | 75878 | 2.00E−82 | 78 | emb\|CAA20466.1\|putative protein [*Arabidopsis thaliana*] | CS | |
| 1247 | 75881 | 7.00E−91 | 89 | ref\|NP_194766.1\|protein binding/ubiquitin-protein ligase/zinc ion binding [*Arabidopsis thaliana*] | LL | |
| 1248 | 77525 | 0 | 95 | ref\|NP_195212.1\|beta-fructofuranosidase [*Arabidopsis thaliana*] | CS | |
| 1249 | 76454 | 1.00E−176 | 88 | ref\|NP_196814.1\|unknown protein [*Arabidopsis thaliana*] | LL | |
| 1250 | 75895 | 2.00E−27 | 78 | ref\|NP_197316.1\|unknown protein [*Arabidopsis thaliana*] | LL | |
| 1251 | 78377 | 1.00E−154 | 85 | ref\|NP_197406.1\|catalytic [*Arabidopsis thaliana*] | HS | |
| 1252 | 75896 | 7.00E−70 | 100 | ref\|NP_197550.1\|arsenate reductase (glutaredoxin)/electron transporter/thiol-disulfide exchange intermediate [*Arabidopsis thaliana*] | CS | |
| 1253 | 77527 | 0 | 85 | ref\|NP_850871.1\|unknown protein [*Arabidopsis thaliana*] | CS | |
| 1254 | 78984 | 0 | 100 | ref\|NP_198084.1\|catalytic [*Arabidopsis thaliana*] | SS | |
| 1255 | 77528 | 0 | 92 | ref\|NP_568564.1\|unknown protein [*Arabidopsis thaliana*] | SS | |
| 1256 | 76752 | 0 | 84 | ref\|NP_199429.1\|unknown protein [*Arabidopsis thaliana*] | LL | |
| 1257 | 78106 | 0 | 100 | gb\|ABK06440.1\|flag-tagged protein kinase domain of putative mitogen-activated protein kinase kinase kinase [synthetic construct] | SS | |
| 1258 | 11720 | 0 | 89 | ref\|NP_565622.1\|RCY1; cyclin-dependent protein kinase regulator [*Arabidopsis thaliana*] | LN | |
| 1259 | 78740 | 1.00E−121 | 75 | ref\|NP_200152.1\|unknown protein [*Arabidopsis thaliana*] | PP | |
| 1260 | 76157 | 1.00E−154 | 88 | ref\|NP_001032094.1\|carrier/steroid binding [*Arabidopsis thaliana*] | LN | |
| 1261 | 77530 | 0 | 83 | ref\|NP_201241.1\|heat shock protein binding/unfolded protein binding [*Arabidopsis thaliana*] | SP | CS |
| 1262 | 76755 | 0 | 87 | gb\|AAM14093.1\|putative bystin [*Arabidopsis thaliana*] | PEG | |
| 1263 | 76166 | 4.00E−99 | 82 | ref\|NP_171940.1\|RIC3 (ROP-INTERACTIVE CRIB MOTIF-CONTAINING PROTEIN 3) [*Arabidopsis thaliana*] | PEG | |
| 1264 | 76756 | 0 | 90 | ref\|NP_171927.1\|ERS2 (ETHYLENE RESPONSE SENSOR 2); receptor [*Arabidopsis thaliana*] | LN | |
| 1265 | 78990 | 0 | 100 | ref\|NP_175364.1\|oxidoreductase, acting on paired donors, with incorporation or reduction of molecular oxygen, 2-oxoglutarate as one donor, and incorporation of one atom each of oxygen into both donors [*Arabidopsis thaliana*] | CS | |
| 1266 | 78460 | 9.00E−97 | 75 | ref\|NP_175584.1\|unknown protein [*Arabidopsis thaliana*] | LN | |
| 1267 | 11022 | 0 | 95 | ref\|NP_192078.1\|PPOX; protoporphyrinogen oxidase [*Arabidopsis thaliana*] | LN | |
| 1268 | 77533 | 0 | 96 | ref\|NP_177399.1\|ATP binding/phenylalanine-tRNA ligase [*Arabidopsis thaliana*] | PEG | |
| 1269 | 76572 | 0 | 100 | ref\|NP_177988.1\|gamma-glutamyl hydrolase [*Arabidopsis thaliana*] | PEG | |
| 1270 | 76186 | 7.00E−48 | 84 | ref\|NP_172210.1\|unknown protein [*Arabidopsis thaliana*] | LL | |
| 1271 | 76190 | 7.00E−35 | 63 | ref\|NP_565499.1\|unknown protein [*Arabidopsis thaliana*] | LL | |

TABLE 3-continued

| PEP Seq ID No. | Construct ID | E-value | % id | Description | Trait | | |
|---|---|---|---|---|---|---|---|
| 1272 | 77071 | 1.00E−160 | 96 | ref|NP_565626.1|unknown protein [*Arabidopsis thaliana*] | SP | | |
| 1273 | 76194 | 3.00E−94 | 79 | ref|NP_565716.1|unknown protein [*Arabidopsis thaliana*] | LN | | |
| 1274 | 78112 | 1.00E−83 | 91 | ref|NP_181610.1|RNA binding/translation initiation factor [*Arabidopsis thaliana*] | CS | | |
| 1275 | 74802 | 0 | 80 | gb|AAO171B3.1|Orf17 [*Photorhabdus luminescens*] | SS | | |
| 1276 | 74851 | 1.00E−163 | 100 | ref|NP_014366.1|Siw14p [*Saccharomyces cerevisiae*] | CK | | |
| 1277 | 74864 | 6.00E−61 | 95 | ref|NP_014486.1|Hxl11p [*Saccharomyces cerevisiae*] | CK | | |
| 1278 | 74805 | 0 | 97 | ref|NP_015359.1|Actin-related protein involved in transcriptional regulation; subunit of the chromatin remodeling Snf/Swi complex [*Saccharomyces cerevisiae*] | HS | | |
| 1279 | 74842 | 2.00E−61 | 65 | ref|NP_001044880.1|Os01g0862200 [*Oryza sativa* (japonica cultivar-group)] | SS | PEG | |
| 1280 | 78231 | 0 | 66 | gb|EAY94228.1|hypothetical protein OsI_01546.1 [*Oryza sativa* (indica cultivar-group)] | LL | | |
| 1281 | 74867 | 1.00E−154 | 65 | gb|EAZ43471.1|hypothetical protein OsJ_026954 [*Oryza sativa* (japonica cultivar-group)] | SS | | |
| 1282 | 74820 | 1.00E−136 | 48 | gb|EAY97430.1|hypothetical protein OsI_018663 [*Oryza sativa* (indica cultivar-group)] | LN | | |
| 1283 | 74868 | 1.00E−101 | 94 | ref|NP_001046499.1|Os02g0265400 [*Oryza sativa* (japonica cultivar-group)] | PP | | |
| 1284 | 74809 | 1.00E−122 | 80 | gb|EAZ13333.1|hypothetical protein OsJ_003158 [*Oryza sativa* (japonica cultivar-group)] | LN | | |
| 1285 | 74845 | 7.00E−43 | 83 | ref|NP_001050930.1|Os03g0685900 [*Oryza sativa* (japonica cultivar-group)] | CS | PP | |
| 1286 | 74870 | 6.00E−91 | 48 | sp|Q5XF85|ATL4J_ARATHRING-H2 finger protein ATL4J precursor emb|CAB43903.1|putative protein [*Arabidopsis thaliana*] | LN | | |
| 1287 | 74859 | 1.00E−109 | 55 | gb|ABD32420.1|Zinc finger, RING-type [*Medicago truncatula*] | CS | | |
| 1288 | 74985 | 3.00E−75 | 94 | ref|NP_001045113.1|Os01g0901800 [*Oryza sativa* (japonica cultivar-group)] | PEG | | |
| 1289 | 74950 | 1.00E−159 | 75 | gb|EAZ00193.1|hypothetical protein OsI_021425 [*Oryza sativa* (indica cultivar-group)] | LN | | |
| 1290 | 74962 | 3.00E−89 | 91 | gb|ABB99414.1|FT-like protein [*Hordeum vulgare* subsp. *vulgare*] | CS | | |
| 1291 | 74939 | 5.00E−42 | 65 | ref|NP_563746.1|transcription factor [*Arabidopsis thaliana*] | LL | | |
| 1292 | 74928 | 1.00E−134 | 87 | ref|NP_001044154.1|Os01g0732200 [*Oryza sativa* (japonica cultivar-group)] | SP | CS | |
| 1293 | 74905 | 0 | 87 | ref|NP_927600.1|glutamine synthetase (*Photorhabdus luminescens* subsp. *laumondii* TTO1) | SP | | |
| 1294 | 74917 | 0 | 99 | ref|YP_346085.1|Inositol phosphatase/fructose-1,6-bisphosphatase [*Pseudomonas fluorescens* PfO-1] | CS | | |
| 1295 | 74989 | 4.00E−69 | 89 | ref|NP_439999.1|hypothetical protein slr0732 [*Synechocystis* sp. PCC 6803] | CS | | |
| 1296 | 74990 | 1.00E−92 | 95 | ref|NP_441647.1|hypothetical protein slr1160 [*Synechocystis* sp. PCC 6803] | LL | | |
| 1297 | 74955 | 1.00E−110 | 99 | ref|NP_441787.1|hypothetical protein slr1649 [*Synechocystis* sp. PCC 6803] | CS | PP | |
| 1298 | 74932 | 1.00E−123 | 83 | ref|NP_441624.1|hypothetical protein slr1530 [*Synechocystis* sp. PCC 6803] | CS | | |
| 1299 | 74944 | 8.00E−76 | 99 | ref|NP_440928.1|hypothetical protein sll0871 [*Synechocystis* sp. PCC 6803] | SS | | |
| 1300 | 74968 | 6.00E−76 | 99 | ref|NP_441307.1|hypothetical protein sll1979 [*Synechocystis* sp. PCC 6803] | CS | | |
| 1301 | 74957 | 1.00E−161 | 100 | ref|NP_440540.1|hypothetical protein slr1699 [*Synechocystis* sp. PCC 6-803] | LL | | |
| 1302 | 75374 | 0 | 72 | ref|NP_001067247.1|Os12g0610500 [*Oryza sativa* (japonica cultivar-group)] | CK | LN | |
| 1303 | 75386 | 1.00E−147 | 74 | emb|CAH67158.1|H0717B12.5 [*Oryza sativa* (indica cultivar-group)] | CS | | |
| 1304 | 77807 | 0 | 85 | ref|NP_001044268.1|Os01g0752700 [*Oryza sativa* (japonica cultivar-group)] | SP | | |
| 1305 | 75388 | 0 | 76 | gb|EAZ29806.1|hypothetical protein OsJ_013289 [*Oryza sativa* (japonica cultivar-group)] | SS | | |
| 1306 | 75365 | 1.00E−82 | 81 | ref|NP_001057701.1|Os06g0498800 [*Oryza sativa* (japonica cultivar-group)] | DS | LL | LN |
| 1307 | 75377 | 3.00E−81 | 77 | gb|EAZ24403.1|hypothetical protein OsJ_007886 [*Oryza sativa* (japonica cultivar-group)] | CK | | |
| 1308 | 75354 | 8.00E−77 | 82 | ref|NP_001062977.1|Os09g0360400 [*Oryza sativa* (japonica cultivar-group)] | LL | | |
| 1309 | 75331 | 1.00E−108 | 84 | ref|NP_001061046.1|Os08g0160000 [*Oryza sativa* (japonica cultivar-group)] | CS | | |
| 1310 | 75343 | 1.00E−122 | 59 | ref|NP_001053728.1|Os04g0594500 [*Oryza sativa* (japonica cultivar-group)] | CS | PEG | |
| 1311 | 77809 | 1.00E−27 | 75 | ref|NP_001059709.1|Os07g0498300 [*Oryza sativa* (japonica cultivar-group)] | LL | | |
| 1312 | 75332 | 1.00E−119 | 72 | dbj|BAD19345.1|2 coiled coil domains of eukaryotic origin (31.3 kD)-like protein [*Oryza sativa* (japonica cultivar-group)] | SP | | |

TABLE 3-continued

| PEP Seq ID No. | Construct ID | Annotation | | | Trait | |
|---|---|---|---|---|---|---|
| | | E-value | % id | Description | | |
| 1313 | 75344 | 1.00E−146 | 81 | gb|EAZ31718.1|hypothetical protein OsJ_015201 [*Oryza sativa* (japonica cultivar-group)] | PP | |
| 1314 | 75333 | 2.00E−78 | 58 | gb|EAZ32939.1|hypothetical protein OsJ_016422 [*Oryza sativa* (japonica cultivar-group)] | LL | |
| 1315 | 75393 | 1.00E−136 | 79 | gb|EAT82167.1|hypothetical protein SNOG_10773 [*Phaeosphaeria nodorum* SN15] | CS | |
| 1316 | 75335 | 2.00E−63 | 79 | ref|NP_001046956.1|Os02g0515600 [*Oryza sativa* (japonica cultivar-group)] | CS | |
| 1317 | 75462 | 1.00E−85 | 90 | dbj|BAD36027.1|putative calcineurin B subunit [*Oryza sativa* (japonica cultivar-group)] | CS | |
| 1318 | 75486 | 1.00E−139 | 89 | ref|NP_001050137.1|Os03g0355800 [*Oryza sativa* (japonica cultivar-group)] | HS | |
| 1319 | 75452 | 1.00E−61 | 91 | ref|NP_001059781.1|Os07g0516200 [*Oryza sativa* (japonica cultivar-group)] | CS | |
| 1320 | 75465 | 2.00E−82 | 29 | ref|NP_974032.1|unknown protein [*Arabidopsis thaliana*] | HS | |
| 1321 | 75489 | 1.00E−115 | 73 | gb|ABE-82748.1|CCT [*Medicago truncatula*] | PP | LN |
| 1322 | 75442 | 3.00E−51 | 51 | emb|CAG26903.1|ALY protein (*Nicotiana benthamiana*) | CS | |
| 1323 | 75466 | 1.00E−147 | 84 | ref|NP_001052646.1|Os04g0391900 [*Oryza sativa* (japonica cultivar-group)] | SP | CS |
| 1324 | 75479 | 1.00E−118 | 87 | ref|NP_001044439.1|Os01g0780800 [*Oryza sativa* (japonica cultivar group)] | LL | |
| 1325 | 75481 | 7.00E−35 | 87 | gb|ABE89387.1|Zinc finger, Tim10/DDP-type [*Medicago truncatula*] | CS | |
| 1326 | 78233 | 0 | 70 | gb|ABE91310.1|F20D23.20 protein - *Arabidopsis thaliana*-related [*Medicago truncatula*] | CK | CS |
| 1327 | 75539 | 2.00E−51 | 79 | ref|NP_564405.1|LOL1 (LSD ONE LIKE 1) [*Arabidopsis thaliana*] | LL | |
| 1328 | 11919 | 0 | 91 | ref|NP_565195.1|AVP2 [*Arabidopsis thaliana*] | PP | |
| 1329 | 75603 | 1.00E−162 | 64 | ref|NP_001067658.1|Os11g0265200 [*Oryza sativa* (japonica cultivar-group)] | LN | |
| 1330 | 75663 | 7.00E−87 | 70 | gb|AAV57783.1|unknown protein [*Oryza sativa* (japonica cultivar-group)] | SS | |
| 1331 | 75616 | 0 | 96 | ref|NP_194004.1|ATP binding/protein kinase/protein serine/threonine kinase/protein-tyrosine kinase [*Arabidopsis thaliana*] | CK | |
| 1332 | 75640 | 1.00E−153 | 81 | ref|NP_001043765.1|Os01g0658700 [*Oryza sativa* (japonica cultivar-group)] | LL | LN |
| 1333 | 75617 | 4.00E−40 | 88 | ref|NP_001054886.1|Os05g0154900 [*Oryza sativa* (japonica cultivar-group)] | SS | |
| 1334 | 75653 | 0 | 92 | ref|NP_568338.2|TOZ (TORMOZEMBRYO DEFECTIVE); nucteotide binding [*Arabidopsis thaliana*] | LN | |
| 1335 | 75665 | 2.00E−95 | 77 | gb|EAY76352.1|hypothetical protein OsI_004199 [*Oryza sativa* indica cultivar-group)] | SS | |
| 1336 | 75618 | 0 | 85 | ref|NP_178381.2|ATP binding/protein kinase/protein serine/threonine kinase [*Arabidopsis thaliana*] | HS | |
| 1337 | 78238 | 0 | 95 | ref|NP_172998.1|nucleotide binding [*Arabidopsis thaliana*] | DS | |
| 1338 | 75608 | 9.00E−72 | 70 | gb|EAZ21409.1|hypothetical protein OsJ_004892 [*Oryza sativa* (japonica cultivar-group)] | LL | |
| 1339 | 75633 | 5.00E−89 | 64 | ref|NP_001046704.1|Os02g0326000 [*Oryza sativa* (japonica cultivar-group)] | HS | |
| 1340 | 75761 | 5.00E−50 | 54 | ref|NP_174505.1|unknown protein [*Arabidopsis thaliana*] | PEG | |
| 1341 | 75785 | 1.00E−74 | 53 | gb|AAK40310.1|putative methyl-binding domain protein MBD111 [*Zea mays*] | CS | |
| 1342 | 75750 | 2.00E−47 | 45 | ref|NP_001042916.1|Os01g0328500 [*Oryza sativa* (japonica cultivar-group)] | PEG | |
| 1343 | 75716 | 0 | 96 | ref|NP_386374.1|PUTATIVE ALDEHYDE DEHYDROGENASE PROTEIN [*Sinorhizobium meliloti* 1021] | DS | LN |
| 1344 | 78129 | 0 | 98 | ref|NP_182096.1|unknown protein [*Arabidopsis thaliana*] | CK | |
| 1345 | 77539 | 1.00E−147 | 88 | ref|NP_187983.1|RNA binding/nucleic acid binding [*Arabidopsis thaliana*] | SP | |
| 1346 | 77540 | 0 | 86 | ref|NP_188270.1|calmodulin binding [*Arabidopsis thaliana*] | LN | |
| 1347 | 77542 | 1.00E−170 | 92 | ref|NP_172882.1|unknown protein [*Arabidopsis thaliana*] | SP | |
| 1348 | 77543 | 0 | 83 | ref|NP_189492.1|ATP binding/ATPase/nucleoside-triphosphatase/nucleotide binding [*Arabidopsis thaliana*] | LL | |
| 1349 | 77545 | 1.00E−141 | 100 | ref|NP_190275.1|unknown protein [*Arabidopsis thaliana*] | SS | |
| 1350 | 77550 | 1.00E−163 | 81 | ref|NP_173191.2|calmodulin binding [*Arabidopsis thaliana*] | SP | |
| 1351 | 77552 | 1.00E−104 | 89 | emb|CAB78029.1|putative protein [*Arabidopsis thaliana*] | CK | |
| 1352 | 77556 | 0 | 94 | ref|NP_173485.1|CYCB; 3; cyclin-dependent protein kinase regulator [*Arabidopsis thaliana*] | PP | SS |
| 1353 | 77559 | 1.00E−174 | 78 | ref|NP_196341.1|calmodulin binding [*Arabidopsis thaliana*] | CS | |
| 1354 | 77957 | 1.00E−168 | 97 | ref|NP_196955.1|unknown protein [*Arabidopsis thaliana*] | CK | |
| 1355 | 77565 | 1.00E−138 | 100 | gb|AAO00857.1|putative protein [*Arabidopsis thaliana*] | DS | LN |
| 1356 | 78508 | 0 | 97 | ref|NP_175058.1|ATP binding/ATPase/nucleoside-triphosphatase/nucleotide binding [*Arabidopsis thaliana*] | LL | LN |
| 1357 | 11748 | 1.00E−105 | 88 | ref|NP_200037.1|MSBP1 [*Arabidopsis thaliana*] | LN | |
| 1358 | 77920 | 0 | 89 | ref|NP_177325.2|RNA binding/nucleic acid binding [*Arabidopsis thaliana*] | CS | DS |

TABLE 3-continued

| PEP Seq ID No. | Construct ID | E-value | % id | Annotation Description | Trait | |
|---|---|---|---|---|---|---|
| 1359 | 77573 | 0 | 81 | ref|NP_177411.1|calmodulin binding [*Arabidopsis thaliana*] | LN | |
| 1360 | 77961 | 0 | 94 | gb|AAD25685.1|putative membrane transporter [*Arabidopsis thaliana*] | CS | |
| 1361 | 77922 | 0 | 100 | ref|NP_181978.1|unknown protein [*Arabidopsis thaliana*] | LL | |
| 1362 | 77337 | 1.00E−121 | 93 | ref|NP_186871.1|unknown protein [*Arabidopsis thaliana*] | PEG | |
| 1363 | 77924 | 4.00E−44 | 100 | ref|NP_566521.1|unknown protein [*Arabidopsis thaliana*] | CK | |
| 1364 | 77926 | 1.00E−136 | 100 | ref|NP_193032.1|catalytic [*Arabidopsis thaliana*] | SS | |
| 1365 | 77964 | 5.00E−91 | 88 | ref|NP_194100.1|unknown protein [*Arabidopsis thaliana*] | CS | |
| 1366 | 77346 | 4.00E−62 | 100 | emb|CAA20568.1|putative protein [*Arabidopsis thaliana*] | CS | |
| 1367 | 77350 | 1.00E−51 | 88 | ref|NP_564175.2|unknown protein [*Arabidopsis thaliana*] | CS | |
| 1368 | 77929 | 0 | 84 | ref|NP_174029.1|unknown protein [*Arabidopsis thaliana*] | CS | |
| 1369 | 77586 | 1.00E−175 | 100 | ref|NP_200984.1|ATIPK2BETA; inositol or phosphatidylinositol kinase [*Arabidopsis thaliana*] | PEG | |
| 1370 | 78510 | 0 | 93 | ref|NP_201011.1|OXA1; protein translocase [*Arabidopsis thaliana*] | LN | |
| 1371 | 77930 | 1.00E−170 | 92 | ref|NP_201115.1|S-adenosylmethionine-dependent methyltransferase [*Arabidopsis thaliana*] | CS | |
| 1372 | 77590 | 1.00E−113 | 84 | ref|NP_172126.1|unknown protein [*Arabidopsis thaliana*] | SS | |
| 1373 | 77592 | 0 | 97 | ref|NP_172535.1|unknown protein [*Arabidopsis thaliana*] | PEG | |
| 1374 | 77361 | 5.00E−99 | 84 | ref|NP_193650.2|protein binding [*Arabidopsis thaliana*] | CK | SS |
| 1375 | 77934 | 0 | 91 | ref|NP_195066.1|unknown protein [*Arabidopsis thaliana*] | PEG | |
| 1376 | 77367 | 2.00E−74 | 66 | ref|NP_196973.1|unknown protein [*Arabidopsis thaliana*] | CS | |
| 1377 | 78121 | 0 | 100 | emb|CAC01785.1|Carboxylesterase-like protein [*Arabidopsis thaliana*] | LL | |
| 1378 | 77370 | 7.00E−70 | 100 | ref|NP_197550.1|arsenate reductase (glutaredoxin)/electron transporter/thiol-disulfide exchange intermediate [*Arabidopsis thaliana*] | CS | |
| 1379 | 78117 | 0 | 96 | ref|NP_851079.1|unknown protein [*Arabidopsis thaliana*] | CS | |
| 1380 | 77950 | 1.00E−177 | 100 | ref|NP_180191.1|urate oxidase [*Arabidopsis thaliana*] | PP | |
| 1381 | 78905 | 1.00E−155 | 75 | ref|NP_565809.1|unknown protein [*Arabidopsis thaliana*] | CK | |
| 1382 | 75913 | 2.00E−73 | 80 | ref|NP_001052968.1|Os04g0456700 [*Oryza sativa* (japonica cultivar-group)] | LL | |
| 1383 | 75925 | 0 | 80 | gb|EAY77273.1|hypothetical protein OsI_005120 [*Oryza sativa* (indica cultivar-group)] | SP | |
| 1384 | 75974 | 0 | 100 | ref|NP_488061.1|fructose-1,6-bisphosphatase [*Nostoc* sp. PCC 7120] | PP | |
| 1385 | 75903 | 0 | 95 | ref|NP_385577.1|PUTATIVE NITRITE REDUCTASE PROTEIN [*Sinorhizobium meliloti* 1021] | SS | |
| 1386 | 75904 | 0 | 97 | ref|NP_244182.1|succinate-semialdehyde dehydrogenase [*Bacillus halodurans* C-125] dbj|BAB07035.1| | CS | LN |
| 1387 | 75916 | 0 | 100 | ref|NP_792120.1|nitrate reductase [*Pseudomonas syringae* pv. tomato str. DC3000] | SP | SS |
| 1388 | 75917 | 0 | 98 | ref|NP_487197.1|phytochrome A, two-component sensor protein [*Nostoc* sp. PCC 7120] | SS | |
| 1389 | 75942 | 0 | 100 | ref|NP_485391.1|ferredoxin-sulfite reductase [*Nostoc* sp. PCC 7120] | CS | |
| 1390 | 75954 | 0 | 100 | ref|NP_662565.1|pyruvate phosphate dikinase [*Chlorobium tepidum* TLS] gb|AAM72907.1| | CS | |
| 1391 | 75943 | 0 | 99 | ref|NP_442685.1|glutamate dehydrogenase (NADP+) [*Synechocystis* sp. PCC 6803] | CS | PEG |
| 1392 | 75967 | 0 | 96 | ref|ZP_00768095.1|Aldehyde dehydrogenase [*Chloroflexus aurantiacus* J-10-fl] | CK | LN |
| 1393 | 75932 |  | 96 | ref|ZP_00767023.1|Phosphoglycerate kinase [*Chloroflexus aurantiacus* J-10-fl] | CS | HS |
| 1394 | 75956 | 0 | 99 | ref|NP_440375.1|glutamate-ammonia ligase [*Synechocystis* sp. PCC 6803] | HS | |
| 1395 | 78135 | 1.00E−170 | 85 | ref|NP_172800.2|sulfotransferase [*Arabidopsis thaliana*] | LL | |
| 1396 | 78612 | 0 | 75 | ref|NP_188602.1|unknown protein [*Arabidopsis thaliana*] | DS | |
| 1397 | 77969 | 0 | 90 | ref|NP_188797.1|unknown protein [*Arabidopsis thaliana*] | PP | |
| 1398 | 78136 | 0 | 93 | ref|NP_171739.1|unknown protein [*Arabidopsis thaliana*] | CS | |
| 1399 | 77627 | 6.00E−69 | 100 | ref|NP_190190.1|structural constituent of ribosome [*Arabidopsis thaliana*] | SS | |
| 1400 | 78142 | 4.00E−43 | 58 | ref|NP_192985.1|PEARLI 1 1; lipid binding [*Arabidopsis thaliana*] | LN | |
| 1401 | 77973 | 1.00E−103 | 92 | emb|CAB36513.1|putative protein [*Arabidopsis thaliana*] | LL | |
| 1402 | 78141 | 0 | 100 | ref|NP_564112.1|pseudouridylate synthase/tRNA-pseudouridine synthase [*Arabidopsis thaliana*] | PEG | |
| 1403 | 78963 | 1.00E−102 | 100 | ref|NP_195300.1|unknown protein [*Arabidopsis thaliana*] | LN | |
| 1404 | 78153 | 0 | 92 | emb|CAB93721.1|hypothetical protein [*Arabidopsis thaliana*] | CS | |
| 1405 | 78156 | 1.00E−160 | 83 | ref|NP_564205.1|unknown protein [*Arabidopsis thaliana*] | LL | |
| 1406 | 11807 | 0 | 83 | ref|NP_181291.1|ASP1 (PDE1 SUPPRESSOR 1); DNA binding [*Arabidopsis thaliana*] | LN | |
| 1407 | 78528 | 0 | 90 | ref|NP_177234.1|unknown protein [*Arabidopsis thaliana*] | LN | |
| 1408 | 78530 | 0 | 100 | ref|NP_177212.2|unknown protein [*Arabidopsis thaliana*] | CK | |
| 1409 | 78618 | 0 | 91 | ref|NP_565086.1|unknown protein [*Arabidopsis thaliana*] | LL | |
| 1410 | 78919 | 0 | 95 | gb|AAG52386.1|AC011765_38unknown protein; 120049-117988 [*Arabidopsis thaliana*] | PP | |

TABLE 3-continued

| PEP Seq ID No. | Construct ID | E-value | % id | Annotation Description | Trait | |
|---|---|---|---|---|---|---|
| 1411 | 77974 | 1.00E−174 | 86 | gb|AAF68123.1|AC010793_18F20B17.8 [*Arabidopsis thaliana*] | CK | |
| 1412 | 77630 | 7.00E−69 | 100 | ref|NP_172256.1|RPS15A (RIBOSOMAL PROTEIN S15A); structural constituent of ribosome [*Arabidopsis thaliana*] | PP | |
| 1413 | 78921 | 0 | 95 | ref|NP_565307.1|inositol or phosphatidylinositol kinase/phosphotransferase, alcohol group as acceptor [*Arabidopsis thaliana*] | LN | |
| 1414 | 78620 | 0 | 100 | gb|AAD03575.1|unknown protein [*Arabidopsis thaliana*] | DS | |
| 1415 | 77975 | 4.00E−40 | 100 | ref|NP_179905.1|zinc ion binding [*Arabidopsis thaliana*] | CS | |
| 1416 | 78536 | 0 | 95 | ref|NP_180034.1|sarcosine oxidase [*Arabidopsis thaliana*] | CS | |
| 1417 | 78537 | 1.00E−179 | 79 | ref|NP_180187.1|calmodulin binding [*Arabidopsis thaliana*] | PEG | |
| 1418 | 78540 | 0 | 100 | ref|NP_565908.1|amino acid binding [*Arabidopsis thaliana*] | SS | LL |
| 1419 | 77993 | 3.00E−86 | 100 | gb|AAF02163.1|AC009853_23unknown protein [*Arabidopsis thaliana*] | PEG | |
| 1420 | 78924 | 0 | 95 | ref|NP_188597.1|catalytic/iron ion binding [*Arabidopsis thaliana*] | LL | |
| 1421 | 78009 | 5.00E−63 | 79 | ref|NP_188798.2|unknown protein [*Arabidopsis thaliana*] | LL | |
| 1422 | 78014 | 1.00E−136 | 88 | ref|NP_189478.2|unknown protein [*Arabidopsis thaliana*] | CS | |
| 1423 | 78015 | 1.00E−165 | 96 | ref|NP_190352.1|DNA binding [*Arabidopsis thaliana*] | CS | |
| 1424 | 78018 | 1.00E−132 | 100 | ref|NP_563661.1|unknown protein [*Arabidopsis thaliana*] | PEG | |
| 1425 | 78021 | 1.00E−108 | 93 | ref|NP_173266.1|hydrolase [*Arabidopsis thaliana*] | CK | |
| 1426 | 78158 | 5.00E−90 | 87 | emb|CAA16775.1|hypothetical protein [*Arabidopsis thaliana*] | CK | |
| 1427 | 78026 | 1.00E−154 | 93 | ref|NP_564109.1|oxidoreductase, acting on paired donors, with incorporation or reduction of molecular oxygen, 2-oxoglutarate as one donor, and incorporation of one atom each of oxygen into both donors [*Arabidopsis thaliana*] | LL | |
| 1428 | 78028 | 1.00E−102 | 80 | ref|NP_564130.1|unknown protein [*Arabidopsis thaliana*] gb|ABD19644.1| | CS | |
| 1429 | 78032 | 5.00E−78 | 91 | gb|ABK28138.1|unknown [*Arabidopsis thaliana*] | PEG | |
| 1430 | 78388 | 2.00E−68 | 100 | ref|NP_171877.1|unknown protein [*Arabidopsis thaliana*] | LL | |
| 1431 | 78044 | 1.00E−156 | 94 | gb|AAF99798.1|AC012463_15T2E6.19 [*Arabidopsis thaliana*] | LL | |
| 1432 | 78047 | 5.00E−78 | 88 | ref|NP_175487.1|unknown protein [*Arabidopsis thaliana*] | CS | |
| 1433 | 78055 | 1.00E−167 | 95 | ref|NP_176410.1|unknown protein [*Arabidopsis thaliana*] | SS | |
| 1434 | 78057 | 1.00E−168 | 100 | ref|NP_176835.1|ubiquitin-protein ligase/zinc ion binding [*Arabidopsis thaliana*] | CK | |
| 1435 | 78059 | 1.00E−167 | 90 | ref|NP_172124.2|iron ion binding/oxidoreductase/stearoyl-CoA 9-desaturase [*Arabidopsis thaliana*] | CS | |
| 1436 | 78553 | 3.00E−77 | 92 | ref|NP_176998.1|unknown protein [*Arabidopsis thaliana*] | SS | |
| 1437 | 78163 | 1.00E−108 | 80 | gb|AAG52601.1|AC016447_10hypothetical protein; 95246-97368 [*Arabidopsis thaliana*] | LN | |
| 1438 | 78060 | 1.00E−118 | 100 | gb|AAD55282.1|AC008263_13ESTs gb|T04387, gb|R84022 and gb|T42239 come from this gene. [*Arabidopsis thaliana*] | DS | PEG |
| 1439 | 78062 | 1.00E−173 | 100 | ref|NP_177653.1|transporter [*Arabidopsis thaliana*] | CS | PP |
| 1440 | 78065 | 1.00E−113 | 100 | gb|AAG52095.1|AC012680_6unknown protein; 48924-49705 [*Arabidopsis thaliana*] | CS | LL |
| 1441 | 78590 | 4.00E−63 | 100 | ref|NP_565623.1|plastoquinol-plastocyanin reductase [*Arabidopsis thaliana*] | LL | |
| 1442 | 78177 | 2.00E−70 | 72 | ref|NP_180909.2|unknown protein [*Arabidopsis thaliana*] | DS | |
| 1443 | 78952 | 1.00E−107 | 95 | ref|NP_565887.1|unknown protein [*Arabidopsis thaliana*] | LL | |
| 1444 | 78559 | 1.00E−155 | 89 | ref|NP_973636.1|unknown protein [*Arabidopsis thaliana*] | LN | |
| 1445 | 78169 | 1.00E−151 | 100 | gb|AAF01548.1|AC009325_18unknown protein [*Arabidopsis thaliana*] | PP | |
| 1446 | 78178 | 1.00E−157 | 100 | ref|NP_187462.1|unknown protein [*Arabidopsis thaliana*] | CS | |
| 1447 | 78932 | 0 | 75 | emb|CAB80914.1|hypothetical protein [*Arabidopsis thaliana*] | CK | |
| 1448 | 78185 | 2.00E−87 | 100 | ref|NP_196768.1|unknown protein [*Arabidopsis thaliana*] | PEG | |
| 1449 | 78186 | 1.00E−99 | 92 | ref|NP_199091.2|unknown protein [*Arabidopsis thaliana*] | CS | |
| 1450 | 78572 | 0 | 96 | ref|NP_171850.1|unknown protein [*Arabidopsis thaliana*] | LL | |
| 1451 | 78631 | 1.00E−98 | 91 | gb|AAD10675.1|Similar to human BC-2 protein, [*Arabidopsis thaliana*] | LL | |
| 1452 | 12425 | 0 | 93 | gb|AAD39650.1|AC007591_15Similar to gb|Z70524 PDR5-like ABC transporter from Spirodela polyrrhiza and is a member of the PF|00005 ABC transporter family. ESTs gb|N97039 and gb|T43169 come from this gene. [*Arabidopsis thaliana*] | LN | |
| 1453 | 78938 | 0 | 95 | ref|NP_175579.1|4CL1 (4-COUMARATE: COA LIGASE 1); 4-coumarate-CoA ligase [*Arabidopsis thaliana*] | PP | |
| 1454 | 78961 | 1.00E−127 | 84 | ref|NP_564988.1|unknown protein [*Arabidopsis thaliana*] | LN | |
| 1455 | 78584 | 1.00E−117 | 75 | ref|NP_178114.1|unknown protein [*Arabidopsis thaliana*] | PP | |
| 1456 | 78589 | 1.00E−106 | 90 | ref|NP_180437.2|unknown protein [*Arabidopsis thaliana*] | CS | |
| 1457 | 78252 | 0 | 61 | ref|NP_001043638.1|Os01g0628900 [*Oryza sativa* (japonica cultivar-group)] | LN | |
| 1458 | 76314 | 1.00E−134 | 76 | gb|AAR01658.1|putative inositol polyphosphate 5-phosphatase [*Oryza sativa* (japonica cultivar-group)] | CK | |
| 1459 | 76326 | 0 | 78 | ref|NP_001048842.1|Os03g0128700 [*Oryza sativa* (japonica cultivar-group)] | CK | |
| 1460 | 76362 | 1.00E−47 | 80 | gb|AAR87161.1|hypotheticat protein [*Oryza sativa* (japonica cultivar-group)] | PEG | |
| 1461 | 76340 | 7.00E−64 | 92 | ref|NP_010440.1|RNA polymerase I subunit A14 [*Saccharomyces cerevisiae*] | LN | |

TABLE 3-continued

| PEP Seq ID No. | Construct ID | Annotation | | | Trait | |
|---|---|---|---|---|---|---|
| | | E-value | % id | Description | | |
| 1462 | 76377 | 0 | 98 | ref|NP_199440.1|ATP binding/DNA binding/DNA-dependent ATPase/nucleoside-triphosphatase/nucleotide binding [*Arabidopsis thaliana*] | CK | |
| 1463 | 76319 | 0 | 93 | ref|NP_850426.1|kinase [*Arabidopsis thaliana*] | LL | LN |
| 1464 | 76343 | 0 | 90 | ref|NP_173578.2|ATP binding/kinase/protein kinase/protein serine/threonine kinase/protein-tyrosine kinase [*Arabidopsis thaliana*] | LN | |
| 1465 | 76320 | 1.00E−109 | 84 | ref|NP_001063406.1|Os09g0463600 [*Oryza sativa* (japonica cultivar-group)] | LL | |
| 1466 | 76380 | 0 | 76 | ref|NP_001044432.1|Os01g0779300 [*Oryza sativa* (japonica cultivar-group)] | LN | |
| 1467 | 77831 | 0 | 80 | gb|ABA91110.1|leucine-rich repeat family protein, putative, expressed [*Oryza sativa* (japonica cultivar-group)] | SS | |
| 1468 | 76334 | 8.00E−21 | 56 | ref|NP_190188.1|RNA binding/nucleic acid binding [*Arabidopsis thaliana*] | LN | |
| 1469 | 76382 | 0 | 78 | emb|CAH66974.1|H0714H04.1 [*Oryza sativa* (indica cultivar-group)] | LN | |
| 1470 | 76838 | 3.00E−98 | 81 | gb|EAY84304.1|hypothetical protein OsI_005537 [*Oryza sativa* (indica cultivar-group)] | LL | LN |
| 1471 | 77841 | 1.00E−102 | 85 | ref|NP_001067006.1|Os12g0557400 [*Oryza sativa* (japonica cultivar-group)] | LL | |
| 1472 | 77838 | 1.00E−134 | 86 | ref|NP_001043004.1|Os01g0356500 [*Oryza sativa* (japonica cultivar-group)] | SS | |
| 1473 | 76865 | 2.00E−79 | 91 | ref|NP_001060126.1|Os07g0585800 [*Oryza sativa* (japonica cultivar-group)] | SP | |
| 1474 | 77834 | 1.00E−166 | 89 | ref|NP_001043134.1|Os01g0501800 [*Oryza sativa* (japonica cultivar-group)] | PEG | |
| 1475 | 76823 | 4.00E−46 | 100 | gb|EAY97498.1|hypothetical protein OsI_018731 [*Oryza sativa* (indica cultivar-group)] | CS | |
| 1476 | 76836 | 1.00E−46 | 65 | ref|NP_001049532.1|Os03g0244000 [*Oryza sativa* (japonica cultivar-group)] | PP | |
| 1477 | 14133 | 0 | 89 | pir||G71435hypothetical protein - *Arabidopsis thaliana* | LN | |
| 1478 | 76927 | 5.00E−58 | 74 | gb|EAY75504.1|hypothetical protein OsI_003351 [*Oryza sativa* (indica cultivar-group)] | LL | |
| 1479 | 76963 | 1.00E−107 | 90 | gb|EAY84610.1|hypothetical protein OsI_005843 [*Oryza sativa* (indica cultivar-group)] | LN | |
| 1480 | 76975 | 3.00E−32 | 62 | ref|NP_001055878.1|Os05g0486200 [*Oryza sativa* (japonica cultivar-group)] | SS | |
| 1481 | 76988 | 4.00E−44 | 81 | ref|NP_001053850.1|Os04g0612900 [*Oryza sativa* (japonica cultivar-group)] dbj|BAF15764.1| | DS | |
| 1482 | 76953 | 7.00E−43 | 75 | sp|Q07764|HVA22_HORVUProtein HVA22 gb|AAA16094.1| A22 | CS | |
| 1483 | 76965 | 3.00E−89 | 75 | gb|EAZ28929.1|hypothetical protein OsJ_012412 [*Oryza sativa* (japonica cultivar-group)] | SP | |
| 1484 | 77161 | 1.00E−123 | 77 | emb|CAH66750.1|H0409D10.8 [*Oryza sativa* (indica cultivar-group)] | CS | |
| 1485 | 77852 | 0 | 87 | ref|NP_001064303.1|Os10g0203000 [*Oryza sativa* (japonica cultivar-group)] | CK | |
| 1486 | 77151 | 0 | 91 | ref|NP_001050897.1|Os03g0679700 [*Oryza sativa* (japonica cultivar-group)] | SS | |
| 1487 | 77116 | 1.00E−133 | 84 | gb|EAY87341.1|hypothetical protein OsI_008574 [*Oryza sativa* (indica cultivar-group)] | SP | |
| 1488 | 77105 | 0 | 81 | gb|EAZ26357.1|hypothetical protein OsJ_009840 [*Oryza sativa* (japonica cultivar-group)] | CK | PP |
| 1489 | 77129 | 0 | 73 | dbj|BAD19329.1|putative eukaryotic translation initiation factor 2A [*Oryza sativa* (japonica cultivar-group)] | CS | |
| 1490 | 77154 | 0 | 98 | ref|NP_001056944.1|Os06g0173100 [*Oryza sativa* (japonica cultivar-group)] | PEG | |
| 1491 | 77190 | 0 | 100 | ref|NP_417002.1|bifunctional GMP synthase/glutamine amidotransferase protein [*Escherichia coli* K12] | LL | |
| 1492 | 77107 | 0 | 100 | ref|NP_486886.1|bifunctional GMP synthase/glutamine amidotransferase protein [*Nostoc* sp. PCC 7120] | SP | CS |
| 1493 | 77167 | 1.00E−141 | 92 | gb|AAZ20768.1|branchy [*Setaria italica*] | PP | |
| 1494 | 77144 | 0 | 100 | ref|NP_416789.1|NADH: ubiquinone oxidoreductase. chain C, D [*Escherichia coli* K12] | CK | |
| 1495 | 77156 | 1.00E−132 | 100 | ref|NP_443063.1|bifunctional phosphoribosyl-AMP cyclohydrolase/phosphoribosyl-ATP pyrophosphatase protein [*Synechocystis* sp. PCC 6803] | CS | |
| 1496 | 77168 | 0 | 83 | ref|NP_001047841.1|Os02g0700600 [*Oryza sativa* (japonica cultivar-group)] | SP | |
| 1497 | 77192 | 7.00E−77 | 84 | dbj|BAD27669.1|putative actin related protein 2/3 complex, 21 kDa subunit [*Oryza sativa* (japonica cultivar-group)] | PEG | |
| 1498 | 77181 | 8.00E−29 | 84 | ref|NP_001049737.1|Os03g0280400 [*Oryza sativa* (japonica cultivar-group)] | LL | |
| 1499 | 77193 | 1.00E−111 | 87 | ref|NP_001049175.1|Os03g0182700 [*Oryza sativa* (japonica cultivar-group)] | PP | PEG |

TABLE 3-continued

| PEP Seq ID No. | Construct ID | Annotation | | | Trait | |
|---|---|---|---|---|---|---|
| | | E-value | % id | Description | | |
| 1500 | 77147 | 1.00E−124 | 64 | emb|CAE04316.1|OSJNBb0016D16.7 [*Oryza sativa* (japonica cultivar-group)] | DS | LL |
| 1501 | 77853 | 0 | 91 | ref|NP_418588.1|predicted carbohydrate kinase [*Escherichia coli* K12] | LN | |
| 1502 | 77854 | 4.00E−68 | 86 | ref|NP_001042156.1|Os01g0173000 [*Oryza sativa* (japonica cultivar-group)] | SS | |
| 1503 | 77287 | 1.00E−46 | 63 | ref|NP_001054446.1|Os05g0111200 [*Oryza sativa* (japonica cultivar-group)] | CS | LL |
| 1504 | 77276 | 2.00E−73 | 66 | ref|NP_001045229.1|Os01g0921600 [*Oryza sativa* (japonica cultivar-group)] | LN | |
| 1505 | 77229 | 1.00E−53 | 90 | gb|AAL67582.1|AC018929_4unknown protein [*Oryza sativa*] | CS | SS |
| 1506 | 77241 | 1.00E−159 | 73 | ref|NP_001045995.1|Os02g0165100 [*Oryza sativa* (japonica cultivar-group)] | SS | |
| 1507 | 77265 | 1.00E−115 | 60 | gb|EAZ04741.1|hypothetical protein OsI_025973 [*Oryza sativa* (indica cultivar-group)] | LN | |
| 1508 | 77233 | 1.00E−113 | 96 | ref|NP_001043339.1|Os01g0559000 [*Oryza sativa* (japonica cultivar-group)] | CS | |
| 1509 | 77293 | 1.00E−102 | 81 | ref|NP_001056330.1|Os05g0564100 [*Oryza sativa* (japonica cultivar-group)] | PEG | |
| 1510 | 77473 | 0 | 75 | ref|NP_001067661.1|Os11g0265600 [*Oryza sativa* (japonica cultivar-group)] | CK | |
| 1511 | 76402 | 0 | 95 | ref|NP_199899.1|ATP binding/protein kinase/protein serine/threonine kinase/protein-tyrosine kinase [*Arabidopsis thaliana*] | CK | PEG |
| 1512 | 77428 | 0 | 86 | dbj|BAC07390.1|putative NAD synthetase [*Oryza sativa* (japonica cultivar-group)] | SS | |
| 1513 | 77429 | 3.00E−93 | 73 | ref|NP_001044830.1|Os01g0853000 [*Oryza sativa* (japonica cultivar-group)] | CS | |
| 1514 | 78277 | 0 | 95 | ref|NP_192815.1|ATOPT7; oligopeptide transporter [*Arabidopsis thaliana*] | DS | |
| 1515 | 11935 | 0 | 97 | ref|NP_188434.2|nucleotide binding [*Arabidopsis thaliana*] | SP | |
| 1516 | 78259 | 0 | 93 | ref|NP_190717.1|carbohydrate transporter/nucleoside transporter/sugar porter [*Arabidopsis thaliana*] | LN | |
| 1517 | 12276 | 0 | 87 | ref|NP_199691.1|protein binding/signal transducer [*Arabidopsis thaliana*] | CS | |
| 1518 | 12365 | 3.00E−66 | 100 | ref|NP_181620.1|FL3-27; cysteine protease inhibitor [*Arabidopsis thaliana*] | CK | |

Trait Enhancement Screens

DS-Enhancement of drought tolerance identified by a soil drought stress tolerance screen: Drought or water deficit conditions impose mainly osmotic stress on plants. Plants are particularly vulnerable to drought during the flowering stage. The drought condition in the screening process disclosed in Example 1B started from the flowering time and was sustained to the end of harvesting. The present invention provides recombinant DNA that can improve the plant survival rate under such sustained drought condition. Exemplary recombinant DNA for conferring such drought tolerance are identified as such in Table 3. Such recombinant DNA may find particular use in generating transgenic plants that are tolerant to the drought condition imposed during flowering time and in other stages of the plant life cycle. As demonstrated from the model plant screen, in some embodiments of transgenic plants with trait-improving recombinant DNA grown under such sustained drought condition can also have increased total seed weight per plant in addition to the increased survival rate within a transgenic population, providing a higher yield potential as compared to control plants.

PEG-Enhancement of drought tolerance identified by PEG induced osmotic stress tolerance screen: Various drought levels can be artificially induced by using various concentrations of polyethylene glycol (PEG) to produce different osmotic potentials (Pilon-Smits e.g., (1995) Plant Physiol. 107:125-130). Several physiological characteristics have been reported as being reliable indications for selection of plants possessing drought tolerance. These characteristics include the rate of seed germination and seedling growth. The traits can be assayed relatively easily by measuring the growth rate of seedling in PEG solution. Thus, a PEG-induced osmotic stress tolerance screen is a useful surrogate for drought tolerance screen. As demonstrated from the model plant screen, embodiments of transgenic plants with trait-improving recombinant DNA identified in the PEG-induced osmotic stress tolerance screen can survive better drought conditions providing a higher yield potential as compared to control plants.

SS-Enhancement of drought tolerance identified by high salinity stress tolerance screen: Three different factors are responsible for salt damages: (1) osmotic effects, (2) disturbances in the mineralization process, and (3) toxic effects caused by the salt ions, e.g., inactivation of enzymes. While the first factor of salt stress results in the wilting of the plants that is similar to drought effect, the ionic aspect of salt stress is clearly distinct from drought. The present invention provides genes that help plants maintain biomass, root growth, and/or plant development in high salinity conditions, which are identified as such in Table 3. Since osmotic effect is one of the major components of salt stress, which is common to the drought stress, trait-improving recombinant DNA identified in a high salinity stress tolerance screen can also provide transgenic crops with enhanced drought tolerance. As demonstrated from the model plant screen, embodiments of transgenic plants with trait-improving recombinant DNA identified in a high salinity stress tolerance screen can survive better drought conditions and/or high salinity conditions providing a higher yield potential as compared to control plants.

HS-Enhancement of drought tolerance identified by heat stress tolerance screen: Heat and drought stress often occur simultaneously, limiting plant growth. Heat stress can cause the reduction in photosynthesis rate, inhibition of leaf growth and osmotic potential in plants. Thus, genes identified by the present invention as heat stress tolerance conferring genes may also impart enhanced drought tolerance to plants. As demonstrated from the model plant screen, embodiments of transgenic plants with trait-improving recombinant DNA identified in a heat stress tolerance screen can survive better heat stress conditions and/or drought conditions providing a higher yield potential as compared to control plants.

CK and CS-Enhancement of tolerance to cold stress: Low temperature may immediately result in mechanical constraints, changes in activities of macromolecules, and reduced osmotic potential. In the present invention, two screening conditions, i.e., cold shock tolerance screen (CK) and cold germination tolerance screen (CS), were set up to look for transgenic plants that display visual growth advantage at lower temperature. In cold germination tolerance screen, the transgenic *Arabidopsis* plants were exposed to a constant temperature of 8° C. from planting until day 28 post plating. The trait-improving recombinant DNA identified by such screen are particular useful for the production of transgenic plant that can germinate more robustly in a cold temperature as compared to the wild type plants. In cold shock tolerance screen, the transgenic plants were first grown under the normal growth temperature of 22° C. until day 8 post plating, and subsequently were placed under 8° C. until day 28 post plating. As demonstrated from the model plant screen, embodiments of transgenic plants with trait-improving recombinant DNA identified in a cold shock stress tolerance screen and/or a cold germination stress tolerance screen can survive better cold conditions providing a higher yield potential as compared to control plants.

Enhancement of tolerance to multiple stresses: Different kinds of stresses often lead to identical or similar reaction in the plants. Genes that are activated or inactivated as a reaction to stress can either act directly in a way the genetic product reduces a specific stress, or they can act indirectly by activating other specific stress genes. By manipulating the activity of such regulatory genes, i.e., multiple stress tolerance genes, the plant can be enabled to react to different kinds of stresses. For examples, PEP SEQ ID NO: 892 can be used to enhance both salt stress tolerance and cold stress tolerance in plants. Of particular interest, plants transformed with PEP SEQ ID NO: 835 can resist heat stress, salt stress and cold stress. Plants transformed with PEP SEQ ID NO: 835 can also improve growth in early stage and under osmotic stress. In addition to these multiple stress tolerance genes, the stress tolerance conferring genes provided by the present invention may be used in combinations to generate transgenic plants that can resist multiple stress conditions.

PP-Enhancement of early plant growth and development: It has been known in the art that to minimize the impact of disease on crop profitability, it is important to start the season with healthy and vigorous plants. This means avoiding seed and seedling diseases, leading to increased nutrient uptake and increased yield potential. Traditionally early planting and applying fertilizer are the methods used for promoting early seedling vigor. In early development stage, plant embryos establish only the basic root-shoot axis, a cotyledon storage organ(s), and stem cell populations, called the root and shoot apical meristems, that continuously generate new organs throughout post-embryonic development. "Early growth and development" used herein encompasses the stages of seed imbibition through the early vegetative phase. The present invention provides genes that are useful to produce transgenic plants that have advantages in one or more processes including, but not limited to, germination, seedling vigor, root growth and root morphology under non-stressed conditions. The transgenic plants starting from a more robust seedling are less susceptible to the fungal and bacterial pathogens that attach germinating seeds and seedling. Furthermore, seedlings with advantage in root growth are more resistant to drought stress due to extensive and deeper root architecture. Therefore, it can be recognized by those skilled in the art that genes conferring the growth advantage in early stages to plants may also be used to generate transgenic plants that are more resistant to various stress conditions due to enhanced early plant development. The present invention provides such exemplary, recombinant DNA that confer both the stress tolerance and growth advantages to plants, identified as such in Table 3, e.g., PEP SEQ ID NO: 799 which can improve the plant early growth and development, and impart heat and cold tolerance to plants. As demonstrated from the model plant screen, embodiments of transgenic plants with trait-improving recombinant DNA identified in the early plant development screen can grow better under non-stress conditions and/or stress conditions providing a higher yield potential as compared to control plants.

SP-Enhancement of late plant growth and development: "Late growth and development" used herein encompasses the stages of leaf development, flower production, and seed maturity. In certain embodiments, transgenic plants produced using genes that confer growth advantages to plants provided by the present invention, identified as such in Table 3, exhibit at least one phenotypic characteristics including, but not limited to, increased rosette radius, increased rosette dry weight, seed dry weight, silique dry weight, and silique length. On one hand, the rosette radius and rosette dry weight are used as the indexes of photosynthesis capacity, and thereby plant source strength and yield potential of a plant. On the other hand, the seed dry weight, silique dry weight and silique length are used as the indexes for plant sink strength, which are considered as the direct determinants of yield. As demonstrated from the model plant screen, embodiments of transgenic plants with trait-improving recombinant DNA identified in the late development screen can grow better and/or have enhanced development during leaf development and seed maturation providing a higher yield potential as compared to control plants.

LL-Enhancement of tolerance to shade stress identified in a low light screen: The effects of light on plant development are especially prominent at the seedling stage. Under normal light conditions with unobstructed direct light, a plant seedling develops according to a characteristic photomorphogenic pattern, in which plants have open and expanded cotyledons and short hypocotyls. Then the plant's energy is devoted to cotyledon and leaf development while longitudinal extension growth is minimized. Under low light condition where light quality and intensity are reduced by shading, obstruction or high population density, a seedling displays a shade-avoidance pattern, in which the seedling displays a reduced cotyledon expansion, and hypocotyls extension is greatly increased. As the result, a plant under low light condition increases significantly its stem length at the expanse of leaf, seed or fruit and storage organ development, thereby adversely affecting of yield. The present invention provides recombinant DNA that enable plants to have an attenuated shade avoidance response so that the source of plant can be contributed to reproductive growth efficiently, resulting higher yield as compared to the wild type plants. As demonstrated from the model plant screen, embodiments of transgenic plants with trait-improving recombinant DNA identified in a shade stress tolerance screen can have attenuated shade response under shade conditions providing a higher yield potential as compared to control plants. The transgenic plants generated by the present invention may be suitable for a higher density planting, thereby resulting increased yield per unit area.

LN-Enhancement of Tolerance to Low Nitrogen Availability Stress

Nitrogen is a key factor in plant growth and crop yield. The metabolism, growth and development of plants are profoundly affected by their nitrogen supply. Restricted nitrogen supply alters shoot to root ratio, root development, activity of enzymes of primary metabolism and the rate of senescence (death) of older leaves. All field crops have a fundamental dependence on inorganic nitrogenous fertilizer. Since fertilizer is rapidly depleted from most soil types, it must be supplied to growing crops two or three times during the growing season. Enhanced nitrogen use efficiency by plants should enable crops cultivated under low nitrogen availability stress condition resulted from low fertilizer input or poor soil quality.

According to the present invention, transgenic plants generated using the recombinant nucleotides, which confer enhanced nitrogen use efficiency, identified as such in Table 3, exhibit one or more desirable traits including, but not limited to, increased seedling weight, greener leaves, increased number of rosette leaves, increased or decreased root length. One skilled in the art may recognize that the transgenic plants provided by the present invention with enhanced nitrogen use efficiency may also have altered amino acid or protein compositions, increased yield and/or better seed quality. The transgenic plants of the present invention may be productively cultivated under low nitrogen growth conditions, i.e., nitrogen-poor soils and low nitrogen fertilizer inputs, which would cause the growth of wild type plants to cease or to be so diminished as to make the wild type plants practically useless. The transgenic plants also may be advantageously used to achieve earlier maturing, faster growing, and/or higher yielding crops and/or produce more nutritious foods and animal feedstocks when cultivated using nitrogen non-limiting growth conditions.

Stacked Traits: The present invention also encompasses transgenic plants with stacked engineered traits, e.g., a crop having an enhanced phenotype resulting from expression of a trait-improving recombinant DNA, in combination with herbicide and/or pest resistance traits. For example, genes of the current invention can be stacked with other traits of agronomic interest, such as a trait providing herbicide resistance, for example a RoundUp Ready® trait, or insect resistance, such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides. To illustrate that the production of transgenic plants with herbicide resistance is a capability of those of ordinary skill in the art, reference is made to U.S. patent application publications 2003/0106096A1 and 2002/0112260A1 and U.S. Pat. Nos. 5,034,322; 5,776,760, 6,107,549 and 6,376,754, all of which are incorporated herein by reference. To illustrate that the production of transgenic plants with pest resistance is a capability of those of ordinary skill in the art reference is made to U.S. Pat. Nos. 5,250,515 and 5,880,275 which disclose plants expressing an endotoxin of *Bacillus thuringiensis* bacteria, to U.S. Pat. No. 6,506,599 which discloses control of invertebrates which feed on transgenic plants which express dsRNA for suppressing a target gene in the invertebrate, to U.S. Pat. No. 5,986,175 which discloses the control of viral pests by transgenic plants which express viral replicase, and to U.S. Patent Application Publication 2003/0150017 A1 which discloses control of pests by a transgenic plant which express a dsRNA targeted to suppressing a gene in the pest, all of which are incorporated herein by reference.

Once one recombinant DNA has been identified as conferring an enhanced trait of interest in transgenic *Arabidopsis* plants, several methods are available for using the sequence of that recombinant DNA and knowledge about the protein it encodes to identify homologs of that sequence from the same plant or different plant species or other organisms, e.g., bacteria and yeast. Thus, in one aspect, the invention provides methods for identifying a homologous gene with a DNA sequence homologous to any of SEQ ID NO: 1 through SEQ ID NO: 759, or a homologous protein with an amino acid sequence homologous to any of SEQ ID NO: 760 through SEQ ID NO: 1518. In another aspect, the present invention provides the protein sequences of identified homologs for a sequence listed, as SEQ ID NO: 1519 through SEQ ID NO: 67778. In yet another aspect, the present invention also includes linking or associating one or more desired traits, or gene function with a homolog sequence provided herein.

The trait-improving recombinant DNA and methods of using such trait-improving recombinant DNA for generating transgenic plants with enhanced traits provided by the present invention are not limited to any particular plant species. Indeed, the plants according to the present invention may be of any plant species, i.e., may be monocotyledonous or dicotyledonous. Preferably, they will be agricultural useful plants, i.e., plants cultivated by man for purposes of food production or technical, particularly industrial applications. Of particular interest in the present invention are corn and soybean plants. The recombinant DNA constructs optimized for soybean transformation and recombinant DNA constructs optimized for corn transformation are provided by the present invention. Other plants of interest in the present invention for production of transgenic plants having enhanced traits include, without limitation, cotton, canola, wheat, sunflower, sorghum, alfalfa, barley, millet, rice, tobacco, fruit and vegetable crops, and turfgrass.

In certain embodiments, the present invention contemplates to use an orthologous gene in generating the transgenic plants with similarly enhanced traits as the transgenic *Arabidopsis* counterpart. Enhanced physiological properties in transgenic plants of the present invention may be confirmed in responses to stress conditions, for example in assays using imposed stress conditions to detect enhanced responses to drought stress, nitrogen deficiency, cold growing conditions, or alternatively, under naturally present stress conditions, for example under field conditions. Biomass measures may be made on greenhouse or field grown plants and may include such measurements as plant height, stem diameter, root and shoot dry weights, and, for corn plants, ear length and diameter.

Trait data on morphological changes may be collected by visual observation during the process of plant regeneration as well as in regenerated plants transferred to soil. Such trait data includes characteristics such as normal plants, bushy plants, taller plants, thicker stalks, narrow leaves, striped leaves, knotted phenotype, chlorosis, albino, anthocyanin production, or altered tassels, ears or roots. Other enhanced traits may be identified by measurements taken under field conditions, such as days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, trait characteristics of harvested grain may be confirmed, including number of kernels per row on the ear, number of rows of kernels on the ear, kernel abortion, kernel weight, kernel size, kernel density and physical grain quality.

To confirm hybrid yield in transgenic corn plants expressing genes of the present invention, it may be desirable to test hybrids over multiple years at multiple locations in a geographical location where maize is conventionally grown, e.g., in Iowa, Illinois or other locations in the midwestern United States, under "normal" field conditions as well as under stress conditions, e.g., under drought or population density stress.

Transgenic plants can be used to provide plant parts according to the invention for regeneration or tissue culture of cells or tissues containing the constructs described herein. Plant parts for these purposes can include leaves, stems, roots, flowers, tissues, epicotyl, meristems, hypocotyls, cotyledons, pollen, ovaries, cells and protoplasts, or any other portion of the plant which can be used to regenerate additional transgenic plants, cells, protoplasts or tissue culture. Seeds of transgenic plants are provided by this invention can be used to propagate more plants containing the trait-improving recombinant DNA constructs of this invention. These descendants are intended to be included in the scope of this invention if they contain a trait-improving recombinant DNA construct of this invention, whether or not these plants are selfed or crossed with different varieties of plants.

The various aspects of the invention are illustrated by means of the following examples which are in no way intended to limit the full breath and scope of claims.

EXAMPLES

Example 1

Identification of Recombinant DNA that Confers Enhanced Trait(s) to Plants

A. Plant Expression Constructs for *Arabidopsis* Transformation

Each gene of interest was amplified from a genomic or cDNA library using primers specific to sequences upstream and downstream of the coding region. Transformation vectors were prepared to constitutively transcribe DNA in either sense orientation (for enhanced protein expression) or antisense orientation (for endogenous gene suppression) under the control of an enhanced Cauliflower Mosaic Virus 35S promoter (U.S. Pat. No. 5,359,142) directly or indirectly (Moore, e.g., PNAS 95:376-381, 1998; Guyer, e.g., Genetics 149: 633-639, 1998; International patent application NO. PCT/EP98/07577). The transformation vectors also contain a bar gene as a selectable marker for resistance to glufosinate herbicide. The transformation of *Arabidopsis* plants was carried out using the vacuum infiltration method known in the art (Bethtold, e.g., Methods Mol. Biol. 82:259-66, 1998). Seeds harvested from the plants, named as T1 seeds, were subsequently grown in a glufosinate-containing selective medium to select for plants which were actually transformed and which produced T2 transgenic seed.

B. Soil Drought Tolerance Screen

This example describes a soil drought tolerance screen to identify *Arabidopsis* plants transformed with recombinant DNA that wilt less rapidly and/or produce higher seed yield when grown in soil under drought conditions T2 seeds were sown in flats filled with Metro/Mix' 200 (The Scotts° Company, USA). Humidity domes were added to each flat and flats were assigned locations and placed in climate-controlled growth chambers. Plants were grown under a temperature regime of 22° C. at day and 20° C. at night, with a photoperiod of 16 hours and average light intensity of 170 µmol/m$^2$/s. After the first true leaves appeared, humidity domes were removed. The plants were sprayed with glufosinate herbicide and put back in the growth chamber for 3 additional days. Flats were watered for I hour the week following the herbicide treatment. Watering was continued every seven days until the flower bud primordia became apparent, at which time plants were watered for the last time.

To identify drought tolerant plants, plants were evaluated for wilting response and seed yield. Beginning ten days after the last watering, plants were examined daily until 4 plants/line had wilted. In the next six days, plants were monitored for wilting response. Five drought scores were assigned according to the visual inspection of the phenotypes: 1 for healthy, 2 for dark green, 3 for wilting, 4 severe wilting, and 5 for dead. A score of 3 or higher was considered as wilted.

At the end of this assay, seed yield measured as seed weight per plant under the drought condition was characterized for the transgenic plants and their controls and analyzed as a quantitative response according to example 1M.

Two approaches were used for statistical analysis on the wilting response. First, the risk score was analyzed for wilting phenotype and treated as a qualitative response according to the example 1L. Alternatively, the survival analysis was carried out in which the proportions of wilted and non-wilted transgenic and control plants were compared over each of the six days under scoring and an overall log rank test was performed to compare the two survival curves using S-PLUS statistical software (S-PLUS 6, Guide to statistics, Insightful, Seattle, Wash., USA). A list of recombinant DNA constructs which improve drought tolerance in transgenic plants is illustrated in Table 4.

TABLE 4

| PEP SEQ ID NO | Construct ID | Nomination ID | Orientation | Drought score Delta mean | P-value | Seed yield Delta mean | P-value | Time to wilting Risk score mean | P-value |
|---|---|---|---|---|---|---|---|---|---|
| 968 | 10359 | CGPG430 | ANTI-SENSE | −0.103 | 0.104 | 0.134 | 0.469 | −0.147 | 1.000 |
| 863 | 10462 | CGPG240 | ANTI-SENSE | 0.133 | 0.006 | −0.101 | 0.331 | 0.306 | 1.000 |
| 1115 | 11149 | CGPG587 | SENSE | −0.021 | 0.741 | 0.277 | 0.158 | −0.105 | 0.852 |
| 769 | 12040 | CGPG1092 | SENSE | 0.025 | 0.240 | 0.227 | 0.258 | 0.058 | 1.000 |
| 771 | 12156 | CGPG1136 | ANTI-SENSE | −0.009 | 0.068 | 0.512 | 0.045 | 0.154 | 0.857 |
| 784 | 12733 | CGPG1291 | ANTI-SENSE | 0.165 | 0.034 | −0.368 | 0.009 | 0.209 | 1.000 |
| 760 | 12792 | CGPG1022 | ANTI-SENSE | 0.070 | 0.184 | 0.223 | 0.077 | 0.083 | 1.000 |
| 786 | 13504 | CGPG1311 | SENSE | −0.055 | 0.704 | 0.109 | 0.445 | −0.042 | 1.000 |
| 1150 | 13518 | CGPG620 | ANTI-SENSE | 0.176 | 0.023 | 0.026 | 0.891 | 0.160 | 1.000 |

TABLE 4-continued

| PEP SEQ ID NO | Construct ID | Nomination ID | Orientation | Drought score Delta mean | P-value | Seed yield Delta mean | P-value | Time to wilting Risk score mean | P-value |
|---|---|---|---|---|---|---|---|---|---|
| 807 | 14271 | CGPG1575 | ANTI-SENSE | 0.163 | 0.014 | −0.144 | 0.536 | −0.186 | 1.000 |
| 822 | 14827 | CGPG1895 | ANTI-SENSE | 0.171 | 0.047 | 0.001 | 0.995 | 0.092 | 1.000 |
| 845 | 16007 | CGPG2142 | ANTI-SENSE | −0.234 | 0.127 | 0.992 | 0.006 | −0.217 | 1.000 |
| 827 | 16182 | CGPG1922 | SENSE | 0.034 | 0.424 | 0.171 | 0.298 | 0.127 | 1.000 |
| 854 | 17003 | CGPG2304 | SENSE | 0.372 | 0.005 | 0.083 | 0.267 | 0.613 | 1.000 |
| 923 | 18408 | CGPG3612 | SENSE | −0.009 | 0.589 | 0.494 | 0.002 | 0.134 | 0.941 |
| 900 | 18644 | CGPG3236 | SENSE | 0.016 | 0.758 | 0.072 | 0.432 | 0.049 | 0.920 |
| 832 | 19133 | CGPG1973 | SENSE | 0.308 | 0.019 | 0.410 | 0.074 | 0.192 | 1.000 |
| 885 | 19166 | CGPG2914 | SENSE | 0.152 | 0.037 | 0.370 | 0.292 | 0.152 | 1.000 |
| 896 | 19256 | CGPG3137 | SENSE | −0.121 | 0.142 | 0.168 | 0.056 | −0.087 | 0.939 |
| 927 | 19328 | CGPG3665 | SENSE | 0.161 | 0.027 | −0.388 | 0.337 | −0.011 | 1.000 |
| 921 | 19623 | CGPG3579 | SENSE | 0.039 | 0.689 | 0.232 | 0.084 | 0.051 | 1.000 |
| 966 | 70632 | CGPG4297 | SENSE | 0.116 | 0.004 | −0.281 | 0.185 | 0.080 | 1.000 |
| 918 | 71115 | CGPG351 | SENSE | 0.240 | 0.005 | −0.793 | 0.088 | 0.257 | 0.936 |
| 1054 | 72067 | CGPG5262 | SENSE | 0.194 | 0.021 | −0.633 | 0.034 | 0.138 | 1.000 |
| 1011 | 72650 | CGPG4882 | SENSE | 0.187 | 0.032 | −1.980 | 0.088 | 0.481 | 1.000 |
| 1098 | 73088 | CGPG5729 | SENSE | −0.134 | 0.488 | 0.027 | 0.792 | 0.066 | 1.000 |
| 982 | 73214 | CGPG4432 | SENSE | 1.524 | 0.033 | — | — | 0.484 | 1.000 |
| 1032 | 73314 | CGPG5100 | SENSE | 0.117 | 0.018 | −1.005 | 0.082 | 0.056 | 1.000 |
| 1195 | 73567 | CGPG6509 | SENSE | 0.216 | 0.159 | 0.581 | 0.020 | 0.067 | 0.961 |
| 1027 | 73683 | CGPG5062 | SENSE | 0.275 | 0.012 | −0.547 | 0.085 | 0.109 | 0.946 |
| 819 | 73986 | CGPG1837 | SENSE | −0.280 | 0.122 | 0.214 | 0.010 | −0.152 | 1.000 |
| 1036 | 74218 | CGPG5159 | SENSE | 0.241 | 0.006 | −0.057 | 0.670 | 0.140 | 0.785 |
| 800 | 74775 | CGPG1492 | SENSE | 0.156 | 0.105 | 0.231 | 0.049 | 0.122 | 0.804 |
| 1306 | 75365 | CGPG7503 | SENSE | 0.830 | 0.001 | −3.139 | 0.047 | 1.008 | 1.000 |
| 1343 | 75716 | CGPG7881 | SENSE | −0.079 | 0.018 | 0.040 | 0.135 | 0.010 | 0.852 |
| 1243 | 75869 | CGPG6974 | SENSE | −0.016 | 0.708 | 0.133 | 0.162 | −0.136 | 0.893 |
| 798 | 76013 | CGPG1445 | SENSE | 0.414 | 0.021 | −0.269 | 0.297 | 0.386 | 1.000 |
| 806 | 76049 | CGPG1568 | SENSE | 0.196 | 0.025 | −0.991 | 0.033 | 0.221 | 1.000 |
| 1123 | 76214 | CGPG5930 | SENSE | −0.069 | 0.101 | 0.158 | 0.001 | −0.157 | 1.000 |
| 1155 | 76226 | CGPG6211 | SENSE | 0.261 | 0.019 | −1.212 | 0.007 | 0.298 | 1.000 |
| 1160 | 76436 | CGPG6233 | SENSE | 0.412 | 0.017 | −0.566 | 0.040 | 0.316 | 0.837 |
| 1173 | 76528 | CGPG6336 | SENSE | 0.732 | 0.009 | −0.069 | 0.624 | 0.898 | 0.833 |
| 1481 | 76988 | CGPG9106 | SENSE | 0.395 | 0.021 | −0.841 | 0.026 | 0.270 | 1.000 |
| 1500 | 77147 | CGPG9201 | SENSE | 0.493 | 0.005 | −1.475 | 0.015 | 0.997 | 0.909 |
| 1355 | 77565 | CGPG7996 | SENSE | 0.778 | 0.049 | −0.185 | 0.190 | 0.170 | 1.000 |
| 891 | 77909 | CGPG3056 | SENSE | −0.140 | 0.118 | 0.093 | 0.458 | −0.220 | 0.813 |
| 1358 | 77920 | CGPG8023 | SENSE | −0.221 | 0.070 | 0.232 | 0.313 | −0.159 | 0.947 |
| 1438 | 78060 | CGPG8640 | SENSE | 0.550 | 0.008 | −2.055 | 0.013 | 0.390 | 0.944 |
| 1442 | 78177 | CGPG8677 | SENSE | 0.029 | 0.548 | 0.496 | 0.007 | 0.020 | 1.000 |
| 1337 | 78238 | CGPG7813 | SENSE | 0.250 | 0.020 | −0.915 | 0.029 | 0.110 | 1.000 |
| 1514 | 78277 | CGPG9327 | SENSE | 0.274 | 0.003 | −0.267 | 0.456 | 0.064 | 1.000 |
| 1172 | 78367 | CGPG6334 | SENSE | 0.169 | 0.037 | −0.691 | 0.039 | 0.305 | 0.941 |
| 1069 | 78434 | CGPG5473 | SENSE | 0.327 | 0.018 | −2.055 | 0.112 | 0.196 | 1.000 |
| 1396 | 78612 | CGPG8320 | SENSE | 0.198 | 0.017 | 0.374 | 0.237 | −0.020 | 0.953 |
| 1414 | 78620 | CGPG8471 | SENSE | 0.248 | 0.030 | −0.127 | 0.108 | 0.016 | 1.000 |
| 960 | 78665 | CGPG4240 | SENSE | 0.605 | 0.035 | −2.631 | 0.047 | 0.376 | 1.000 |

If $p<0.05$ and delta or risk score mean $>0$, the transgenic plants showed statistically significant trait enhancement as compared to the reference (p value, of the delta of a quantitative response or of the risk score of a qualitative response, is the probability that the observed difference between the transgenic plants and the reference occur by chance) If $p<0.2$ and delta or risk score mean $>0$, the transgenic plants showed a trend of trait enhancement as compared to the reference.

C. Heat Stress Tolerance Screen

Under high temperatures, *Arabidopsis* seedlings become chlorotic and root growth is inhibited. This example sets forth the heat stress tolerance screen to identify *Arabidopsis* plants transformed with the gene of interest that are more resistant to heat stress based on primarily their seedling weight and root growth under high temperature.

T2 seeds were plated on ½× MS salts, 11% phytagel, with 10 µg/ml BASTA (7 per plate with 2 control seeds; 9 seeds total per plate). Plates were placed at 4° C. for 3 days to stratify seeds. Plates were then incubated at room temperature for 3 hours and then held vertically for 11 additional days at temperature of 34° C. at day and 20° C. at night. Photoperiod was 16 h. Average light intensity was ~140 µmol/m²/s. After 14 days of growth, plants were scored for glufosinate resistance, root length, final growth stage, visual color, and seedling fresh weight. A photograph of the whole plate was taken on day 14.

The seedling weight and root length were analyzed as quantitative responses according to example 1M. The final grow stage at day 14 was scored as success if 50% of the plants had reached 3 rosette leaves and size of leaves are greater than 1 mm (Boyes, e.g., (2001) The Plant Cell 13, 1499-1510). The growth stage data was analyzed as a qualitative response according to example 1L. A list of recombinant DNA constructs that improve heat tolerance in transgenic plants illustrated in Table 5.

TABLE 5

| PEP SEQ ID NO | Construct ID | Nomination ID | Orientation | Root length at day 14 Delta mean | P-value | Growth stage at day 14 Risk score mean | P-value | Seedling weight at day 14 Delta mean | P-value |
|---|---|---|---|---|---|---|---|---|---|
| 763 | 10174 | CGPG105 | ANTI-SENSE | 0.263 | 0.011 | −0.010 | 0.930 | 1.029 | 0.003 |
| 778 | 14803 | CGPG1192 | SENSE | 0.202 | 0.011 | 1.151 | 0.391 | 0.828 | 0.015 |
| 835 | 14909 | CGPG2005 | ANTI-SENSE | 0.394 | 0.050 | 0.093 | 0.553 | 1.084 | 0.044 |
| 847 | 17310 | CGPG2190 | SENSE | 0.140 | 0.039 | 1.726 | 0.160 | 1.100 | 0.027 |
| 920 | 19619 | CGPG3575 | SENSE | 0.342 | 0.020 | 1.537 | 0.108 | 1.277 | 0.000 |
| 1018 | 70822 | CGPG499 | SENSE | 0.402 | 0.015 | 0.644 | 0.180 | 1.386 | 0.005 |
| 1080 | 73173 | CGPG5596 | SENSE | 0.686 | 0.003 | 1.254 | 0.054 | 1.482 | 0.002 |
| 1180 | 73416 | CGPG6388 | SENSE | 0.184 | 0.013 | 0.640 | 0.454 | 0.830 | 0.008 |
| 1147 | 74658 | CGPG6174 | SENSE | 0.298 | 0.036 | 1.390 | 0.166 | 0.933 | 0.008 |
| 1278 | 74805 | CGPG7327 | SENSE | 0.441 | 0.017 | 0.071 | 0.080 | 1.258 | 0.019 |
| 839 | 75221 | CGPG2065 | SENSE | 0.345 | 0.049 | 0.686 | 0.402 | 1.294 | 0.005 |
| 1320 | 75465 | CGPG7599 | SENSE | 0.160 | 0.030 | 0.000 | 0.998 | 1.010 | 0.007 |
| 1318 | 75486 | CGPG7577 | SENSE | 0.361 | 0.024 | −0.046 | 0.172 | 1.009 | 0.008 |
| 1336 | 75618 | CGPG7801 | SENSE | 0.364 | 0.038 | 0.136 | 0.664 | 1.246 | 0.006 |
| 1339 | 75633 | CGPG7826 | SENSE | 0.325 | 0.010 | 0.100 | 0.609 | 0.948 | 0.024 |
| 1245 | 75876 | CGPG6996 | SENSE | 0.186 | 0.041 | −0.162 | 0.005 | 0.834 | 0.032 |
| 1393 | 75932 | CGPG8269 | SENSE | 0.379 | 0.000 | 0.377 | 0.333 | 0.836 | 0.008 |
| 1394 | 75956 | CGPG8271 | SENSE | 0.265 | 0.047 | 0.751 | 0.248 | 1.071 | 0.011 |
| 806 | 76049 | CGPG1568 | SENSE | 0.422 | 0.035 | 0.795 | 0.179 | 1.058 | 0.088 |
| 1125 | 76118 | CGPG5958 | SENSE | 0.248 | 0.032 | 0.316 | 0.503 | 0.921 | 0.002 |
| 1177 | 77725 | CGPG6364 | SENSE | 0.181 | 0.029 | 0.469 | 0.266 | 1.059 | 0.005 |
| 1003 | 78207 | CGPG4713 | SENSE | 0.330 | 0.039 | 0.578 | 0.488 | 1.079 | 0.006 |
| 1251 | 78377 | CGPG7075 | SENSE | 0.519 | 0.004 | 0.051 | 0.442 | 0.908 | 0.004 |
| 962 | 78970 | CGPG4248 | SENSE | 0.251 | 0.017 | 1.680 | 0.056 | 1.044 | 0.007 |

If p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference.

D. Salt Stress Tolerance Screen

This example sets forth the high salinity stress screen to identify *Arabidopsis* plants transformed with the gene of interest that are tolerant to high levels of salt based on their rate of development, root growth and chlorophyll accumulation under high salt conditions.

T2 seeds were plated on glufosinate selection plates containing 90 mM NaCl and grown under standard light and temperature conditions. All seedlings used in the experiment were grown at a temperature of 22° C. at day and 20° C. at night, a 16-hour photoperiod, an average light intensity of approximately 120 umol/m$^2$. On day 11, plants were measured for primary root length. After 3 more days of growth (day 14), plants were scored for transgenic status, primary root length, growth stage, visual color, and the seedlings were pooled for fresh weight measurement. A photograph of the whole plate was also taken on day 14.

The seedling weight and root length were analyzed as quantitative responses according to example 1M. The final growth stage at day 14 was scored as success if 50% of the plants reached 3 rosette leaves and size of leaves are greater than 1 mm (Boyes, D. C., et al., (2001), The Plant Cell 13, 1499/1510). The growth stage data was analyzed as a qualitative response according to example 1L. A list of recombinant DNA constructs that improve high salinity tolerance in transgenic plants illustrated in Table 6.

TABLE 6

| PEP SEQ ID | Construct ID | Root length at day 11 Delta mean | P-value | Root length at day 14 Delta mean | P-value | Growth stage at day 14 Delta mean | P-value | Seedling weight at day 14 Delta mean | P-value |
|---|---|---|---|---|---|---|---|---|---|
| 799 | 10192 | 0.372 | 0.009 | 0.330 | 0.001 | 0.915 | 0.033 | 0.668 | 0.005 |
| 772 | 11853 | 0.141 | 0.208 | 0.082 | 0.241 | — | — | 0.319 | 0.025 |
| 792 | 12766 | 0.317 | 0.048 | 0.253 | 0.112 | — | — | 0.360 | 0.006 |
| 1031 | 12772 | 0.150 | 0.111 | 0.178 | 0.014 | — | — | 0.223 | 0.175 |
| 761 | 13673 | 0.101 | 0.216 | 0.174 | 0.009 | 0.134 | 0.521 | 0.534 | 0.002 |
| 813 | 14341 | 0.490 | 0.012 | 0.487 | 0.014 | 2.561 | 0.007 | 1.051 | 0.025 |
| 835 | 14909 | 0.406 | 0.004 | 0.504 | 0.001 | 1.099 | 0.100 | 0.802 | 0.015 |
| 849 | 15627 | 0.168 | 0.123 | 0.208 | 0.000 | 0.735 | 0.500 | 0.512 | 0.089 |
| 796 | 15806 | 0.180 | 0.003 | 0.122 | 0.025 | — | — | −0.023 | 0.780 |
| 838 | 16553 | 0.229 | 0.004 | 0.243 | 0.016 | 0.399 | 0.157 | 0.552 | 0.104 |
| 854 | 17003 | 0.214 | 0.002 | 0.174 | 0.006 | 0.672 | 0.060 | 0.383 | 0.021 |
| 844 | 17014 | 0.080 | 0.200 | 0.182 | 0.080 | 0.912 | 0.283 | 0.468 | 0.022 |
| 870 | 17813 | 0.385 | 0.044 | 0.428 | 0.038 | 2.319 | 0.112 | 1.246 | 0.006 |
| 882 | 17930 | 0.330 | 0.021 | 0.224 | 0.102 | 0.860 | 0.133 | 0.414 | 0.009 |
| 922 | 18381 | 0.209 | 0.200 | 0.191 | 0.041 | 0.521 | 0.192 | 0.496 | 0.301 |

TABLE 6-continued

| PEP | | Root length at day 11 | | Root length at day 14 | | Growth stage at day 14 | | Seedling weight at day 14 | |
|---|---|---|---|---|---|---|---|---|---|
| SEQ ID | Construct ID | Delta mean | P-value | Delta mean | P-value | Delta mean | P-value | Delta mean | P-value |
| 919 | 18406 | 0.272 | 0.077 | 0.351 | 0.022 | 1.292 | 0.106 | 0.783 | 0.046 |
| 888 | 18418 | 0.203 | 0.070 | 0.186 | 0.014 | 0.031 | 0.823 | 0.086 | 0.365 |
| 883 | 18442 | 0.186 | 0.152 | 0.205 | 0.038 | 0.341 | 0.307 | 0.417 | 0.072 |
| 894 | 18874 | 0.238 | 0.058 | 0.182 | 0.278 | 0.854 | 0.044 | 0.462 | 0.026 |
| 895 | 18875 | 0.299 | 0.003 | 0.316 | 0.009 | 0.332 | 0.102 | 0.569 | 0.022 |
| 928 | 19312 | 0.309 | 0.066 | 0.293 | 0.008 | 0.549 | 0.025 | 0.475 | 0.024 |
| 892 | 19656 | 0.093 | 0.126 | 0.198 | 0.008 | 0.054 | 0.698 | 0.453 | 0.031 |
| 954 | 19927 | 0.454 | 0.033 | 0.401 | 0.018 | 0.887 | 0.023 | 0.499 | 0.013 |
| 946 | 19966 | 0.184 | 0.210 | 0.345 | 0.052 | 0.088 | 0.490 | 0.514 | 0.038 |
| 860 | 70123 | 0.175 | 0.019 | 0.119 | 0.026 | 0.367 | 0.171 | 0.335 | 0.026 |
| 1138 | 70243 | 0.347 | 0.036 | 0.386 | 0.026 | 0.479 | 0.331 | 0.551 | 0.007 |
| 937 | 70477 | 0.123 | 0.093 | 0.045 | 0.570 | 0.682 | 0.218 | 0.278 | 0.008 |
| 929 | 70538 | 0.455 | 0.003 | 0.356 | 0.006 | 1.166 | 0.321 | 0.598 | 0.005 |
| 963 | 71250 | 0.262 | 0.147 | 0.299 | 0.033 | 0.999 | 0.124 | 0.592 | 0.067 |
| 1050 | 72037 | 0.336 | 0.054 | 0.356 | 0.004 | 0.046 | 0.770 | 0.564 | 0.016 |
| 1071 | 72713 | 0.064 | 0.675 | 0.204 | 0.183 | 0.520 | 0.383 | 0.528 | 0.030 |
| 1093 | 73009 | 0.383 | 0.028 | 0.323 | 0.030 | 2.526 | 0.076 | 0.749 | 0.013 |
| 1102 | 73042 | 0.278 | 0.087 | 0.216 | 0.031 | 0.703 | 0.011 | 0.360 | 0.158 |
| 1097 | 73158 | 0.210 | 0.259 | 0.251 | 0.101 | 0.655 | 0.229 | 0.482 | 0.009 |
| 1086 | 73163 | 0.327 | 0.016 | 0.422 | 0.028 | 1.516 | 0.357 | 0.666 | 0.034 |
| 789 | 73333 | 0.024 | 0.728 | 0.012 | 0.855 | 0.380 | 0.191 | 0.400 | 0.032 |
| 1189 | 73436 | 0.340 | 0.106 | 0.315 | 0.016 | 3.045 | 0.086 | 0.697 | 0.055 |
| 1178 | 73437 | 0.232 | 0.100 | 0.268 | 0.030 | 0.239 | 0.433 | 0.157 | 0.592 |
| 1181 | 73452 | −0.026 | 0.593 | 0.238 | 0.029 | −0.028 | — | 0.345 | 0.274 |
| 1183 | 73454 | −0.072 | 0.456 | 0.020 | 0.863 | −0.307 | 0.041 | 0.337 | 0.026 |
| 1070 | 73932 | 0.191 | 0.068 | 0.254 | 0.058 | 2.253 | .0.125 | 0.524 | 0.006 |
| 1081 | 73979 | 0.323 | 0.014 | 0.241 | 0.207 | 1.728 | 0.066 | 0.957 | 0.000 |
| 1213 | 74172 | 0.235 | 0.015 | 0.261 | 0.024 | 0.476 | 0.513 | 0.276 | 0.567 |
| 1214 | 74184 | 0.183 | 0.139 | 0.193 | 0.049 | −0.143 | 0.317 | 0.308 | 0.305 |
| 899 | 74233 | — | — | — | — | — | — | 0.599 | 0.029 |
| 1068 | 74238 | 0.129 | 0.171 | 0.147 | 0.030 | 1.234 | 0.173 | 0.492 | 0.047 |
| 1063 | 74272 | 0.187 | 0.339 | 0.226 | 0.051 | 1.278 | 0.447 | 0.553 | 0.040 |
| 1140 | 74373 | 0.058 | 0.684 | 0.102 | 0.644 | 1.245 | 0.465 | 0.734 | 0.049 |
| 1220 | 74430 | 0.286 | 0.054 | 0.128 | 0.086 | 2.820 | 0.139 | 0.500 | 0.001 |
| 1218 | 74461 | 0.324 | 0.001 | 0.197 | 0.025 | −0.064 | 0.428 | 0.457 | 0.017 |
| 1141 | 74615 | 0.245 | 0.042 | 0.223 | 0.045 | 2.483 | 0.082 | 0.600 | 0.035 |
| 1149 | 74673 | 0.083 | 0.465 | 0.160 | 0.052 | −0.241 | 0.465 | 0.422 | 0.012 |
| 1175 | 74677 | 0.319 | 0.032 | 0.317 | 0.000 | 2.140 | 0.155 | 0.724 | 0.003 |
| 1113 | 74738 | −0.081 | 0.388 | −0.050 | 0.733 | 0.471 | 0.274 | 0.310 | 0.018. |
| 1275 | 74802 | 0.256 | 0.035 | 0.251 | 0.027 | 1.218 | 0.019 | 0.481 | 0.096 |
| 1279 | 74842 | 0.091 | 0.269 | 0.196 | 0.001 | 0.858 | 0.085 | 0.410 | 0.055 |
| 1281 | 74867 | 0.195 | 0.125 | 0.170 | 0.041 | −0.518 | 0.560 | −0.101 | 0.439 |
| 1299 | 74944 | — | — | — | — | — | — | 0.499 | 0.002 |
| 967 | 75205 | 0.195 | 0.114 | 0.210 | 0.085 | 0.941 | 0.098 | 0.458 | 0.010 |
| 1170 | 75292 | −0.056 | 0.658 | −0.086 | 0.593 | 1.203 | 0.180 | 0.380 | 0.026 |
| 1305 | 75388 | 0.263 | 0.028 | 0.305 | 0.006 | 1.879 | 0.037 | 0.655 | 0.027 |
| 1333 | 75617 | 0.352 | 0.044 | 0.366 | 0.025 | 0.878 | 0.179 | 0.854 | 0.010 |
| 1330 | 75663 | 0.151 | 0.148 | 0.147 | 0.044 | — | — | 0.251 | 0.102 |
| 1335 | 75665 | 0.468 | 0.009 | 0.276 | 0.109 | 0.302 | 0.052 | 0.779 | 0.001 |
| 1128 | 75810 | 0.238 | 0.058 | 0.230 | 0.002 | 1.794 | 0.286 | 0.599 | 0.006 |
| 1385 | 75903 | 0.198 | 0.104 | 0.176 | 0.049 | — | — | 0.171 | 0.401 |
| 1387 | 75916 | 0.318 | 0.041 | 0.360 | 0.049 | 0.819 | 0.245 | 0.677 | 0.015 |
| 1388 | 75917 | 0.391 | 0.012 | 0.428 | 0.006 | 0.269 | 0.200 | 0.861 | 0.013 |
| 1234 | 76548 | 0.237 | 0.051 | 0.266 | 0.014 | 0.385 | 0.336 | 0.680 | 0.049 |
| 1480 | 76975 | 0.216 | 0.114 | 0.198 | 0.001 | −0.162 | 0.362 | 0.316 | 0.061 |
| 1486 | 77151 | 0.181 | 0.001 | 0.235 | 0.017 | 0.641 | 0.099 | 0.365 | 0.034 |
| 1505 | 77229 | 0.265 | 0.226 | 0.338 | 0.088 | 1.988 | 0.005 | 1.093 | 0.003 |
| 1506 | 77241 | 0.039 | 0.795 | 0.038 | 0.632 | 0.903 | 0.388 | 0.350 | 0.038 |
| 1374 | 77361 | 0.271 | 0.000 | 0.232 | 0.156 | 0.508 | 0.273 | 0.238 | 0.016 |
| 1512 | 77428 | 0.355 | 0.005 | 0.429 | 0.012 | 1.455 | 0.381 | 0.800 | 0.042 |
| 1255 | 77528 | 0.284 | 0.126 | 0.254 | 0.031 | 0.608 | 0.368 | 0.753 | 0.087 |
| 1349 | 77545 | 0.469 | 0.004 | 0.324 | 0.072 | 0.283 | 0.300 | 0.652 | 0.022 |
| 1352 | 77556 | 0.068 | 0.597 | 0.017 | 0.884 | 1.080 | 0.379 | 0.320 | 0.044 |
| 1372 | 77590 | 0.342 | 0.026 | 0.250 | 0.145 | 2.393 | 0.019 | 0.549 | 0.039 |
| 1399 | 77627 | 0.192 | 0.005 | 0.146 | 0.011 | −0.147 | 0.734 | 0.275 | 0.025 |
| 1467 | 77831 | 0.299 | 0.087 | 0.332 | 0.062 | 3.081 | 0.079 | 0.774 | 0.006 |
| 1472 | 77838 | 0.301 | 0.041 | 0.296 | 0.005 | 0.121 | 0.423 | 1.151 | 0.258 |
| 1502 | 77854 | 0.131 | 0.183 | 0.205 | 0.082 | 0.341 | 0.470 | 0.419 | 0.036 |
| 1364 | 77926 | 0.232 | 0.030 | 0.219 | 0.049 | 2.642 | 0.061 | 0.321 | 0.089 |
| 1433 | 78055 | 0.244 | 0.007 | 0.393 | 0.011 | 1.371 | 0.410 | 0.634 | 0.024 |
| 1257 | 78106 | 0.276 | 0.017 | 0.327 | 0.003 | 2.062 | 0.024 | 0.900 | 0.001 |
| 830 | 78355 | 0.295 | 0.044 | 0.309 | 0.005 | 1.146 | 0.284 | 0.549 | 0.028 |
| 1067 | 78361 | 0.217 | 0.032 | 0.220 | 0.016 | 1.351 | 0.181 | 0.463 | 0.057 |

TABLE 6-continued

| PEP | | Root length at day 11 | | Root length at day 14 | | Growth stage at day 14 | | Seedling weight at day 14 | |
|---|---|---|---|---|---|---|---|---|---|
| SEQ ID | Construct ID | Delta mean | P-value | Delta mean | P-value | Delta mean | P-value | Delta mean | P-value |
| 1418 | 78540 | 0.116 | 0.039 | 0.166 | 0.021 | 1.290 | 0.473 | 0.170 | 0.191 |
| 1436 | 78553 | 0.236 | 0.083 | 0.190 | 0.016 | — | — | 0.219 | 0.253 |
| 965 | 78677 | 0.126 | 0.074 | 0.217 | 0.005 | — | — | 0.205 | 0.068 |
| 1254 | 78984 | 0.206 | 0.183 | 0.283 | 0.044 | — | — | 0.575 | 0.019 |

If $p<0.05$ and delta or risk score mean $>0$, the transgenic plants showed statistically significant trait enhancement as compared to the reference. If $p<0.2$ and delta or risk score mean $>0$, the transgenic plants showed a trend of trait enhancement as compared to the reference.

E. Polyethylene Glycol (PEG) Induced Osmotic Stress Tolerance Screen

There are numerous factors, which can influence seed germination and subsequent seedling growth, one being the availability of water. Genes, which can directly affect the success rate of germination and early seedling growth, are potentially useful agronomic traits for improving the germination and growth of crop plants under drought stress. In this assay, PEG was used to induce osmotic stress on germinating transgenic lines of *Arabiclopsis thaliana* seeds in order to screen for osmotically resistant seed lines.

T2 seeds were plated on BASTA selection plates containing 3% PEG and grown under standard light and temperature conditions. Seeds were plated on each plate containing 3% PEG, ½× MS salts, 1% phytagel, and 10 µg/ml glufosinate. Plates were placed at 4° C. for 3 days to stratify seeds. On day 11, plants were measured for primary root length. After 3 more days of growth, i.e., at day 14, plants were scored for transgenic status, primary root length, growth stage, visual color, and the seedlings were pooled for fresh weight measurement. A photograph of the whole plate was taken on day14.

Seedling weight and root length were analyzed as quantitative responses according to example 1 M. The final growth stage at day 14 was scored as success or failure based on whether the plants reached 3 rosette leaves and size of leaves are greater than 1 mm. The growth stage data was analyzed as a qualitative response according to example 1L. A list of recombinant DNA constructs that improve osmotic stress tolerance in transgenic plants illustrated in Table 7.

TABLE 7

| PEP | | Root length at day 11 | | Root length at day 14 | | Growth stage at day 14 | | Seedling weight at day 14 | |
|---|---|---|---|---|---|---|---|---|---|
| SEQ ID | Construct ID | Delta mean | P-value | Delta mean | P-value | Delta mean | P-value | Delta mean | P-value |
| 763 | 10174 | 0.193 | 0.202 | 0.148 | 0.120 | 0.926 | 0.610 | 0.228 | 0.043 |
| 1040 | 12773 | 0.142 | 0.020 | 0.138 | 0.086 | 3.109 | 0.073 | 0.465 | 0.020 |
| 835 | 14909 | 0.167 | 0.038 | 0.057 | 0.383 | 3.041 | 0.087 | 0.411 | 0.014 |
| 850 | 15409 | 0.017 | 0.742 | −0.042 | 0.706 | 1.533 | 0.369 | 0.299 | 0.014 |
| 844 | 17014 | 0.164 | 0.005 | 0.116 | 0.074 | 4.000 | 0.000 | 0.287 | 0.002 |
| 850 | 17201 | 0.305 | 0.041 | 0.290 | 0.023 | 2.929 | 0.112 | 0.122 | 0.441 |
| 903 | 18830 | 0.038 | 0.553 | −0.100 | 0.008 | 1.463 | 0.372 | 0.427 | 0.004 |
| 826 | 70401 | 0.041 | 0.558 | 0.025 | 0.833 | 3.230 | 0.052 | 0.281 | 0.033 |
| 840 | 70746 | — | — | — | — | — | — | 0.462 | 0.003 |
| 952 | 70902 | 0.268 | 0.064 | 0.276 | 0.021 | 4.000 | 0.000 | 0.510 | 0.013 |
| 955 | 70976 | 0.198 | 0.199 | 0.159 | 0.200 | — | — | 0.477 | 0.033 |
| 971 | 71839 | 0.269 | 0.008 | 0.185 | 0.019 | 1.178 | 0.506 | 0.108 | 0.316 |
| 1073 | 72678 | 0.373 | 0.087 | 0.404 | 0.027 | 2.998 | 0.096 | 0.188 | 0.527 |
| 1077 | 72755 | 0.206 | 0.089 | 0.132 | 0.048 | 4.000 | 0.000 | 0.397 | 0.136 |
| 1074 | 72765 | 0.169 | 0.040 | −0.006 | 0.836 | 4.000 | 0.000 | 0.335 | 0.008 |
| 1084 | 72960 | 0.111 | 0.065 | 0.197 | 0.050 | 3.068 | 0.081 | 0.243 | 0.110 |
| 1085 | 73021 | 0.364 | 0.011 | 0.300 | 0.018 | 4.000 | 0.000 | 0.758 | 0.023 |
| 1094 | 73109 | 0.261 | 0.045 | 0.202 | 0.004 | 4.000 | 0.000 | 0.344 | 0.027 |
| 1095 | 73121 | 0.503 | 0.003 | 0.508 | 0.013 | 4.000 | 0.000 | 0.713 | 0.029 |
| 1088 | 73188 | 0.298 | 0.109 | 0.539 | 0.048 | 3.140 | 0.067 | 0.860 | 0.029 |
| 1198 | 73545 | 0.115 | 0.037 | 0.110 | 0.275 | 4.000 | 0.000 | 0.378 | 0.023 |
| 1034 | 73676 | 0.169 | 0.005 | 0.130 | 0.118 | 4.000 | 0.000 | 0.405 | 0.008 |
| 1033 | 73861 | 0.055 | 0.321 | 0.009 | 0.777 | 0.510 | 0.151 | 0.203 | 0.036 |
| 1081 | 73979 | 0.274 | 0.063 | 0.249 | 0.202 | 4.000 | 0.000 | 0.325 | 0.017 |
| 1200 | 74138 | 0.146 | 0.006 | 0.141 | 0.008 | 2.512 | 0.233 | 0.080 | 0.734 |
| 1225 | 74495 | 0.091 | 0.636 | 0.294 | 0.028 | 2.352 | 0.290 | −0.029 | 0.911 |
| 1227 | 74514 | 0.181 | 0.342 | 0.219 | 0.232 | 4.000 | 0.000 | 0.441 | 0.036 |
| 1229 | 74552 | 0.238 | 0.100 | 0.177 | 0.092 | 3.055 | 0.084 | 0.261 | 0.005 |
| 1167 | 74674 | 0.196 | 0.073 | 0.289 | 0.008 | 2.780 | 0.150 | 0.261 | 0.138 |
| 1279 | 74842 | 0.012 | 0.920 | −0.027 | 0.757 | 4.000 | 0.000 | 0.281 | 0.021 |
| 1288 | 74985 | 0.401 | 0.014 | 0.421 | 0.036 | 2.179 | 0.139 | 0.756 | 0.041 |
| 1124 | 75238 | 0.176 | 0.226 | 0.123 | 0.362 | 4.000 | 0.000 | 0.364 | 0.040 |
| 1310 | 75343 | 0.216 | 0.078 | 0.465 | 0.025 | 1.251 | 0.464 | 0.420 | 0.005 |
| 1342 | 75750 | 0.161 | 0.266 | 0.216 | 0.094 | 4.000 | 0.000 | 0.281 | 0.004 |

TABLE 7-continued

| PEP SEQ ID | Construct ID | Root length at day 11 Delta mean | P-value | Root length at day 14 Delta mean | P-value | Growth stage at day 14 Delta mean | P-value | Seedling weight at day 14 Delta mean | P-value |
|---|---|---|---|---|---|---|---|---|---|
| 1340 | 75761 | 0.437 | 0.006 | 0.385 | 0.024 | 4.000 | 0.000 | 0.473 | 0.023 |
| 1391 | 75943 | 0.316 | 0.001 | 0.390 | 0.025 | 1.263 | 0.454 | −0.029 | 0.627 |
| 793 | 76025 | 0.356 | 0.074 | 0.309 | 0.076 | 2.832 | 0.136 | 0.519 | 0.019 |
| 1263 | 76166 | 0.179 | 0.190 | 0.003 | 0.894 | 0.470 | 0.590 | 0.397 | 0.038 |
| 1460 | 76362 | 0.153 | 0.302 | 0.174 | 0.385 | 2.051 | 0.403 | 0.746 | 0.043 |
| 1511 | 76402 | 0.224 | 0.153 | 0.215 | 0.192 | 4.000 | 0.000 | 0.448 | 0.006 |
| 1269 | 76572 | 0.256 | 0.026 | 0.289 | 0.106 | 2.708 | 0.171 | 0.294 | 0.031 |
| 1262 | 76755 | 0.245 | 0.141 | 0.153 | 0.143 | 1.174 | 0.493 | 0.299 | 0.043 |
| 1490 | 77154 | 0.208 | 0.114 | 0.215 | 0.043 | 4.000 | 0.000 | 0.403 | 0.060 |
| 1497 | 77192 | 0.075 | 0.400 | −0.036 | 0.402 | 4.000 | 0.000 | 0.559 | 0.009 |
| 1499 | 77193 | 0.256 | 0.116 | 0.207 | 0.141 | 3.235 | 0.052 | 0.498 | 0.041 |
| 1509 | 77293 | 0.424 | 0.034 | 0.280 | 0.106 | 2.931 | 0.111 | 0.609 | 0.002 |
| 1362 | 77337 | 0.182 | 0.077 | 0.109 | 0.098 | 4.000 | 0.000 | 0.571 | 0.032 |
| 1268 | 77533 | 0.143 | 0.089 | 0.146 | 0.002 | 1.381 | 0.404 | 0.257 | 0.030 |
| 1369 | 77586 | 0.227 | 0.020 | 0.160 | 0.138 | 3.298 | 0.042 | 0.723 | 0.014 |
| 1373 | 77592 | — | — | — | — | — | — | 0.397 | 0.014 |
| 1474 | 77834 | 0.180 | 0.025 | 0.211 | 0.009 | — | — | −0.019 | 0.787 |
| 1375 | 77934 | 0.179 | 0.081 | 0.183 | 0.327 | 0.556 | 0.316 | 0.349 | 0.003 |
| 1419 | 77993 | 0.074 | 0.395 | 0.131 | 0.147 | 1.394 | 0.406 | 0.380 | 0.004 |
| 1424 | 78018 | 0.192 | 0.073 | 0.135 | 0.014 | 0.322 | 0.626 | 0.284 | 0.096 |
| 1429 | 78032 | 0.142 | 0.010 | 0.099 | 0.050 | 4.000 | 0.000 | 0.266 | 0.049 |
| 1438 | 78060 | 0.235 | 0.207 | 0.381 | 0.030 | 1.696 | 0.325 | 0.285 | 0.327 |
| 1118 | 78113 | 0.122 | 0.032 | −0.106 | 0.179 | 2.732 | 0.164 | 0.353 | 0.002 |
| 1402 | 78141 | 0.119 | 0.497 | 0.152 | 0.349 | 2.567 | 0.215 | 0.202 | 0.033 |
| 1448 | 78185 | 0.283 | 0.048 | 0.344 | 0.079 | 4.000 | 0.000 | 0.513 | 0.000 |
| 1024 | 78341 | 0.148 | 0.031 | 0.270 | 0.010 | −0.914 | 0.129 | −0.182 | 0.172 |
| 1417 | 78537 | −0.001 | 0.988 | 0.191 | 0.014 | 1.801 | 0.499 | −0.171 | 0.287 |
| 974 | 78717 | −0.022 | 0.692 | 0.106 | 0.037 | 1.170 | 0.497 | 0.284 | 0.042 |
| 1164 | 78734 | 0.145 | 0.233 | 0.068 | 0.620 | 4.000 | 0.000 | 0.375 | 0.012 |

If $p<0.05$ and delta or risk score mean $>0$, the transgenic plants showed statistically significant trait enhancement as compared to the reference.

If $p<0.2$ and delta or risk score mean $>0$, the transgenic plants showed a trend of trait enhancement as compared to the reference.

F. Cold Shock Tolerance Screen

This example set forth a screen to identify *Arabidopsis* plants transformed with the genes of interest that are more tolerant to cold stress subjected during day 8 to day 28 after seed planting. During these crucial early stages, seedling growth and leaf area increase were measured to assess tolerance when *Arabidopsis* seedlings were exposed to low temperatures. Using this screen, genetic alterations can be found that enable plants to germinate and grow better than wild type plants under sudden exposure to low temperatures.

Eleven seedlings from T2 seeds of each transgenic line plus one control line were plated together on a plate containing ½× Gamborg Salts with 0.8 Phytagel™, 1% Phytagel, and 0.3% Sucrose. Plates were then oriented horizontally and stratified for three days at 4° C. At day three, plates were removed from stratification and exposed to standard conditions (16 hr photoperiod, 22° C. at day and 20° C. at night) until day 8. At day eight, plates were removed from standard conditions and exposed to cold shock conditions (24 hr photoperiod, 8° C. at both day and night) until the final day of the assay, i.e., day 28. Rosette areas were measured to at day 8 and day 28, which were analyzed as quantitative responses according to example 1M. A list of recombinant nucleotides that improve cold shock stress tolerance in plants illustrated in Table 8.

TABLE 8

| PEP SEQ ID | Construct ID | Orientation | Rosette area at day 8 Delta mean | P-value | Rosette area at day 28 Risk score mean | P-value | Rosette area difference Delta mean | P-value |
|---|---|---|---|---|---|---|---|---|
| 943 | 10366 | ANTI-SENSE | 0.361 | 0.009 | 0.569 | 0.038 | 0.588 | 0.036 |
| 1518 | 12365 | SENSE | −0.114 | 0.771 | 0.663 | 0.009 | 0.717 | 0.008 |
| 939 | 12601 | SENSE | −0.240 | 0.390 | 0.612 | 0.034 | 1.531 | 0.003 |
| 781 | 12714 | ANTI-SENSE | 0.818 | 0.064 | 0.896 | 0.025 | 0.901 | 0.016 |
| 850 | 15409 | ANTI-SENSE | 0.637 | 0.157 | 0.426 | 0.220 | 0.615 | 0.050 |
| 851 | 15903 | ANTI-SENSE | −0.276 | 0.592 | 0.287 | 0.041 | 0.247 | 0.102 |
| 842 | 15966 | ANTI-SENSE | 0.140 | 0.650 | 0.282 | 0.015 | 0.297 | 0.003 |
| 915 | 18403 | SENSE | 0.366 | 0.197 | 0.729 | 0.007 | 0.785 | 0.004 |
| 888 | 18418 | SENSE | −0.236 | 0.125 | 0.379 | 0.023 | 0.366 | 0.026 |
| 924 | 18720 | SENSE | 0.620 | 0.144 | 0.740 | 0.015 | 0.659 | 0.014 |

TABLE 8-continued

| PEP SEQ ID | Construct ID | Orientation | Rosette area at day 8 | | Rosette area at day 28 Risk | | Rosette area difference | |
|---|---|---|---|---|---|---|---|---|
| | | | Delta mean | P-value | score mean | P-value | Delta mean | P-value |
| 948 | 19906 | SENSE | 0.788 | 0.005 | 0.635 | 0.030 | 0.560 | 0.039 |
| 860 | 70123 | SENSE | 0.556 | 0.114 | 0.968 | 0.067 | 1.245 | 0.028 |
| 908 | 70415 | SENSE | 0.334 | 0.147 | 0.763 | 0.009 | 0.977 | 0.023 |
| 930 | 70440 | SENSE | −0.175 | 0.249 | 0.541 | 0.049 | 0.622 | 0.067 |
| 817 | 70748 | ANTI-SENSE | 0.503 | 0.075 | 0.700 | 0.048 | 0.527 | 0.116 |
| 1150 | 70824 | SENSE | −0.134 | 0.679 | 0.829 | 0.002 | 0.921 | 0.011 |
| 989 | 71347 | SENSE | −0.346 | 0.381 | 0.401 | 0.003 | 0.412 | 0.014 |
| 1053 | 72007 | SENSE | 0.161 | 0.573 | 1.180 | 0.026 | 1.302 | 0.042 |
| 1056 | 72022 | SENSE | 0.976 | 0.025 | 1.051 | 0.001 | 1.124 | 0.002 |
| 1059 | 72138 | SENSE | 0.486 | 0.009 | 0.817 | 0.005 | 0.669 | 0.000 |
| 994 | 72469 | SENSE | 0.335 | 0.300 | 0.767 | 0.025 | 0.948 | 0.023 |
| 1007 | 72526 | SENSE | 0.323 | 0.223 | 0.413 | 0.003 | 0.505 | 0.002 |
| 1076 | 72707 | SENSE | 0.146 | 0.596 | 0.396 | 0.012 | 0.400 | 0.074 |
| 1089 | 73153 | SENSE | 0.728 | 0.031 | 0.290 | 0.044 | 0.311 | 0.047 |
| 1101 | 73171 | SENSE | 0.333 | 0.336 | 0.320 | 0.059 | 0.378 | 0.038 |
| 1087 | 73187 | SENSE | 0.454 | 0.037 | 0.492 | 0.008 | 0.460 | 0.003 |
| 1182 | 73453 | SENSE | 0.672 | 0.013 | 0.708 | 0.010 | 0.879 | 0.004 |
| 1012 | 73686 | SENSE | 0.704 | 0.040 | 0.906 | 0.000 | 0.888 | 0.000 |
| 1090 | 73983 | SENSE | −0.071 | 0.867 | 0.431 | 0.004 | 0.286 | 0.037 |
| 1036 | 74218 | SENSE | 0.002 | 0.993 | 0.294 | 0.020 | 0.089 | 0.625 |
| 1276 | 74851 | SENSE | 0.626 | 0.184 | 0.917 | 0.074 | 1.028 | 0.033 |
| 1277 | 74864 | SENSE | 0.879 | 0.041 | 0.742 | 0.031 | 0.752 | 0.044 |
| 1302 | 75374 | SENSE | 0.278 | 0.273 | 2.374 | 0.016 | 2.950 | 0.013 |
| 1307 | 75377 | SENSE | −0.307 | 0.316 | 0.085 | 0.166 | 0.212 | 0.009 |
| 1331 | 75616 | SENSE | 0.399 | 0.473 | 0.807 | 0.022 | 1.015 | 0.015 |
| 1392 | 75967 | SENSE | 0.714 | 0.027 | 1.588 | 0.007 | 1.793 | 0.006 |
| 1458 | 76314 | SENSE | 0.420 | 0.049 | 0.787 | 0.004 | 0.970 | 0.002 |
| 1459 | 76326 | SENSE | 0.232 | 0.383 | 0.894 | 0.018 | 0.930 | 0.034 |
| 1462 | 76377 | SENSE | 0.263 | 0.137 | 0.254 | 0.014 | 0.227 | 0.435 |
| 1511 | 76402 | SENSE | −0.265 | 0.435 | 0.402 | 0.024 | 0.490 | 0.046 |
| 1065 | 76709 | SENSE | −0.566 | 0.063 | 0.091 | 0.110 | 0.250 | 0.016 |
| 1488 | 77105 | SENSE | 0.954 | 0.016 | 0.817 | 0.015 | 0.925 | 0.011 |
| 1494 | 77144 | SENSE | 0.163 | 0.523 | 0.946 | 0.003 | 0.906 | 0.000 |
| 1374 | 77361 | SENSE | 0.595 | 0.065 | 1.056 | 0.006 | 1.207 | 0.016 |
| 1510 | 77473 | SENSE | −0.048 | 0.732 | 0.170 | 0.019 | 0.091 | 0.057 |
| 1238 | 77522 | SENSE | 0.132 | 0.616 | 1.709 | 0.011 | 2.008 | 0.009 |
| 1351 | 77552 | SENSE | 1.221 | 0.028 | 1.687 | 0.004 | 1.900 | 0.004 |
| 1106 | 77723 | SENSE | 0.342 | 0.151 | 0.100 | 0.051 | 0.141 | 0.037 |
| 1485 | 77852 | SENSE | 0.236 | 0.151 | 0.416 | 0.197 | 0.587 | 0.040 |
| 891 | 77909 | SENSE | 0.722 | 0.034 | 1.330 | 0.003 | 1.285 | 0.010 |
| 1363 | 77924 | SENSE | 0.547 | 0.057 | 0.480 | 0.017 | 0.576 | 0.016 |
| 1354 | 77957 | SENSE | 0.417 | 0.256 | 0.930 | 0.026 | 0.827 | 0.013 |
| 1411 | 77974 | SENSE | 0.512 | 0.030 | 1.175 | 0.013 | 1.036 | 0.013 |
| 1425 | 78021 | SENSE | 0.391 | 0.250 | 0.460 | 0.005 | 0.532 | 0.009 |
| 1434 | 78057 | SENSE | 0.086 | 0.766 | 0.534 | 0.007 | 0.588 | 0.013 |
| 1344 | 78129 | SENSE | 1.189 | 0.001 | 0.613 | 0.030 | 0.599 | 0.111 |
| 1426 | 78158 | SENSE | 1.261 | 0.005 | 0.732 | 0.001 | 1.040 | 0.016 |
| 1002 | 78202 | SENSE | 0.842 | 0.004 | 0.835 | 0.000 | 0.865 | 0.000 |
| 1326 | 78233 | SENSE | 0.162 | 0.477 | 0.771 | 0.013 | 0.822 | 0.007 |
| 1172 | 78367 | SENSE | −0.153 | 0.668 | 0.522 | 0.047 | 0.514 | 0.068 |
| 1408 | 78530 | SENSE | 2.039 | 0.005 | 2.026 | 0.002 | 2.244 | 0.002 |
| 1381 | 78905 | SENSE | 0.615 | 0.181 | 0.863 | 0.007 | 0.925 | 0.007 |
| 1447 | 78932 | SENSE | 0.472 | 0.046 | 0.626 | 0.027 | 0.715 | 0.030 |

If p<0.05 and delta or risk score mean >0, the transgenic plants showed statistically significant trait enhancement as compared to the reference (p value, of the delta of a quantitative response or of the risk score of a qualitative response, is the probability that the observed difference between the transgenic plants and the reference occur by chance) If p<0.2 and delta or risk score mean >0, the transgenic plants showed a trend of trait enhancement as compared to the reference.

G. Cold Germination Tolerance Screen

This example sets forth a screen to identify *Arabidopsis* plants transformed with the genes of interests are resistant to cold stress based on their rate of development, root growth and chlorophyll accumulation under low temperature conditions.

T2 seeds were plated and all seedlings used in the experiment were grown at 8° C. Seeds were first surface disinfested using chlorine gas and then seeded on assay plates containing an aqueous solution of ½× Garnborg's B/5 Basal Salt Mixture (Sigma/Aldrich Corp., St. Louis, Mo., USA G/5788), 1% Phytagel™ (Sigma-Aldrich, P-8169), and 10 ug/ml glufosinate with the final pH adjusted to 5.8 using KOH. Test plates were held vertically for 28 days at a constant temperature of 8° C., a photoperiod of 16 hr, and average light intensity of approximately 100 umol/m²/s. At 28 days post plating, root length was measured, growth stage was observed, the visual color was assessed, and a whole plate photograph was taken.

The root length at day 28 was analyzed as a quantitative response according to example 1M. The growth stage at day 7 was analyzed as a qualitative response according to example 1L. A list of recombinant DNA constructs that improve cold stress tolerance in transgenic plants illustrated in Table 9.

TABLE 9

| PEP SEQ ID | Construct ID | Nomination ID | Orientation | Root length at day 28 | | Growth stage at day 28 | |
|---|---|---|---|---|---|---|---|
| | | | | Delta-mean | P-value | Delta mean | P-value |
| 799 | 10192 | CGPG146 | ANTI-SENSE | 0.461 | 0.094 | 4.000 | 0.000 |
| 1517 | 12276 | CGPG967 | ANTI-SENSE | 0.203 | 0.217 | 4.000 | 0.000 |
| 835 | 14909 | CGPG2005 | ANTI-SENSE | 0.311 | 0.005 | 4.000 | 0.000 |
| 828 | 15126 | CGPG1929 | SENSE | 0.216 | 0.016 | 4.000 | 0.000 |
| 829 | 15628 | CGPG1938 | ANTI-SENSE | 0.132 | 0.205 | 4.000 | 0.000 |
| 846 | 16208 | CGPG2148 | SENSE | −0.068 | 0.734 | 4.000 | 0.000 |
| 864 | 17402 | CGPG2426 | SENSE | 0.105 | 0.581 | 4.000 | 0.000 |
| 780 | 18011 | CGPG126 | SENSE | −0.248 | 0.184 | 4.000 | 0.000 |
| 812 | 18116 | CGPG1656 | ANTI-SENSE | −0.231 | 0.358 | 4.000 | 0.000 |
| 905 | 18226 | CGPG3269 | SENSE | 0.196 | 0.313 | 4.000 | 0.000 |
| 887 | 18415 | CGPG3004 | SENSE | −0.024 | 0.845 | 4.000 | 0.000 |
| 901 | 18827 | CGPG3248 | SENSE | 0.023 | 0.845 | 4.000 | 0.000 |
| 889 | 19532 | CGPG3030 | SENSE | 0.332 | 0.044 | 4.000 | 0.000 |
| 912 | 19608 | CGPG3400 | SENSE | −0.053 | 0.705 | 4.000 | 0.000 |
| 892 | 19656 | CGPG3084 | SENSE | 0.037 | 0.746 | 4.000 | 0.000 |
| 951 | 19746 | CGPG4099 | SENSE | 0.328 | 0.209 | 4.000 | 0.000 |
| 940 | 19747 | CGPG3931 | SENSE | −0.008 | 0.938 | 4.000 | 0.000 |
| 950 | 19802 | CGPG4071 | SENSE | 0.150 | 0.602 | 4.000 | 0.000 |
| 954 | 19927 | CGPG4153 | SENSE | — | — | 4.000 | 0.000 |
| 1168 | 70225 | CGPG63 | SENSE | 0.291 | 0.006 | 4.000 | 0.000 |
| 816 | 70240 | CGPG177 | SENSE | 0.033 | 0.755 | 4.000 | 0.000 |
| 932 | 70443 | CGPG3724 | SENSE | −0.087 | 0.321 | 4.000 | 0.000 |
| 831 | 70560 | CGPG1964 | SENSE | 0.401 | 0.128 | 4.000 | 0.000 |
| 818 | 70807 | CGPG182 | SENSE | 0.200 | 0.055 | 4.000 | 0.000 |
| 985 | 70834 | CGPG445 | SENSE | −0.300 | 0.322 | 4.000 | 0.000 |
| 871 | 70845 | CGPG253 | SENSE | 0.094 | 0.290 | 4.000 | 0.000 |
| 944 | 70935 | CGPG3975 | SENSE | −0.087 | 0.236 | 4.000 | 0.000 |
| 942 | 70965 | CGPG3964 | SENSE | 0.318 | 0.030 | 4.000 | 0.000 |
| 956 | 71440 | CGPG4169 | SENSE | 0.046 | 0.154 | 4.000 | 0.000 |
| 999 | 71638 | CGPG4691 | SENSE | 0.362 | 0.225 | 4.000 | 0.000 |
| 1049 | 72025 | CGPG5223 | SENSE | — | — | 4.000 | 0.000 |
| 1057 | 72096 | CGPG5304 | SENSE | — | — | 4.000 | 0.000 |
| 1005 | 72457 | CGPG4747 | SENSE | −0.010 | 0.907 | 4.000 | 0.000 |
| 1008 | 72531 | CGPG4779 | SENSE | 0.062 | 0.704 | 4.000 | 0.000 |
| 910 | 72606 | CGPG3361 | SENSE | 0.133 | 0.315 | 4.000 | 0.000 |
| 1075 | 72730 | CGPG5546 | SENSE | 0.179 | 0.134 | 4.000 | 0.000 |
| 1100 | 73005 | CGPG5732 | SENSE | — | — | 4.000 | 0.000 |
| 1085 | 73021 | CGPG5642 | SENSE | 0.110 | 0.531 | 4.000 | 0.000 |
| 1107 | 73048 | CGPG5797 | SENSE | — | — | 4.000 | 0.000 |
| 1103 | 73067 | CGPG5771 | SENSE | −0.244 | 0.395 | 4.000 | 0.000 |
| 1104 | 73148 | CGPG5778 | SENSE | 0.211 | 0.260 | 4.000 | 0.000 |
| 1096 | 73157 | CGPG5715 | SENSE | 0.168 | 0.440 | 4.000 | 0.000 |
| 1086 | 73163 | CGPG5644 | SENSE | 0.327 | 0.003 | 4.000 | 0.000 |
| 884 | 73207 | CGPG2874 | SENSE | −0.185 | 0.626 | 4.000 | 0.000 |
| 986 | 73215 | CGPG4453 | SENSE | 0.433 | 0.010 | 4.000 | 0.000 |
| 1016 | 73230 | CGPG4949 | SENSE | 0.273 | 0.150 | 4.000 | 0.000 |
| 1039 | 73251 | CGPG5186 | SENSE | 0.061 | 0.636 | 4.000 | 0.000 |
| 1041 | 73254 | CGPG5190 | SENSE | 0.205 | 0.018 | 4.000 | 0.000 |
| 1030 | 73313 | CGPG5097 | SENSE | 0.638 | 0.006 | 3.090 | 0.077 |
| 1187 | 73434 | CGPG6437 | SENSE | 0.116 | 0.345 | 4.000 | 0.000 |
| 1179 | 73450 | CGPG6375 | SENSE | 0.174 | 0.250 | 4.000 | 0.000 |
| 1186 | 73469 | CGPG6432 | SENSE | — | — | 4.000 | 0.000 |
| 1188 | 73471 | CGPG6445 | SENSE | −0.101 | 0.604 | 4.000 | 0.000 |
| 1184 | 73491 | CGPG6418 | SENSE | 0.061 | 0.230 | 4.000 | 0.000 |
| 1193 | 73519 | CGPG6505 | SENSE | 0.118 | 0.064 | 4.000 | 0.000 |
| 1194 | 73543 | CGPG6507 | SENSE | 0.219 | 0.385 | 4.000 | 0.000 |
| 1195 | 73567 | CGPG6509 | SENSE | 0.371 | 0.101 | 4.000 | 0.000 |
| 833 | 73602 | CGPG1977 | SENSE | −0.037 | 0.762 | 4.000 | 0.000 |
| 1006 | 73639 | CGPG4755 | SENSE | 0.035 | 0.724 | 4.000 | 0.000 |
| 865 | 73707 | CGPG2433 | SENSE | 0.149 | 0.133 | 4.000 | 0.000 |
| 1010 | 73722 | CGPG4879 | SENSE | 0.022 | 0.763 | 4.000 | 0.000 |
| 1038 | 73731 | CGPG5161 | SENSE | 0.050 | 0.825 | 3.321 | 0.039 |
| 808 | 73927 | CGPG1619 | SENSE | 0.083 | 0.050 | 4.000 | 0.000 |
| 811 | 73948 | CGPG1651 | SENSE | 0.203 | 0.154 | 4.000 | 0.000 |
| 995 | 73951 | CGPG4660 | SENSE | 0.220 | 0.104 | 4.000 | 0.000 |
| 1209 | 74170 | CGPG6619 | SENSE | −0.054 | 0.750 | 4.000 | 0.000 |
| 1207 | 74179 | CGPG6596 | SENSE | 0.258 | 0.237 | 4.000 | 0.000 |
| 1214 | 74184 | CGPG6636 | SENSE | 0.415 | 0.000 | 4.000 | 0.000 |

TABLE 9-continued

| PEP SEQ ID | Construct ID | Nomination ID | Orientation | Root length at day 28 Delta-mean | P-value | Growth stage at day 28 Delta mean | P-value |
|---|---|---|---|---|---|---|---|
| 1201 | 74186 | CGPG6557 | SENSE | −0.426 | 0.017 | 4.000 | 0.000 |
| 916 | 74206 | CGPG3465 | SENSE | 0.346 | 0.088 | 4.000 | 0.000 |
| 1045 | 74231 | CGPG5211 | SENSE | 0.191 | 0.235 | 4.000 | 0.000 |
| 1061 | 74264 | CGPG5355 | SENSE | — | — | 4.000 | 0.000 |
| 1062 | 74271 | CGPG5376 | SENSE | 0.390 | 0.096 | 4.000 | 0.000 |
| 1140 | 74373 | CGPG6082 | SENSE | — | — | 4.000 | 0.000 |
| 1223 | 74434 | CGPG6729 | SENSE | −0.073 | 0.551 | 4.000 | 0.000 |
| 1228 | 74515 | CGPG6768 | SENSE | 0.333 | 0.170 | 4.000 | 0.000 |
| 1231 | 74519 | CGPG6800 | SENSE | 0.245 | 0.075 | 4.000 | 0.000 |
| 1230 | 74529 | CGPG6785 | SENSE | 0.186 | 0.034 | 4.000 | 0.000 |
| 876 | 74535 | CGPG268 | SENSE | 0.085 | 0.201 | 4.000 | 0.000 |
| 857 | 74567 | CGPG2349 | SENSE | 0.223 | 0.189 | 4.000 | 0.000 |
| 1215 | 74582 | CGPG6641 | SENSE | — | — | 4.000 | 0.000 |
| 1216 | 74584 | CGPG6642 | SENSE | 0.065 | 0.795 | 4.000 | 0.000 |
| 1146 | 74656 | CGPG6172 | SENSE | 0.225 | 0.005 | 4.000 | 0.000 |
| 1148 | 74659 | CGPG6176 | SENSE | −0.112 | 0.271 | 4.000 | 0.000 |
| 1015 | 74715 | CGPG4937 | SENSE | 0.167 | 0.043 | 4.000 | 0.000 |
| 1116 | 74739 | CGPG5889 | SENSE | 0.154 | 0.356 | 4.000 | 0.000 |
| 1285 | 74845 | CGPG7362 | SENSE | 0.248 | 0.021 | 4.000 | 0.000 |
| 1287 | 74859 | CGPG7379 | SENSE | 0.331 | 0.115 | 4.000 | 0.000 |
| 1294 | 74917 | CGPG7424 | SENSE | 0.028 | 0.885 | 4.000 | 0.000 |
| 1292 | 74928 | CGPG7417 | SENSE | 0.227 | 0.263 | 4.000 | 0.000 |
| 1298 | 74932 | CGPG7449 | SENSE | 0.053 | 0.562 | 4.000 | 0.000 |
| 1297 | 74955 | CGPG7443 | SENSE | 0.232 | 0.010 | 4.000 | 0.000 |
| 1290 | 74962 | CGPG7404 | SENSE | 0.194 | 0.433 | 4.000 | 0.000 |
| 1300 | 74968 | CGPG7452 | SENSE | 0.184 | 0.204 | 4.000 | 0.000 |
| 1295 | 74989 | CGPG7430 | SENSE | 0.098 | 0.494 | 4.000 | 0.000 |
| 1066 | 75002 | CGPG539 | SENSE | 0.529 | 0.001 | 4.000 | 0.000 |
| 1129 | 75094 | CGPG5994 | SENSE | 0.087 | 0.017 | 4.000 | 0.000 |
| 839 | 75221 | CGPG2065 | SENSE | 0.447 | 0.028 | 4.000 | 0.000 |
| 1114 | 75225 | CGPG5868 | SENSE | −0.063 | 0.602 | 4.000 | 0.000 |
| 1119 | 75233 | CGPG5914 | SENSE | — | — | 4.000 | 0.000 |
| 1126 | 75243 | CGPG5977 | SENSE | 0.298 | 0.017 | 4.000 | 0.000 |
| 1165 | 75274 | CGPG6267 | SENSE | −0.038 | 0.744 | 4.000 | 0.000 |
| 1169 | 75291 | CGPG6311 | SENSE | −0.095 | 0.371 | 4.000 | 0.000 |
| 1309 | 75331 | CGPG7516 | SENSE | −0.336 | 0.022 | 4.000 | 0.000 |
| 1316 | 75335 | CGPG7548 | SENSE | −0.059 | 0.778 | 4.000 | 0.000 |
| 1310 | 75343 | CGPG7517 | SENSE | 0.098 | 0.652 | 4.000 | 0.000 |
| 1303 | 75386 | CGPG7481 | SENSE | 0.463 | 0.072 | 4.000 | 0.000 |
| 1315 | 75393 | CGPG7537 | SENSE | −0.122 | 0.605 | 4.000 | 0.000 |
| 1322 | 75442 | CGPG7605 | SENSE | 0.183 | 0.133 | 4.000 | 0.000 |
| 1319 | 75452 | CGPG7590 | SENSE | 0.554 | 0.054 | 4.000 | 0.000 |
| 1317 | 75462 | CGPG7575 | SENSE | 0.244 | 0.345 | 4.000 | 0.000 |
| 1323 | 75466 | CGPG7607 | SENSE | 0.028 | 0.042 | 4.000 | 0.000 |
| 1325 | 75481 | CGPG7632 | SENSE | 0.110 | 0.284 | 4.000 | 0.000 |
| 1341 | 75785 | CGPG7863 | SENSE | −0.038 | 0.826 | 4.000 | 0.000 |
| 1162 | 75814 | CGPG6243 | SENSE | 0.008 | 0.952 | 4.000 | 0.000 |
| 1130 | 75818 | CGPG5996 | SENSE | 0.050 | 0.550 | 4.000 | 0.000 |
| 1236 | 75856 | CGPG6920 | SENSE | 0.118 | 0.579 | 4.000 | 0.000 |
| 1246 | 75878 | CGPG7002 | SENSE | 0.182 | 0.165 | 4.000 | 0.000 |
| 1252 | 75896 | CGPG7080 | SENSE | — | — | 4.000 | 0.000 |
| 1386 | 75904 | CGPG8235 | SENSE | 0.089 | 0.730 | 4.000 | 0.000 |
| 1393 | 75932 | CGPG8269 | SENSE | 0.567 | 0.067 | 4.000 | 0.000 |
| 788 | 75935 | CGPG1335 | SENSE | 0.306 | 0.098 | 4.000 | 0.000 |
| 862 | 75936 | CGPG2397 | SENSE | 0.212 | 0.090 | 4.000 | 0.000 |
| 1389 | 75942 | CGPG8254 | SENSE | 0.038 | 0.373 | 4.000 | 0.000 |
| 1391 | 75943 | CGPG8262 | SENSE | 0.121 | 0.566 | 4.000 | 0.000 |
| 1390 | 75954 | CGPG8255 | SENSE | 0.215 | 0.436 | 4.000 | 0.000 |
| 856 | 76041 | CGPG2348 | SENSE | 0.362 | 0.096 | 4.000 | 0.000 |
| 1241 | 76275 | CGPG6946 | SENSE | −0.079 | 0.533 | 4.000 | 0.000 |
| 1137 | 76610 | CGPG6069 | SENSE | 0.521 | 0.112 | 4.000 | 0.000 |
| 1475 | 76823 | CGPG9060 | SENSE | 0.068 | 0.707 | 4.000 | 0.000 |
| 1482 | 76953 | CGPG9111 | SENSE | −0.271 | 0.139 | 4.000 | 0.000 |
| 820 | 77005 | CGPG1873 | SENSE | 0.235 | 0.102 | 4.000 | 0.000 |
| 1121 | 77008 | CGPG5925 | SENSE | 0.076 | 0.709 | 4.000 | 0.000 |
| 1163 | 77016 | CGPG6248 | SENSE | 0.121 | 0.325 | 4.000 | 0.000 |
| 1492 | 77107 | CGPG9166 | SENSE | 0.036 | 0.900 | 4.000 | 0.000 |
| 1489 | 77129 | CGPG9152 | SENSE | 0.198 | 0.069 | 4.000 | 0.000 |
| 1495 | 77156 | CGPG9178 | SENSE | 0.440 | 0.110 | 4.000 | 0.000 |
| 1484 | 77161 | CGPG9123 | SENSE | 0.265 | 0.223 | 4.000 | 0.000 |
| 1505 | 77229 | CGPG9248 | SENSE | −0.024 | 0.810 | 4.000 | 0.000 |
| 1508 | 77233 | CGPG9280 | SENSE | 0.451 | 0.020 | 4.000 | 0.000 |
| 1503 | 77287 | CGPG9237 | SENSE | 0.249 | 0.157 | 4.000 | 0.000 |
| 1174 | 77319 | CGPG6349 | SENSE | −0.144 | 0.485 | 4.000 | 0.000 |

TABLE 9-continued

| PEP SEQ ID | Construct ID | Nomination ID | Orientation | Root length at day 28 Delta-mean | Root length at day 28 P-value | Growth stage at day 28 Delta mean | Growth stage at day 28 P-value |
|---|---|---|---|---|---|---|---|
| 1122 | 77321 | CGPG5926 | SENSE | −0.241 | 0.172 | 4.000 | 0.000 |
| 1366 | 77346 | CGPG8076 | SENSE | 0.001 | 0.993 | 4.000 | 0.000 |
| 1367 | 77350 | CGPG8084 | SENSE | −0.221 | 0.300 | 4.000 | 0.000 |
| 1376 | 77367 | CGPG8157 | SENSE | 0.130 | 0.228 | 4.000 | 0.000 |
| 1378 | 77370 | CGPG8165 | SENSE | −0.114 | 0.477 | 4.000 | 0.000 |
| 1513 | 77429 | CGPG9315 | SENSE | 0.336 | 0.042 | 4.000 | 0.000 |
| 1239 | 77516 | CGPG6934 | SENSE | 0.452 | 0.002 | 1.413 | 0.409 |
| 1248 | 77525 | CGPG7021 | SENSE | 0.450 | 0.038 | 4.000 | 0.000 |
| 1253 | 77527 | CGPG7094 | SENSE | 0.300 | 0.045 | 4.000 | 0.000 |
| 1261 | 77530 | CGPG7166 | SENSE | −0.031 | 0.790 | 4.000 | 0.000 |
| 925 | 77537 | CGPG3631 | SENSE | 0.167 | 0.539 | 4.000 | 0.000 |
| 1353 | 77559 | CGPG7967 | SENSE | −0.205 | 0.278 | 4.000 | 0.000 |
| 945 | 77717 | CGPG3983 | SENSE | 0.147 | 0.350 | 4.000 | 0.000 |
| 1106 | 77723 | CGPG5785 | SENSE | −0.078 | 0.573 | 4.000 | 0.000 |
| 1358 | 77920 | CGPG8023 | SENSE | — | — | 4.000 | 0.000 |
| 1368 | 77929 | CGPG8093 | SENSE | 0.445 | 0.031 | 4.000 | 0.000 |
| 1371 | 77930 | CGPG8097 | SENSE | 0.039 | 0.737 | 4.000 | 0.000 |
| 1360 | 77961 | CGPG8038 | SENSE | 0.218 | 0.019 | 4.000 | 0.000 |
| 1365 | 77964 | CGPG8073 | SENSE | 0.270 | 0.022 | 2.762 | 0.156 |
| 1415 | 77975 | CGPG8474 | SENSE | 0.116 | 0.035 | 1.333 | 0.423 |
| 1422 | 78014 | CGPG8544 | SENSE | 0.415 | 0.030 | 4.000 | 0.000 |
| 1423 | 78015 | CGPG8546 | SENSE | 0.157 | 0.597 | 4.000 | 0.000 |
| 1428 | 78028 | CGPG8573 | SENSE | 0.238 | 0.346 | 4.000 | 0.000 |
| 1432 | 78047 | CGPG8611 | SENSE | — | — | 4.000 | 0.000 |
| 1435 | 78059 | CGPG8634 | SENSE | −0.009 | 0.947 | 4.000 | 0.000 |
| 1439 | 78062 | CGPG8642 | SENSE | −0.034 | 0.909 | 4.000 | 0.000 |
| 1440 | 78065 | CGPG8646 | SENSE | 0.004 | 0.782 | 4.000 | 0.000 |
| 1176 | 78109 | CGPG6353 | SENSE | 0.198 | 0.277 | 4.000 | 0.000 |
| 1274 | 78112 | CGPG7291 | SENSE | −0.173 | 0.212 | 4.000 | 0.000 |
| 1379 | 78117 | CGPG8169 | SENSE | 0.319 | 0.051 | 4.000 | 0.000 |
| 1398 | 78136 | CGPG8344 | SENSE | 0.410 | 0.030 | 4.000 | 0.000 |
| 1404 | 78153 | CGPG8378 | SENSE | 0.102 | 0.238 | 4.000 | 0.000 |
| 1446 | 78178 | CGPG8716 | SENSE | −0.027 | 0.861 | 4.000 | 0.000 |
| 1449 | 78186 | CGPG8774 | SENSE | −0.002 | 0.993 | 4.000 | 0.000 |
| 998 | 78203 | CGPG4689 | SENSE | 0.001 | 0.995 | 4.000 | 0.000 |
| 1003 | 78207 | CGPG4713 | SENSE | 0.131 | 0.276 | 4.000 | 0.000 |
| 1052 | 78213 | CGPG5254 | SENSE | 0.260 | 0.001 | 4.000 | 0.000 |
| 1326 | 78233 | CGPG7673 | SENSE | 0.169 | 0.183 | 4.000 | 0.000 |
| 1026 | 78349 | CGPG5061 | SENSE | 0.096 | 0.479 | 4.000 | 0.000 |
| 881 | 78362 | CGPG2832 | SENSE | — | — | 4.000 | 0.000 |
| 1416 | 78536 | CGPG8475 | SENSE | −0.104 | 0.537 | 4.000 | 0.000 |
| 1456 | 78589 | CGPG8853 | SENSE | −0.154 | 0.060 | 4.000 | 0.000 |
| 1265 | 78990 | CGPG7192 | SENSE | — | — | 4.000 | 0.000 |

If p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference.

H. Shade Tolerance Screen

Plants undergo a characteristic morphological response in shade that includes the elongation of the petiole, a change in the leaf angle, and a reduction in chlorophyll content. While these changes may confer a competitive advantage to individuals, in a monoculture the shade avoidance response is thought to reduce the overall biomass of the population. Thus, genetic alterations that prevent the shade avoidance response may be associated with higher yields. Genes that favor growth under low light conditions may also promote yield, as inadequate light levels frequently limit yield. This protocol describes a screen to look for *Arabidopsis* plants that show an attenuated shade avoidance response and/or grow better than control plants under low light intensity. Of particular interest, we were looking for plants that didn't extend their petiole length, had an increase in seedling weight relative to the reference and had leaves that were more close to parallel with the plate surface.

T2 seeds were plated on glufosinate selection plates with ½ MS medium. Seeds were sown on ½× MS salts, 1% Phytagel, 10 ug/ml BASTA. Plants were grown on vertical plates at a temperature of 22° C. at day, 20° C. at night and under low light (approximately 30 uE/m$^2$/s, far/red ratio (655/665/725/735) ~0.35 using PLAQ lights with GAM color filter #680). Twenty-three days after seedlings were sown, measurements were recorded including seedling status, number of rosette leaves, status of flower bud, petiole leaf angle, petiole length, and pooled fresh weights. A digital image of the whole plate was taken on the measurement day. Seedling weight and petiole length were analyzed as quantitative responses according to example 1M. The number of rosette leaves, flowering bud formation and leaf angel were analyzed as qualitative responses according to example 1L.

A list of recombinant DNA constructs that improve shade tolerance in plants illustrated in Table 10:

TABLE 10

| PEP SEQ ID | Construct ID | Nomination ID | Orientation | Seedling weight at day 23 Delta mean | Seedling weight at day 23 P-value | Petiole length at day 23 Delta mean | Petiole length at day 23 P-value |
|---|---|---|---|---|---|---|---|
| 877 | 10204 | CGPG274 | ANTI-SENSE | 0.763 | 0.001 | 0.617 | 0.141 |
| 1136 | 11152 | CGPG606 | SENSE | 0.658 | 0.006 | 0.784 | 0.002 |
| 968 | 11408 | CGPG430 | SENSE | −0.458 | 0.210 | −0.311 | 0.065 |
| 773 | 12224 | CGPG1143 | SENSE | 0.010 | 0.974 | −0.378 | 0.055 |
| 823 | 19122 | CGPG1899 | SENSE | −0.397 | 0.110 | −0.291 | 0.043 |
| 897 | 19537 | CGPG3156 | SENSE | −0.299 | 0.107 | −0.245 | 0.054 |
| 934 | 70466 | CGPG3781 | SENSE | −0.531 | 0.071 | −0.342 | 0.031 |
| 992 | 70680 | CGPG4583 | SENSE | 0.051 | 0.591 | −0.345 | 0.038 |
| 991 | 70764 | CGPG4553 | SENSE | −0.407 | 0.550 | −0.991 | 0.012 |
| 926 | 70833 | CGPG365 | SENSE | −0.195 | 0.201 | −0.247 | 0.084 |
| 997 | 71613 | CGPG4684 | SENSE | −0.464 | 0.031 | −0.328 | 0.014 |
| 1000 | 71631 | CGPG4702 | SENSE | −0.806 | 0.032 | −0.607 | 0.011 |
| 834 | 71702 | CGPG1996 | SENSE | 0.385 | 0.053 | 0.293 | 0.032 |
| 990 | 71820 | CGPG4506 | SENSE | −0.663 | 0.053 | −0.921 | 0.094 |
| 973 | 71952 | CGPG4344 | SENSE | −1.336 | 0.011 | −0.931 | 0.054 |
| 1055 | 72008 | CGPG5265 | SENSE | −0.515 | 0.042 | −0.379 | 0.043 |
| 867 | 72665 | CGPG2452 | SENSE | −0.229 | 0.236 | −0.314 | 0.052 |
| 873 | 72675 | CGPG2567 | SENSE | −1.355 | 0.051 | −1.051 | 0.024 |
| 874 | 72677 | CGPG2571 | SENSE | −1.011 | 0.070 | −1.259 | 0.017 |
| 1092 | 73179 | CGPG5686 | SENSE | 0.230 | 0.030 | 0.186 | 0.133 |
| 1021 | 73309 | CGPG5032 | SENSE | −0.347 | 0.026 | −0.277 | 0.007 |
| 1009 | 73336 | CGPG4848 | SENSE | −1.640 | 0.045 | −1.744 | 0.008 |
| 1199 | 73511 | CGPG6531 | SENSE | 0.103 | 0.505 | −0.210 | 0.016 |
| 1192 | 73551 | CGPG6476 | SENSE | −0.881 | 0.070 | −0.744 | 0.050 |
| 1012 | 73686 | CGPG4892 | SENSE | 0.080 | 0.905 | −1.178 | 0.007 |
| 1079 | 73953 | CGPG5576 | SENSE | 0.381 | 0.054 | 0.325 | 0.098 |
| 1210 | 74123 | CGPG6623 | SENSE | −0.442 | 0.002 | −0.424 | 0.048 |
| 1035 | 74212 | CGPG5155 | SENSE | −0.380 | 0.069 | −0.262 | 0.026 |
| 1023 | 74222 | CGPG5045 | SENSE | −0.913 | 0.051 | −1.766 | 0.051 |
| 1060 | 74261 | CGPG5350 | SENSE | −0.207 | 0.140 | −0.532 | 0.022 |
| 1112 | 74332 | CGPG5837 | SENSE | −0.544 | 0.015 | −0.630 | 0.019 |
| 1219 | 74403 | CGPG6671 | SENSE | −1.289 | 0.039 | −1.057 | 0.038 |
| 1221 | 74443 | CGPG6706 | SENSE | −0.664 | 0.057 | −0.968 | 0.015 |
| 1222 | 74457 | CGPG6723 | SENSE | −0.913 | 0.008 | −0.993 | 0.066 |
| 1226 | 74513 | CGPG6752 | SENSE | −0.405 | 0.010 | −0.356 | 0.042 |
| 1228 | 74515 | CGPG6768 | SENSE | −0.523 | 0.258 | −0.227 | 0.070 |
| 857 | 74567 | CGPG2349 | SENSE | −0.424 | 0.132 | −0.532 | 0.026 |
| 1132 | 74605 | CGPG6027 | SENSE | −0.353 | 0.268 | −0.652 | 0.097 |
| 1135 | 74611 | CGPG6049 | SENSE | −0.732 | 0.015 | −0:985 | 0.023 |
| 1143 | 74626 | CGPG6128 | SENSE | −0.638 | 0.084 | −0.691 | 0.030 |
| 1145 | 74636 | CGPG6149 | SENSE | −0.259 | 0.527 | −0.597 | 0.095 |
| 1217 | 74687 | CGPG6645 | SENSE | −0.882 | 0.027 | −0.431 | 0.024 |
| 1117 | 74748 | CGPG5893 | SENSE | −0.731 | 0.175 | −0.825 | 0.080 |
| 1291 | 74939 | CGPG7410 | SENSE | −0.867 | 0.020 | −0.620 | 0.001 |
| 1301 | 74957 | CGPG7459 | SENSE | −1.058 | 0.008 | −0.937 | 0.088 |
| 1296 | 74990 | CGPG7438 | SENSE | −1.717 | 0.007 | −1.271 | 0.032 |
| 975 | 75040 | CGPG4349 | SENSE | −0.643 | 0.100 | −0.406 | 0.000 |
| 1131 | 75248 | CGPG6021 | SENSE | −0.504 | 0.069 | −0.247 | 0.051 |
| 1133 | 75252 | CGPG6035 | SENSE | −0.395 | 0.097 | −0.290 | 0.072 |
| 1151 | 75267 | CGPG6201 | SENSE | −0.243 | 0.267 | −0.193 | 0.080 |
| 1314 | 75333 | CGPG7532 | SENSE | −0.632 | 0.031 | −0.362 | 0.089 |
| 1308 | 75354 | CGPG7510 | SENSE | −0.658 | 0.018 | −1.165 | 0.019 |
| 1306 | 75365 | CGPG7503 | SENSE | −0.329 | 0.033 | −0.526 | 0.061 |
| 1324 | 75479 | CGPG7616 | SENSE | −1.296 | 0.018 | −1.485 | 0.027. |
| 1327 | 75539 | CGPG7683 | SENSE | −0.463 | 0.183 | −1.074 | 0.052 |
| 1338 | 75608 | CGPG7816 | SENSE | −0.392 | 0.145 | −0.101 | 0.046 |
| 1332 | 75640 | CGPG7787 | SENSE | −0.603 | 0.006 | −0.539 | 0.041 |
| 1047 | 75823 | CGPG5213 | SENSE | −0.433 | 0.132 | −0.505 | 0.076 |
| 1240 | 75864 | CGPG6945 | SENSE | 0.596 | 0.008 | 0.045 | 0.730 |
| 1247 | 75881 | CGPG7013 | SENSE | −1.632 | 0.014 | −1.898 | 0.000 |
| 1250 | 75895 | CGPG7071 | SENSE | −0.808 | 0.006 | −0.543 | 0.084 |
| 1382 | 75913 | CGPG8212 | SENSE | −0.866 | 0.072 | −0.779 | 0.030 |
| 815 | 75957 | CGPG1740 | SENSE | −0.514 | 0.006 | −0.383 | 0.032 |
| 790 | 75993 | CGPG1352 | SENSE | −0.606 | 0.040 | −0.590 | 0.008 |
| 856 | 76041 | CGPG2348 | SENSE | 0.642 | 0.006 | 0.151 | 0.187 |
| 1270 | 76186 | CGPG7243 | SENSE | −0.603 | 0.016 | −0.427 | 0.080 |
| 1271 | 76190 | CGPG7258 | SENSE | −0.032 | 0.887 | −0.125 | 0.011 |
| 1156 | 76222 | CGPG6214 | SENSE | −0.653 | 0.011 | −0.632 | 0.046 |
| 1158 | 76228 | CGPG6222 | SENSE | −0.259 | 0.179 | −0.310 | 0.013 |
| 1463 | 76319 | CGPG8917 | SENSE | −0.354 | 0.147 | −0.767 | 0.097 |
| 1465 | 76320 | CGPG8925 | SENSE | −0.655 | 0.087 | −1.218 | 0.010 |
| 980 | 76410 | CGPG4405 | SENSE | −1.709 | 0.008 | −2.126 | 0.042 |
| 1159 | 76435 | CGPG6229 | SENSE | −0.308 | 0.051 | −0.453 | 0.078 |
| 1249 | 76454 | CGPG7056 | SENSE | −0.603 | 0.016 | −0.821 | 0.052 |

TABLE 10-continued

| PEP SEQ ID | Construct ID | Nomination ID | Orientation | Seedling weight at day 23 | | Petiole length at day 23 | |
|---|---|---|---|---|---|---|---|
| | | | | Delta mean | P-value | Delta mean | P-value |
| 1173 | 76528 | CGPG6336 | SENSE | −0.086 | 0.245 | −0.337 | 0.069 |
| 1157 | 76611 | CGPG6215 | SENSE | −0.624 | 0.077 | −0.668 | 0.008 |
| 1237 | 76642 | CGPG6921 | SENSE | −1.027 | 0.010 | −0.738 | 0.041 |
| 1256 | 76752 | CGPG7118 | SENSE | −0.345 | 0.286 | −0.600 | 0.066 |
| 1470 | 76838 | CGPG8990 | SENSE | −1.442 | 0.073 | −1.521 | 0.049 |
| 1478 | 76927 | CGPG9093 | SENSE | −0.384 | 0.161 | −0.261 | 0.039 |
| 1500 | 77147 | CGPG9201 | SENSE | −0.975 | 0.035 | −0.888 | 0.099 |
| 1498 | 77181 | CGPG9188 | SENSE | −1.360 | 0.000 | −1.347 | 0.016 |
| 1491 | 77190 | CGPG9165 | SENSE | 0.005 | 0.954 | −0.239 | 0.021 |
| 1503 | 77287 | CGPG9237 | SENSE | −0.315 | 0.377 | −0.602 | 0.097 |
| 1348 | 77543 | CGPG7911 | SENSE | −0.166 | 0.104 | −0.676 | 0.072 |
| 1311 | 77809 | CGPG7523 | SENSE | −0.466 | 0.063 | −0.144 | 0.035 |
| 1471 | 77841 | CGPG9001 | SENSE | −0.651 | 0.072 | −0.316 | 0.022 |
| 1361 | 77922 | CGPG8053 | SENSE | −0.447 | 0.020 | −0.270 | 0.050 |
| 1401 | 77973 | CGPG8370 | SENSE | −0.722 | 0.059 | −1.092 | 0.036 |
| 1421 | 78009 | CGPG8533 | SENSE | −0.468 | 0.072 | −0.268 | 0.034 |
| 1427 | 78026 | CGPG8569 | SENSE | −0.555 | 0.154 | −0.467 | 0.085 |
| 1431 | 78044 | CGPG8607 | SENSE | −0.838 | 0.007 | −0.803 | 0.013 |
| 1440 | 78065 | CGPG8646 | SENSE | −0.085 | 0.595 | −0.517 | 0.096 |
| 1377 | 78121 | CGPG8158 | SENSE | 0.274 | 0.079 | 0.172 | 0.036 |
| 1395 | 78135 | CGPG8305 | SENSE | −1.246 | 0.024 | −1.112 | 0.023 |
| 1405 | 78156 | CGPG8383 | SENSE | −0.343 | 0.243 | −1.089 | 0.002 |
| 1280 | 78231 | CGPG7347 | SENSE | −0.441 | 0.022 | −0.297 | 0.084 |
| 1020 | 78339 | CGPG5028 | SENSE | −0.295 | 0.147 | −0.334 | 0.042 |
| 1025 | 78342 | CGPG5051 | SENSE | −1.534 | 0.023 | −1.513 | 0.022 |
| 1013 | 78353 | CGPG4903 | SENSE | −1.018 | 0.043 | −1.290 | 0.020 |
| 970 | 78358 | CGPG4307 | SENSE | −0.531 | 0.022 | −0.430 | 0.066 |
| 1111 | 78371 | CGPG5822 | SENSE | −0.743 | 0.091 | −1.382 | 0.002 |
| 1430 | 78388 | CGPG8597 | SENSE | −0.200 | 0.409 | −0.417 | 0.055 |
| 1064 | 78442 | CGPG5382 | SENSE | −1.106 | 0.000 | −1.187 | 0.012 |
| 1356 | 78508 | CGPG8006 | SENSE | −1.184 | 0.009 | −0.784 | 0.071 |
| 1418 | 78540 | CGPG8490 | SENSE | 0.253 | 0.057 | 0.289 | 0.137 |
| 1450 | 78572 | CGPG8778 | SENSE | −0.586 | 0.088 | −0.474 | 0.070 |
| 1441 | 78590 | CGPG8666 | SENSE | −0.854 | 0.073 | −0.875 | 0.043 |
| 1409 | 78618 | CGPG8450 | SENSE | −0.953 | 0.037 | −1.088 | 0.008 |
| 1451 | 78631 | CGPG8784 | SENSE | −1.128 | 0.250 | −1.224 | 0.048 |
| 1420 | 78924 | CGPG8530 | SENSE | 0.213 | 0.001 | 0.305 | 0.058 |
| 1443 | 78952 | CGPG8688 | SENSE | −0.264 | 0.282 | −0.721 | 0.023 |

For "seeding weight", if p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference with p<0.2.

For "petiole length", if p<0.05 and delta <0, the transgenic plants showed statistically significant trait enhancement as compared to the reference. If p<0.2 and delta <0, the transgenic plants showed a trend of trait enhancement as compared to the reference.

I. Early Plant Growth and Development Screen

This example sets forth a plate based phenotypic analysis platform for the rapid detection of phenotypes that are evident during the first two weeks of growth. In this screen, we were looking for genes that confer advantages in the processes of germination, seedling vigor, root growth and root morphology under non-stressed growth conditions to plants. The transgenic plants with advantages in seedling growth and development were determined by the seedling weight and root length at day14 after seed planting.

T2 seeds were plated on glufosinate selection plates and grown under standard conditions (~100 uE/m$^2$/s, 16 h photoperiod, 22° C. at day, 20° C. at night). Seeds were stratified for 3 days at 4° C. Seedlings were grown vertically (at a temperature of 22° C. at day 20° C. at night). Observations were taken on day 10 and day 14. Both seedling weight and root length at day 14 were analyzed as quantitative responses according to example 1M.

A list recombinant DNA constructs that improve early plant growth and development illustrated in Table 11.

TABLE 11

| PEP SEQ ID | Construct ID | Orientation | Root length at day 10 | | Root length at day 14 | | Seedling weight at day 14 | |
|---|---|---|---|---|---|---|---|---|
| | | | Delta mean | P-value | Delta mean | P-value | Delta mean | P-value |
| 799 | 10192 | ANTI-SENSE | 0.269 | 0.024 | 0.222 | 0.026 | 0.417 | 0.021 |
| 877 | 10204 | ANTI-SENSE | 0.290 | 0.057 | 0.234 | 0.095 | 0.512 | 0.014 |
| 1328 | 11919 | ANTI-SENSE | 0.207 | 0.249 | 0.115 | 0.330 | 0.537 | 0.035 |

TABLE 11-continued

| PEP SEQ ID | Construct ID | Orientation | Root length at day 10 Delta mean | Root length at day 10 P-value | Root length at day 14 Delta mean | Root length at day 14 P-value | Seedling weight at day 14 Delta mean | Seedling weight at day 14 P-value |
|---|---|---|---|---|---|---|---|---|
| 1083 | 12776 | ANTI-SENSE | 0.237 | 0.002 | 0.092 | 0.280 | 0.233 | 0.147 |
| 835 | 14909 | ANTI-SENSE | 0.151 | 0.053 | 0.074 | 0.582 | 0.398 | 0.001 |
| 858 | 15809 | ANTI-SENSE | 0.212 | 0.184 | 0.066 | 0.493 | 0.403 | 0.061 |
| 938 | 19713 | SENSE | 0.139 | 0.141 | 0.008 | 0.954 | 0.177 | 0.090 |
| 841 | 70403 | SENSE | 0.295 | 0.017 | 0.077 | 0.280 | 0.337 | 0.044 |
| 1037 | 71218 | SENSE | 0.208 | 0.308 | 0.145 | 0.034 | 0.554 | 0.138 |
| 983 | 71963 | SENSE | 0.151 | 0.099 | −0.094 | 0.359 | 0.106 | 0.030 |
| 933 | 72357 | SENSE | 0.164 | 0.073 | −0.033 | 0.571 | −0.168 | 0.023 |
| 1077 | 72755 | SENSE | 0.339 | 0.014 | 0.218 | 0.047 | 0.307 | 0.281 |
| 1074 | 72765 | SENSE | 0.295 | 0.075 | 0.158 | 0.196 | 0.419 | 0.094 |
| 1072 | 72773 | SENSE | 0.185 | 0.051 | 0.111 | 0.183 | 0.239 | 0.057 |
| 880 | 72906 | SENSE | 0.224 | 0.086 | 0.074 | 0.246 | 0.150 | 0.027 |
| 1085 | 73021 | SENSE | 0.134 | 0.098 | 0.141 | 0.083 | 0.217 | 0.036 |
| 1099 | 73135 | SENSE | 0.255 | 0.073 | 0.214 | 0.057 | 0.329 | 0.082 |
| 1046 | 73266 | SENSE | 0.222 | 0.085 | 0.038 | 0.745 | 0.175 | 0.183 |
| 1183 | 73454 | SENSE | 0.276 | 0.046 | 0.201 | 0.131 | 0.277 | 0.234 |
| 1190 | 73525 | SENSE | 0.204 | 0.016 | −0.109 | 0.216 | 0.245 | 0.265 |
| 1196 | 73579 | SENSE | 0.166 | 0.028 | 0.257 | 0.011 | 0.379 | 0.024 |
| 1211 | 74159 | SENSE | 0.413 | 0.025 | 0.218 | 0.012 | 0.548 | 0.010 |
| 1202 | 74163 | SENSE | 0.188 | 0.140 | 0.126 | 0.244 | 0.408 | 0.096 |
| 1214 | 74184 | SENSE | 0.153 | 0.068 | 0.042 | 0.555 | −0.084 | 0.710 |
| 875 | 74534 | SENSE | 0.143 | 0.026 | 0.055 | 0.136 | 0.066 | 0.416 |
| 1285 | 74845 | SENSE | 0.190 | 0.183 | 0.035 | 0.622 | 0.383 | 0.044 |
| 1283 | 74868 | SENSE | 0.111 | 0.017 | 0.081 | 0.014 | 0.257 | 0.041 |
| 1297 | 74955 | SENSE | 0.345 | 0.006 | 0.256 | 0.002 | 0.464 | 0.011 |
| 1066 | 75002 | SENSE | 0.126 | 0.027 | 0.110 | 0.013 | 0.144 | 0.081 |
| 1313 | 75344 | SENSE | 0.100 | 0.079 | 0.015 | 0.296 | 0.083 | 0.541 |
| 1321 | 75489 | SENSE | −0.047 | 0.839 | 0.037 | 0.763 | 0.405 | 0.091 |
| 1162 | 75814 | SENSE | 0.246 | 0.021 | 0.144 | 0.041 | 0.233 | 0.107 |
| 1384 | 75974 | SENSE | 0.133 | 0.034 | 0.103 | 0.037 | 0.214 | 0.109 |
| 843 | 76076 | SENSE | 0.417 | 0.050 | 0.250 | 0.028 | 0.347 | 0.034 |
| 1125 | 76118 | SENSE | 0.200 | 0.035 | 0.127 | 0.024 | 0.311 | 0.125 |
| 1154 | 76221 | SENSE | 0.188 | 0.086 | −0.010 | 0.913 | 0.353 | 0.039 |
| 1233 | 76547 | SENSE | 0.198 | 0.038 | 0.080 | 0.307 | 0.105 | 0.183 |
| 1244 | 76558 | SENSE | 0.279 | 0.036 | 0.239 | 0.005 | 0.290 | 0.026 |
| 1476 | 76836 | SENSE | 0.263 | 0.012 | 0.200 | 0.003 | 0.292 | 0.089 |
| 1488 | 77105 | SENSE | 0.325 | 0.114 | 0.235 | 0.056 | 0.224 | 0.170 |
| 1493 | 77167 | SENSE | 0.186 | 0.004 | −0.068 | 0.308 | 0.235 | 0.068 |
| 1499 | 77193 | SENSE | 0.312 | 0.027 | 0.275 | 0.007 | 0.444 | 0.005 |
| 1352 | 77556 | SENSE | — | — | — | — | 0.468 | 0.001 |
| 1412 | 77630 | SENSE | 0.146 | 0.199 | 0.180 | 0.025 | 0.236 | 0.060 |
| 1380 | 77950 | SENSE | 0.121 | 0.084 | 0.088 | 0.302 | 0.141 | 0.259 |
| 1397 | 77969 | SENSE | 0.461 | 0.009 | 0.375 | 0.008 | 0.503 | 0.001 |
| 1439 | 78062 | SENSE | 0.163 | 0.060 | 0.185 | 0.043 | 0.380 | 0.080 |
| 1445 | 78169 | SENSE | 0.104 | 0.358 | 0.143 | 0.014 | 0.096 | 0.071 |
| 1455 | 78584 | SENSE | 0.164 | 0.056 | −0.020 | 0.749 | −0.108 | 0.303 |
| 1259 | 78740 | SENSE | — | — | — | — | 0.367 | 0.099 |
| 1410 | 78919 | SENSE | 0.273 | 0.052 | 0.155 | 0.085 | 0.225 | 0.310 |
| 1453 | 78938 | SENSE | 0.187 | 0.107 | 0.113 | 0.010 | 0.309 | 0.303 |

If $p<0.05$ and delta or risk score mean >0, the transgenic plants showed statistically significant trait enhancement as compared to the reference. If $p<0.2$ and delta or risk score mean >0, the transgenic plants showed a trend of trait enhancement as compared to the reference.

J. Late Plant Growth and Development Screen

This example sets forth a soil based phenotypic platform to identify genes that confer advantages in the processes of leaf development, flowering production and seed maturity to plants.

*Arabidopsis* plants were grown on a commercial potting mixture (Metro Mix 360, Scotts Co., Marysville, Ohio) consisting of 30-40% medium grade horticultural vermiculite, 35-55% sphagnum peat moss, 10-20% processed bark ash, 1-15% pine bark and a starter nutrient charge. Soil was supplemented with Osmocote time-release fertilizer at a rate of 30 mg/ft$^3$. T2 seeds were imbibed in 1% agarose solution for 3 days at 4° C. and then sown at a to density of ~5 per 2½" pot. Thirty-two pots were ordered in a 4 by 8 grid in standard greenhouse flat. Plants were grown in environmentally controlled rooms under a 16 h day length with an average light intensity of ~200 μmoles/m$^2$/s. Day and night temperature set points were 22° C. and 20° C., respectively. Humidity was maintained at 65%. Plants were watered by sub-irrigation every two days on average until mid-flowering, at which point the plants were watered daily until flowering was complete.

Application of the herbicide glufosinate was performed to select T2 individuals containing the target transgene. A single application of glufosinate was applied when the first true leaves were visible. Each pot was thinned to leave a single glufosinate-resistant seedling ~3 days after the selection was applied.

The rosette radius was measured at day 25. The silique length was measured at day 40. The plant parts were harvested at day 49 for dry weight measurements if flowering production was stopped. Otherwise, the dry weights of rosette and silique were carried out at day 53. The seeds were harvested at day 58. All measurements were analyzed as quantitative responses according to example 1M.

A list of recombinant DNA constructs that improve late plant growth and development illustrated in Table 12.

TABLE 12

| PEP SEQ ID | Construct ID | Rosette dry weight at day 53 | | Rosette radius at day 25 | | Seed net dry weight at day 62 | | Silique dry weight at day 53 | | Silique length at day 40 | |
|---|---|---|---|---|---|---|---|---|---|---|---|
| | | Delta mean | P-value | Delta mean | P-value | Delta mean | P-value | Delta mean | P-value | Delta mean | P-value |
| 1515 | 11935 | 0.099 | 0.072 | −0.093 | 0.030 | 1.235 | 0.027 | 0.041 | 0.679 | 0.039 | 0.247 |
| 762 | 12020 | −0.040 | 0.812 | −0.191 | 0.054 | 0.871 | 0.010 | −0.060 | 0.746 | −0.075 | 0.107 |
| 787 | 12932 | 0.438 | 0.013 | — | — | −0.701 | 0.057 | 0.618 | 0.012 | −0.013 | 0.692 |
| 810 | 14730 | −0.045 | 0.534 | 0.325 | 0.001 | 0.817 | 0.003 | 0.236 | 0.140 | 0.017 | 0.123 |
| 824 | 16446 | −0.152 | 0.214 | −0.097 | 0.367 | 0.701 | 0.032 | 0.055 | 0.450 | −0.017 | 0.832 |
| 902 | 18220 | 0.209 | 0.049 | −0.182 | 0.052 | 0.295 | 0.259 | −0.205 | 0.036 | −0.134 | 0.072 |
| 907 | 18239 | 0.482 | 0.004 | 0.071 | 0.077 | −0.245 | 0.113 | −0.024 | 0.818 | −0.045 | 0.346 |
| 953 | 19933 | 0.211 | 0.020 | — | — | −0.755 | 0.005 | 0.257 | 0.154 | 0.045 | 0.214 |
| 821 | 70410 | −0.208 | 0.070 | — | — | 0.505 | 0.028 | −0.348 | 0.015 | −0.081 | 0.421 |
| 978 | 71846 | −0.285 | 0.012 | — | — | 0.511 | 0.017 | 0.277 | 0.185 | −0.046 | 0.534 |
| 983 | 71963 | −0.146 | 0.231 | −0.035 | 0.312 | 0.421 | 0.037 | 0.120 | 0.131 | 0.037 | 0.048 |
| 1051 | 72049 | 0.351 | 0.153 | −0.047 | 0.683 | 0.419 | 0.025 | −0.108 | 0.180 | 0.024 | 0.493 |
| 1001 | 72368 | 0.282 | 0.013 | −0.407 | 0.051 | −0.912 | 0.082 | −0.244 | 0.208 | −0.096 | 0.017 |
| 993 | 72375 | 0.327 | 0.002 | — | — | −0.261 | 0.014 | 0.022 | 0.324 | 0.042 | 0.076 |
| 1185 | 73445 | −0.042 | 0.704 | −0.126 | 0.091 | 1.499 | 0.015 | −0.037 | 0.330 | 0.009 | 0.633 |
| 852 | 10332 | 0.108 | 0.156 | 0.101 | 0.449 | 0.799 | 0.038 | — | — | −0.072 | 0.208 |
| 810 | 13938 | 0.450 | 0.064 | 0.225 | 0.094 | 0.874 | 0.021 | 0.331 | 0.029 | 0.258 | 0.005 |
| 814 | 13960 | −0.042 | 0.697 | 0.191 | 0.010 | 0.387 | 0.033 | 0.657 | 0.005 | 0.098 | 0.005 |
| 872 | 16607 | 0.246 | 0.041 | 0.170 | 0.076 | −1.029 | 0.012 | −0.675 | 0.018 | 0.197 | 0.029 |
| 914 | 18347 | −0.240 | 0.238 | 0.188 | 0.026 | 1.183 | 0.017 | −0.019 | 0.873 | 0.071 | 0.236 |
| 935 | 70241 | −0.146 | 0.264 | 0.116 | 0.068 | 0.851 | 0.012 | 0.245 | 0.007 | 0.023 | 0.640 |
| 947 | 70909 | −0.163 | 0.084 | −0.026 | 0.345 | 0.792 | 0.004 | 0.484 | 0.011 | 0.647 | 0.001 |
| 949 | 70974 | −0.111 | 0.119 | −0.036 | 0.794 | 1.359 | 0.002 | — | — | −0.027 | 0.476 |
| 979 | 71314 | −0.076 | 0.209 | −0.007 | 0.793 | 0.426 | 0.027 | — | — | 0.021 | 0.098 |
| 987 | 71334 | 1.355 | 0.001 | −0.002 | 0.971 | −0.472 | 0.206 | 0.328 | 0.052 | −0.134 | 0.322 |
| 1109 | 72923 | 0.331 | 0.002 | −0.108 | 0.335 | 1.545 | 0.005 | 0.345 | 0.297 | 0.630 | 0.002 |
| 1042 | 73255 | 0.147 | 0.018 | −0.001 | 0.972 | 0.581 | 0.005 | 0.829 | 0.002 | 0.080 | 0.016 |
| 1028 | 73280 | −0.377 | 0.134 | −0.042 | 0.512 | 0.824 | 0.014 | 0.324 | 0.202 | 0.003 | 0.976 |
| 1189 | 73436 | 0.563 | 0.014 | 0.072 | 0.106 | 0.766 | 0.052 | 0.335 | 0.120 | −0.049 | 0.171 |
| 1191 | 73514 | −0.409 | 0.051 | −0.027 | 0.588 | 0.384 | 0.006 | 0.103 | 0.575 | −0.032 | 0.335 |
| 1197 | 73556 | 0.282 | 0.275 | 0.049 | 0.055 | 0.975 | 0.011 | 0.203 | 0.273 | −0.106 | 0.220 |
| 1208 | 74110 | 0.745 | 0.014 | 0.177 | 0.116 | −0.983 | 0.178 | 1.131 | 0.009 | −0.104 | 0.214 |
| 814 | 74391 | 0.299 | 0.002 | 0.036 | 0.095 | −0.578 | 0.004 | — | — | 0.076 | 0.044 |
| 861 | 74702 | −0.335 | 0.019 | 0.092 | 0.173 | 1.364 | 0.003 | 0.080 | 0.546 | 0.083 | 0.041 |
| 1293 | 74905 | 0.143 | 0.537 | −0.085 | 0.246 | 1.488 | 0.002 | 0.092 | 0.454 | −0.004 | 0.910 |
| 1292 | 74928 | 0.330 | 0.031 | 0.087 | 0.114 | 0.303 | 0.173 | 0.542 | 0.050 | 0.082 | 0.019 |
| 1312 | 75332 | −0.145 | 0.035 | 0.222 | 0.027 | 0.919 | 0.021 | 0.149 | 0.476 | 0.012 | 0.694 |
| 1323 | 75466 | 0.137 | 0.237 | 0.264 | 0.009 | 0.479 | 0.039 | 0.539 | 0.010 | 0.062 | 0.171 |
| 1387 | 75916 | 0.342 | 0.027 | 0.029 | 0.549 | −0.137 | 0.634 | 0.257 | 0.042 | 0.027 | 0.655 |
| 1383 | 75925 | −0.207 | 0.072 | 0.038 | 0.662 | 1.374 | 0.001 | −0.025 | 0.853 | −0.009 | 0.727 |
| 837 | 75945 | 0.550 | 0.001 | −0.188 | 0.113 | 0.440 | 0.022 | 0.050 | 0.769 | −0.236 | 0.045 |
| 1154 | 76221 | −0.042 | 0.742 | 0.090 | 0.132 | 0.863 | 0.002 | 0.295 | 0.139 | 0.029 | 0.469 |
| 1166 | 76233 | 0.115 | 0.162 | 0.110 | 0.160 | 1.062 | 0.008 | 0.196 | 0.005 | 0.065 | 0.343 |
| 1242 | 76276 | 0.295 | 0.029 | 0.058 | 0.333 | 0.732 | 0.022 | 0.258 | 0.110 | −0.060 | 0.400 |
| 1473 | 76865 | −0.084 | 0.474 | −0.155 | 0.034 | 0.719 | 0.039 | 0.267 | 0.104 | −0.005 | 0.968 |
| 1483 | 76965 | 0.107 | 0.469 | −0.329 | 0.058 | 0.446 | 0.001 | 0.067 | 0.770 | −0.174 | 0.320 |
| 1272 | 77071 | −0.354 | 0.006 | 0.108 | 0.020 | 0.854 | 0.002 | −0.200 | 0.125 | 0.012 | 0.647 |
| 1492 | 77107 | 0.077 | 0.748 | −0.026 | 0.709 | 1.343 | 0.003 | −0.451 | 0.256 | −0.092 | 0.349 |
| 1487 | 77116 | −0.064 | 0.634 | 0.048 | 0.066 | 1.289 | 0.003 | 0.006 | 0.935 | 0.004 | 0.475 |
| 1496 | 77168 | −0.287 | 0.410 | −0.105 | 0.148 | 0.389 | 0.018 | −0.407 | 0.281 | −0.069 | 0.161 |
| 1261 | 77530 | 0.535 | 0.050 | −0.055 | 0.706 | −1.462 | 0.041 | — | — | −0.240 | 0.224 |
| 1345 | 77539 | 0.655 | 0.009 | −0.079 | 0.264 | 0.618 | 0.022 | — | — | 0.041 | 0.044 |
| 1347 | 77542 | 0.161 | 0.003 | 0.035 | 0.273 | 0.708 | 0.010 | −0.480 | 0.039 | 0.025 | 0.461 |
| 1350 | 77550 | 0.606 | 0.015 | −0.187 | 0.043 | −0.907 | 0.002 | — | — | −0.338 | 0.044 |
| 1304 | 77807 | −0.079 | 0.511 | 0.078 | 0.184 | 0.770 | 0.008 | 0.162 | 0.258 | 0.039 | 0.112 |
| 1110 | 78501 | 0.073 | 0.568 | −0.202 | 0.040 | 0.292 | 0.006 | — | — | −0.009 | 0.796 |
| 1185 | 73445 | | | | | | | | | | |

If p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference.

K. Limited Nitrogen Tolerance Screen

Under low nitrogen conditions, *Arabidopsis* seedlings become chlorotic and have less to biomass. This example sets forth the limited nitrogen tolerance screen to identify *Arabidopsis* plants transformed with the gene of interest that are altered in their ability to accumulate biomass and/or retain chlorophyll under low nitrogen condition.

T2 seeds were plated on glufosinate selection plates containing 0.5× N-Free Hoagland's T 0.1 mM NH₄NO₃ T 0.1% sucrose T 1% phytagel media and grown under standard light and temperature conditions. At 12 days of growth, plants were scored for seedling status (i.e., viable or nonviable) and root length. After 21 days of growth, plants were scored for BASTA resistance, visual color, seedling weight, number of green leaves, number of rosette leaves, root length and formation of flowering buds. A photograph of each plant was also taken at this time point.

The seedling weight and root length were analyzed as quantitative responses according to example 1M. The number green leaves, the number of rosette leaves and the flowerbud formation were analyzed as qualitative responses according to example 1L. The leaf color raw data were collected on each plant as the percentages of five color elements (Green, DarkGreen, LightGreen, RedPurple, YellowChlorotic) using a computer imaging system. A statistical logistic regression model was developed to predict an overall value based on five colors for each plant.

A list of recombinant DNA constructs that improve low nitrogen availability tolerance in plants illustrated in Table 13.

TABLE 13

| PEP SEQ ID | Construct ID | Orientation | Root length at day 21 Delta mean | P-value | Leaf color at day 21 Risk score mean | P-value | Rosette weight at day 21 Delta mean | P-value |
|---|---|---|---|---|---|---|---|---|
| 779 | 10176 | ANTI-SENSE | −0.448 | 0.045 | 2.804 | 0.082 | 0.174 | 0.077 |
| 893 | 10217 | ANTI-SENSE | −0.237 | 0.066 | 0.820 | 0.051 | 0.027 | 0.787 |
| 911 | 10230 | ANTI-SENSE | — | — | 3.346 | 0.001 | −0.006 | 0.844 |
| 917 | 10234 | ANTI-SENSE | −0.415 | 0.068 | 7.023 | 0.002 | 0.028 | 0.772 |
| 957 | 10413 | ANTI-SENSE | −0.401 | 0.084 | 3.636 | 0.046 | −0.026 | 0.767 |
| 879 | 10431 | ANTI-SENSE | −0.476 | 0.022 | 3.731 | 0.010 | −0.037 | 0.731 |
| 886 | 10469 | SENSE | −0.570 | 0.002 | 5.909 | 0.004 | 0.019 | 0.652 |
| 878 | 10472 | SENSE | −0.337 | 0.013 | 3.669 | 0.035 | −0.089 | 0.173 |
| 782 | 10507 | ANTI-SENSE | −0.494 | 0.011 | 4.504 | 0.014 | −0.134 | 0.200 |
| 1078 | 10610 | ANTI-SENSE | −0.379 | 0.078 | 0.591 | 0.016 | −0.039 | 0.413 |
| 1108 | 10616 | ANTI-SENSE | −0.462 | 0.013 | 4.827 | 0.058 | −0.122 | 0.054 |
| 1134 | 10620 | ANTI-SENSE | −0.279 | 0.002 | 2.695 | 0.022 | −0.057 | 0.244 |
| 1144 | 10622 | ANTI-SENSE | −0.567 | 0.021 | 4.506 | 0.010 | −0.160 | 0.252 |
| 1212 | 10633 | ANTI-SENSE | −0.320 | 0.051 | 3.471 | 0.012 | −0.165 | 0.055 |
| 1232 | 10638 | ANTI-SENSE | −0.692 | 0.004 | 5.933 | 0.026 | −0.089 | 0.346 |
| 1058 | 10811 | ANTI-SENSE | −0.290 | 0.005 | 1.439 | 0.021 | −0.002 | 0.952 |
| 996 | 11003 | ANTI-SENSE | — | — | 3.118 | 0.019 | −0.138 | 0.054 |
| 1267 | 11022 | ANTI-SENSE | −0.273 | 0.033 | 4.514 | 0.044 | 0.000 | 0.987 |
| 1044 | 11049 | SENSE | −0.173 | 0.177 | 0.986 | 0.059 | 0.086 | 0.406 |
| 941 | 11117 | ANTI-SENSE | −0.707 | 0.027 | 5.220 | 0.004 | −0.112 | 0.488 |
| 958 | 11119 | ANTI-SENSE | — | — | 6.165 | 0.025 | −0.012 | 0.899 |
| 931 | 11319 | ANTI-SENSE | −0.334 | 0.293 | 1.469 | 0.062 | −0.099 | 0.149 |
| 1048 | 11353 | SENSE | −0.152 | 0.034 | 1.063 | 0.058 | −0.072 | 0.044 |
| 1091 | 11516 | ANTI-SENSE | −0.293 | 0.016 | 4.740 | 0.030 | 0.050 | 0.594 |
| 1258 | 11720 | ANTI-SENSE | −0.553 | 0.007 | 4.801 | 0.007 | −0.044 | 0.519 |
| 1357 | 11748 | ANTI-SENSE | −0.181 | 0.032 | 1.491 | 0.022 | 0.034 | 0.679 |
| 1406 | 11807 | ANTI-SENSE | −0.538 | 0.080 | 5.467 | 0.057 | −0.001 | 0.985 |
| 764 | 11827 | ANTI-SENSE | −0.510 | 0.005 | 6.450 | 0.001 | 0.080 | 0.391 |
| 767 | 11836 | ANTI-SENSE | −0.154 | 0.001 | 0.513 | 0.099 | −0.112 | 0.127 |
| 774 | 11856 | ANTI-SENSE | −0.127 | 0.273 | 2.401 | 0.035 | −0.023 | 0.788 |
| 766 | 12015 | SENSE | −0.402 | 0.088 | 0.799 | 0.030 | −0.104 | 0.162 |
| 775 | 12065 | SENSE | 0.264 | 0.121 | 174.221 | 0.424 | 0.193 | 0.012 |
| 768 | 12141 | ANTI-SENSE | −0.343 | 0.001 | 1.939 | 0.010 | −0.059 | 0.278 |
| 777 | 12208 | SENSE | 0.064 | 0.731 | 1.066 | 0.453 | 0.209 | 0.073 |
| 776 | 12419 | ANTI-SENSE | −0.399 | 0.128 | 4.501 | 0.068 | 0.095 | 0.183 |
| 1452 | 12425 | ANTI-SENSE | −0.894 | 0.160 | 4.996 | 0.056 | −0.176 | 0.184 |
| 765 | 12435 | SENSE | 0.101 | 0.355 | −0.040 | 0.909 | 0.135 | 0.066 |
| 770 | 12437 | SENSE | — | — | 1.828 | 0.051 | −0.077 | 0.324 |
| 785 | 13237 | SENSE | −0.287 | 0.009 | 4.272 | 0.017 | 0.169 | 0.174 |
| 795 | 13305 | ANTI-SENSE | −0.221 | 0.051 | 0.981 | 0.076 | −0.062 | 0.543 |
| 943 | 13404 | SENSE | −0.372 | 0.121 | 3.277 | 0.059 | 0.089 | 0.096 |
| 804 | 13650 | ANTI-SENSE | — | — | 3.220 | 0.055 | 0.302 | 0.004 |
| 809 | 13657 | ANTI-SENSE | −0.500 | 0.018 | 5.368 | 0.037 | −0.059 | 0.462 |
| 794 | 13708 | ANTI-SENSE | −0.527 | 0.021 | 4.121 | 0.079 | 0.077 | 0.402 |
| 1153 | 13805 | SENSE | — | — | 5.349 | 0.049 | −0.085 | 0.433 |
| 801 | 13841 | ANTI-SENSE | −0.460 | 0.009 | 5.012 | 0.009 | 0.162 | 0.031 |
| 805 | 13855 | ANTI-SENSE | −0.141 | 0.024 | 1.477 | 0.072 | 0.056 | 0.426 |
| 1477 | 14133 | ANTI-SENSE | −0.461 | 0.074 | 3.450 | 0.085 | 0.012 | 0.868 |
| 803 | 14253 | ANTI-SENSE | — | — | 4.232 | 0.034 | 0.023 | 0.906 |
| 1235 | 14703 | SENSE | −0.450 | 0.039 | 4.394 | 0.019 | −0.001 | 0.990 |
| 797 | 14712 | SENSE | −0.429 | 0.034 | 4.370 | 0.025 | 0.152 | 0.112 |
| 836 | 14927 | ANTI-SENSE | −0.293 | 0.083 | 4.557 | 0.006 | 0.134 | 0.255 |
| 783 | 15039 | SENSE | −0.491 | 0.102 | 4.688 | 0.003 | −0.096 | 0.230 |
| 825 | 15143 | SENSE | — | — | 5.445 | 0.010 | −0.028 | 0.831 |
| 848 | 15716 | ANTI-SENSE | −0.473 | 0.018 | 3.843 | 0.014 | −0.087 | 0.024 |
| 802 | 15805 | SENSE | −0.347 | 0.073 | 3.195 | 0.001 | −0.003 | 0.931 |
| 866 | 17129 | ANTI-SENSE | −0.356 | 0.185 | 2.082 | 0.099 | −0.095 | 0.068 |
| 869 | 17151 | ANTI-SENSE | — | — | 4.021 | 0.022 | 0.024 | 0.747 |
| 868 | 18206 | SENSE | −0.160 | 0.337 | 1.069 | 0.052 | 0.643 | 0.014 |

TABLE 13-continued

| PEP SEQ ID | Construct ID | Orientation | Root length at day 21 Delta mean | P-value | Leaf color at day 21 Risk score mean | P-value | Rosette weight at day 21 Delta mean | P-value |
|---|---|---|---|---|---|---|---|---|
| 906 | 18227 | SENSE | −0.273 | 0.185 | 1.990 | 0.020 | −0.045 | 0.201 |
| 913 | 18271 | SENSE | −0.036 | 0.744 | 0.278 | 0.082 | 0.004 | 0.925 |
| 909 | 18329 | SENSE | −0.220 | 0.418 | 5.264 | 0.067 | 0.118 | 0.119 |
| 890 | 18423 | SENSE | −0.304 | 0.018 | 3.789 | 0.079 | 0.025 | 0.771 |
| 904 | 19205 | SENSE | −0.313 | 0.084 | 0.702 | 0.004 | −0.061 | 0.491 |
| 791 | 19401 | SENSE | −0.032 | 0.850 | 0.086 | 0.874 | 0.161 | 0.096 |
| 859 | 70110 | SENSE | −0.264 | 0.020 | 2.237 | 0.076 | 0.105 | 0.354 |
| 930 | 70440 | SENSE | −0.347 | 0.017 | 1.576 | 0.032 | 0.115 | 0.251 |
| 936 | 70476 | SENSE | −0.297 | 0.072 | 0.965 | 0.044 | −0.141 | 0.095 |
| 977 | 70666 | SENSE | −0.351 | 0.007 | 3.536 | 0.039 | −0.085 | 0.127 |
| 963 | 71250 | SENSE | −0.018 | 0.901 | 2.025 | 0.110 | 0.278 | 0.022 |
| 981 | 71322 | SENSE | −0.046 | 0.431 | 1.676 | 0.080 | 0.026 | 0.628 |
| 984 | 71326 | SENSE | −0.380 | 0.065 | 3.996 | 0.032 | −0.047 | 0.399 |
| 987 | 71334 | SENSE | −0.482 | 0.028 | 3.737 | 0.074 | 0.042 | 0.322 |
| 988 | 71335 | SENSE | −0.264 | 0.060 | 3.812 | 0.035 | 0.133 | 0.220 |
| 971 | 71839 | SENSE | 0.052 | 0.538 | 2.437 | 0.013 | 0.140 | 0.150 |
| 976 | 71843 | SENSE | −0.316 | 0.045 | 1.660 | 0.219 | 0.232 | 0.038 |
| 1127 | 72602 | SENSE | 0.021 | 0.833 | 0.410 | 0.025 | 0.043 | 0.751 |
| 1017 | 72663 | SENSE | 0.002 | 0.989 | −0.270 | 0.862 | 0.199 | 0.016 |
| 873 | 72675 | SENSE | −0.173 | 0.135 | 1.435 | 0.055 | −0.117 | 0.096 |
| 1019 | 72827 | SENSE | −0.264 | 0.054 | 1.909 | 0.080 | 0.000 | 0.995 |
| 1105 | 72933 | SENSE | −0.245 | 0.122 | 3.963 | 0.025 | 0.076 | 0.442 |
| 1043 | 73257 | SENSE | — | — | 4.972 | 0.090 | −0.045 | 0.609 |
| 1029 | 73281 | SENSE | −0.305 | 0.097 | 4.638 | 0.040 | −0.043 | 0.175 |
| 1181 | 73452 | SENSE | 0.043 | 0.102 | 0.097 | 0.808 | 0.154 | 0.053 |
| 969 | 73616 | SENSE | 0.307 | 0.023 | 1.292 | 0.012 | −0.036 | 0.222 |
| 1014 | 73726 | SENSE | −0.049 | 0.097 | 2.396 | 0.041 | −0.024 | 0.788 |
| 855 | 73847 | SENSE | −0.100 | 0.149 | 1.517 | 0.044 | −0.075 | 0.036 |
| 1082 | 73966 | SENSE | −0.273 | 0.001 | 2.969 | 0.035 | −0.179 | 0.224 |
| 853 | 73968 | SENSE | — | — | 4.339 | 0.056 | −0.022 | 0.584 |
| 1205 | 74141 | SENSE | −0.362 | 0.112 | 1.484 | 0.051 | −0.224 | 0.015 |
| 1203 | 74175 | SENSE | −0.305 | 0.069 | 3.974 | 0.023 | −0.007 | 0.901 |
| 1204 | 74176 | SENSE | 0.048 | 0.225 | 1.673 | 0.005 | −0.042 | 0.558 |
| 1206 | 74178 | SENSE | −0.546 | 0.051 | 3.934 | 0.038 | −0.117 | 0.062 |
| 898 | 74201 | SENSE | −0.223 | 0.046 | 1.264 | 0.077 | −0.200 | 0.018 |
| 1023 | 74222 | SENSE | — | — | 5.858 | 0.048 | −0.076 | 0.268 |
| 1139 | 74371 | SENSE | — | — | 4.728 | 0.007 | −0.117 | 0.322 |
| 1140 | 74373 | SENSE | −0.027 | 0.715 | −0.646 | 0.465 | 0.106 | 0.051 |
| 1224 | 74447 | SENSE | −0.867 | 0.064 | 3.200 | 0.055 | −0.197 | 0.206 |
| 1135 | 74611 | SENSE | −0.189 | 0.350 | 2.233 | 0.060 | −0.118 | 0.205 |
| 1142 | 74620 | SENSE | −0.736 | 0.094 | 5.605 | 0.047 | 0.004 | 0.979 |
| 1113 | 74738 | SENSE | 0.036 | 0.145 | −0.181 | 0.528 | 0.168 | 0.098 |
| 1284 | 74809 | SENSE | −0.256 | 0.031 | 2.481 | 0.053 | −0.021 | 0.606 |
| 1282 | 74820 | SENSE | −0.173 | 0.032 | 1.129 | 0.036 | −0.168 | 0.064 |
| 1286 | 74870 | SENSE | −0.448 | 0.051 | 4.227 | 0.061 | −0.103 | 0.154 |
| 1289 | 74950 | SENSE | −0.115 | 0.085 | 1.801 | 0.070 | −0.107 | 0.291 |
| 1004 | 75209 | SENSE | −0.231 | 0.065 | 2.947 | 0.046 | 0.008 | 0.887 |
| 1152 | 75283 | SENSE | −0.190 | 0.011 | 0.627 | 0.047 | −0.038 | 0.323 |
| 1306 | 75365 | SENSE | 0.125 | 0.219 | 1.830 | 0.047 | −0.056 | 0.569 |
| 1302 | 75374 | SENSE | −0.326 | 0.031 | 2.123 | 0.080 | −0.193 | 0.015 |
| 1321 | 75489 | SENSE | 0.208 | 0.053 | −4.236 | 0.035 | 0.184 | 0.054 |
| 1329 | 75603 | SENSE | 0.035 | 0.604 | 0.552 | 0.179 | 0.124 | 0.009 |
| 1332 | 75640 | SENSE | −0.353 | 0.018 | 3.264 | 0.026 | −0.152 | 0.231 |
| 1334 | 75653 | SENSE | −0.256 | 0.151 | 3.269 | 0.076 | −0.023 | 0.755 |
| 1343 | 75716 | SENSE | 0.292 | 0.079 | 2.436 | 0.028 | −0.066 | 0.580 |
| 1386 | 75904 | SENSE | 0.254 | 0.052 | −1.863 | 0.084 | 0.312 | 0.025 |
| 1392 | 75967 | SENSE | — | — | 1.628 | 0.003 | −0.038 | 0.729 |
| 1260 | 76157 | SENSE | — | — | 2.689 | 0.064 | 0.155 | 0.058 |
| 1273 | 76194 | SENSE | — | — | 7.881 | 0.009 | −0.078 | 0.728 |
| 1463 | 76319 | SENSE | — | — | 7.442 | 0.029 | −0.388 | 0.417 |
| 1468 | 76334 | SENSE | −0.338 | 0.068 | 1.019 | 0.036 | −0.036 | 0.517 |
| 1461 | 76340 | SENSE | −0.159 | 0.020 | 0.346 | 0.061 | −0.026 | 0.682 |
| 1464 | 76343 | SENSE | −0.042 | 0.710 | 0.257 | 0.390 | 0.111 | 0.081 |
| 1466 | 76380 | SENSE | — | — | 2.459 | 0.019 | −0.130 | 0.254 |
| 1469 | 76382 | SENSE | −0.693 | 0.013 | 5.109 | 0.008 | −0.304 | 0.007 |
| 980 | 76410 | SENSE | −0.203 | 0.007 | 3.337 | 0.004 | −0.107 | 0.294 |
| 1264 | 76756 | SENSE | — | — | 3.459 | 0.034 | −0.147 | 0.126 |
| 1470 | 76838 | SENSE | — | — | 4.610 | 0.021 | −0.067 | 0.168 |
| 1479 | 76963 | SENSE | — | — | 1.779 | 0.046 | −0.188 | 0.096 |
| 1507 | 77265 | SENSE | — | — | 2.573 | 0.025 | −0.097 | 0.265 |
| 1504 | 77276 | SENSE | — | — | 3.580 | 0.010 | −0.113 | 0.219 |
| 1120 | 77311 | SENSE | — | — | 2.744 | 0.032 | −0.035 | 0.696 |

TABLE 13-continued

| PEP SEQ ID | Construct ID | Orientation | Root length at day 21 Delta mean | P-value | Leaf color at day 21 Risk score mean | P-value | Rosette weight at day 21 Delta mean | P-value |
|---|---|---|---|---|---|---|---|---|
| 1346 | 77540 | SENSE | −0.322 | 0.016 | 3.433 | 0.004 | −0.164 | 0.013 |
| 1355 | 77565 | SENSE | — | — | 2.221 | 0.006 | −0.026 | 0.272 |
| 1359 | 77573 | SENSE | −0.404 | 0.005 | 5.266 | 0.007 | 0.092 | 0.178 |
| 1501 | 77853 | SENSE | — | — | 4.686 | 0.004 | −0.072 | 0.264 |
| 1400 | 78142 | SENSE | — | — | 3.787 | 0.059 | 0.010 | 0.566 |
| 1437 | 78163 | SENSE | — | — | 1.541 | 0.029 | 0.038 | 0.603 |
| 1457 | 78252 | SENSE | — | — | 5.384 | 0.026 | −0.043 | 0.728 |
| 1516 | 78259 | SENSE | — | — | 3.387 | 0.036 | 0.004 | 0.928 |
| 1024 | 78341 | SENSE | — | — | 4.261 | 0.040 | −0.056 | 0.478 |
| 1025 | 78342 | SENSE | −0.469 | 0.027 | 7.592 | 0.050 | −0.272 | 0.023 |
| 1013 | 78353 | SENSE | — | — | 7.028 | 0.040 | 0.013 | 0.930 |
| 972 | 78417 | SENSE | 0.041 | 0.366 | −0.590 | 0.551 | 0.282 | 0.076 |
| 1266 | 78460 | SENSE | — | — | 2.353 | 0.087 | −0.159 | 0.017 |
| 1356 | 78508 | SENSE | — | — | 4.369 | 0.001 | −0.241 | 0.000 |
| 1370 | 78510 | SENSE | −0.216 | 0.041 | 3.626 | 0.043 | −0.125 | 0.126 |
| 1407 | 78528 | SENSE | — | — | 4.716 | 0.014 | −0.241 | 0.075 |
| 1444 | 78559 | SENSE | — | — | 4.385 | 0.022 | −0.029 | 0.877 |
| 1171 | 78607 | SENSE | — | — | 4.547 | 0.049 | −0.162 | 0.319 |
| 959 | 78659 | SENSE | — | — | 6.713 | 0.013 | −0.060 | 0.637 |
| 974 | 78717 | SENSE | — | — | 1.926 | 0.179 | 0.121 | 0.013 |
| 1022 | 78725 | SENSE | −0.157 | 0.213 | 1.656 | 0.054 | 0.028 | 0.683 |
| 1161 | 78743 | SENSE | — | — | 2.003 | 0.048 | 0.107 | 0.258 |
| 1413 | 78921 | SENSE | — | — | 2.641 | 0.040 | 0.039 | 0.795 |
| 1454 | 78961 | SENSE | −0.475 | 0.006 | 4.949 | 0.000 | 0.002 | 0.972 |
| 1403 | 78963 | SENSE | — | — | 5.358 | 0.057 | 0.042 | 0.725 |
| 961 | 78969 | SENSE | — | — | 2.921 | 0.097 | 0.196 | 0.127 |
| 964 | 78972 | SENSE | — | — | 1.621 | 0.050 | 0.009 | 0.814 |

For rosette weight, if p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference with p<0.2. For root length, if p<0.05, the transgenic plants showed statistically significant trait enhancement as compared to the reference. if p<0.2, the transgenic plants showed a trend of trait enhancement as compared to the reference.

L. Statistic Analysis for Qualitative Responses

A list of responses that were analyzed as qualitative responses illustrated in Table 14.

TABLE 14

| response | Screen | categories (success vs. failure) |
|---|---|---|
| Wilting response Risk Score | Soil drought tolerance screen | non-wilted vs. wilted |
| growth stage at day 14 | heat stress tolerance screen | 50% of plants reach stage1.03 vs. not |
| growth stage at day 14 | salt stress tolerance screen | 50% of plants reach stage1.03 vs. not |
| growth stage at day 14 | PEG induced osmotic stress tolerance screen | 50% of plants reach stage1.03 vs. not |
| growth stage at day 7 | cold germination tolerance screen | 50% of plants reach stage 0.5 vs. not |
| number of rosette leaves at day 23 | Shade tolerance screen | 5 leaves appeared vs. not |
| Flower bud formation at day 23 | Shade tolerance screen | flower buds appear vs. not |
| leaf angle at day 23 | Shade tolerance screen | >60 degree vs. <60 degree |
| number of green leaves at day 21 | limited nitrogen tolerance screen | 6 or 7 leaves appeared vs. not |
| number of rosette leaves at day 21 | limited nitrogen tolerance screen | 6 or 7 leaves appeared vs. not |
| Flower bud formation at day 21 | limited nitrogen tolerance screen | flower buds appear vs. not |

Plants were grouped into transgenic and reference groups and were scored as success or failure according to Table 14. First, the risk (R) was calculated, which is the proportion of plants that were scored as of failure plants within the group. Then the relative risk (RR) was calculated as the ratio of R (transgenic) to R (reference). Risk score (RS) was calculated as $-\log_2{RR}$. Subsequently the risk scores from multiple events for each transgene of interest were evaluated for statistical significance by t-test using SAS statistical software (SAS 9, SAS/STAT User's Guide, SAS institute Inc, Cary, N.C., USA). RS with a value greater than 0 indicates that the transgenic plants perform better than the reference. RS with a value less than 0 indicates that the transgenic plants perform worse than the reference. The RS with a value equal to 0 indicates that the performance of the transgenic plants and the reference don't show any difference.

M. Statistic Analysis for Quantitative Responses

A list of responses that were analyzed as quantitative responses illustrated in Table 15.

TABLE 15

| response | screen |
|---|---|
| seed yield | Soil drought stress tolerance screen |
| seedling weight at day 14 | heat stress tolerance screen |
| root length at day 14 | heat stress tolerance screen |
| seedling weight at day 14 | salt stress tolerance screen |
| root length at day 14 | salt stress tolerance screen |
| root length at day 11 | salt stress tolerance screen |
| seedling weight at day 14 | PEG induced osmotic stress tolerance screen |
| root length at day 11 | PEG induced osmotic stress tolerance screen |
| root length at day 14 | PEG induced osmotic stress tolerance screen |
| rosette area at day 8 | cold shock tolerance screen |
| rosette area at day 28 | cold shock tolerance screen |

TABLE 15-continued

| response | screen |
| --- | --- |
| difference in rosette area from day 8 to day 28 | cold shock tolerance screen |
| root length at day 28 | cold germination tolerance screen |
| seedling weight at day 23 | Shade tolerance screen |
| petiole length at day 23 | Shade tolerance screen |
| root length at day 14 | Early plant growth and development screen |
| Seedling weight at day 14 | Early plant growth and development screen |
| Rosette dry weight at day 53 | Late plant growth and development screen |
| rosette radius at day 25 | Late plant growth and development screen |
| seed dry weight at day 58 | Late plant growth and development screen |
| silique dry weight at day 53 | Late plant growth and development screen |
| silique length at day 40 | Late plant growth and development screen |
| Seedling weight at day 21 | Limited nitrogen tolerance screen |
| Root length at day 21 | Limited nitrogen tolerance screen |

The measurements (M) of each plant were transformed by $\log_2$ calculation. The Delta was calculated as $\log_2 M$(transgenic)–$\log_2 M$(reference). Subsequently the mean delta from multiple events of the transgene of interest was evaluated for statistical significance by t-test using SAS statistical software (SAS 9, SAS/STAT User's Guide, SAS Institute Inc, Cary, N.C., USA). The Delta with a value greater than 0 indicates that the transgenic plants perform better than the reference. The Delta with a value less than 0 indicates that the transgenic plants perform worse than the reference. The Delta with a value equal to 0 indicates that the performance of the transgenic plants and the reference don't show any difference.

Example 2

Identification of Homologs

A BLAST searchable "All Protein Database" is constructed of known protein sequences using a proprietary sequence database and the National Center for Biotechnology Information (NCBI) non-redundant amino acid database (nr.aa). For each organism from which a DNA sequence provided herein was obtained, an "Organism Protein Database" is constructed of known protein sequences of the organism; the Organism Protein Database is a subset of the All Protein Database based on the NCBI taxonomy ID for the organism.

The All Protein Database is queried using amino acid sequence of cognate protein for gene DNA used in trait-improving recombinant DNA, i.e., sequences of SEQ ID NO: 760 through SEQ ID NO: 1518 using "blastp" with E-value cutoff of 1e-8. Up to 1000 top hits were kept, and separated by organism names. For each organism other than that of the query sequence, a list is kept for hits from the query organism itself with a more significant E-value than the best hit of the organism. The list contains likely duplicated genes, and is referred to as the Core List. Another list was kept for all the hits from each organism, sorted by E-value, and referred to as the Hit List.

The Organism Protein Database is queried using amino acid sequences of SEQ ID NO: 760 through SEQ ID NO: 1518 using "blastp" with E-value cutoff of 1e-4. Up to 1000 top hits are kept. A BLAST searchable database is constructed based on these hits, and is referred to as "SubDB".

SubDB was queried with each sequence in the Hit List using "blastp" with E-value cutoff of 1e-8. The hit with the best E-value is compared with the Core List from the corresponding organism. The hit is deemed a likely ortholog if it belongs to the Core List, otherwise it is deemed not a likely ortholog and there is no further search of sequences in the Hit List for the same organism. Likely orthologs from a large number of distinct organisms were identified and are reported by amino acid sequences of SEQ ID NO: 1519 to SEQ ID NO: 67778. These orthologs are reported in Tables 16 as homologs to the proteins cognate to genes used in trait-improving recombinant DNA.

Example 3

Consensus Sequence Build

ClustalW program is selected for multiple sequence alignments of an amino acid sequence of SEQ ID NO: 760 and its homologs, through SEQ ID NO: 1518 and its homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of 1 were chosen for multiple sequence alignment. The consensus sequence of SEQ ID NO: 768 and its 17 homologs were derived according to the procedure described above and is displayed in FIGS. 4A-4D.

Example 4

Pfam Module Annoation

This example illustrates the identification of domain and domain module by Pfam analysis.

The amino acid sequence of the expressed proteins that were shown to be associated with an enhanced trait were analyzed for Pfam protein family against the current Pfam collection of multiple sequence alignments and hidden Markov models using the HMMER software. The Pfam domain modules and individual protein domain for the proteins of SEQ ID NO: 760 through 1518 are shown in Table 17 and Table 18 respectively. The Hidden Markov model databases for the identified patent families allow identification of other homologous proteins and their cognate encoding DNA to enable the full breadth of the invention for a person of ordinary skill in the art. Certain proteins are identified by a single Pfam domain and others by multiple Pfam domains. For instance, the protein with amino acids of SEQ ID NO: 766 is characterized by two Pfam domains, i.e. "FHA" and "PP2C". See also the protein with amino acids of SEQ ID NO: 1515 which is characterized by seven copies of the Pfam domain "WD40". In Table 18 "score" is the gathering score for the Hidden Markov Model of the domain which exceeds the gathering cutoff reported in Table 19.

TABLE 17

| PEP SEQ ID | Construct ID | Module | Position |
|---|---|---|---|
| 760 | CGPG1022.pep | RRM_1 | 95-165 |
| 761 | CGPG1035.pep | Peptidase_C54 | 82-373 |
| 763 | CGPG105.pep | AP2 | 48-112 |
| 764 | CGPG1060.pep | DUF788 | 1-169 |
| 765 | CGPG1069.pep | NDUF_B7 | 2-81 |
| 766 | CGPG108.pep | FHA::PP2C | 208-284::309-570 |
| 771 | CGPG1136.pep | RRM_1 | 22-87 |
| 774 | CGPG1145.pep | NUDIX | 24-160 |
| 776 | CGPG1173.pep | adh_short | 6-181 |
| 777 | CGPG1176.pep | F-box | 2-50 |
| 779 | CGPG122.pep | PTR2 | 113-517 |
| 780 | CGPG126.pep | Response_reg | 34-158 |
| 781 | CGPG1262.pep | Gar1 | 51-152 |
| 782 | CGPG128.pep | Response_reg | 25-149 |
| 783 | CGPG1280.pep | DUF676 | 515-717 |
| 784 | CGPG1291.pep | DUF862 | 2-156 |
| 785 | CGPG1295.pep | TMEM14 | 7-104 |
| 787 | CGPG1315.pep | Brix | 60-255 |
| 788 | CGPG1335.pep | LRR_1 | 424-447 |
| 789 | CGPG1344.pep | Pkinase | 496-767 |
| 790 | CGPG1352.pep | Pkinase_Tyr | 154-425 |
| 791 | CGPG1364.pep | Pkinase | 38-416 |
| 793 | CGPG1396.pep | malic::Malic_M | 106-295::297-550 |
| 794 | CGPG1398.pep | Glycolytic | 11-358 |
| 795 | CGPG1399.pep | Metallophos | 161-360 |
| 796 | CGPG1429.pep | NTP_transferase::Hexapep::Hexapep | 86-365::413-430::466-483 |
| 797 | CGPG1430.pep | E1_dh | 89-393 |
| 798 | CGPG1445.pep | Pkinase | 33-294 |
| 799 | CGPG146.pep | p450 | 38-482 |
| 800 | CGPG1492.pep | Aldedh | 29-491 |
| 801 | CGPG1528.pep | ATP_synt_H | 1-70 |
| 802 | CGPG1530.pep | ArfGap::C2 | 15-137::183-262 |
| 803 | CGPG1535.pep | SPT2 | 230-329 |
| 804 | CGPG1546.pep | CTP_transf_1 | 101-300 |
| 805 | CGPG1567.pep | Ribosomal_L19 | 107-212 |
| 806 | CGPG1568.pep | FAD_binding_4 | 82-221 |
| 807 | CGPG1575.pep | DUF740 | 24-595 |
| 808 | CGPG1619.pep | Pyr_redox_2::Pyr_redox_dim | 27-343::373-483 |
| 810 | CGPG1641.pep | Di19 | 11-219 |
| 811 | CGPG1651.pep | DEAD::Helicase_C::DSHCT | 69-220::378-462::800-988 |
| 812 | CGPG1656.pep | Cyt-b5::FA_desaturase | 9-82::145-399 |
| 813 | CGPG1668.pep | DUF791::MFS_1 | 4-358::42-406 |
| 815 | CGPG1740.pep | DUF860 | 25-364 |
| 816 | CGPG177.pep | WD40::WD40 | 168-205::257-296 |
| 817 | CGPG1785.pep | PB1::Pkinase_Tyr | 179-266::863-1126 |
| 818 | CGPG182.pep | LRR_1::LRR_1::LRR_1::LRR_1::LRR_1::LRR_1::LRR_1::LRR_1::LRR_1::LRR_1::LRR_1::LRR_1::LRR_1::LRR_1 | 46-67::69-90::115-136::161-183::208-229::231-252::276-297::382-403::405-427::429-451::477-498::500-521::523-544 |
| 819 | CGPG1837.pep | TFIIS_M::SPOC | 328-445::656-762 |
| 820 | CGPG1873.pep | Pkinase::NAF | 20-275::314-374 |
| 823 | CGPG1899.pep | F-box::Kelch_1::Kelch_1 | 18-65::139-186::189-235 |
| 824 | CGPG1913.pep | F-box::FBA_1 | 31-78::268-416 |
| 825 | CGPG1918.pep | F-box | 30-77 |
| 826 | CGPG1919.pep | F-box | 65-112 |
| 827 | CGPG1922.pep | F-box::Kelch_1::Kelch_1 | 25-72::118-163::165-210 |
| 828 | CGPG1929.pep | F-box | 1-44 |
| 829 | CGPG1938.pep | F-box::LRR_2 | 8-55::159-185 |
| 830 | CGPG1956.pep | Pre-SET::SET | 409-558::560-702 |
| 831 | CGPG1964.pep | zf-C3HC4::YDG_SRA | 109-147::228-345 |
| 832 | CGPG1973.pep | zf-UBR | 40-109 |
| 833 | CGPG1977.pep | TFIIF_alpha | 18-542 |
| 834 | CGPG1996.pep | Pkinase | 3-286 |
| 835 | CGPG2005.pep | NADPH_Ox::Ferric_reduct::FAD_binding_8::NAD_binding_6 | 130-229::352-511::552-671::677-850 |
| 837 | CGPG2044.pep | PTR2 | 99-507 |
| 838 | CGPG2059.pep | Nuc_sug_transp | 104-340 |
| 839 | CGPG2065.pep | PEARLI-4 | 342-611 |
| 841 | CGPG2072.pep | DUF1639 | 264-300 |
| 842 | CGPG2074.pep | HMA::HMA | 75-138::173-235 |
| 843 | CGPG2116.pep | NOI | 1-67 |
| 845 | CGPG2142.pep | MATH::MATH | 101-233::258-375 |
| 847 | CGPG2190.pep | DJ-1_PfpI::DJ-1_PfpI | 34-174::240-378 |
| 849 | CGPG221.pep | DnaJ::DnaJ_CXXCXGXG::DnaJ_C | 35-96::160-243::256-378 |
| 850 | CGPG2213.pep | RNA_pol_I_A49 | 83-441 |
| 851 | CGPG2247.pep | DUF23 | 256-497 |
| 852 | CGPG228.pep | p450 | 67-511 |
| 853 | CGPG2301.pep | PC_rep::PC_rep::PC_rep::PC_rep::PC_rep::PC_rep | 414-447::448-484::485-519::523-557::671-705::706-740 |

TABLE 17-continued

| PEP SEQ ID | Construct ID | Module | Position |
|---|---|---|---|
| 854 | CGPG2304.pep | Phi_1 | 32-309 |
| 856 | CGPG2348.pep | Gal-bind_lectin::Galactosyl_T | 165-343::385-580 |
| 857 | CGPG2349.pep | IQ::IQ | 120-140::142-162 |
| 858 | CGPG2354.pep | ABC1 | 183-306 |
| 859 | CGPG2369.pep | DAGK_cat | 228-368 |
| 860 | CGPG2382.pep | WD40::WD40::WD40::WD40 | 65-103::106-144::197-235::240-278 |
| 861 | CGPG2392.pep | UBX | 311-392 |
| 862 | CGPG2397.pep | AA_permease | 64-510 |
| 863 | CGPG240.pep | Hydrolase | 22-210 |
| 865 | CGPG2433.pep | DUF23 | 289-544 |
| 868 | CGPG2464.pep | Glyco_transf_8 | 83-345 |
| 869 | CGPG2472.pep | Band_7 | 35-227 |
| 870 | CGPG2480.pep | Prefoldin | 53-175 |
| 871 | CGPG253.pep | HEAT::HEAT::HEAT::HEAT::HEAT::HEAT::HEAT::HEAT::HEAT::HEAT::HEAT::HEAT | 82-117::158-194::197-233::236-272::275-311::314-350::353-389::392-428::431-467::470-506::509-545::548-584 |
| 872 | CGPG2538.pep | PfkB | 7-297 |
| 873 | CGPG2567.pep | zf-C3HC4 | 372-412 |
| 874 | CGPG2571.pep | zf-C3HC4 | 146-187 |
| 875 | CGPG258.pep | Cyclin_N::Cyclin_C | 185-310::312-433 |
| 876 | CGPG268.pep | PTR2 | 97-514 |
| 877 | CGPG274.pep | WD40::WD40::WD40 | 259-298::303-342::350-389 |
| 878 | CGPG275.pep | PP2C | 32-271 |
| 879 | CGPG277.pep | IGPD | 103-247 |
| 880 | CGPG2785.pep | SIR2 | 52-216 |
| 881 | CGPG2832.pep | Myb_DNA-binding | 195-243 |
| 883 | CGPG2865.pep | SRF-TF | 17-67 |
| 884 | CGPG2874.pep | polyprenyl_synt | 123-383 |
| 885 | CGPG2914.pep | AP2 | 84-142 |
| 886 | CGPG295.pep | Pro_isomerase | 96-256 |
| 888 | CGPG3009.pep | Arf | 4-184 |
| 889 | CGPG3030.pep | Pkinase | 4-301 |
| 890 | CGPG3048.pep | adh_short | 18-186 |
| 891 | CGPG3056.pep | PP2C | 76-341 |
| 893 | CGPG309.pep | Cyclin_N | 4-143 |
| 894 | CGPG3094.pep | C2 | 6-87 |
| 895 | CGPG3095.pep | F-box::LRR_2::FBD | 5-52::163-188::374-426 |
| 896 | CGPG3137.pep | Spermine_synth | 54-313 |
| 897 | CGPG3156.pep | DEAD::Helicase_C | 33-212::279-355 |
| 898 | CGPG3157.pep | DEAD::Helicase_C | 175-355::427-503 |
| 899 | CGPG3205.pep | F-box::Kelch_1::Kelch_1 | 130-177::220-269::347-389 |
| 900 | CGPG3236.pep | Thioredoxin | 4-108 |
| 901 | CGPG3248.pep | Copine | 102-250 |
| 902 | CGPG3255.pep | NTP_transferase::Hexapep::Hexapep::Hexapep::Hexapep | 10-246::294-311::312-329::335-352::379-396 |
| 903 | CGPG3258.pep | UDPGT | 23-484 |
| 904 | CGPG3261.pep | Pkinase | 79-334 |
| 907 | CGPG3283.pep | Mo25 | 1-339 |
| 908 | CGPG3302.pep | SRF-TF::K-box | 9-59::76-174 |
| 909 | CGPG3334.pep | GRP | 1-113 |
| 910 | CGPG3361.pep | DUF1644 | 38-255 |
| 911 | CGPG337.pep | Glyco_transf_8 | 19-264 |
| 912 | CGPG3400.pep | IQ | 304-324 |
| 914 | CGPG3424.pep | TFIIS_C | 79-117 |
| 915 | CGPG3428.pep | DUF914 | 136-435 |
| 916 | CGPG3465.pep | zf-MYND::UCH | 57-94::326-630 |
| 917 | CGPG347.pep | DREPP | 1-225 |
| 919 | CGPG3567.pep | DUF581 | 63-121 |
| 920 | CGPG3575.pep | Mago-bind | 22-48 |
| 921 | CGPG3579.pep | SNARE | 141-203 |
| 926 | CGPG365.pep | MATH::BTB | 53-182::206-328 |
| 927 | CGPG3665.pep | BNR::BNR::BNR | 138-149::189-200::239-250 |
| 928 | CGPG3684.pep | Pro_dh | 113-464 |
| 929 | CGPG3690.pep | MtN3_slv::MtN3_slv | 10-97::131-217 |
| 930 | CGPG3717.pep | OTU | 219-331 |
| 931 | CGPG372.pep | SET | 83-212 |
| 934 | CGPG3781.pep | SRF-TF | 11-65 |
| 935 | CGPG380.pep | Histone | 25-94 |
| 936 | CGPG3821.pep | F-box::FBA_3 | 5-52::205-281 |
| 937 | CGPG3824.pep | WRKY | 107-169 |
| 938 | CGPG3901.pep | 2OG-FeII_Oxy | 166-271 |
| 939 | CGPG391.pep | Histone | 58-132 |
| 941 | CGPG394.pep | DUF6::TPT | 11-152::170-319 |
| 942 | CGPG3964.pep | Pyr_redox | 174-248 |
| 943 | CGPG397.pep | SOR_SNZ::ThiG | 24-229::123-290 |
| 945 | CGPG3983.pep | DUF6::DUF6 | 31-164::213-342 |
| 946 | CGPG3986.pep | WD40::WD40 | 160-197::249-288 |
| 947 | CGPG3991.pep | SNARE_assoc | 111-232 |

TABLE 17-continued

| PEP SEQ ID | Construct ID | Module | Position |
|---|---|---|---|
| 948 | CGPG4050.pep | PP2C | 49-327 |
| 949 | CGPG4070.pep | Not3::NOT2_3_5 | 2-246::693-881 |
| 950 | CGPG4071.pep | Pkinase_Tyr | 135-389 |
| 951 | CGPG4099.pep | 14-3-3 | 6-243 |
| 952 | CGPG4138.pep | adh_short | 44-217 |
| 953 | CGPG4152.pep | RRM_1 | 11-78 |
| 954 | CGPG4153.pep | HMG-CoA_red | 190-583 |
| 955 | CGPG4164.pep | PP2C | 22-322 |
| 956 | CGPG4169.pep | WD40::WD40::WD40::WD40 | 253-291::298-336::340-378::510-549 |
| 957 | CGPG421.pep | Pkinase::efhand::efhand::efhand::efhand | 22-280::327-355::363-391::399-427::433-461 |
| 958 | CGPG4222.pep | Pkinase | 73-331 |
| 959 | CGPG4223.pep | SRF-TF | 23-76 |
| 960 | CGPG4240.pep | F-box | 8-56 |
| 961 | CGPG4242.pep | PP2C | 58-341 |
| 962 | CGPG4248.pep | efhand::efhand::efhand | 10-38::89-117::127-155 |
| 963 | CGPG425.pep | Pkinase_Tyr | 8-260 |
| 964 | CGPG4265.pep | Cys_Met_Meta_PP | 42-432 |
| 965 | CGPG4283.pep | Dehydrin | 36-183 |
| 966 | CGPG4297.pep | Globin | 10-149 |
| 967 | CGPG43.pep | Aa_trans | 46-481 |
| 968 | CGPG430.pep | Pkinase | 8-264 |
| 969 | CGPG4305.pep | Rib_5-P_isom_A | 85-273 |
| 970 | CGPG4307.pep | Orn_Arg_deC_N::Orn_DAP_Arg_deC | 98-348::351-459 |
| 971 | CGPG4315.pep | PPR::PPR::PPR::PPR::PPR::PPR | 139-173::209-243::286-320::321-355::356-390::391-425 |
| 972 | CGPG4320.pep | DUF6::DUF6 | 20-153::190-319 |
| 973 | CGPG4344.pep | Mito_carr::Mito_carr::Mito_carr | 13-98::104-199::203-297 |
| 975 | CGPG4349.pep | Aha1_N::AHSA1 | 29-165::233-291 |
| 976 | CGPG4365.pep | CCT | 220-258 |
| 978 | CGPG4389.pep | Aminotran_1_2 | 23-376 |
| 979 | CGPG4404.pep | p450 | 37-514 |
| 980 | CGPG4405.pep | p450 | 69-504 |
| 981 | CGPG4419.pep | p450 | 33-477 |
| 982 | CGPG4432.pep | p450 | 70-528 |
| 984 | CGPG4443.pep | p450 | 32-551 |
| 985 | CGPG445.pep | PLAT::Lipoxygenase | 54-159::171-843 |
| 986 | CGPG4453.pep | p450 | 40-500 |
| 987 | CGPG4481.pep | Glyco_hydro_17 | 34-352 |
| 988 | CGPG4490.pep | AMP-binding | 42-473 |
| 989 | CGPG4498.pep | Glyco_hydro_1 | 40-516 |
| 990 | CGPG4506.pep | RRM_1 | 18-89 |
| 991 | CGPG4553.pep | DUF313 | 158-265 |
| 992 | CGPG4583.pep | HIT | 43-142 |
| 993 | CGPG4643.pep | Pkinase | 400-656 |
| 994 | CGPG4650.pep | Pkinase | 141-425 |
| 996 | CGPG468.pep | Fer4::Fer4 | 116-139::155-178 |
| 997 | CGPG4684.pep | MIP | 11-232 |
| 998 | CGPG4689.pep | LRRNT_2::LRR_1::LRR_1::Pkinase | 29-70::120-144::144-165::261-532 |
| 999 | CGPG4691.pep | PCI | 281-385 |
| 1000 | CGPG4702.pep | DUF6::TPT | 106-231::240-385 |
| 1001 | CGPG4703.pep | TPT | 205-349 |
| 1002 | CGPG4710.pep | CPSase_L_chain::CPSase_L_D2::CPSase_L_D3::CPSase_L_chain::CPSase_L_D2::MGS | 97-217::219-455::515-638::648-775::777-989::1061-1148 |
| 1003 | CGPG4713.pep | DUF231 | 241-420 |
| 1004 | CGPG4730.pep | DHquinase_I::Shikimate_dh_N::Shikimate_DH | 96-313::328-408::440-558 |
| 1005 | CGPG4747.pep | UQ_con | 8-145 |
| 1006 | CGPG4755.pep | Cpn60_TCP1 | 30-520 |
| 1008 | CGPG4779.pep | Peptidase_M22 | 27-305 |
| 1009 | CGPG4848.pep | PGAM | 77-246 |
| 1010 | CGPG4879.pep | SIS::CBS | 64-197::229-350 |
| 1011 | CGPG4882.pep | TFIIS | 121-206 |
| 1012 | CGPG4892.pep | DUF260 | 5-105 |
| 1013 | CGPG4903.pep | DUF260 | 7-108 |
| 1014 | CGPG4925.pep | WD40::WD40::WD40::WD40 | 74-112::116-153::207-245::249-287 |
| 1015 | CGPG4937.pep | NLE::WD40::WD40::WD40::WD40 | 11-79::140-182::195-233::262-299::348-387 |
| 1016 | CGPG4949.pep | Pkinase | 208-470 |
| 1017 | CGPG4971.pep | SKI | 11-177 |
| 1018 | CGPG499.pep | Voltage_CLC::CBS | 138-560::593-759 |
| 1019 | CGPG5004.pep | Adh_short | 53-224 |
| 1020 | CGPG5028.pep | Adh_short | 42-200 |
| 1021 | CGPG5032.pep | Adh_short | 48-216 |
| 1022 | CGPG5038.pep | DUF26::DUF26::Pkinase | 74-134::200-254::345-620 |
| 1023 | CGPG5045.pep | LRRNT_2::LRR_1::LRR_1::LRR_1::LRR_1::Pkinase | 24-67::97-119::122-144::146-168::170-192::306-576 |
| 1024 | CGPG5048.pep | LRRNT_2::LRR_1::LRR_1::LRR_1::LRR_1::LRR_1::Pkinase | 22-59::89-111::113-135::137-159::161-182::183-205::307-578 |
| 1025 | CGPG5051.pep | AOX | 45-323 |

TABLE 17-continued

| PEP SEQ ID | Construct ID | Module | Position |
|---|---|---|---|
| 1026 | CGPG5061.pep | Fibrillarin | 1-99 |
| 1027 | CGPG5062.pep | Skp1_POZ::Skp1 | 6-66::86-163 |
| 1028 | CGPG5069.pep | Skp1_POZ::Skp1 | 4-64::89-167 |
| 1029 | CGPG5070.pep | Skp1_POZ::Skp1 | 4-64::72-150 |
| 1030 | CGPG5097.pep | Pkinase | 295-579 |
| 1031 | CGPG510.pep | Rho_GDI | 20-223 |
| 1032 | CGPG5100.pep | Pkinase | 353-615 |
| 1033 | CGPG5117.pep | efhand_like::PI-PLC-X::PI-PLC-Y::C2 | 25-105::107-251::294-412::430-523 |
| 1034 | CGPG5151.pep | p450 | 1-282 |
| 1035 | CGPG5155.pep | p450 | 27-493 |
| 1036 | CGPG5159.pep | p450 | 26-520 |
| 1037 | CGPG516.pep | HD::RelA_SpoT | 233-337::427-537 |
| 1038 | CGPG5161.pep | p450 | 31-503 |
| 1039 | CGPG5186.pep | Thioredoxin | 70-172 |
| 1040 | CGPG519.pep | Abhydrolase_1 | 59-279 |
| 1041 | CGPG5190.pep | Ribosomal_L37 | 15-125 |
| 1042 | CGPG5191.pep | TPR_2 | 166-199 |
| 1044 | CGPG521.pep | Abhydrolase_1 | 65-282 |
| 1045 | CGPG5211.pep | DUF827 | 16-271 |
| 1047 | CGPG5213.pep | DUF623 | 143-203 |
| 1048 | CGPG522.pep | FA_desaturase | 62-277 |
| 1049 | CGPG5223.pep | PGM_PMM_I::PGM_PMM_II::PGM_PMM_III::PGM_PMM_IV | 79-222::251-360::362-486::507-612 |
| 1050 | CGPG5224.pep | LRR_1::LRR_1::LRR_1::LRR_1::LRR_1::LRR_1::LRR_1::LRR_1 | 231-252::254-275::277-298::300-321::323-344::369-390::392-413::440-461 |
| 1051 | CGPG5225.pep | p450 | 37-452 |
| 1052 | CGPG5254.pep | 2OG-FeII_Oxy | 162-279 |
| 1053 | CGPG5257.pep | SpoIIE | 130-374 |
| 1054 | CGPG5262.pep | SH3_1 | 303-359 |
| 1056 | CGPG5282.pep | F-box::Sel1::Sel1::zf-MYND | 17-69::129-167::168-203::273-317 |
| 1058 | CGPG532.pep | Transket_pyr::Transketolase_C | 30-207::222-342 |
| 1059 | CGPG5336.pep | adh_short | 19-188 |
| 1060 | CGPG5350.pep | Aminotran_4 | 107-395 |
| 1061 | CGPG5355.pep | GRAM | 95-173 |
| 1062 | CGPG5376.pep | DUF21::CBS | 14-191::210-326 |
| 1063 | CGPG5377.pep | CBS | 81-226 |
| 1064 | CGPG5382.pep | B56 | 93-416 |
| 1065 | CGPG5385.pep | Pyridoxal_deC | 146-452 |
| 1066 | CGPG539.pep | Citrate_synt | 78-455 |
| 1067 | CGPG5437.pep | IQ | 115-135 |
| 1068 | CGPG5450.pep | DHDPS | 64-341 |
| 1069 | CGPG5473.pep | Xan_ur_permease | 31-438 |
| 1070 | CGPG55.pep | Sugar_tr | 6-719 |
| 1071 | CGPG5505.pep | AlaDh_PNT_N::AlaDh_PNT_C::Saccharop_dh_N::Saccharop_dh | 18-154::194-400::477-583::589-1060 |
| 1073 | CGPG5514.pep | Cyclin_N::Cyclin_C | 165-294::296-422 |
| 1074 | CGPG5541.pep | Pkinase | 316-590 |
| 1075 | CGPG5546.pep | Cyclin | 108-264 |
| 1076 | CGPG5552.pep | Cornichon | 2-125 |
| 1077 | CGPG5556.pep | SAC3_GANP | 20-211 |
| 1078 | CGPG557.pep | Chitin_bind_1::Barwin | 21-62::73-191 |
| 1079 | CGPG5576.pep | zf-PARP::zf-PARP::PADR1::BRCT::WGR::PARP_reg::PARP | 11-88::117-195::290-343::394-471::517-605::633-765::767-979 |
| 1080 | CGPG5596.pep | Response_reg | 9-143 |
| 1081 | CGPG5605.pep | DEAD::Helicase_C | 52-221::290-366 |
| 1082 | CGPG5606.pep | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 21-62::90-113::115-137::140-162::164-186::188-211::213-235::237-259::261-283::308-330::332-354::356-375::380-402::404-426::428-450::452-474::500-522::524-546::548-570::571-592::683-964 |
| 1083 | CGPG561.pep | XG_FTase | 54-532 |
| 1084 | CGPG5618.pep | Lectin_legB::Pkinase | 20-247::376-651 |
| 1085 | CGPG5642.pep | Aldedh | 18-477 |
| 1086 | CGPG5644.pep | ELFV_dehydrog_N::ELFV_dehydrog | 51-181::197-428 |
| 1087 | CGPG5647.pep | Aldedh | 46-511 |
| 1088 | CGPG5655.pep | Glutaminase | 23-309 |
| 1089 | CGPG5660.pep | Glutaminase | 24-308 |
| 1090 | CGPG5662.pep | Aminotran_3 | 47-381 |
| 1091 | CGPG568.pep | FTHFS | 14-634 |
| 1092 | CGPG5686.pep | Aminotran_3 | 31-387 |
| 1093 | CGPG5702.pep | Gln-synt_N::Gln-synt_C | 28-109::116-397 |
| 1094 | CGPG5712.pep | Pribosyltran | 22-158 |
| 1095 | CGPG5713.pep | Rib_5-P_isom_A | 55-229 |
| 1096 | CGPG5715.pep | Pribosyltran | 27-163 |
| 1097 | CGPG5723.pep | NDK | 4-138 |
| 1098 | CGPG5729.pep | Cyclin_N::Cyclin_C | 210-336::338-457 |

TABLE 17-continued

| PEP SEQ ID | Construct ID | Module | Position |
|---|---|---|---|
| 1099 | CGPG5730.pep | Lung_7-TM_R | 151-444 |
| 1101 | CGPG5741.pep | NIF | 165-344 |
| 1102 | CGPG5752.pep | CAF1 | 161-404 |
| 1103 | CGPG5771.pep | Acyltransferase | 84-277 |
| 1104 | CGPG5778.pep | Aa_trans | 51-498 |
| 1105 | CGPG5782.pep | Sugar_tr | 65-525 |
| 1106 | CGPG5785.pep | Sugar_tr | 69-530 |
| 1107 | CGPG5797.pep | AA_permease | 94-562 |
| 1108 | CGPG580.pep | MGDG_synth::Glyco_tran_28_C | 155-323::349-512 |
| 1109 | CGPG5805.pep | AA_permease | 57-511 |
| 1110 | CGPG5810.pep | Ank::Ank::Pkinase_Tyr | 74-106::107-139::200-468 |
| 1111 | CGPG5822.pep | Pkinase | 131-418 |
| 1112 | CGPG5837.pep | Pkinase | 14-275 |
| 1113 | CGPG5855.pep | Pkinase | 81-363 |
| 1114 | CGPG5868.pep | Pkinase_Tyr | 45-312 |
| 1115 | CGPG587.pep | FKBP_C | 104-208 |
| 1117 | CGPG5893.pep | Pkinase | 52-314 |
| 1118 | CGPG5909.pep | ADH_zinc_N | 163-310 |
| 1119 | CGPG5914.pep | ADH_N::ADH_zinc_N | 54-188::219-362 |
| 1123 | CGPG5930.pep | Mov34 | 328-437 |
| 1124 | CGPG5945.pep | Pyr_redox_2 | 8-305 |
| 1125 | CGPG5958.pep | Pyr_redox_2 | 8-304 |
| 1126 | CGPG5977.pep | Ank::Ank::Ank::Pkinase | 48-80::81-113::114-146::166-424 |
| 1127 | CGPG598.pep | Nramp | 66-429 |
| 1128 | CGPG5986.pep | Pkinase | 43-329 |
| 1129 | CGPG5994.pep | F-box::LRR_2 | 62-108::314-340 |
| 1130 | CGPG5996.pep | Tetraspannin | 4-230 |
| 1131 | CGPG6021.pep | RRM_1::RRM_1 | 8-77::108-178 |
| 1132 | CGPG6027.pep | RRM_1 | 42-113 |
| 1133 | CGPG6035.pep | Pyr_redox_2::efhand | 51-370::376-404 |
| 1134 | CGPG604.pep | PSI_PsaH | 6-145 |
| 1136 | CGPG606.pep | Phytochelatin::DUF1984 | 46-178::179-259 |
| 1137 | CGPG6069.pep | RNA_pol_A_bac | 124-268 |
| 1138 | CGPG608.pep | TB2_DP1_HVA22 | 11-108 |
| 1139 | CGPG6080.pep | Str_synth | 144-232 |
| 1140 | CGPG6082.pep | Ras | 8-179 |
| 1141 | CGPG6089.pep | NicO | 153-372 |
| 1143 | CGPG6128.pep | Reticulon | 22-197 |
| 1144 | CGPG614.pep | cobW | 74-246 |
| 1145 | CGPG6149.pep | Glutaredoxin | 84-148 |
| 1146 | CGPG6172.pep | Ras | 11-173 |
| 1147 | CGPG6174.pep | Ras | 19-180 |
| 1148 | CGPG6176.pep | Ras | 15-177 |
| 1149 | CGPG6197.pep | Phi_1 | 55-334 |
| 1150 | CGPG620.pep | tRNA-synt_1g | 71-430 |
| 1152 | CGPG6204.pep | mTERF | 75-357 |
| 1153 | CGPG621.pep | RRM_1 | 19-90 |
| 1154 | CGPG6210.pep | Sugar_tr | 29-459 |
| 1155 | CGPG6211.pep | Sugar_tr | 24-479 |
| 1156 | CGPG6214.pep | Sugar_tr | 26-487 |
| 1157 | CGPG6215.pep | PTR2 | 93-486 |
| 1158 | CGPG6222.pep | Sugar_tr | 27-490 |
| 1159 | CGPG6229.pep | Sugar_tr | 28-490 |
| 1160 | CGPG6233.pep | MFS_1 | 37-473 |
| 1161 | CGPG6237.pep | Sugar_tr | 25-483 |
| 1162 | CGPG6243.pep | Pkinase | 25-333 |
| 1163 | CGPG6248.pep | Pkinase::NAF | 22-276::306-366 |
| 1164 | CGPG6252.pep | Pkinase::NAF | 12-266::298-358 |
| 1165 | CGPG6267.pep | Pkinase | 68-306 |
| 1166 | CGPG6272.pep | Pkinase | 74-349 |
| 1167 | CGPG6294.pep | Pkinase | 75-352 |
| 1168 | CGPG63.pep | p450 | 44-511 |
| 1170 | CGPG6317.pep | PTR2 | 101-488 |
| 1171 | CGPG6328.pep | Trehalose_PPase | 121-354 |
| 1172 | CGPG6334.pep | Sterol_desat | 34-245 |
| 1173 | CGPG6336.pep | Sterol_desat | 38-247 |
| 1174 | CGPG6349.pep | LRR_1::LRR_1::LRR_1::LRR_1::LRR_1::LRR_1::LRR_1 | 42-62::64-84::108-128::130-151::153-174::176-197::199-219 |
| 1175 | CGPG6352.pep | zf-CCHC | 81-98 |
| 1177 | CGPG6364.pep | Gp_dh_N::Gp_dh_C | 3-152::157-313 |
| 1178 | CGPG6366.pep | Gp_dh_N::Gp_dh_C | 3-153::158-314 |
| 1179 | CGPG6375.pep | Aminotran_1_2 | 36-390 |
| 1180 | CGPG6388.pep | NTP_transferase | 15-285 |
| 1181 | CGPG6391.pep | ADH_N::ADH_zinc_N | 32-143::172-312 |
| 1182 | CGPG6399.pep | ADH_N::ADH_zinc_N | 27-155::186-332 |
| 1183 | CGPG6407.pep | Glucokinase | 5-341 |
| 1184 | CGPG6418.pep | ADH_N::ADH_zinc_N | 28-156::187-333 |
| 1185 | CGPG6430.pep | Iso_dh | 6-355 |

TABLE 17-continued

| PEP SEQ ID | Construct ID | Module | Position |
|---|---|---|---|
| 1186 | CGPG6432.pep | ADH_N::ADH_zinc_N | 25-135::166-305 |
| 1187 | CGPG6437.pep | TPT | 205-388 |
| 1188 | CGPG6445.pep | Aldedh | 45-511 |
| 1189 | CGPG6450.pep | Aldedh | 26-491 |
| 1190 | CGPG6458.pep | Aldedh | 22-480 |
| 1191 | CGPG6465.pep | PfkB | 10-314 |
| 1192 | CGPG6476.pep | PFK | 3-278 |
| 1193 | CGPG6505.pep | Aminotran_3 | 123-449 |
| 1194 | CGPG6507.pep | Gln-synt_N::Gln-synt_C | 105-187::193-446 |
| 1195 | CGPG6509.pep | Glutaminase | 112-396 |
| 1196 | CGPG6510.pep | Aldedh | 17-476 |
| 1197 | CGPG6515.pep | Aldedh | 19-476 |
| 1198 | CGPG6520.pep | Aldedh | 29-491 |
| 1199 | CGPG6531.pep | Enolase_N::Enolase_C | 3-133::138-425 |
| 1200 | CGPG6553.pep | Aldedh | 103-563 |
| 1201 | CGPG6557.pep | ELFV_dehydrog_N::ELFV_dehydrog | 145-275::290-533 |
| 1202 | CGPG6563.pep | Aminotran_1_2 | 120-472 |
| 1203 | CGPG6564.pep | iPGM_N::Metalloenzyme | 90-451::461-576 |
| 1204 | CGPG6572.pep | Gp_dh_N::Gp_dh_C | 91-241::246-402 |
| 1205 | CGPG6577.pep | iPGM_N::Metalloenzyme | 92-451::461-577 |
| 1206 | CGPG6588.pep | Pyr_redox_2::Pyr_redox_dim | 92-409::437-546 |
| 1207 | CGPG6596.pep | Biotin_lipoyl::E3_binding::2-oxoacid_dh | 91-164::228-264::296-521 |
| 1209 | CGPG6619.pep | Transketolase_N::Transket_pyr::Transketolase_C | 101-435::450-627::639-754 |
| 1210 | CGPG6623.pep | PGAM | 96-330 |
| 1211 | CGPG6626.pep | OstA | 109-219 |
| 1212 | CGPG663.pep | Pro_CA | 155-325 |
| 1213 | CGPG6635.pep | Cytochrom_C | 126-204 |
| 1215 | CGPG6641.pep | AstE_AspA | 93-372 |
| 1216 | CGPG6642.pep | Transket_pyr::Transketolase_C | 125-303::319-443 |
| 1217 | CGPG6645.pep | TIM | 95-336 |
| 1218 | CGPG6660.pep | CBS | 97-214 |
| 1219 | CGPG6671.pep | NTP_transferase | 102-374 |
| 1220 | CGPG6697.pep | Transaldolase | 100-400 |
| 1221 | CGPG6706.pep | iPGM_N::Metalloenzyme | 90-451:461-576 |
| 1222 | CGPG6723.pep | Aminotran_1_2 | 124-478 |
| 1223 | CGPG6729.pep | Gln-synt_N::Gln-synt_C | 100-182::189-470 |
| 1224 | CGPG6738.pep | Aminotran_1_2 | 123-473 |
| 1225 | CGPG6742.pep | Aldedh | 105-563 |
| 1226 | CGPG6752.pep | TIM | 92-334 |
| 1227 | CGPG6760.pep | GATase_2::Asn_synthase | 2-164::241-531 |
| 1228 | CGPG6768.pep | PGI | 55-545 |
| 1229 | CGPG6779.pep | Isoamylase_N::Alpha-amylase | 105-182::219-613 |
| 1230 | CGPG6785.pep | Molybdop_Fe4S4::Molybdopterin::Molydop_binding | 44-105::108-660::892-1011 |
| 1231 | CGPG6800.pep | PGI | 52-541 |
| 1232 | CGPG686.pep | RRM_1::zf-CCHC | 9-80::118-135 |
| 1233 | CGPG6898.pep | Hin1 | 28-163 |
| 1234 | CGPG6900.pep | Pkinase | 97-365 |
| 1236 | CGPG6920.pep | Dehydrin | 14-128 |
| 1237 | CGPG6921.pep | CorA | 48-440 |
| 1240 | CGPG6945.pep | SNARE | 37-99 |
| 1241 | CGPG6946.pep | MATH | 13-133 |
| 1242 | CGPG6948.pep | PAP2 | 100-233 |
| 1243 | CGPG6974.pep | DUF538 | 7-146 |
| 1244 | CGPG6976.pep | DUF926 | 293-406 |
| 1245 | CGPG6996.pep | CPDase | 1-179 |
| 1246 | CGPG7002.pep | zf-C3HC4 | 123-157 |
| 1247 | CGPG7013.pep | zf-C3HC4 | 115-156 |
| 1248 | CGPG7021.pep | Invertase_neut | 98-564 |
| 1251 | CGPG7075.pep | DUF1749 | 77-349 |
| 1252 | CGPG7080.pep | Glutaredoxin | 44-106 |
| 1253 | CGPG7094.pep | DUF300 | 6-281 |
| 1254 | CGPG7095.pep | Abhydrolase_3 | 107-321 |
| 1255 | CGPG7104.pep | Saccharop_dh | 13-445 |
| 1256 | CGPG7118.pep | F-box | 25-73 |
| 1257 | CGPG7122.pep | Pkinase | 20-280 |
| 1258 | CGPG713.pep | Cyclin_N | 5-135 |
| 1259 | CGPG7130.pep | CS | 145-220 |
| 1260 | CGPG7145.pep | Transthyretin | 191-310 |
| 1261 | CGPG7166.pep | DnaJ | 79-141 |
| 1262 | CGPG7179.pep | Bystin | 127-423 |
| 1263 | CGPG7184.pep | PBD | 27-127 |
| 1264 | CGPG7185.pep | GAF::HisKA | 190-346::382-445 |
| 1265 | CGPG7192.pep | 2OG-FeII_Oxy | 201-301 |
| 1266 | CGPG7199.pep | RWD | 3-122 |
| 1267 | CGPG72.pep | Amino_oxidase | 66-528 |
| 1268 | CGPG7231.pep | B3_4::B5 | 118-280::305-378 |
| 1269 | CGPG7241.pep | Peptidase_C26 | 58-281 |

TABLE 17-continued

| PEP SEQ ID | Construct ID | Module | Position |
|---|---|---|---|
| 1272 | CGPG7265.pep | ARM_1 | 12-296 |
| 1273 | CGPG7274.pep | DUF640 | 36-168 |
| 1274 | CGPG7291.pep | eIF-1a | 20-91 |
| 1275 | CGPG7303.pep | Aldedh | 20-484 |
| 1276 | CGPG7315.pep | Y_phosphatase2 | 116-280 |
| 1278 | CGPG7327.pep | Actin | 2-470 |
| 1280 | CGPG7347.pep | Tcp11 | 648-1133 |
| 1281 | CGPG7348.pep | CorA | 90-467 |
| 1283 | CGPG7356.pep | Metallophos | 2-120 |
| 1284 | CGPG7359.pep | Methyltransf_12 | 38-133 |
| 1286 | CGPG7372.pep | zf-C3HC4 | 119-160 |
| 1287 | CGPG7379.pep | zf-C3HC4 | 36-76 |
| 1288 | CGPG7398.pep | DUF212 | 22-167 |
| 1289 | CGPG7403.pep | TLD | 203-341 |
| 1290 | CGPG7404.pep | PBP | 25-170 |
| 1291 | CGPG7410.pep | HLH | 36-83 |
| 1292 | CGPG7417.pep | MMR_HSR1 | 131-252 |
| 1293 | CGPG7423.pep | Gln-synt_N::Gln-synt_C | 102-183::190-471 |
| 1294 | CGPG7424.pep | FBPase | 92-424 |
| 1297 | CGPG7443.pep | DUF1001 | 92-274 |
| 1298 | CGPG7449.pep | ScpA_ScpB | 104-347 |
| 1301 | CGPG7459.pep | DUF1350 | 90-360 |
| 1303 | CGPG7481.pep | Abhydrolase_1 | 113-361 |
| 1304 | CGPG7483.pep | GTP_EFTU::GTP_EFTU_D2::EFG_C | 62-260::281-355::461-551 |
| 1306 | CGPG7503.pep | PBP | 19-170 |
| 1307 | CGPG7504.pep | MSF1 | 15-187 |
| 1309 | CGPG7516.pep | DUF783 | 25-229 |
| 1312 | CGPG7524.pep | lsy1 | 1-292 |
| 1313 | CGPG7525.pep | UFD1 | 10-184 |
| 1315 | CGPG7537.pep | KTI12 | 1-291 |
| 1317 | CGPG7575.pep | Efhand | 95-123 |
| 1318 | CGPG7577.pep | TP_methylase | 1-213 |
| 1319 | CGPG7590.pep | Ribonuc_L-PSP | 61-179 |
| 1321 | CGPG7601.pep | CCT | 237-275 |
| 1322 | CGPG7605.pep | RRM_1 | 88-158 |
| 1323 | CGPG7607.pep | Amidohydro_2 | 10-289 |
| 1325 | CGPG7632.pep | zf-Tim10_DDP | 12-77 |
| 1326 | CGPG7673.pep | zf-MYND::UCH | 76-113::468-774 |
| 1327 | CGPG7683.pep | zf-LSD1::zf-LSD1::zf-LSD1 | 28-52::67-91::105-129 |
| 1328 | CGPG773.pep | H_PPase | 64-798 |
| 1329 | CGPG7776.pep | DUF525 | 311-445 |
| 1330 | CGPG7781.pep | SapB_1::SapB_2::SapB_1::SapB_2 | 45-83::86-119::131-169::172-206 |
| 1331 | CGPG7785.pep | LRRNT_2::LRR_1::LRR_1::LRR_1::LRR_1::LRR_1::LRR_1::Pkinase | 24-65::93-115::117-139::141-163::165-187::189-211::213-235::415-682 |
| 1332 | CGPG7787.pep | Aldose_epim | 26-301 |
| 1334 | CGPG7796.pep | WD40::WD40::WD40::WD40::WD40::WD40::WD40::WD40::WD40::WD40::Utp13 | 50-88::92-130::134-174::182-220::391-432::436-475::489-527::531-569::573-611::615-653::674-809 |
| 1335 | CGPG7797.pep | GILT | 35-144 |
| 1336 | CGPG7801.pep | LRR_1::LRR_1::LRR_1::LRR_1::LRR_1::LRR_1::LRR_1::LRR_1::Pkinase | 106-129::132-154::156-178::180-199::201-223::225-246::249-272::273-294::456-716 |
| 1337 | CGPG7813.pep | WD40::WD40::WD40::WD40::PWP2 | 379-417::421-459::507-545::549-587::785-900 |
| 1341 | CGPG7863.pep | zf-CW::MBD | 100-153::162-237 |
| 1342 | CGPG7868.pep | BCNT | 165-244 |
| 1343 | CGPG7881.pep | Aldedh | 99-558 |
| 1344 | CGPG7887.pep | HEAT::Arm::HEAT::Arm | 191-222::262-302::389-424::423-463 |
| 1345 | CGPG7899.pep | RRM_1 | 225-295 |
| 1346 | CGPG7901.pep | IQ::IQ | 107-127::129-149 |
| 1347 | CGPG7909.pep | DUF383::DUF384 | 92-271::272-330 |
| 1348 | CGPG7911.pep | AAA | 245-447 |
| 1349 | CGPG7919.pep | Cullin | 30-191 |
| 1350 | CGPG7935.pep | IQ::IQ | 93-113::115-135 |
| 1351 | CGPG7940.pep | RRM_1 | 96-161 |
| 1352 | CGPG7959.pep | Cyclin_N::Cyclin_C | 180-306::308-428 |
| 1353 | CGPG7967.pep | IQ::IQ | 106-126::128-148 |
| 1354 | CGPG7975.pep | Arm::Arm | 28-68::70-110 |
| 1355 | CGPG7996.pep | efhand | 136-164 |
| 1356 | CGPG8006.pep | AAA | 241-440 |
| 1357 | CGPG801.pep | Cyt-b5 | 74-171 |
| 1358 | CGPG8023.pep | RRM_1 | 11-82 |
| 1359 | CGPG8025.pep | IQ::IQ | 93-113::115-135 |
| 1360 | CGPG8038.pep | MFS_1 | 36-433 |
| 1361 | CGPG8053.pep | DUF246 | 182-525 |
| 1364 | CGPG8070.pep | GILT | 32-136 |
| 1365 | CGPG8073.pep | Dirigent | 17-183 |
| 1366 | CGPG8076.pep | Tryp_alpha_amyl | 32-107 |
| 1369 | CGPG8095.pep | IPK | 16-279 |

TABLE 17-continued

| PEP SEQ ID | Construct ID | Module | Position |
|---|---|---|---|
| 1370 | CGPG8096.pep | 60KD_IMP | 151-348 |
| 1374 | CGPG8129.pep | Ank::Ank::Ank | 49-81::82-114::115-147 |
| 1378 | CGPG8165.pep | Glutaredoxin | 44-106 |
| 1379 | CGPG8169.pep | Nol1_Nop2_Fmu | 226-505 |
| 1380 | CGPG8203.pep | Uricase::Uricase | 11-140::147-300 |
| 1381 | CGPG8205.pep | DZC | 113-148 |
| 1383 | CGPG8213.pep | Phosphoesterase | 27-388 |
| 1384 | CGPG8225.pep | FBPase | 25-348 |
| 1385 | CGPG8227.pep | NIR_SIR_ferr::NIR_SIR::NIR_SIR_ferr::NIR_SIR | 44-111::119-275::331-399::405-553 |
| 1386 | CGPG8235.pep | Aldedh | 12-471 |
| 1387 | CGPG8236.pep | Molybdop_Fe4S4::Molybdopterin::Molydop_binding::Fer2_BFD | 9-63::66-495::593-703::852-903 |
| 1388 | CGPG8244.pep | PAS_2::GAF::Phytochrome::HisKA::HATPase_c | 15-125::152-320::331-513::528-596::637-747 |
| 1389 | CGPG8254.pep | NIR_SIR_ferr::NIR_SIR::NIR_SIR_ferr::NIR_SIR | 66-133::166-347::362-434::443-591 |
| 1390 | CGPG8255.pep | PPDK_N::PEP-utilizers::PEP-utilizers_C | 16-384::439-531::559-914 |
| 1391 | CGPG8262.pep | ELFV_dehydrog_N::ELFV_dehydrog | 33-163::179-420 |
| 1392 | CGPG8264.pep | Aldedh | 17-480 |
| 1393 | CGPG8269.pep | PGK | 1-396 |
| 1394 | CGPG8271.pep | Gln-synt_N::Gln-synt_C | 16-97::104-386 |
| 1395 | CGPG8305.pep | Sulfotransfer_1 | 70-336 |
| 1396 | CGPG8320.pep | DUF1005 | 282-487 |
| 1397 | CGPG8326.pep | Senescence | 35-369 |
| 1398 | CGPG8344.pep | PPR::PPR::PPR::PPR::PPR::PPR::PPR | 173-207::208-242::243-277::279-312::314-348::349-383::384-418 |
| 1399 | CGPG8347.pep | Ribosomal_S8 | 5-130 |
| 1400 | CGPG8359.pep | Tryp_alpha_amyl | 85-167 |
| 1401 | CGPG8370.pep | Tim17 | 40-156 |
| 1402 | CGPG8371.pep | PseudoU_synth_1::PseudoU_synth_1 | 62-167::324-431 |
| 1404 | CGPG8378.pep | LysM | 78-121 |
| 1406 | CGPG841.pep | ArfGap | 4-120 |
| 1408 | CGPG8438.pep | DUF239 | 174-368 |
| 1409 | CGPG8450.pep | DUF793 | 1-390 |
| 1410 | CGPG8451.pep | IQ::IQ | 105-125::127-147 |
| 1411 | CGPG8459.pep | ubiquitin::UBA::XPC-binding::UBA | 6-78::145-187::242-298::322-361 |
| 1412 | CGPG8461.pep | Ribosomal_S8 | 5-130 |
| 1413 | CGPG8463.pep | PI3_PI4_kinase | 163-421 |
| 1414 | CGPG8471.pep | F-box::FBA_1 | 1-46::211-383 |
| 1415 | CGPG8474.pep | Metallothio_PEC | 12-85 |
| 1416 | CGPG8475.pep | DAO | 10-372 |
| 1417 | CGPG8476.pep | IQ::IQ | 84-104::106-126 |
| 1418 | CGPG8490.pep | ACT::ACT | 21-85::110-174 |
| 1419 | CGPG8510.pep | DUF538 | 9-149 |
| 1420 | CGPG8530.pep | Radical_SAM | 119-283 |
| 1421 | CGPG8533.pep | DUF212 | 27-172 |
| 1425 | CGPG8555.pep | NUDIX | 59-196 |
| 1426 | CGPG8561.pep | zf-C3HC4 | 154-191 |
| 1427 | CGPG8569.pep | 2OG-FeII_Oxy | 159-282 |
| 1428 | CGPG8573.pep | DUF617 | 83-242 |
| 1431 | CGPG8607.pep | DUF862 | 69-219 |
| 1432 | CGPG8611.pep | Stig1 | 13-154 |
| 1434 | CGPG8632.pep | Sina | 86-273 |
| 1435 | CGPG8634.pep | FA_desaturase | 55-278 |
| 1436 | CGPG8635.pep | DUF59 | 36-117 |
| 1438 | CGPG8640.pep | DUF581 | 119-176 |
| 1439 | CGPG8642.pep | CRAL_TRIO_N::CRAL_TRIO | 5-80::93-266 |
| 1441 | CGPG8666.pep | PetM | 69-120 |
| 1443 | CGPG8688.pep | Polyketide_cyc | 60-191 |
| 1444 | CGPG8689.pep | DUF506 | 74-282 |
| 1445 | CGPG8704.pep | GHMP_kinases_N::GHMP_kinases_C | 24-93::166-249 |
| 1448 | CGPG8769.pep | Self-incomp_S1 | 35-144 |
| 1449 | CGPG8774.pep | Maf | 1-207 |
| 1450 | CGPG8778.pep | PPR::PPR::PPR::PPR::PPR::PPR | 13-47::115-149::249-283::284-318::320-354::386-420 |
| 1451 | CGPG8784.pep | Snf7 | 16-189 |
| 1452 | CGPG879.pep | ABC_tran::ABC2_membrane::PDR_assoc::ABC_tran::ABC2_membrane | 195-418::520-733::738-812::887-1077::1174-1388 |
| 1453 | CGPG8797.pep | AMP-binding | 67-488 |
| 1454 | CGPG8810.pep | DUF1645 | 80-252 |
| 1455 | CGPG8827.pep | DUF623 | 199-263 |
| 1456 | CGPG8853.pep | DUF1635 | 1-218 |
| 1457 | CGPG8873.pep | p450 | 72-518 |
| 1458 | CGPG8877.pep | Exo_endo_phos | 33-310 |
| 1459 | CGPG8878.pep | Pkinase::efhand::efhand | 79-337::400-428::434-462 |
| 1460 | CGPG8881.pep | DUF1677 | 3-107 |
| 1461 | CGPG8895.pep | RNA_poll_A14 | 1-137 |

TABLE 17-continued

| PEP SEQ ID | Construct ID | Module | Position |
|---|---|---|---|
| 1462 | CGPG8906.pep | MCM | 272-635 |
| 1463 | CGPG8917.pep | Pkinase | 363-697 |
| 1464 | CGPG8919.pep | Usp::Pkinase | 11-141::405-676 |
| 1465 | CGPG8925.pep | DUF617 | 82-260 |
| 1466 | CGPG8930.pep | Lectin_legB::Pkinase | 26-261::347-617 |
| 1467 | CGPG8937.pep | LRR_1::LRR_1::LRR_1::Pkinase | 440-461::463-485::487-510::602-873 |
| 1468 | CGPG8942.pep | RRM_1 | 23-94 |
| 1469 | CGPG8946.pep | Pkinase | 516-786 |
| 1470 | CGPG8990.pep | V-SNARE | 71-221 |
| 1472 | CGPG9008.pep | TPK_catalytic::TPK_B1_binding | 40-180::191-259 |
| 1473 | CGPG9016.pep | ETC_C1_NDUFA4 | 54-156 |
| 1474 | CGPG9036.pep | MSP | 93-329 |
| 1475 | CGPG9060.pep | LSM | 22-101 |
| 1477 | CGPG908.pep | PPR::PPR::PPR::PPR::PPR::PPR::PPR::PPR | 62-96::125-158::187-221::250-284::351-385::386-419::422-456::488-522 |
| 1478 | CGPG9093.pep | AWPM-19 | 15-156 |
| 1479 | CGPG9096.pep | OTU | 11-121 |
| 1482 | CGPG9111.pep | TB2_DP1_HVA22 | 4-101 |
| 1483 | CGPG9112.pep | DUF778 | 10-177 |
| 1484 | CGPG9123.pep | DUF833 | 1-264 |
| 1485 | CGPG9124.pep | Exo_endo_phos | 20-427 |
| 1486 | CGPG9138.pep | ThiC | 165-588 |
| 1488 | CGPG9150.pep | Pkinase | 56-326 |
| 1489 | CGPG9152.pep | eIF2A | 217-410 |
| 1490 | CGPG9162.pep | AAA | 211-398 |
| 1491 | CGPG9165.pep | GATase::GMP_synt_C | 11-201::432-524 |
| 1492 | CGPG9166.pep | GATase::GMP_synt_C | 28-210::447-539 |
| 1493 | CGPG9171.pep | Zip | 5-266 |
| 1494 | CGPG9177.pep | Complex1_30 kDa::Complex1_49 kDa | 113-181::329-600 |
| 1495 | CGPG9178.pep | PRA-CH::PRA-PH | 54-129::142-230 |
| 1496 | CGPG9179.pep | Pkinase | 4-283 |
| 1497 | CGPG9181.pep | P21-Arc | 17-187 |
| 1499 | CGPG9189.pep | SAC3_GANP | 19-164 |
| 1500 | CGPG9201.pep | TPT | 201-350 |
| 1501 | CGPG9222.pep | YjeF_N::Carb_kinase | 34-199::257-496 |
| 1502 | CGPG9234.pep | DUF393 | 65-183 |
| 1503 | CGPG9237.pep | Tim17 | 18-146 |
| 1504 | CGPG9244.pep | TOM20_plant | 9-200 |
| 1506 | CGPG9249.pep | Pkinase | 46-330 |
| 1507 | CGPG9251.pep | Cyclin_N::Cyclin_C | 54-186::188-314 |
| 1508 | CGPG9280.pep | DUF1000 | 53-168 |
| 1510 | CGPG9302.pep | Diphthamide_syn | 30-398 |
| 1511 | CGPG931.pep | Pkinase | 114-398 |
| 1512 | CGPG9313.pep | CN_hydrolase::NAD_synthase | 5-200::338-652 |
| 1514 | CGPG9327.pep | OPT | 74-729 |
| 1515 | CGPG933.pep | WD40:WD40::WD40::WD40::WD40::WD40::WD40 | 46-84::134-173::177-215::222-260::314-353::524-562::568-605 |
| 1516 | CGPG9334.pep | Sugar_tr | 7-720 |
| 1517 | CGPG967.pep | BTB::NPH3 | 38-135::218-460 |
| 1518 | CGPG988.pep | Cystatin | 36-124 |

TABLE 18

| PEP SEQ ID | Construct ID | Pfam domain name | begin | start | score | E-value |
|---|---|---|---|---|---|---|
| 760 | CGPG1022 | RRM_1 | 95 | 165 | 58.4 | 2.40E-14 |
| 761 | CGPG1035 | Peptidase_C54 | 82 | 373 | 558.5 | 6.50E-165 |
| 763 | CGPG105 | AP2 | 48 | 112 | 146.2 | 8.50E-41 |
| 764 | CGPG1060 | DUF788 | 1 | 169 | 339.1 | 7.70E-99 |
| 765 | CGPG1069 | NDUF_B7 | 2 | 81 | 20.4 | 9.50E-08 |
| 766 | CGPG108 | FHA | 208 | 284 | 59.7 | 9.90E-15 |
| 766 | CGPG108 | PP2C | 309 | 570 | 282.3 | 9.50E-82 |
| 771 | CGPG1136 | RRM_1 | 22 | 87 | 32.4 | 1.60E-06 |
| 774 | CGPG1145 | NUDIX | 24 | 160 | 79.2 | 1.30E-20 |
| 776 | CGPG1173 | adh_short | 6 | 181 | −32 | 0.00071 |
| 777 | CGPG1176 | F-box | 2 | 50 | 21.6 | 0.0027 |
| 779 | CGPG122 | PTR2 | 113 | 517 | 661.3 | 7.40E-196 |
| 780 | CGPG126 | Response_reg | 34 | 158 | 86 | 1.10E-22 |
| 781 | CGPG1262 | Gar1 | 51 | 152 | 251.2 | 2.10E-72 |
| 782 | CGPG128 | Response_reg | 25 | 149 | 84.9 | 2.50E-22 |
| 783 | CGPG1280 | DUF676 | 515 | 717 | 301.1 | 2.10E-87 |
| 784 | CGPG1291 | DUF862 | 2 | 156 | 209.3 | 8.70E-60 |
| 785 | CGPG1295 | TMEM14 | 7 | 104 | 166.9 | 5.20E-47 |
| 787 | CGPG1315 | Brix | 60 | 255 | 139.3 | 1.00E-38 |

TABLE 18-continued

| PEP SEQ ID | Construct ID | Pfam domain name | begin | start | score | E-value |
|---|---|---|---|---|---|---|
| 788 | CGPG1335 | LRR_1 | 424 | 447 | 10.1 | 3.6 |
| 789 | CGPG1344 | Pkinase | 496 | 767 | 132.9 | 8.60E−37 |
| 789 | CGPG1344 | Pkinase_Tyr | 497 | 767 | 81.2 | 3.30E−21 |
| 790 | CGPG1352 | Pkinase | 154 | 425 | 140.3 | 5.20E−39 |
| 790 | CGPG1352 | Pkinase_Tyr | 154 | 425 | 142.1 | 1.50E−39 |
| 791 | CGPG1364 | Pkinase | 38 | 416 | 177.6 | 3.00E−50 |
| 793 | CGPG1396 | malic | 106 | 295 | 422.9 | 4.50E−124 |
| 793 | CGPG1396 | Malic_M | 297 | 550 | 466.9 | 2.50E−137 |
| 794 | CGPG1398 | Glycolytic | 11 | 358 | 877.1 | 8.10E−261 |
| 795 | CGPG1399 | Metallophos | 161 | 360 | 87.4 | 4.50E−23 |
| 796 | CGPG1429 | NTP_transferase | 86 | 365 | 444 | 2.00E−130 |
| 796 | CGPG1429 | Hexapep | 413 | 430 | 3.5 | 55 |
| 796 | CGPG1429 | Hexapep | 466 | 483 | 19.6 | 0.011 |
| 797 | CGPG1430 | E1_dh | 89 | 393 | 468.9 | 6.30E−138 |
| 798 | CGPG1445 | Pkinase | 33 | 294 | 257.4 | 2.90E−74 |
| 798 | CGPG1445 | Pkinase_Tyr | 33 | 294 | 99.8 | 8.00E−27 |
| 799 | CGPG146 | p450 | 38 | 482 | 75.2 | 2.00E−19 |
| 800 | CGPG1492 | Aldedh | 29 | 491 | 535.5 | 5.80E−158 |
| 801 | CGPG1528 | ATP_synt_H | 1 | 70 | 128.2 | 2.30E−35 |
| 802 | CGPG1530 | ArfGap | 15 | 137 | 169.4 | 9.00E−48 |
| 802 | CGPG1530 | C2 | 183 | 262 | 103 | 8.90E−28 |
| 803 | CGPG1535 | SPT2 | 230 | 329 | 31.1 | 9.80E−07 |
| 804 | CGPG1546 | CTP_transf_1 | 101 | 300 | 20 | 2.00E−07 |
| 805 | CGPG1567 | Ribosomal_L19 | 107 | 212 | 72.7 | 1.20E−18 |
| 806 | CGPG1568 | FAD_binding_4 | 82 | 221 | 53.1 | 9.10E−13 |
| 807 | CGPG1575 | DUF740 | 24 | 595 | 626.7 | 1.90E−185 |
| 808 | CGPG1619 | Pyr_redox_2 | 27 | 343 | 213.2 | 5.80E−61 |
| 808 | CGPG1619 | Pyr_redox | 205 | 297 | 93.6 | 6.00E−25 |
| 808 | CGPG1619 | Pyr_redox_dim | 373 | 483 | 158.2 | 2.10E−44 |
| 810 | CGPG1641 | Di19 | 11 | 219 | 487.1 | 2.10E−143 |
| 811 | CGPG1651 | DEAD | 69 | 220 | 110.3 | 5.50E−30 |
| 811 | CGPG1651 | Helicase_C | 378 | 462 | 45.3 | 2.00E−10 |
| 811 | CGPG1651 | DSHCT | 800 | 988 | 358.6 | 1.00E−104 |
| 812 | CGPG1656 | Cyt-b5 | 9 | 82 | 94.5 | 3.30E−25 |
| 812 | CGPG1656 | FA_desaturase | 145 | 399 | 256.9 | 4.10E−71 |
| 813 | CGPG1668 | DUF791 | 4 | 358 | 877.2 | 7.80E−261 |
| 813 | CGPG1668 | MFS_1 | 42 | 406 | 33.6 | 6.70E−07 |
| 815 | CGPG1740 | DUF860 | 25 | 364 | 615 | 6.40E−182 |
| 816 | CGPG177 | WD40 | 168 | 205 | 23.2 | 0.00096 |
| 816 | CGPG177 | WD40 | 257 | 296 | 36 | 1.30E−07 |
| 817 | CGPG1785 | PB1 | 179 | 266 | 108.9 | 1.40E−29 |
| 817 | CGPG1785 | Pkinase | 863 | 1126 | 202.7 | 8.80E−58 |
| 817 | CGPG1785 | Pkinase_Tyr | 863 | 1126 | 253 | 6.30E−73 |
| 818 | CGPG182 | LRR_1 | 46 | 67 | 11.1 | 2.3 |
| 818 | CGPG182 | LRR_1 | 69 | 90 | 12.4 | 1.4 |
| 818 | CGPG182 | LRR_1 | 115 | 136 | 11.8 | 1.8 |
| 818 | CGPG182 | LRR_1 | 161 | 183 | 8.6 | 7 |
| 818 | CGPG182 | LRR_1 | 208 | 229 | 12.9 | 1.1 |
| 818 | CGPG182 | LRR_1 | 231 | 252 | 9.4 | 4.9 |
| 818 | CGPG182 | LRR_1 | 276 | 297 | 18.4 | 0.026 |
| 818 | CGPG182 | LRR_1 | 382 | 403 | 8.8 | 6.5 |
| 818 | CGPG182 | LRR_1 | 405 | 427 | 10.2 | 3.5 |
| 818 | CGPG182 | LRR_1 | 429 | 451 | 8.8 | 6.5 |
| 818 | CGPG182 | LRR_1 | 477 | 498 | 9.9 | 3.9 |
| 818 | CGPG182 | LRR_1 | 500 | 521 | 17 | 0.069 |
| 818 | CGPG182 | LRR_1 | 523 | 544 | 20.7 | 0.0052 |
| 819 | CGPG1837 | TFIIS_M | 328 | 445 | 155 | 1.90E−43 |
| 819 | CGPG1837 | SPOC | 656 | 762 | 92.5 | 1.30E−24 |
| 820 | CGPG1873 | Pkinase | 20 | 275 | 323.7 | 3.20E−94 |
| 820 | CGPG1873 | NAF | 314 | 374 | 112 | 1.70E−30 |
| 823 | CGPG1899 | F-box | 18 | 65 | 34.8 | 3.00E−07 |
| 823 | CGPG1899 | Kelch_1 | 139 | 186 | 33.7 | 6.30E−07 |
| 823 | CGPG1899 | Kelch_2 | 188 | 235 | 16.7 | 0.082 |
| 823 | CGPG1899 | Kelch_1 | 189 | 235 | 51.4 | 3.00E−12 |
| 824 | CGPG1913 | F-box | 31 | 78 | 39.4 | 1.20E−08 |
| 824 | CGPG1913 | FBA_1 | 268 | 416 | −16.6 | 6.10E−05 |
| 825 | CGPG1918 | F-box | 30 | 77 | 36 | 1.30E−07 |
| 826 | CGPG1919 | F-box | 65 | 112 | 43.1 | 9.70E−10 |
| 827 | CGPG1922 | F-box | 25 | 72 | 46.6 | 8.30E−11 |
| 827 | CGPG1922 | Kelch_2 | 118 | 163 | 24.4 | 0.0004 |
| 827 | CGPG1922 | Kelch_1 | 118 | 163 | 39.1 | 1.50E−08 |
| 827 | CGPG1922 | Kelch_2 | 165 | 208 | 26.7 | 8.10E−05 |
| 827 | CGPG1922 | Kelch_1 | 165 | 210 | 49.6 | 1.00E−11 |
| 828 | CGPG1929 | F-box | 1 | 44 | 14.8 | 0.31 |
| 829 | CGPG1938 | F-box | 8 | 55 | 35.4 | 2.00E−07 |
| 829 | CGPG1938 | LRR_2 | 159 | 185 | 29.1 | 1.60E−05 |
| 830 | CGPG1956 | Pre-SET | 409 | 558 | 20.9 | 5.60E−06 |

TABLE 18-continued

| PEP SEQ ID | Construct ID | Pfam domain name | begin | start | score | E-value |
|---|---|---|---|---|---|---|
| 830 | CGPG1956 | SET | 560 | 702 | 157.5 | 3.40E-44 |
| 831 | CGPG1964 | zf-C3HC4 | 109 | 147 | 35.2 | 2.30E-07 |
| 831 | CGPG1964 | YDG_SRA | 228 | 345 | 212.8 | 8.10E-61 |
| 832 | CGPG1973 | zf-UBR | 40 | 109 | 73.4 | 7.10E-19 |
| 833 | CGPG1977 | TFIIF_alpha | 18 | 542 | 984.3 | 4.60E-293 |
| 834 | CGPG1996 | Pkinase | 3 | 286 | 373.9 | 2.50E-109 |
| 835 | CGPG2005 | NADPH_Ox | 130 | 229 | 245.7 | 9.80E-71 |
| 835 | CGPG2005 | Ferric_reduct | 352 | 511 | 177.6 | 3.00E-50 |
| 835 | CGPG2005 | FAD_binding_8 | 552 | 671 | 227.3 | 3.40E-65 |
| 835 | CGPG2005 | NAD_binding_6 | 677 | 850 | 271.5 | 1.60E-78 |
| 837 | CGPG2044 | PTR2 | 99 | 507 | 587.7 | 1.10E-173 |
| 838 | CGPG2059 | Nuc_sug_transp | 104 | 340 | 26.5 | 4.50E-15 |
| 839 | CGPG2065 | PEARLI-4 | 342 | 611 | 652.6 | 3.30E-193 |
| 841 | CGPG2072 | DUF1639 | 264 | 300 | 60.4 | 5.90E-15 |
| 842 | CGPG2074 | HMA | 75 | 138 | 46.4 | 9.40E-11 |
| 842 | CGPG2074 | HMA | 173 | 235 | 50.6 | 5.40E-12 |
| 843 | CGPG2116 | NOI | 1 | 67 | 147.8 | 2.80E-41 |
| 845 | CGPG2142 | MATH | 101 | 233 | 5.3 | 0.028 |
| 845 | CGPG2142 | MATH | 258 | 375 | 33 | 1.00E-06 |
| 847 | CGPG2190 | DJ-1_Pfpl | 34 | 174 | 110.4 | 5.10E-30 |
| 847 | CGPG2190 | DJ-1_Pfpl | 240 | 378 | 129.9 | 6.90E-36 |
| 849 | CGPG221 | DnaJ | 35 | 96 | 137.6 | 3.30E-38 |
| 849 | CGPG221 | DnaJ_CXXCXGXG | 160 | 243 | 101 | 3.60E-27 |
| 849 | CGPG221 | DnaJ_C | 256 | 378 | 210.4 | 4.00E-60 |
| 850 | CGPG2213 | RNA_pol_I_A49 | 83 | 441 | 629.1 | 3.80E-186 |
| 851 | CGPG2247 | DUF23 | 256 | 497 | 99.8 | 8.20E-27 |
| 852 | CGPG228 | p450 | 67 | 511 | 252.1 | 1.10E-72 |
| 853 | CGPG2301 | PC_rep | 414 | 447 | 28.8 | 1.90E-05 |
| 853 | CGPG2301 | PC_rep | 448 | 484 | 28 | 3.20E-05 |
| 853 | CGPG2301 | PC_rep | 485 | 519 | 33.7 | 6.30E-07 |
| 853 | CGPG2301 | PC_rep | 523 | 557 | 10.4 | 0.45 |
| 853 | CGPG2301 | PC_rep | 671 | 705 | 11.9 | 0.28 |
| 853 | CGPG2301 | PC_rep | 706 | 740 | 32.7 | 1.30E-06 |
| 854 | CGPG2304 | Phi_1 | 32 | 309 | 680.3 | 1.40E-201 |
| 856 | CGPG2348 | Gal-bind_lectin | 165 | 343 | 143.9 | 4.40E-40 |
| 856 | CGPG2348 | Galactosyl_T | 385 | 580 | 105.4 | 1.60E-28 |
| 857 | CGPG2349 | IQ | 120 | 140 | 33.4 | 7.70E-07 |
| 857 | CGPG2349 | IQ | 142 | 162 | 13.6 | 0.74 |
| 858 | CGPG2354 | ABC1 | 183 | 306 | 132.6 | 1.00E-36 |
| 859 | CGPG2369 | DAGK_cat | 228 | 368 | 129.9 | 7.20E-36 |
| 860 | CGPG2382 | WD40 | 65 | 103 | 48.6 | 2.20E-11 |
| 860 | CGPG2382 | WD40 | 106 | 144 | 32.1 | 2.00E-06 |
| 860 | CGPG2382 | WD40 | 197 | 235 | 34.5 | 3.70E-07 |
| 860 | CGPG2382 | WD40 | 240 | 278 | 47.3 | 5.30E-11 |
| 861 | CGPG2392 | UBX | 311 | 392 | 104 | 4.40E-28 |
| 862 | CGPG2397 | AA_permease | 64 | 510 | 34.5 | 3.70E-07 |
| 863 | CGPG240 | Hydrolase | 22 | 210 | 118.1 | 2.50E-32 |
| 865 | CGPG2433 | DUF23 | 289 | 544 | 209.9 | 6.00E-60 |
| 868 | CGPG2464 | Glyco_transf_8 | 83 | 345 | 341.2 | 1.70E-99 |
| 869 | CGPG2472 | Band_7 | 35 | 227 | 90.6 | 4.80E-24 |
| 870 | CGPG2480 | Prefoldin | 53 | 175 | 140.5 | 4.40E-39 |
| 871 | CGPG253 | HEAT | 82 | 117 | 18.6 | 0.022 |
| 871 | CGPG253 | HEAT | 158 | 194 | 22.9 | 0.0012 |
| 871 | CGPG253 | HEAT | 197 | 233 | 15.3 | 0.22 |
| 871 | CGPG253 | HEAT | 236 | 272 | 31.1 | 3.80E-06 |
| 871 | CGPG253 | HEAT | 275 | 311 | 27.5 | 4.80E-05 |
| 871 | CGPG253 | HEAT | 314 | 350 | 26.6 | 8.60E-05 |
| 871 | CGPG253 | HEAT | 353 | 389 | 27.9 | 3.60E-05 |
| 871 | CGPG253 | HEAT | 392 | 428 | 24.6 | 0.00035 |
| 871 | CGPG253 | HEAT | 431 | 467 | 24.2 | 0.00045 |
| 871 | CGPG253 | HEAT | 470 | 506 | 21.3 | 0.0036 |
| 871 | CGPG253 | HEAT | 509 | 545 | 18.9 | 0.019 |
| 871 | CGPG253 | HEAT | 548 | 584 | 17.9 | 0.036 |
| 872 | CGPG2538 | PfkB | 7 | 297 | 115.2 | 1.40E-31 |
| 873 | CGPG2567 | zf-C3HC4 | 372 | 412 | 42.6 | 1.40E-09 |
| 874 | CGPG2571 | zf-C3HC4 | 146 | 187 | 39.3 | 1.30E-08 |
| 875 | CGPG258 | Cyclin_N | 185 | 310 | 240.4 | 3.70E-69 |
| 875 | CGPG258 | Cyclin_C | 312 | 433 | 188.8 | 1.30E-53 |
| 876 | CGPG268 | PTR2 | 97 | 514 | 458.7 | 7.20E-135 |
| 877 | CGPG274 | WD40 | 259 | 298 | 36.8 | 7.40E-08 |
| 877 | CGPG274 | WD40 | 303 | 342 | 26.9 | 7.30E-05 |
| 877 | CGPG274 | WD40 | 350 | 389 | 26.6 | 9.10E-05 |
| 878 | CGPG275 | PP2C | 32 | 271 | 205.2 | 1.50E-58 |
| 879 | CGPG277 | IGPD | 103 | 247 | 372.6 | 6.20E-109 |
| 880 | CGPG2785 | SIR2 | 52 | 216 | 107.2 | 4.70E-29 |
| 881 | CGPG2832 | Myb_DNA-binding | 195 | 243 | 33.6 | 6.80E-07 |
| 883 | CGPG2865 | SRF-TF | 17 | 67 | 94.4 | 3.50E-25 |

TABLE 18-continued

| PEP SEQ ID | Construct ID | Pfam domain name | begin | start | score | E-value |
|---|---|---|---|---|---|---|
| 884 | CGPG2874 | polyprenyl_synt | 123 | 383 | 275.6 | 9.70E−80 |
| 885 | CGPG2914 | AP2 | 84 | 142 | 18 | 5.20E−06 |
| 886 | CGPG295 | Pro_isomerase | 96 | 256 | 405.8 | 6.30E−119 |
| 888 | CGPG3009 | Arf | 4 | 184 | 165.1 | 1.80E−46 |
| 889 | CGPG3030 | Pkinase | 4 | 301 | 322.2 | 9.20E−94 |
| 890 | CGPG3048 | adh_short | 18 | 186 | 135.3 | 1.60E−37 |
| 890 | CGPG3048 | KR | 18 | 188 | −35.3 | 2.60E−05 |
| 891 | CGPG3056 | PP2C | 76 | 341 | 261.8 | 1.40E−75 |
| 893 | CGPG309 | Cyclin_N | 4 | 143 | 8.9 | 2.50E−05 |
| 894 | CGPG3094 | C2 | 6 | 87 | 73.4 | 7.30E−19 |
| 895 | CGPG3095 | F-box | 5 | 52 | 34.8 | 2.90E−07 |
| 895 | CGPG3095 | LRR_2 | 163 | 188 | 34.7 | 3.30E−07 |
| 895 | CGPG3095 | FBD | 374 | 426 | 83.7 | 5.60E−22 |
| 896 | CGPG3137 | Spermine_synth | 54 | 313 | 429.1 | 6.20E−126 |
| 897 | CGPG3156 | DEAD | 33 | 212 | 223 | 6.80E−64 |
| 897 | CGPG3156 | Helicase_C | 279 | 355 | 131.8 | 1.90E−36 |
| 898 | CGPG3157 | DEAD | 175 | 355 | 231.2 | 2.30E−66 |
| 898 | CGPG3157 | Helicase_C | 427 | 503 | 130.3 | 5.40E−36 |
| 899 | CGPG3205 | F-box | 130 | 177 | 35.8 | 1.50E−07 |
| 899 | CGPG3205 | Kelch_1 | 220 | 269 | 34.4 | 4.00E−07 |
| 899 | CGPG3205 | Kelch_2 | 220 | 269 | 16.3 | 0.11 |
| 899 | CGPG3205 | Kelch_1 | 347 | 389 | 11.8 | 0.18 |
| 900 | CGPG3236 | Thioredoxin | 4 | 108 | 67.2 | 5.20E−17 |
| 901 | CGPG3248 | Copine | 102 | 250 | 294.3 | 2.20E−85 |
| 902 | CGPG3255 | NTP_transferase | 10 | 246 | 50.6 | 2.10E−13 |
| 902 | CGPG3255 | Hexapep | 294 | 311 | 4.4 | 42 |
| 902 | CGPG3255 | Hexapep | 312 | 329 | 16.7 | 0.083 |
| 902 | CGPG3255 | Hexapep | 335 | 352 | 10.7 | 5.2 |
| 902 | CGPG3255 | Hexapep | 379 | 396 | 1.8 | 85 |
| 903 | CGPG3258 | UDPGT | 23 | 484 | −66 | 2.70E−07 |
| 904 | CGPG3261 | Pkinase | 79 | 334 | 261.2 | 2.00E−75 |
| 907 | CGPG3283 | Mo25 | 1 | 339 | 584.5 | 1.00E−172 |
| 908 | CGPG3302 | SRF-TF | 9 | 59 | 118.3 | 2.20E−32 |
| 908 | CGPG3302 | K-box | 76 | 174 | 130.2 | 5.60E−36 |
| 909 | CGPG3334 | GRP | 1 | 113 | 129.8 | 7.40E−36 |
| 910 | CGPG3361 | DUF1644 | 38 | 255 | 215.2 | 1.50E−61 |
| 911 | CGPG337 | Glyco_transf_8 | 19 | 264 | 298.7 | 1.10E−86 |
| 912 | CGPG3400 | IQ | 304 | 324 | 14.7 | 0.33 |
| 914 | CGPG3424 | TFIIS_C | 79 | 117 | 31.8 | 2.40E−06 |
| 915 | CGPG3428 | DUF914 | 136 | 435 | −191.9 | 0.0045 |
| 916 | CGPG3465 | zf-MYND | 57 | 94 | 50.2 | 6.80E−12 |
| 916 | CGPG3465 | UCH | 326 | 630 | 175.9 | 1.00E−49 |
| 917 | CGPG347 | DREPP | 1 | 225 | 483.5 | 2.50E−142 |
| 917 | CGPG347 | PPAK | 172 | 197 | 0.5 | 17 |
| 919 | CGPG3567 | DUF581 | 63 | 121 | 135.5 | 1.40E−37 |
| 920 | CGPG3575 | Mago-bind | 22 | 48 | 58.7 | 2.00E−14 |
| 921 | CGPG3579 | SNARE | 141 | 203 | 59.8 | 8.90E−15 |
| 926 | CGPG365 | MATH | 53 | 182 | 59.9 | 8.30E−15 |
| 926 | CGPG365 | BTB | 206 | 328 | 86.5 | 7.90E−23 |
| 927 | CGPG3665 | BNR | 138 | 149 | 10.5 | 5.1 |
| 927 | CGPG3665 | BNR | 189 | 200 | 8.4 | 9.7 |
| 927 | CGPG3665 | BNR | 239 | 250 | 10.7 | 4.8 |
| 928 | CGPG3684 | Pro_dh | 113 | 464 | 472.8 | 4.30E−139 |
| 929 | CGPG3690 | MtN3_slv | 10 | 97 | 116 | 1.10E−31 |
| 929 | CGPG3690 | MtN3_slv | 131 | 217 | 119 | 1.30E−32 |
| 930 | CGPG3717 | OTU | 219 | 331 | 154.2 | 3.50E−43 |
| 931 | CGPG372 | SET | 83 | 212 | 181.8 | 1.70E−51 |
| 934 | CGPG3781 | SRF-TF | 11 | 65 | 30.5 | 6.00E−06 |
| 935 | CGPG380 | Histone | 25 | 94 | 67.1 | 5.70E−17 |
| 936 | CGPG3821 | F-box | 5 | 52 | 36.5 | 9.50E−08 |
| 936 | CGPG3821 | FBA_3 | 205 | 281 | −0.8 | 0.00013 |
| 937 | CGPG3824 | WRKY | 107 | 169 | 89.8 | 8.20E−24 |
| 938 | CGPG3901 | 2OG-FeII_Oxy | 166 | 271 | 67.5 | 4.30E−17 |
| 939 | CGPG391 | Histone | 58 | 132 | 144.1 | 3.60E−40 |
| 941 | CGPG394 | DUF6 | 11 | 152 | 22.3 | 0.0018 |
| 941 | CGPG394 | TPT | 170 | 319 | 165.1 | 1.80E−46 |
| 942 | CGPG3964 | Pyr_redox | 174 | 248 | 7.9 | 0.0034 |
| 943 | CGPG397 | SOR_SNZ | 24 | 229 | 449.4 | 4.60E−132 |
| 943 | CGPG397 | ThiG | 123 | 290 | −178.1 | 0.0011 |
| 945 | CGPG3983 | DUF6 | 31 | 164 | 50.3 | 6.60E−12 |
| 945 | CGPG3983 | DUF6 | 213 | 342 | 60.5 | 5.40E−15 |
| 946 | CGPG3986 | WD40 | 160 | 197 | 27.3 | 5.50E−05 |
| 946 | CGPG3986 | WD40 | 249 | 288 | 33.1 | 9.60E−07 |
| 947 | CGPG3991 | SNARE_assoc | 111 | 232 | 91.5 | 2.60E−24 |
| 948 | CGPG4050 | PP2C | 49 | 327 | 107 | 5.40E−29 |
| 949 | CGPG4070 | Not3 | 2 | 246 | 527.4 | 1.50E−155 |
| 949 | CGPG4070 | NOT2_3_5 | 693 | 881 | 217 | 4.30E−62 |

TABLE 18-continued

| PEP SEQ ID | Construct ID | Pfam domain name | begin | start | score | E-value |
|---|---|---|---|---|---|---|
| 950 | CGPG4071 | Pkinase_Tyr | 135 | 389 | 256.4 | 5.90E−74 |
| 950 | CGPG4071 | Pkinase | 135 | 389 | 221.3 | 2.20E−63 |
| 951 | CGPG4099 | 14-3-3 | 6 | 243 | 509.5 | 3.80E−150 |
| 952 | CGPG4138 | adh_short | 44 | 217 | 55.7 | 1.60E−13 |
| 953 | CGPG4152 | RRM_1 | 11 | 78 | 44.3 | 4.00E−10 |
| 954 | CGPG4153 | HMG-CoA_red | 190 | 583 | 1044.7 | 0 |
| 955 | CGPG4164 | PP2C | 22 | 322 | 276.7 | 4.60E−80 |
| 956 | CGPG4169 | WD40 | 253 | 291 | 38.4 | 2.40E−08 |
| 956 | CGPG4169 | WD40 | 298 | 336 | 30.8 | 4.80E−06 |
| 956 | CGPG4169 | WD40 | 340 | 378 | 24.8 | 0.00031 |
| 956 | CGPG4169 | WD40 | 510 | 549 | 55.3 | 2.00E−13 |
| 957 | CGPG421 | Pkinase | 22 | 280 | 354.8 | 1.40E−103 |
| 957 | CGPG421 | efhand | 327 | 355 | 39.1 | 1.50E−08 |
| 957 | CGPG421 | efhand | 363 | 391 | 26.9 | 7.30E−05 |
| 957 | CGPG421 | efhand | 399 | 427 | 30.3 | 6.70E−06 |
| 957 | CGPG421 | efhand | 433 | 461 | 37.9 | 3.50E−08 |
| 958 | CGPG422 | Pkinase | 73 | 331 | 363.9 | 2.50E−106 |
| 959 | CGPG4223 | SRF-TF | 23 | 76 | 25.8 | 0.00015 |
| 960 | CGPG4240 | F-box | 8 | 56 | 30.1 | 7.90E−06 |
| 961 | CGPG4242 | PP2C | 58 | 341 | 195.8 | 1.00E−55 |
| 962 | CGPG4248 | efhand | 10 | 38 | 30.5 | 6.00E−06 |
| 962 | CGPG4248 | efhand | 89 | 117 | 37 | 6.70E−08 |
| 962 | CGPG4248 | efhand | 127 | 155 | 27.1 | 6.10E−05 |
| 963 | CGPG425 | Pkinase_Tyr | 8 | 260 | 238.9 | 1.10E−68 |
| 963 | CGPG425 | Pkinase | 8 | 260 | 224.7 | 2.00E−64 |
| 964 | CGPG4265 | Cys_Met_Meta_PP | 42 | 432 | 263.8 | 3.50E−76 |
| 965 | CGPG4283 | Dehydrin | 36 | 183 | 171.1 | 2.70E−48 |
| 966 | CGPG4297 | Globin | 10 | 149 | 102.6 | 1.10E−27 |
| 967 | CGPG43 | Aa_trans | 46 | 481 | 587.5 | 1.30E−173 |
| 968 | CGPG430 | Pkinase_Tyr | 8 | 264 | 127.5 | 3.70E−35 |
| 968 | CGPG430 | Pkinase | 8 | 264 | 297.5 | 2.50E−86 |
| 969 | CGPG4305 | Rib_5-P_isom_A | 85 | 273 | −27.7 | 1.60E−07 |
| 970 | CGPG4307 | Orn_Arg_deC_N | 98 | 348 | 174.8 | 2.20E−49 |
| 970 | CGPG4307 | Orn_DAP_Arg_deC | 351 | 459 | 125.2 | 1.80E−34 |
| 971 | CGPG4315 | PPR | 139 | 173 | 7.5 | 0.97 |
| 971 | CGPG4315 | PPR | 209 | 243 | 26.1 | 0.00013 |
| 971 | CGPG4315 | PPR | 286 | 320 | 36.6 | 8.60E−08 |
| 971 | CGPG4315 | PPR | 321 | 355 | 11.6 | 0.32 |
| 971 | CGPG4315 | PPR | 356 | 390 | 3.1 | 3.2 |
| 971 | CGPG4315 | PPR | 391 | 425 | 11.4 | 0.33 |
| 972 | CGPG4320 | DUF6 | 20 | 153 | 52.8 | 1.20E−12 |
| 972 | CGPG4320 | DUF6 | 190 | 319 | 40.8 | 4.70E−09 |
| 973 | CGPG4344 | Mito_carr | 13 | 98 | 65.1 | 2.30E−16 |
| 973 | CGPG4344 | Mito_carr | 104 | 199 | 103.1 | 8.20E−28 |
| 973 | CGPG4344 | Mito_carr | 203 | 297 | 83.2 | 8.20E−22 |
| 975 | CGPG4349 | Aha1_N | 29 | 165 | 185 | 1.80E−52 |
| 975 | CGPG4349 | AHSA1 | 233 | 291 | 17.7 | 0.0027 |
| 976 | CGPG4365 | CCT | 220 | 258 | 75.3 | 2.00E−19 |
| 978 | CGPG4389 | Aminotran_1_2 | 23 | 376 | 250.1 | 4.70E−72 |
| 979 | CGPG4404 | p450 | 37 | 514 | 135.5 | 1.40E−37 |
| 980 | CGPG4405 | p450 | 69 | 504 | 265.7 | 9.60E−77 |
| 981 | CGPG4419 | p450 | 33 | 477 | 342.6 | 6.60E−100 |
| 982 | CGPG4432 | p450 | 70 | 528 | 261.7 | 1.50E−75 |
| 984 | CGPG4443 | p450 | 32 | 551 | 268.9 | 1.00E−77 |
| 985 | CGPG445 | PLAT | 54 | 159 | 137.1 | 4.70E−38 |
| 985 | CGPG445 | Lipoxygenase | 171 | 843 | 1610.6 | 0 |
| 986 | CGPG4453 | p450 | 40 | 500 | 373.2 | 4.20E−109 |
| 987 | CGPG4481 | Glyco_hydro_17 | 34 | 352 | 365.3 | 9.40E−107 |
| 988 | CGPG4490 | AMP-binding | 42 | 473 | 358 | 1.50E−104 |
| 989 | CGPG4498 | Glyco_hydro_1 | 40 | 516 | 757.2 | 1.10E−224 |
| 990 | CGPG4506 | RRM_1 | 18 | 89 | 95.5 | 1.60E−25 |
| 991 | CGPG4553 | DUF313 | 158 | 265 | 219 | 1.10E−62 |
| 992 | CGPG4583 | HIT | 43 | 142 | 152.5 | 1.10E−42 |
| 993 | CGPG4643 | Pkinase | 400 | 656 | 303.4 | 4.20E−88 |
| 993 | CGPG4643 | Pkinase_Tyr | 400 | 656 | 149.3 | 1.00E−41 |
| 994 | CGPG4650 | Pkinase | 141 | 425 | 320.1 | 4.00E−93 |
| 996 | CGPG468 | Fer4 | 116 | 139 | 30.6 | 5.60E−06 |
| 996 | CGPG468 | Fer4 | 155 | 178 | 38.5 | 2.30E−08 |
| 997 | CGPG4684 | MIP | 11 | 232 | 407.1 | 2.60E−119 |
| 998 | CGPG4689 | LRRNT_2 | 29 | 70 | 63.6 | 6.40E−16 |
| 998 | CGPG4689 | LRR_1 | 120 | 142 | 10.7 | 2.8 |
| 998 | CGPG4689 | LRR_1 | 144 | 165 | 8.2 | 8.5 |
| 998 | CGPG4689 | Pkinase | 261 | 532 | 154.6 | 2.70E−43 |
| 998 | CGPG4689 | Pkinase_Tyr | 261 | 532 | 77.7 | 3.80E−20 |
| 999 | CGPG4691 | PCI | 281 | 385 | 116.6 | 6.90E−32 |
| 1000 | CGPG4702 | UAA | 92 | 388 | −129.1 | 0.00058 |
| 1000 | CGPG4702 | DUF6 | 106 | 231 | 27.4 | 5.10E−05 |

TABLE 18-continued

| PEP SEQ ID | Construct ID | Pfam domain name | begin | start | score | E-value |
|---|---|---|---|---|---|---|
| 1000 | CGPG4702 | TPT | 240 | 385 | 193.4 | 5.60E−55 |
| 1001 | CGPG4703 | UAA | 55 | 355 | −71.5 | 7.60E−07 |
| 1001 | CGPG4703 | TPT | 205 | 349 | 160.4 | 4.80E−45 |
| 1002 | CGPG4710 | CPSase_L_chain | 97 | 217 | 196.1 | 8.20E−56 |
| 1002 | CGPG4710 | CPSase_L_D2 | 219 | 455 | 449.7 | 3.80E−132 |
| 1002 | CGPG4710 | CPSase_L_D3 | 515 | 638 | 255.2 | 1.30E−73 |
| 1002 | CGPG4710 | CPSase_L_chain | 648 | 775 | 68.2 | 2.60E−17 |
| 1002 | CGPG4710 | CPSase_L_D2 | 777 | 989 | 118.2 | 2.40E−32 |
| 1002 | CGPG4710 | MGS | 1061 | 1148 | 105.9 | 1.20E−28 |
| 1003 | CGPG4713 | DUF231 | 241 | 420 | 229.6 | 6.60E−66 |
| 1004 | CGPG4730 | DHquinase_I | 96 | 313 | 281.4 | 1.80E−81 |
| 1004 | CGPG4730 | Shikimate_dh_N | 328 | 408 | 148.1 | 2.40E−41 |
| 1004 | CGPG4730 | Shikimate_DH | 440 | 558 | 118.7 | 1.60E−32 |
| 1005 | CGPG4747 | UQ_con | 8 | 145 | 267.3 | 3.00E−77 |
| 1006 | CGPG4755 | Cpn60_TCP1 | 30 | 520 | 556.6 | 2.60E−164 |
| 1008 | CGPG4779 | Peptidase_M22 | 27 | 305 | 238.7 | 1.20E−68 |
| 1009 | CGPG4848 | PGAM | 77 | 246 | 22.5 | 4.10E−05 |
| 1010 | CGPG4879 | SIS | 64 | 197 | 71.5 | 2.60E−18 |
| 1010 | CGPG4879 | CBS | 229 | 350 | 83.4 | 6.80E−22 |
| 1011 | CGPG4882 | TFIIS | 121 | 206 | 127 | 5.10E−35 |
| 1012 | CGPG4892 | DUF260 | 5 | 105 | 193.4 | 5.60E−55 |
| 1013 | CGPG4903 | DUF260 | 7 | 108 | 237 | 4.20E−68 |
| 1014 | CGPG4925 | WD40 | 74 | 112 | 34.3 | 4.30E−07 |
| 1014 | CGPG4925 | WD40 | 116 | 153 | 27.5 | 4.60E−05 |
| 1014 | CGPG4925 | WD40 | 207 | 245 | 42.3 | 1.60E−09 |
| 1014 | CGPG4925 | WD40 | 249 | 287 | 47.1 | 6.10E−11 |
| 1015 | CGPG4937 | NLE | 11 | 79 | 115.3 | 1.70E−31 |
| 1015 | CGPG4937 | WD40 | 140 | 182 | 33.3 | 8.30E−07 |
| 1015 | CGPG4937 | WD40 | 195 | 233 | 31.2 | 3.50E−06 |
| 1015 | CGPG4937 | WD40 | 262 | 299 | 29.4 | 1.20E−05 |
| 1015 | CGPG4937 | WD40 | 348 | 387 | 34.5 | 3.70E−07 |
| 1016 | CGPG4949 | Pkinase | 208 | 470 | −29.3 | 8.10E−07 |
| 1017 | CGPG4971 | SKI | 11 | 177 | 104 | 4.30E−28 |
| 1018 | CGPG499 | Voltage_CLC | 138 | 560 | 690.2 | 1.50E−204 |
| 1018 | CGPG499 | CBS | 593 | 759 | 42.9 | 1.10E−09 |
| 1019 | CGPG5004 | adh_short | 53 | 224 | 50.1 | 7.30E−12 |
| 1020 | CGPG5028 | adh_short | 42 | 200 | −2.3 | 7.90E−06 |
| 1021 | CGPG5032 | adh_short | 48 | 216 | 81.4 | 2.80E−21 |
| 1022 | CGPG5038 | DUF26 | 74 | 134 | 74.3 | 3.90E−19 |
| 1022 | CGPG5038 | DUF26 | 200 | 254 | 94 | 4.40E−25 |
| 1022 | CGPG5038 | Pkinase | 345 | 620 | 172.1 | 1.40E−48 |
| 1022 | CGPG5038 | Pkinase_Tyr | 345 | 620 | 130.8 | 3.70E−36 |
| 1023 | CGPG5045 | LRRNT_2 | 24 | 67 | 38.3 | 2.70E−08 |
| 1023 | CGPG5045 | LRR_1 | 97 | 119 | 16.6 | 0.092 |
| 1023 | CGPG5045 | LRR_1 | 122 | 144 | 10.9 | 2.6 |
| 1023 | CGPG5045 | LRR_1 | 146 | 168 | 12.9 | 1.1 |
| 1023 | CGPG5045 | LRR_1 | 170 | 192 | 14.8 | 0.31 |
| 1023 | CGPG5045 | Pkinase | 306 | 576 | 6.1 | 6.30E−09 |
| 1024 | CGPG5048 | LRRNT_2 | 22 | 59 | 39.5 | 1.20E−08 |
| 1024 | CGPG5048 | LRR_1 | 89 | 111 | 16.8 | 0.08 |
| 1024 | CGPG5048 | LRR_1 | 113 | 135 | 13.6 | 0.72 |
| 1024 | CGPG5048 | LRR_1 | 137 | 159 | 20.2 | 0.0076 |
| 1024 | CGPG5048 | LRR_1 | 161 | 182 | 14.5 | 0.4 |
| 1024 | CGPG5048 | LRR_1 | 183 | 205 | 14.1 | 0.49 |
| 1024 | CGPG5048 | Pkinase | 307 | 578 | 47.4 | 2.20E−11 |
| 1025 | CGPG5051 | AOX | 45 | 323 | 739.1 | 3.00E−219 |
| 1026 | CGPG5061 | Fibrillarin | 1 | 99 | 56.9 | 6.50E−14 |
| 1027 | CGPG5062 | Skp1_POZ | 6 | 66 | 115.7 | 1.30E−31 |
| 1027 | CGPG5062 | Skp1 | 86 | 163 | 168.3 | 2.00E−47 |
| 1028 | CGPG5069 | Skp1_POZ | 4 | 64 | 108.8 | 1.60E−29 |
| 1028 | CGPG5069 | Skp1 | 89 | 167 | 169.2 | 1.10E−47 |
| 1029 | CGPG5070 | Skp1_POZ | 4 | 64 | 93.5 | 6.40E−25 |
| 1029 | CGPG5070 | Skp1 | 72 | 150 | 113.9 | 4.50E−31 |
| 1030 | CGPG5097 | Pkinase | 295 | 579 | 140.1 | 5.90E−39 |
| 1030 | CGPG5097 | Pkinase_Tyr | 295 | 579 | 68.2 | 2.60E−17 |
| 1031 | CGPG510 | Rho_GDI | 20 | 223 | 44 | 6.20E−12 |
| 1032 | CGPG5100 | Pkinase | 353 | 615 | −2.8 | 2.10E−08 |
| 1033 | CGPG5117 | efhand_like | 25 | 105 | 66.7 | 7.50E−17 |
| 1033 | CGPG5117 | PI-PLC-X | 107 | 251 | 133 | 8.30E−37 |
| 1033 | CGPG5117 | PI-PLC-Y | 294 | 412 | 87.5 | 4.20E−23 |
| 1033 | CGPG5117 | C2 | 430 | 523 | 64.2 | 4.10E−16 |
| 1034 | CGPG5151 | p450 | 1 | 282 | 11.9 | 1.60E−11 |
| 1035 | CGPG5155 | p450 | 27 | 493 | 112.9 | 9.10E−31 |
| 1036 | CGPG5159 | p450 | 26 | 520 | 145.4 | 1.50E−40 |
| 1037 | CGPG516 | HD | 233 | 337 | 53.7 | 6.00E−13 |
| 1037 | CGPG516 | RelA_SpoT | 427 | 537 | 165 | 1.90E−46 |
| 1037 | CGPG516 | p450 | 31 | 503 | 89.9 | 8.00E−24 |

TABLE 18-continued

| PEP SEQ ID | Construct ID | Pfam domain name | begin | start | score | E-value |
|---|---|---|---|---|---|---|
| 1039 | CGPG5186 | Thioredoxin | 70 | 172 | 137.3 | 4.20E−38 |
| 1040 | CGPG519 | Abhydrolase_1 | 59 | 279 | 29.7 | 1.10E−05 |
| 1041 | CGPG5190 | Ribosomal_L37 | 15 | 125 | 143.9 | 4.40E−40 |
| 1042 | CGPG5191 | TPR_2 | 166 | 199 | 22 | 0.0022 |
| 1044 | CGPG521 | Abhydrolase_1 | 65 | 282 | 21 | 0.00018 |
| 1044 | CGPG521 | DUF827 | 16 | 271 | 333.9 | 2.80E−97 |
| 1047 | CGPG5213 | DUF623 | 143 | 203 | 116.7 | 6.40E−32 |
| 1048 | CGPG522 | FA_desaturase | 62 | 277 | 200.7 | 3.50E−57 |
| 1049 | CGPG5223 | PG-M_PMM_I | 79 | 222 | 166.1 | 8.80E−47 |
| 1049 | CGPG5223 | PGM_PMM_II | 251 | 360 | 96.4 | 8.30E−26 |
| 1049 | CGPG5223 | PGM_PMM_III | 362 | 486 | 138.1 | 2.50E−38 |
| 1049 | CGPG5223 | PGM_PMM_IV | 507 | 612 | 75.4 | 1.80E−19 |
| 1050 | CGPG5224 | LRR_1 | 231 | 252 | 9.5 | 4.7 |
| 1050 | CGPG5224 | LRR_1 | 254 | 275 | 15.2 | 0.24 |
| 1050 | CGPG5224 | LRR_1 | 277 | 298 | 18.3 | 0.027 |
| 1050 | CGPG5224 | LRR_1 | 300 | 321 | 17.8 | 0.039 |
| 1050 | CGPG5224 | LRR_1 | 323 | 344 | 12.7 | 1.2 |
| 1050 | CGPG5224 | LRR_1 | 369 | 390 | 7.8 | 10 |
| 1050 | CGPG5224 | LRR_1 | 392 | 413 | 13.5 | 0.75 |
| 1050 | CGPG5224 | LRR_1 | 440 | 461 | 17.7 | 0.041 |
| 1051 | CGPG5225 | p450 | 37 | 452 | 209.6 | 7.00E−60 |
| 1052 | CGPG5254 | 2OG-FeII_Oxy | 162 | 279 | 65.3 | 1.90E−16 |
| 1053 | CGPG5257 | SpoIIE | 130 | 374 | 52.9 | 1.00E−12 |
| 1054 | CGPG5262 | SH3_1 | 303 | 359 | 75.4 | 1.80E−19 |
| 1054 | CGPG5262 | SH3_2 | 304 | 359 | 35.8 | 1.50E−07 |
| 1056 | CGPG5282 | F-box | 17 | 69 | 14.5 | 0.39 |
| 1056 | CGPG5282 | Sel1 | 129 | 167 | 19.9 | 0.0091 |
| 1056 | CGPG5282 | Sel1 | 168 | 203 | 12.2 | 0.47 |
| 1056 | CGPG5282 | zf-MYND | 273 | 317 | 38.2 | 2.80E−08 |
| 1058 | CGPG532 | Transket_pyr | 30 | 207 | 261.4 | 1.90E−75 |
| 1058 | CGPG532 | Transketolase_C | 222 | 342 | 175.3 | 1.50E−49 |
| 1059 | CGPG5336 | adh_short | 19 | 188 | 81.3 | 3.10E−21 |
| 1059 | CGPG5336 | KR | 19 | 205 | −66.7 | 0.0017 |
| 1060 | CGPG5350 | Aminotran_4 | 107 | 395 | 353.2 | 4.30E−103 |
| 1061 | CGPG5355 | GRAM | 95 | 173 | 41.4 | 3.20E−09 |
| 1062 | CGPG5376 | DUF21 | 14 | 191 | 162.9 | 8.00E−46 |
| 1062 | CGPG5376 | CBS | 210 | 326 | 27 | 6.60E−05 |
| 1063 | CGPG5377 | CBS | 81 | 226 | 138.6 | 1.70E−38 |
| 1064 | CGPG5382 | B56 | 93 | 416 | 759.8 | 1.80E−225 |
| 1065 | CGPG5385 | Pyridoxal_deC | 146 | 452 | −54.5 | 1.00E−10 |
| 1065 | CGPG5385 | Aminotran_5 | 150 | 491 | −148.7 | 7.00E−05 |
| 1066 | CGPG539 | Citrate_synt | 78 | 455 | 764.2 | 8.10E−227 |
| 1067 | CGPG5437 | IQ | 115 | 135 | 31.3 | 3.40E−06 |
| 1068 | CGPG5450 | DHDPS | 64 | 341 | 486.2 | 4.00E−143 |
| 1069 | CGPG5473 | Xan_ur_permease | 31 | 438 | 164.5 | 2.70E−46 |
| 1070 | CGPG55 | Sugar_tr | 6 | 719 | 208.1 | 2.10E−59 |
| 1070 | CGPG55 | MFS_1 | 11 | 678 | 137.1 | 4.70E−3B |
| 1071 | CGPG5505 | AlaDh_PNT_N | 18 | 154 | 81.4 | 2.80E−21 |
| 1071 | CGPG5505 | AlaDh_PNT_C | 194 | 400 | 134 | 4.10E−37 |
| 1071 | CGPG5505 | Saccharop_dh_N | 477 | 583 | 228.5 | 1.50E−65 |
| 1071 | CGPG5505 | ThiF | 585 | 714 | −36.3 | 0.0039 |
| 1071 | CGPG5505 | Saccharop_dh | 589 | 1060 | 377.2 | 2.50E−110 |
| 1073 | CGPG5514 | Cyclin_N | 165 | 294 | 211.1 | 2.60E−60 |
| 1073 | CGPG5514 | Cyclin_C | 296 | 422 | 111.3 | 2.70E−30 |
| 1074 | CGPG5541 | Pkinase | 316 | 590 | 319.8 | 4.80E−93 |
| 1075 | CGPG5546 | Cyclin | 108 | 264 | 289.2 | 7.70E−84 |
| 1076 | CGPG5552 | Cornichon | 2 | 125 | 268.7 | 1.20E−77 |
| 1077 | CGPG5556 | SAC3_GANP | 20 | 211 | 214.5 | 2.30E−61 |
| 1078 | CGPG557 | Chitin_bind_1 | 21 | 62 | 72.3 | 1.50E−18 |
| 1078 | CGPG557 | Barwin | 73 | 191 | 311.7 | 1.30E−90 |
| 1079 | CGPG5576 | zf-PARP | 11 | 88 | 88.5 | 2.10E−23 |
| 1079 | CGPG5576 | zf-PARP | 117 | 195 | 65.3 | 2.00E−16 |
| 1079 | CGPG5576 | PADR1 | 290 | 343 | 120.6 | 4.40E−33 |
| 1079 | CGPG5576 | BRCT | 394 | 471 | 47.4 | 4.80E−11 |
| 1079 | CGPG5576 | WGR | 517 | 605 | 153 | 7.90E−43 |
| 1079 | CGPG5576 | PARP_reg | 633 | 765 | 87.7 | 3.60E−23 |
| 1079 | CGPG5576 | PARP | 767 | 979 | 434.2 | 1.80E−127 |
| 1080 | CGPG5596 | Response_reg | 9 | 143 | 77.4 | 4.60E−20 |
| 1081 | CGPG5605 | DEAD | 52 | 221 | 246.1 | 7.20E−71 |
| 1081 | CGPG5605 | Helicase_C | 290 | 366 | 89.9 | 7.50E−24 |
| 1082 | CGPG5606 | LRRNT_2 | 21 | 62 | 49.4 | 1.20E−11 |
| 1082 | CGPG5606 | LRR_1 | 90 | 113 | 14.1 | 0.52 |
| 1082 | CGPG5606 | LRR_1 | 115 | 137 | 14.7 | 0.35 |
| 1082 | CGPG5606 | LRR_1 | 140 | 162 | 19.3 | 0.014 |
| 1082 | CGPG5606 | LRR_1 | 164 | 186 | 17.2 | 0.059 |
| 1082 | CGPG5606 | LRR_1 | 188 | 211 | 11.7 | 1.9 |
| 1082 | CGPG5606 | LRR_1 | 213 | 235 | 14.2 | 0.47 |

TABLE 18-continued

| PEP SEQ ID | Construct ID | Pfam domain name | begin | start | score | E-value |
|---|---|---|---|---|---|---|
| 1082 | CGPG5606 | LRR_1 | 237 | 259 | 16.1 | 0.13 |
| 1082 | CGPG5606 | LRR_1 | 261 | 283 | 8.9 | 6.3 |
| 1082 | CGPG5606 | LRR_1 | 308 | 330 | 12 | 1.6 |
| 1082 | CGPG5606 | LRR_1 | 332 | 354 | 11.1 | 2.4 |
| 1082 | CGPG5606 | LRR_1 | 356 | 375 | 9.3 | 5.1 |
| 1082 | CGPG5606 | LRR_1 | 380 | 402 | 10.8 | 2.7 |
| 1082 | CGPG5606 | LRR_1 | 404 | 426 | 17.1 | 0.065 |
| 1082 | CGPG5606 | LRR_1 | 428 | 450 | 11 | 1.6 |
| 1082 | CGPG5606 | LRR_1 | 452 | 474 | 14.6 | 0.36 |
| 1082 | CGPG5606 | LRR_1 | 500 | 522 | 14.3 | 0.44 |
| 1082 | CGPG5606 | LRR_1 | 524 | 546 | 14.9 | 0.28 |
| 1082 | CGPG5606 | LRR_1 | 548 | 570 | 15.1 | 0.25 |
| 1082 | CGPG5606 | LRR_1 | 571 | 592 | 15.6 | 0.18 |
| 1082 | CGPG5606 | Pkinase | 683 | 964 | 125.6 | 1.40E−34 |
| 1082 | CGPG5606 | Pkinase_Tyr | 683 | 964 | 85 | 2.30E−22 |
| 1083 | CGPG561 | XG_FTase | 54 | 532 | 1264.7 | 0 |
| 1084 | CGPG5618 | Lectin_legB | 20 | 247 | 260.2 | 4.30E−75 |
| 1084 | CGPG5618 | Pkinase | 376 | 651 | 185.1 | 1.70E−52 |
| 1084 | CGPG5618 | Pkinase_Tyr | 376 | 651 | 141.6 | 2.10E−39 |
| 1085 | CGPG5642 | Aldedh | 18 | 477 | 674.3 | 9.50E−200 |
| 1086 | CGPG5644 | ELFV_dehydrog_N | 51 | 181 | 278.1 | 1.80E−80 |
| 1086 | CGPG5644 | ELFV_dehydrog | 197 | 428 | 394.9 | 1.20E−115 |
| 1087 | CGPG5647 | Aldedh | 46 | 511 | 669.6 | 2.50E−198 |
| 1088 | CGPG5655 | Glutaminase | 23 | 309 | 642.2 | 4.30E−190 |
| 1089 | CGPG5660 | Glutaminase | 24 | 308 | 599 | 4.30E−177 |
| 1090 | CGPG5662 | Aminotran_3 | 47 | 381 | 473.1 | 3.30E−139 |
| 1091 | CGPG568 | FTHFS | 14 | 634 | 1422.6 | 0 |
| 1092 | CGPG5686 | Aminotran_3 | 31 | 387 | 365.8 | 7.00E−107 |
| 1093 | CGPG5702 | Gln-synt_N | 28 | 109 | 171.5 | 2.10E−48 |
| 1093 | CGPG5702 | Gln-synt_C | 116 | 397 | 581.1 | 1.10E−171 |
| 1094 | CGPG5712 | Pribosyltran | 22 | 158 | 167.1 | 4.50E−47 |
| 1095 | CGPG5713 | Rib_5-P_isom_A | 55 | 229 | 353.2 | 4.30E−103 |
| 1096 | CGPG5715 | Pribosyltran | 27 | 163 | 131.6 | 2.20E−36 |
| 1097 | CGPG5723 | NDK | 4 | 138 | 304.7 | 1.80E−88 |
| 1098 | CGPG5729 | Cyclin_N | 210 | 336 | 218.9 | 1.20E−62 |
| 1098 | CGPG5729 | Cyclin_C | 338 | 457 | 133.1 | 7.50E−37 |
| 1099 | CGPG5730 | Lung_7-TM_R | 151 | 444 | 474.5 | 1.30E−139 |
| 1101 | CGPG5741 | NIF | 165 | 344 | 184.2 | 3.20E−52 |
| 1102 | CGPG5752 | CAF1 | 161 | 404 | 356.1 | 5.80E−104 |
| 1103 | CGPG5771 | Acyltransferase | 84 | 277 | 123.8 | 4.90E−34 |
| 1104 | CGPG5778 | Aa_trans | 51 | 498 | 498.7 | 6.60E−147 |
| 1105 | CGPG5782 | Sugar_tr | 65 | 525 | 819.5 | 1.80E−243 |
| 1105 | CGPG5782 | MFS_1 | 69 | 485 | 103.5 | 6.40E−28 |
| 1106 | CGPG5785 | Sugar_tr | 69 | 530 | 791.6 | 4.50E−235 |
| 1106 | CGPG5785 | MFS_1 | 73 | 490 | 88.2 | 2.50E−23 |
| 1107 | CGPG5797 | AA_permease | 94 | 562 | 588.2 | 7.60E−174 |
| 1108 | CGPG580 | MGDG_synth | 155 | 323 | 316.4 | 5.00E−92 |
| 1108 | CGPG580 | Glyco_tran_28_C | 349 | 512 | 5.9 | 0.0004 |
| 1109 | CGPG5805 | AA_permease | 57 | 511 | 619.8 | 2.40E−183 |
| 1110 | CGPG5810 | Ank | 74 | 106 | 1.8 | 17 |
| 1110 | CGPG5810 | Ank | 107 | 139 | 51.9 | 2.10E−12 |
| 1110 | CGPG5810 | Pkinase | 197 | 468 | 93.7 | 5.40E−25 |
| 1110 | CGPG5810 | Pkinase_Tyr | 200 | 468 | 100.3 | 5.80E−27 |
| 1111 | CGPG5822 | Pkinase | 131 | 418 | 302.6 | 7.40E−88 |
| 1112 | CGPG5837 | Pkinase | 14 | 275 | 128.1 | 2.50E−35 |
| 1113 | CGPG5855 | Pkinase_Tyr | 81 | 363 | 133.4 | 6.10E−37 |
| 1113 | CGPG5855 | Pkinase | 81 | 363 | 158.3 | 2.00E−44 |
| 1114 | CGPG5868 | Pkinase_Tyr | 45 | 312 | 154.4 | 3.00E−43 |
| 1114 | CGPG5868 | Pkinase | 45 | 312 | 150.1 | 6.00E−42 |
| 1115 | CGPG587 | FKBP_C | 104 | 208 | 138.8 | 1.50E−38 |
| 1117 | CGPG5893 | Pkinase | 52 | 314 | −49.3 | 1.30E−05 |
| 1118 | CGPG5909 | ADH_zinc_N | 163 | 310 | 104.4 | 3.40E−28 |
| 1119 | CGPG5914 | ADH_N | 54 | 188 | 144.5 | 2.80E−40 |
| 1119 | CGPG5914 | ADH_zinc_N | 219 | 362 | 157.2 | 4.30E−44 |
| 1123 | CGPG5930 | Mov34 | 328 | 437 | 81.7 | 2.30E−21 |
| 1124 | CGPG5945 | Pyr_redox_2 | 8 | 305 | 125.3 | 1.70E−34 |
| 1124 | CGPG5945 | Pyr_redox | 167 | 262 | 104.5 | 3.00E−28 |
| 1125 | CGPG5958 | Pyr_redox_2 | 8 | 304 | 126.4 | 8.20E−35 |
| 1125 | CGPG5958 | Pyr_redox | 166 | 261 | 115.1 | 2.00E−31 |
| 1126 | CGPG5977 | Ank | 48 | 80 | 1.7 | 18 |
| 1126 | CGPG5977 | Ank | 81 | 113 | 39.4 | 1.30E−08 |
| 1126 | CGPG5977 | Ank | 114 | 146 | 18.6 | 0.023 |
| 1126 | CGPG5977 | Pkinase | 166 | 424 | 186.4 | 6.90E−53 |
| 1126 | CGPG5977 | Pkinase_Tyr | 166 | 424 | 172.3 | 1.20E−48 |
| 1127 | CGPG598 | Nramp | 66 | 429 | 644.5 | 8.90E−191 |
| 1128 | CGPG5986 | Pkinase | 43 | 329 | 323.5 | 3.60E−94 |
| 1129 | CGPG5994 | F-box | 62 | 108 | 15.1 | 0.26 |

TABLE 18-continued

| PEP SEQ ID | Construct ID | Pfam domain name | begin | start | score | E-value |
|---|---|---|---|---|---|---|
| 1129 | CGPG5994 | LRR_2 | 314 | 340 | 17.1 | 0.063 |
| 1130 | CGPG5996 | Tetraspannin | 4 | 230 | 244.3 | 2.60E−70 |
| 1131 | CGPG6021 | RRM_1 | 8 | 77 | 73.1 | 8.60E−19 |
| 1131 | CGPG6021 | RRM_1 | 108 | 178 | 81.2 | 3.20E−21 |
| 1132 | CGPG6027 | RRM_1 | 42 | 113 | 104.5 | 3.10E−28 |
| 1133 | CGPG6035 | Pyr_redox_2 | 51 | 370 | 86.5 | 8.30E−23 |
| 1133 | CGPG6035 | Pyr_redox | 216 | 323 | 55.5 | 1.80E−13 |
| 1133 | CGPG6035 | efhand | 376 | 404 | 23.3 | 0.00087 |
| 1134 | CGPG604 | PSI_PsaH | 6 | 145 | 342.9 | 5.50E−100 |
| 1136 | CGPG606 | Phytochelatin | 46 | 178 | 381.8 | 1.10E−111 |
| 1136 | CGPG606 | DUF1984 | 179 | 259 | 206.3 | 7.10E−59 |
| 1137 | CGPG6069 | RNA_pol_L | 90 | 382 | 75.5 | 1.60E−19 |
| 1137 | CGPG6069 | RNA_pol_A_bac | 124 | 268 | 113 | 8.80E−31 |
| 1138 | CGPG608 | TB2_DP1_HVA22 | 11 | 108 | 188.4 | 1.70E−53 |
| 1139 | CGPG6080 | Str_synth | 144 | 232 | 164.7 | 2.40E−46 |
| 1140 | CGPG6082 | Miro | 8 | 121 | 62.7 | 1.20E−15 |
| 1140 | CGPG6082 | Ras | 8 | 179 | 254 | 3.00E−73 |
| 1141 | CGPG6089 | NicO | 153 | 372 | 147.1 | 4.70E−41 |
| 1143 | CGPG6128 | Reticulon | 22 | 197 | 303.7 | 3.40E−88 |
| 1144 | CGPG614 | cobW | 74 | 246 | 232.9 | 6.80E−67 |
| 1145 | CGPG6149 | Glutaredoxin | 84 | 148 | 115.9 | 1.10E−31 |
| 1146 | CGPG6172 | Miro | 11 | 126 | 74.1 | 4.60E−19 |
| 1146 | CGPG6172 | Ras | 11 | 173 | 288.8 | 1.00E−83 |
| 1147 | CGPG6174 | Miro | 19 | 133 | 75.8 | 1.30E−19 |
| 1147 | CGPG6174 | Ras | 19 | 180 | 326.5 | 4.80E−95 |
| 1148 | CGPG6176 | Miro | 15 | 130 | 63.8 | 5.50E−16 |
| 1148 | CGPG6176 | Ras | 15 | 177 | 285.5 | 1.00E−82 |
| 1149 | CGPG6197 | Phi_1 | 55 | 334 | 656.6 | 2.00E−194 |
| 1150 | CGPG620 | tRNA-synt_1g | 71 | 430 | 627.4 | 1.20E−185 |
| 1152 | CGPG6204 | mTERF | 75 | 357 | 69.9 | 8.00E−18 |
| 1153 | CGPG621 | RRM_1 | 19 | 90 | 20.7 | 0.0017 |
| 1154 | CGPG6210 | MFS_1 | 26 | 419 | 55.8 | 1.40E−13 |
| 1154 | CGPG6210 | Sugar_tr | 29_ | 459 | 239.3 | 8.30E−69 |
| 1155 | CGPG6211 | Sugar_tr | 24 | 479 | 469.9 | 3.00E−138 |
| 1155 | CGPG6211 | MFS_1 | 30 | 443 | 98.8 | 1.60E−26 |
| 1156 | CGPG6214 | Sugar_tr | 26 | 487 | 541.1 | 1.20E−159 |
| 1156 | CGPG6214 | MFS_1 | 32 | 448 | 89.3 | 1.20E−23 |
| 1157 | CGPG6215 | MFS_1 | 34 | 498 | 52.2 | 1.80E−12 |
| 1157 | CGPG6215 | PTR2 | 93 | 486 | 181.3 | 2.40E−51 |
| 1158 | CGPG6222 | Sugar_tr | 27 | 490 | 523.9 | 1.70E−154 |
| 1158 | CGPG6222 | MFS_1 | 31 | 447 | 92.4 | 1.40E−24 |
| 1159 | CGPG6229 | MFS_1 | 23 | 447 | 97.4 | 4.40E−26 |
| 1159 | CGPG6229 | Sugar_tr | 28 | 490 | 565.7 | 4.40E−167 |
| 1160 | CGPG6233 | Sugar_tr | 22 | 512 | 23.1 | 1.30E−07 |
| 1160 | CGPG6233 | MFS_1 | 37 | 473 | 69.1 | 1.40E−17 |
| 1161 | CGPG6237 | Sugar_tr | 25 | 483 | 398.5 | 1.00E−116 |
| 1161 | CGPG6237 | MFS_1 | 29 | 442 | 110 | 6.80E−30 |
| 1162 | CGPG6243 | Pkinase | 25 | 333 | 289.3 | 7.40E−84 |
| 1163 | CGPG6248 | Pkinase | 22 | 276 | 338.1 | 1.50E−98 |
| 1163 | CGPG6248 | NAF | 306 | 366 | 64.3 | 3.90E−16 |
| 1164 | CGPG6252 | Pkinase | 12 | 266 | 340.3 | 3.20E−99 |
| 1164 | CGPG6252 | NAF | 298 | 358 | 110.9 | 3.70E−30 |
| 1165 | CGPG6267 | Pkinase | 68 | 306 | −7.3 | 4.00E−08 |
| 1166 | CGPG6272 | Pkinase | 74 | 349 | 167.4 | 3.70E−47 |
| 1166 | CGPG6272 | Pkinase_Tyr | 74 | 349 | 134.3 | 3.20E−37 |
| 1167 | CGPG6294 | Pkinase | 75 | 352 | −1.8 | 1.90E−08 |
| 1168 | CGPG63 | p450 | 44 | 511 | 425.2 | 8.90E−125 |
| 1170 | CGPG6317 | MFS_1 | 39 | 504 | 44.5 | 3.50E−10 |
| 1170 | CGPG6317 | PTR2 | 101 | 488 | 297.8 | 2.00E−86 |
| 1171 | CGPG6328 | Trehalose_PPase | 121 | 354 | 380.5 | 2.60E−111 |
| 1172 | CGPG6334 | Sterol_desat | 34 | 245 | 281.2 | 2.00E−81 |
| 1173 | CGPG6336 | Sterol_desat | 38 | 247 | 261.6 | 1.60E−75 |
| 1174 | CGPG6349 | LRR_1 | 42 | 62 | 15.7 | 0.17 |
| 1174 | CGPG6349 | LRR_1 | 64 | 84 | 7.9 | 9.3 |
| 1174 | CGPG6349 | LRR_1 | 108 | 128 | 11.6 | 1.9 |
| 1174 | CGPG6349 | LRR_1 | 130 | 151 | 12.5 | 1.3 |
| 1174 | CGPG6349 | LRR_1 | 153 | 174 | 10.7 | 2.9 |
| 1174 | CGPG6349 | LRR_1 | 176 | 197 | 11.9 | 1.7 |
| 1174 | CGPG6349 | LRR_1 | 199 | 219 | 7.9 | 9.6 |
| 1175 | CGPG6352 | zf-CCHC | 81 | 98 | 18.4 | 0.00091 |
| 1177 | CGPG6364 | Gp_dh_N | 3 | 152 | 341.6 | 1.30E−99 |
| 1177 | CGPG6364 | Gp_dh_C | 157 | 313 | 381.4 | 1.40E−111 |
| 1178 | CGPG6366 | Gp_dh_N | 3 | 153 | 301.7 | 1.40E−87 |
| 1178 | CGPG6366 | Gp_dh_C | 158 | 314 | 334 | 2.60E−97 |
| 1179 | CGPG6375 | Aminotran_1_2 | 36 | 390 | 217 | 4.30E−62 |
| 1180 | CGPG6388 | NTP_transferase | 15 | 285 | 397.9 | 1.50E−116 |
| 1181 | CGPG6391 | ADH_N | 32 | 143 | 172.7 | 9.30E−49 |

TABLE 18-continued

| PEP SEQ ID | Construct ID | Pfam domain name | begin | start | score | E-value |
|---|---|---|---|---|---|---|
| 1181 | CGPG6391 | ADH_zinc_N | 172 | 312 | 193.2 | 6.00E−55 |
| 1182 | CGPG6399 | ADH_N | 27 | 155 | 135.6 | 1.30E−37 |
| 1182 | CGPG6399 | ADH_zinc_N | 186 | 332 | 115.4 | 1.70E−31 |
| 1183 | CGPG6407 | Glucokinase | 5 | 341 | 569.2 | 4.00E−168 |
| 1184 | CGPG6418 | ADH_N | 28 | 156 | 128.2 | 2.40E−35 |
| 1184 | CGPG6418 | ADH_zinc_N | 187 | 333 | 135.1 | 2.00E−37 |
| 1185 | CGPG6430 | Iso_dh | 6 | 355 | 346.2 | 5.40E−101 |
| 1186 | CGPG6432 | ADH_N | 25 | 135 | 157.5 | 3.40E−44 |
| 1186 | CGPG6432 | ADH_zinc_N | 166 | 305 | 114.8 | 2.40E−31 |
| 1187 | CGPG6437 | TPT | 205 | 388 | 167.3 | 4.00E−47 |
| 1188 | CGPG6445 | Aldedh | 45 | 511 | 720.6 | 1.10E−213 |
| 1189 | CGPG6450 | Aldedh | 26 | 491 | 797.6 | 7.00E−237 |
| 1190 | CGPG6458 | Aldedh | 22 | 480 | 796.6 | 1.40E−236 |
| 1191 | CGPG6465 | PfkB | 10 | 314 | 274.5 | 2.10E−79 |
| 1192 | CGPG6476 | PFK | 3 | 278 | 659.8 | 2.20E−195 |
| 1193 | CGPG6505 | Aminotran_3 | 123 | 449 | 321.7 | 1.30E−93 |
| 1194 | CGPG6507 | Gln-synt_N | 105 | 187 | 85.7 | 1.50E−22 |
| 1194 | CGPG6507 | Gln-synt_C | 193 | 446 | 528.1 | 9.40E−156 |
| 1195 | CGPG6509 | Glutaminase | 112 | 396 | 599 | 4.30E−177 |
| 1196 | CGPG6510 | Aldedh | 17 | 476 | 689.2 | 3.10E−204 |
| 1197 | CGPG6515 | Aldedh | 19 | 476 | 789.7 | 1.70E−234 |
| 1198 | CGPG6520 | Aldedh | 29 | 491 | 790.7 | 8.30E−235 |
| 1199 | CGPG6531 | Enolase_N | 3 | 133 | 215.5 | 1.20E−61 |
| 1199 | CGPG6531 | Enolase_C | 138 | 425 | 571.7 | 7.20E−169 |
| 1200 | CGPG6553 | Aldedh | 103 | 563 | 768.4 | 4.40E−228 |
| 1201 | CGPG6557 | ELFV_dehydrog_N | 145 | 275 | 294.9 | 1.50E−85 |
| 1201 | CGPG6557 | ELFV_dehydrog | 290 | 533 | 486.7 | 2.80E−143 |
| 1202 | CGPG6563 | Aminotran_1_2 | 120 | 472 | 403.3 | 3.50E−118 |
| 1203 | CGPG6564 | iPGM_N | 90 | 451 | 876.8 | 1.00E−260 |
| 1203 | CGPG6564 | Metalloenzyme | 461 | 576 | 173.3 | 5.90E−49 |
| 1204 | CGPG6572 | Gp_dh_N | 91 | 241 | 301.7 | 1.40E−87 |
| 1204 | CGPG6572 | Gp_dh_C | 246 | 402 | 334 | 2.60E−97 |
| 1205 | CGPG6577 | iPGM_N | 92 | 451 | 863.6 | 9.30E−257 |
| 1205 | CGPG6577 | Metalloenzyme | 461 | 577 | 195.7 | 1.10E−55 |
| 1206 | CGPG6588 | DAO | 92 | 493 | −24.3 | 0.00021 |
| 1206 | CGPG6588 | FAD_binding_2 | 92 | 421 | −110.2 | 0.0013 |
| 1206 | CGPG6588 | GIDA | 92 | 418 | −223.3 | 0.0021 |
| 1206 | CGPG6588 | Pyr_redox_2 | 92 | 409 | 252.3 | 9.90E−73 |
| 1206 | CGPG6588 | Pyr_redox | 265 | 362 | 125.3 | 1.70E−34 |
| 1206 | CGPG6588 | Pyr_redox_dim | 437 | 546 | 222.4 | 9.80E−64 |
| 1207 | CGPG6596 | Biotin_lipoyl | 91 | 164 | 76 | 1.20E−19 |
| 1207 | CGPG6596 | E3_binding | 228 | 264 | 68.1 | 2.70E−17 |
| 1207 | CGPG6596 | 2-oxoacid_dh | 296 | 521 | 326.6 | 4.20E−95 |
| 1209 | CGPG6619 | Transketolase_N | 101 | 435 | 777.9 | 5.90E−231 |
| 1209 | CGPG6619 | Transket_pyr | 450 | 627 | 245.4 | 1.20E−70 |
| 1209 | CGPG6619 | Transketolase_C | 639 | 754 | 36.1 | 1.30E−07 |
| 1210 | CGPG6623 | PGAM | 96 | 330 | 130.8 | 3.80E−36 |
| 1211 | CGPG6626 | OstA | 109 | 219 | 106.8 | 6.20E−29 |
| 1212 | CGPG663 | Pro_CA | 155 | 325 | 357.7 | 1.90E−104 |
| 1213 | CGPG6635 | Cytochrom_C | 126 | 204 | 55.4 | 1.90E−13 |
| 1215 | CGPG6641 | AstE_AspA | 93 | 372 | 312.6 | 7.00E−91 |
| 1216 | CGPG6642 | Transket_pyr | 125 | 303 | 234.2 | 2.70E−67 |
| 1216 | CGPG6642 | Transketolase_C | 319 | 443 | 196.1 | 8.20E−56 |
| 1217 | CGPG6645 | TIM | 95 | 336 | 398.9 | 7.60E−117 |
| 1218 | CGPG6660 | CBS | 97 | 214 | 118.4 | 2.00E−32 |
| 1219 | CGPG6671 | NTP_transferase | 102 | 374 | 277.3 | 2.90E−80 |
| 1220 | CGPG6697 | Transaldolase | 100 | 400 | 657.9 | 7.90E−195 |
| 1221 | CGPG6706 | iPGM_N | 90 | 451 | 870.1 | 1.00E−258 |
| 1221 | CGPG6706 | Metalloenzyme | 461 | 576 | 191.4 | 2.10E−54 |
| 1222 | CGPG6723 | Aminotran_1_2 | 124 | 478 | 217 | 4.30E−62 |
| 1223 | CGPG6729 | Gln-synt_N | 100 | 182 | 148.3 | 2.00E−41 |
| 1223 | CGPG6729 | Gln-synt_C | 189 | 470 | 568.5 | 6.70E−168 |
| 1224 | CGPG6738 | Aminotran_1_2 | 123 | 473 | 205.6 | 1.10E−58 |
| 1225 | CGPG6742 | Aldedh | 105 | 563 | 730.5 | 1.10E−216 |
| 1226 | CGPG6752 | TIM | 92 | 334 | 465.9 | 5.00E−137 |
| 1227 | CGPG6760 | GATase_2 | 2 | 164 | −6.7 | 1.70E−10 |
| 1227 | CGPG6760 | Asn_synthase | 241 | 531 | 383.2 | 3.80E−112 |
| 1228 | CGPG6768 | PGI | 55 | 545 | 770.6 | 9.60E−229 |
| 1229 | CGPG6779 | Isoamylase_N | 105 | 182 | 91.3 | 2.90E−24 |
| 1229 | CGPG6779 | Alpha-amylase | 219 | 613 | 30.3 | 8.20E−08 |
| 1230 | CGPG6785 | Molybdop_Fe4S4 | 44 | 105 | 86.1 | 1.10E−22 |
| 1230 | CGPG6785 | Molybdopterin | 108 | 660 | 93.7 | 5.70E−25 |
| 1230 | CGPG6785 | Molydop_binding | 892 | 1011 | 60.2 | 6.90E−15 |
| 1231 | CGPG6800 | PGI | 52 | 541 | 1093.7 | 0 |
| 1232 | CGPG686 | RRM_1 | 9 | 80 | 101 | 3.50E−27 |
| 1232 | CGPG686 | zf-CCHC | 118 | 135 | 37.8 | 3.90E−08 |
| 1233 | CGPG6898 | Hin1 | 28 | 163 | 112.4 | 1.30E−30 |

TABLE 18-continued

| PEP SEQ ID | Construct ID | Pfam domain name | begin | start | score | E-value |
|---|---|---|---|---|---|---|
| 1234 | CGPG6900 | Pkinase | 97 | 365 | 172.1 | 1.40E-48 |
| 1236 | CGPG6920 | Dehydrin | 14 | 128 | 165.3 | 1.50E-46 |
| 1237 | CGPG6921 | CorA | 48 | 440 | 576.8 | 2.10E-170 |
| 1240 | CGPG6945 | SNARE | 37 | 99 | 67.1 | 5.60E-17 |
| 1241 | CGPG6946 | MATH | 13 | 133 | 30.7 | 5.10E-06 |
| 1242 | CGPG6948 | PAP2 | 100 | 233 | 71.2 | 3.40E-18 |
| 1243 | CGPG6974 | DUF538 | 7 | 146 | 248.7 | 1.20E-71 |
| 1244 | CGPG6976 | DUF926 | 293 | 406 | 220 | 5.20E-63 |
| 1245 | CGPG6996 | CPDase | 1 | 179 | 275.9 | 7.80E-80 |
| 1246 | CGPG7002 | zf-C3HC4 | 123 | 157 | 25 | 0.00026 |
| 1247 | CGPG7013 | zf-C3HC4 | 115 | 156 | 26.2 | 0.00011 |
| 1248 | CGPG7021 | Invertase_neut | 98 | 564 | 1154 | 0 |
| 1248 | CGPG7021 | GDE_C | 151 | 537 | −212.6 | 0.0022 |
| 1251 | CGPG7075 | DUF1749 | 77 | 349 | 217.1 | 3.80E-62 |
| 1252 | CGPG7080 | Glutaredoxin | 44 | 106 | 97.2 | 5.10E-26 |
| 1253 | CGPG7094 | DUF300 | 6 | 281 | 574.1 | 1.40E-169 |
| 1254 | CGPG7095 | Abhydrolase_3 | 107 | 321 | 295.6 | 9.10E-86 |
| 1255 | CGPG7104 | Saccharop_dh | 13 | 445 | 35.1 | 6.50E-09 |
| 1256 | CGPG7118 | F-box | 25 | 73 | 25 | 0.00026 |
| 1257 | CGPG7122 | Pkinase | 20 | 280 | 206.6 | 5.70E-59 |
| 1257 | CGPG7122 | Pkinase_Tyr | 20 | 280 | 199.1 | 1.10E-56 |
| 1258 | CGPG713 | Cyclin_N | 5 | 135 | 6.2 | 4.30E-05 |
| 1259 | CGPG7130 | CS | 145 | 220 | 109.9 | 7.50E-30 |
| 1260 | CGPG7145 | Transthyretin | 191 | 310 | 185.5 | 1.30E-52 |
| 1261 | CGPG7166 | DnaJ | 79 | 141 | 29.6 | 5.80E-06 |
| 1262 | CGPG7179 | Bystin | 127 | 423 | 795.6 | 2.90E-236 |
| 1263 | CGPG7184 | PBD | 27 | 127 | 24 | 0.0002 |
| 1264 | CGPG7185 | GAF | 190 | 346 | 32.9 | 1.10E-06 |
| 1264 | CGPG7185 | HisKA | 382 | 445 | 24.6 | 0.00036 |
| 1265 | CGPG7192 | 2OG-FeII_Oxy | 201 | 301 | 136.6 | 6.60E-38 |
| 1266 | CGPG7199 | RWD | 3 | 122 | 126.7 | 6.30E-35 |
| 1267 | CGPG72 | Amino_oxidase | 66 | 528 | 217.5 | 3.10E-62 |
| 1268 | CGPG7231 | B3_4 | 118 | 280 | 89.3 | 1.10E-23 |
| 1268 | CGPG7231 | B5 | 305 | 378 | 94.9 | 2.40E-25 |
| 1269 | CGPG7241 | Peptidase_C26 | 58 | 281 | 149 | 1.20E-41 |
| 1272 | CGPG7265 | ARM_1 | 12 | 296 | 531.9 | 6.60E-157 |
| 1273 | CGPG7274 | DUF640 | 36 | 168 | 312.1 | 1.00E-90 |
| 1274 | CGPG7291 | eIF-1a | 20 | 91 | 71.9 | 2.00E-18 |
| 1275 | CGPG7303 | Aldedh | 20 | 484 | 779 | 2.80E-231 |
| 1276 | CGPG7315 | Y_phosphatase2 | 116 | 280 | 346.6 | 4.00E-101 |
| 1278 | CGPG7327 | Actin | 2 | 470 | 33.2 | 5.40E-16 |
| 1280 | CGPG7347 | Tcp11 | 648 | 1133 | 261.8 | 1.40E-75 |
| 1281 | CGPG7348 | CorA | 90 | 467 | 408.2 | 1.20E-119 |
| 1283 | CGPG7356 | Metallophos | 2 | 120 | 28.1 | 3.10E-05 |
| 1284 | CGPG7359 | Methyltransf_11 | 38 | 135 | 43.8 | 5.80E-10 |
| 1284 | CGPG7359 | Methyltransf_12 | 38 | 133 | 46 | 1.30E-10 |
| 1286 | CGPG7372 | zf-C3HC4 | 119 | 160 | 38.8 | 1.90E-08 |
| 1287 | CGPG7379 | zf-C3HC4 | 36 | 76 | 39.6 | 1.10E-08 |
| 1288 | CGPG7398 | DUF212 | 22 | 167 | 141.6 | 2.10E-39 |
| 1289 | CGPG7403 | TLD | 203 | 341 | 176.8 | 5.30E-50 |
| 1290 | CGPG7404 | PBP | 25 | 170 | 217.5 | 2.90E-62 |
| 1291 | CGPG7410 | HLH | 36 | 83 | 14 | 0.0047 |
| 1292 | CGPG7417 | MMR_HSR1 | 131 | 252 | 120.2 | 6.00E-33 |
| 1293 | CGPG7423 | Gln-synt_N | 102 | 183 | 171.5 | 2.10E-48 |
| 1293 | CGPG7423 | Gln-synt_C | 190 | 471 | 581.1 | 1.10E-171 |
| 1294 | CGPG7424 | FBPase | 92 | 424 | 521.2 | 1.20E-153 |
| 1297 | CGPG7443 | DUF1001 | 92 | 274 | 425.2 | 9.10E-125 |
| 1298 | CGPG7449 | ScpA_ScpB | 104 | 347 | 405 | 1.10E-118 |
| 1301 | CGPG7459 | DUF1350 | 90 | 360 | 812.2 | 2.80E-241 |
| 1303 | CGPG7481 | Abhydrolase_1 | 113 | 361 | 29.1 | 1.50E-05 |
| 1304 | CGPG7483 | GTP_EFTU | 62 | 260 | 227.2 | 3.70E-65 |
| 1304 | CGPG7483 | GTP_EFTU_D2 | 281 | 355 | 38.5 | 2.30E-08 |
| 1304 | CGPG7483 | EFG_C | 461 | 551 | 54.5 | 3.60E-13 |
| 1306 | CGPG7503 | PBP | 19 | 170 | 159.9 | 6.70E-45 |
| 1307 | CGPG7504 | MSF1 | 15 | 187 | 125.9 | 1.10E-34 |
| 1309 | CGPG7516 | DUF783 | 25 | 229 | 255.1 | 1.40E-73 |
| 1312 | CGPG7524 | Isy1 | 1 | 292 | 519.5 | 3.70E-153 |
| 1313 | CGPG7525 | UFD1 | 10 | 184 | 417.5 | 1.90E-122 |
| 1315 | CGPG7537 | KTI12 | 1 | 291 | 406.2 | 4.80E-119 |
| 1317 | CGPG7575 | efhand | 95 | 123 | 31.4 | 3.20E-06 |
| 1318 | CGPG7577 | TP_methylase | 1 | 213 | 89.5 | 1.00E-23 |
| 1319 | CGPG7590 | Ribonuc_L-PSP | 61 | 179 | 210.1 | 5.20E-60 |
| 1321 | CGPG7601 | CCT | 237 | 275 | 74 | 4.80E-19 |
| 1322 | CGPG7605 | RRM_1 | 88 | 158 | 65 | 2.40E-16 |
| 1323 | CGPG7607 | Amidohydro_2 | 10 | 289 | 102.2 | 1.50E-271 |
| 1325 | CGPG7632 | zf-Tim10_DDP | 12 | 77 | 105 | 2.30E-28 |
| 1326 | CGPG7673 | zf-MYND | 76 | 113 | 47.5 | 4.40E-11 |

TABLE 18-continued

| PEP SEQ ID | Construct ID | Pfam domain name | begin | start | score | E-value |
|---|---|---|---|---|---|---|
| 1326 | CGPG7673 | UCH | 468 | 774 | 192.5 | 1.00E−54 |
| 1327 | CGPG7683 | zf-LSD1 | 28 | 52 | 40.3 | 6.70E−09 |
| 1327 | CGPG7683 | zf-LSD1 | 67 | 91 | 54.8 | 2.80E−13 |
| 1327 | CGPG7683 | zf-LSD1 | 105 | 129 | 54.1 | 4.70E−13 |
| 1328 | CGPG773 | H_PPase | 64 | 798 | 1699.2 | 0 |
| 1329 | CGPG7776 | DUF525 | 311 | 445 | 155.8 | 1.10E−43 |
| 1330 | CGPG7781 | SapB_1 | 45 | 83 | 37.9 | 3.60E−08 |
| 1330 | CGPG7781 | SapB_2 | 86 | 119 | 18.1 | 0.025 |
| 1330 | CGPG7781 | SapB_1 | 131 | 169 | 27.7 | 4.20E−05 |
| 1330 | CGPG7781 | SapB_2 | 172 | 206 | 20.8 | 0.0049 |
| 1331 | CGPG7785 | LRRNT_2 | 24 | 65 | 39.3 | 1.30E−08 |
| 1331 | CGPG7785 | LRR_1 | 93 | 115 | 11.4 | 2.1 |
| 1331 | CGPG7785 | LRR_1 | 117 | 139 | 8.8 | 6.4 |
| 1331 | CGPG7785 | LRR_1 | 141 | 163 | 12.5 | 1.3 |
| 1331 | CGPG7785 | LRR_1 | 165 | 187 | 15.6 | 0.18 |
| 1331 | CGPG7785 | LRR_1 | 189 | 211 | 8.7 | 6.8 |
| 1331 | CGPG7785 | LRR_1 | 213 | 235 | 16.9 | 0.075 |
| 1331 | CGPG7785 | Pkinase | 415 | 682 | 18.7 | 1.10E−09 |
| 1332 | CGPG7787 | Aldose_epim | 26 | 301 | 257.4 | 3.00E−74 |
| 1334 | CGPG7796 | WD40 | 50 | 88 | 32 | 2.10E−06 |
| 1334 | CGPG7796 | WD40 | 92 | 130 | 43 | 1.00E−09 |
| 1334 | CGPG7796 | WD40 | 134 | 174 | 47.8 | 3.70E−11 |
| 1334 | CGPG7796 | WD40 | 182 | 220 | 37.9 | 3.40E−08 |
| 1334 | CGPG7796 | WD40 | 391 | 432 | 33.3 | 8.40E−07 |
| 1334 | CGPG7796 | WD40 | 436 | 475 | 40.4 | 6.20E−09 |
| 1334 | CGPG7796 | WD40 | 489 | 527 | 28.9 | 1.80E−05 |
| 1334 | CGPG7796 | WD40 | 531 | 569 | 31 | 4.30E−06 |
| 1334 | CGPG7796 | WD40 | 573 | 611 | 43.9 | 5.30E−10 |
| 1334 | CGPG7796 | WD40 | 615 | 653 | 28.6 | 2.20E−05 |
| 1334 | CGPG7796 | Utp13 | 674 | 809 | 231.1 | 2.40E−66 |
| 1335 | CGPG7797 | GILT | 35 | 144 | 133.6 | 5.40E−37 |
| 1336 | CGPG7801 | LRR_1 | 106 | 129 | 8.1 | 8.7 |
| 1336 | CGPG7801 | LRR_1 | 132 | 154 | 16.9 | 0.071 |
| 1336 | CGPG7801 | LRR_1 | 156 | 178 | 10.9 | 2.6 |
| 1336 | CGPG7801 | LRR_1 | 180 | 199 | 9.2 | 5.4 |
| 1336 | CGPG7801 | LRR_1 | 201 | 223 | 9.4 | 4.9 |
| 1336 | CGPG7801 | LRR_1 | 225 | 246 | 17.1 | 0.062 |
| 1336 | CGPG7801 | LRR_1 | 249 | 272 | 12.8 | 1.1 |
| 1336 | CGPG7801 | LRR_1 | 273 | 294 | 10.3 | 3.4 |
| 1336 | CGPG7801 | Pkinase | 456 | 716 | −45.5 | 7.60E−06 |
| 1337 | CGPG7813 | WD40 | 379 | 417 | 43.1 | 9.20E−10 |
| 1337 | CGPG7813 | WD40 | 421 | 459 | 39.8 | 9.60E−09 |
| 1337 | CGPG7813 | WD40 | 507 | 545 | 46.9 | 6.80E−11 |
| 1337 | CGPG7813 | WD40 | 549 | 587 | 29.5 | 1.20E−05 |
| 1337 | CGPG7813 | PWP2 | 785 | 900 | 243.1 | 5.70E−70 |
| 1341 | CGPG7863 | zf-CW | 100 | 153 | 85.7 | 1.40E−22 |
| 1341 | CGPG7863 | MBD | 162 | 237 | 43.4 | 7.80E−10 |
| 1342 | CGPG7868 | BCNT | 165 | 244 | 123.2 | 7.40E−34 |
| 1343 | CGPG7881 | Aldedh | 99 | 558 | 694.8 | 6.40E−206 |
| 1344 | CGPG7887 | HEAT | 191 | 222 | 12 | 1.5 |
| 1344 | CGPG7887 | Arm | 262 | 302 | 27.2 | 6.00E−05 |
| 1344 | CGPG7887 | HEAT | 389 | 424 | 14.1 | 0.52 |
| 1344 | CGPG7887 | Arm | 423 | 463 | 32.8 | 1.20E−06 |
| 1345 | CGPG7899 | RRM_1 | 225 | 295 | 27.8 | 3.80E−05 |
| 1346 | CGPG7901 | IQ | 107 | 127 | 30.9 | 4.40E−06 |
| 1346 | CGPG7901 | IQ | 129 | 149 | 18.8 | 0.02 |
| 1347 | CGPG7909 | DUF383 | 92 | 271 | 353 | 4.90E−103 |
| 1347 | CGPG7909 | DUF384 | 272 | 330 | 107.8 | 3.20E−29 |
| 1348 | CGPG7911 | AAA | 245 | 447 | 58.7 | 1.90E−14 |
| 1349 | CGPG7919 | Cullin | 30 | 191 | −9.6 | 7.00E−09 |
| 1350 | CGPG7935 | IQ | 93 | 113 | 26.3 | 0.00011 |
| 1350 | CGPG7935 | IQ | 115 | 135 | 17.6 | 0.046 |
| 1351 | CGPG7940 | RRM_1 | 96 | 161 | 37.7 | 3.90E−08 |
| 1352 | CGPG7959 | Cyclin_N | 180 | 306 | 218.1 | 2.00E−62 |
| 1352 | CGPG7959 | Cyclin_C | 308 | 428 | 179 | 1.20E−50 |
| 1353 | CGPG7967 | IQ | 106 | 126 | 30.4 | 6.50E−06 |
| 1353 | CGPG7967 | IQ | 128 | 148 | 15.1 | 0.26 |
| 1354 | CGPG7975 | Arm | 28 | 68 | 23.4 | 0.00079 |
| 1354 | CGPG7975 | Arm | 70 | 110 | 17.4 | 0.052 |
| 1355 | CGPG7996 | efhand | 136 | 164 | 22.7 | 0.0013 |
| 1356 | CGPG8006 | AAA | 241 | 440 | 50.9 | 4.10E−12 |
| 1357 | CGPG801 | Cyt-b5 | 74 | 171 | 81.3 | 3.00E−21 |
| 1358 | CGPG8023 | RRM_1 | 11 | 82 | 114.5 | 3.00E−31 |
| 1359 | CGPG8025 | IQ | 93 | 113 | 27 | 6.80E−05 |
| 1359 | CGPG8025 | IQ | 115 | 135 | 20.6 | 0.0056 |
| 1360 | CGPG8038 | MFS_1 | 36 | 433 | 124.8 | 2.40E−34 |
| 1361 | CGPG8053 | DUF246 | 182 | 525 | 691.9 | 4.70E−205 |

TABLE 18-continued

| PEP SEQ ID | Construct ID | Pfam domain name | begin | start | score | E-value |
|---|---|---|---|---|---|---|
| 1364 | CGPG8070 | GILT | 32 | 136 | 193.2 | 6.30E−55 |
| 1365 | CGPG8073 | Dirigent | 17 | 183 | 330.8 | 2.30E−96 |
| 1366 | CGPG8076 | Tryp_alpha_amyl | 32 | 107 | 47.1 | 5.90E−11 |
| 1369 | CGPG8095 | IPK | 16 | 279 | 434.8 | 1.20E−127 |
| 1370 | CGPG8096 | 60KD_IMP | 151 | 348 | 35.5 | 1.70E−13 |
| 1374 | CGPG8129 | Ank | 49 | 81 | 32.1 | 1.90E−06 |
| 1374 | CGPG8129 | Ank | 82 | 114 | 24.1 | 0.00049 |
| 1374 | CGPG8129 | Ank | 115 | 147 | 43.2 | 8.90E−10 |
| 1378 | CGPG8165 | Glutaredoxin | 44 | 106 | 97.2 | 5.10E−26 |
| 1379 | CGPG8169 | Nol1_Nop2_Fmu | 226 | 505 | 21.9 | 3.60E−09 |
| 1380 | CGPG8203 | Uricase | 11 | 140 | 134.3 | 3.40E−37 |
| 1380 | CGPG8203 | Uricase | 147 | 300 | 177.6 | 3.00E−50 |
| 1381 | CGPG8205 | DZC | 113 | 148 | 81 | 3.70E−21 |
| 1383 | CGPG8213 | Phosphoesterase | 27 | 388 | 519.2 | 2.70E−153 |
| 1384 | CGPG8225 | FBPase | 25 | 348 | 464.4 | 1.40E−136 |
| 1385 | CGPG8227 | NIR_SIR_ferr | 44 | 111 | 90.7 | 4.50E−24 |
| 1385 | CGPG8227 | NIR_SIR | 119 | 275 | 207.5 | 3.00E−59 |
| 1385 | CGPG8227 | NIR_SIR_ferr | 331 | 399 | 57.3 | 5.00E−14 |
| 1385 | CGPG8227 | NIR_SIR | 405 | 553 | 28.9 | 1.40E−05 |
| 1386 | CGPG8235 | Aldedh | 12 | 471 | 791.5 | 4.70E−235 |
| 1387 | CGPG8236 | Molybdop_Fe4S4 | 9 | 63 | 76 | 1.20E−19 |
| 1387 | CGPG8236 | Molybdopterin | 66 | 495 | 428.7 | 8.00E−126 |
| 1387 | CGPG8236 | Molydop_binding | 593 | 703 | 111.8 | 2.00E−30 |
| 1387 | CGPG8236 | Fer2_BFD | 852 | 903 | 50.3 | 6.50E−12 |
| 1388 | CGPG8244 | PAS_2 | 15 | 125 | 151.7 | 2.00E−42 |
| 1388 | CGPG8244 | GAF | 152 | 320 | 93.4 | 7.10E−25 |
| 1388 | CGPG8244 | Phytochrome | 331 | 513 | 88.8 | 1.70E−23 |
| 1388 | CGPG8244 | HisKA | 528 | 596 | 43.1 | 9.40E−10 |
| 1388 | CGPG8244 | HATPase_c | 637 | 747 | 127 | 5.20E−35 |
| 1389 | CGPG8254 | NIR_SIR_ferr | 66 | 133 | 48.1 | 2.90E−11 |
| 1389 | CGPG8254 | NIR_SIR | 166 | 347 | 198.6 | 1.40E−56 |
| 1389 | CGPG8254 | NIR_SIR_ferr | 362 | 434 | 77.4 | 4.50E−20 |
| 1389 | CGPG8254 | NIR_SIR | 443 | 591 | 15.1 | 0.00014 |
| 1390 | CGPG8255 | PPDK_N | 16 | 384 | 620.2 | 1.80E−183 |
| 1390 | CGPG8255 | PEP-utilizers | 439 | 531 | 141.1 | 3.00E−39 |
| 1390 | CGPG8255 | PEP-utilizers_C | 559 | 914 | 485.9 | 4.80E−143 |
| 1391 | CGPG8262 | ELFV_dehydrog_N | 33 | 163 | 239.1 | 9.20E−69 |
| 1391 | CGPG8262 | ELFV_dehydrog | 179 | 420 | 400.7 | 2.10E−117 |
| 1392 | CGPG8264 | Aldedh | 17 | 480 | 795.7 | 2.70E−236 |
| 1393 | CGPG8269 | PGK | 1 | 396 | 769.8 | 1.70E−228 |
| 1394 | CGPG8271 | Gln-synt_N | 16 | 97 | 149.9 | 6.70E−42 |
| 1394 | CGPG8271 | Gln-synt_C | 104 | 386 | 584.6 | 9.60E−173 |
| 1395 | CGPG8305 | Sulfotransfer_1 | 70 | 336 | 352.4 | 7.40E−103 |
| 1396 | CGPG8320 | DUF1005 | 282 | 487 | 545.7 | 4.80E−161 |
| 1397 | CGPG8326 | Senescence | 35 | 369 | 791.4 | 5.30E−235 |
| 1398 | CGPG8344 | PPR | 173 | 207 | 17.6 | 0.046 |
| 1398 | CGPG8344 | PPR | 208 | 242 | 19.4 | 0.013 |
| 1398 | CGPG8344 | PPR | 243 | 277 | 10.4 | 0.44 |
| 1398 | CGPG8344 | PPR | 279 | 312 | 13.4 | 0.19 |
| 1398 | CGPG8344 | PPR | 314 | 348 | 2 | 4.3 |
| 1398 | CGPG8344 | PPR | 349 | 383 | 8.3 | 0.79 |
| 1398 | CGPG8344 | PPR | 384 | 418 | 2.3 | 4 |
| 1399 | CGPG8347 | Ribosomal_S8 | 5 | 130 | 214.4 | 2.60E−61 |
| 1400 | CGPG8359 | Tryp_alpha_amyl | 85 | 167 | 93.5 | 6.40E−25 |
| 1401 | CGPG8370 | Tim17 | 40 | 156 | 129.2 | 1.10E−35 |
| 1402 | CGPG8371 | PseudoU_synth_1 | 62 | 167 | 44.3 | 4.10E−10 |
| 1402 | CGPG8371 | PseudoU_synth_1 | 324 | 431 | 18.3 | 0.00016 |
| 1404 | CGPG8378 | LysM | 78 | 121 | 22 | 0.0021 |
| 1406 | CGPG841 | ArfGap | 4 | 120 | 173.8 | 4.20E−49 |
| 1405 | CGPG8383 | DUF239 | 174 | 368 | 401.1 | 1.60E−117 |
| 1409 | CGPG8450 | DUF793 | 1 | 390 | 976.4 | 1.10E−290 |
| 1410 | CGPG8451 | IQ | 105 | 125 | 21.2 | 0.0038 |
| 1410 | CGPG8451 | IQ | 127 | 147 | 21.5 | 0.0031 |
| 1411 | CGPG8459 | ubiquitin | 6 | 78 | 58.1 | 2.90E−14 |
| 1411 | CGPG8459 | UBA | 145 | 187 | 49.6 | 1.10E−11 |
| 1411 | CGPG8459 | XPC-binding | 242 | 298 | 56.4 | 9.40E−14 |
| 1411 | CGPG8459 | UBA | 322 | 361 | 46 | 1.20E−10 |
| 1412 | CGPG8461 | Ribosomal_S8 | 5 | 130 | 219 | 1.10E−62 |
| 1413 | CGPG8463 | PI3_PI4_kinase | 163 | 421 | 280.6 | 3.00E−81 |
| 1414 | CGPG8471 | F-box | 1 | 46 | 36.9 | 6.90E−08 |
| 1414 | CGPG8471 | FBA_1 | 211 | 383 | 295.9 | 7.50E−86 |
| 1415 | CGPG8474 | Metallothio_PEC | 12 | 85 | 150 | 6.10E−42 |
| 1416 | CGPG8475 | DAO | 10 | 372 | 186.6 | 5.80E−53 |
| 1417 | CGPG8476 | IQ | 84 | 104 | 30 | 8.20E−06 |
| 1417 | CGPG8476 | IQ | 106 | 126 | 14.4 | 0.41 |
| 1418 | CGPG8490 | ACT | 21 | 85 | 3.9 | 1.3 |
| 1418 | CGPG8490 | ACT | 110 | 174 | 36.6 | 8.60E−08 |

TABLE 18-continued

| PEP SEQ ID | Construct ID | Pfam domain name | begin | start | score | E-value |
|---|---|---|---|---|---|---|
| 1419 | CGPG8510 | DUF538 | 9 | 149 | 250.2 | 4.20E−72 |
| 1420 | CGPG8530 | Radical_SAM | 119 | 283 | 51.3 | 3.30E−12 |
| 1421 | CGPG8533 | DUF212 | 27 | 172 | 104.1 | 4.20E−28 |
| 1425 | CGPG8555 | NUDIX | 59 | 196 | 82 | 1.90E−21 |
| 1426 | CGPG8561 | zf-C3HC4 | 154 | 191 | 34 | 5.30E−07 |
| 1427 | CGPG8569 | 2OG-FeII_Oxy | 159 | 282 | 61.8 | 2.20E−15 |
| 1428 | CGPG8573 | DUF617 | 83 | 242 | 392.1 | 8.40E−115 |
| 1431 | CGPG8607 | DUF862 | 69 | 219 | 244 | 3.20E−70 |
| 1432 | CGPG8611 | Stig1 | 13 | 154 | 165.9 | 1.00E−46 |
| 1434 | CGPG8632 | Sina | 86 | 273 | −41.1 | 0.00037 |
| 1435 | CGPG8634 | FA_desaturase | 55 | 278 | 132.1 | 1.60E−36 |
| 1436 | CGPG8635 | DUF59 | 36 | 117 | 47 | 6.30E−11 |
| 1438 | CGPG8640 | DUF581 | 119 | 176 | 133.1 | 7.60E−37 |
| 1439 | CGPG8642 | CRAL_TRIO_N | 5 | 80 | 30.8 | 4.60E−06 |
| 1439 | CGPG8642 | CRAL_TRIO | 93 | 266 | 84.7 | 2.80E−22 |
| 1441 | CGPG8666 | PetM | 69 | 120 | 81.9 | 2.00E−21 |
| 1443 | CGPG8688 | Bet_v_I | 55 | 192 | −31.7 | 0.0014 |
| 1443 | CGPG8688 | Polyketide_cyc | 60 | 191 | 28.7 | 2.00E−05 |
| 1444 | CGPG8689 | DUF506 | 74 | 282 | 436 | 5.20E−128 |
| 1445 | CGPG8704 | GHMP_kinases_N | 24 | 93 | 39.2 | 1.40E−08 |
| 1445 | CGPG8704 | GHMP_kinases_C | 166 | 249 | 32.3 | 1.70E−06 |
| 1448 | CGPG8769 | Self-incomp_S1 | 35 | 144 | 175.9 | 9.80E−50 |
| 1449 | CGPG8774 | Maf | 1 | 207 | −0.7 | 4.20E−09 |
| 1450 | CGPG8778 | PPR | 13 | 47 | 5.4 | 1.7 |
| 1450 | CGPG8778 | PPR | 115 | 149 | 24.7 | 0.00032 |
| 1450 | CGPG8778 | PPR | 249 | 283 | 40.8 | 4.70E−09 |
| 1450 | CGPG8778 | PPR | 284 | 318 | 12.2 | 0.27 |
| 1450 | CGPG8778 | PPR | 320 | 354 | 16.7 | 0.078 |
| 1450 | CGPG8778 | PPR | 386 | 420 | 9.5 | 0.56 |
| 1451 | CGPG8784 | Snf7 | 16 | 189 | 208.6 | 1.50E−59 |
| 1452 | CGPG879 | ABC_tran | 195 | 418 | 49.2 | 7.50E−12 |
| 1452 | CGPG879 | ABC2_membrane | 520 | 733 | 231.7 | 1.60E−66 |
| 1452 | CGPG879 | PDR_assoc | 738 | 812 | 107.4 | 4.30E−29 |
| 1452 | CGPG879 | ABC_tran | 887 | 1077 | 109 | 1.40E−29 |
| 1452 | CGPG879 | ABC2_membrane | 1174 | 1388 | 249.2 | 8.80E−72 |
| 1453 | CGPG8797 | AMP-binding | 67 | 488 | 430.1 | 3.10E−126 |
| 1454 | CGPG8810 | DUF1645 | 80 | 252 | 310.1 | 4.00E−90 |
| 1455 | CGPG8827 | DUF623 | 199 | 263 | 128.8 | 1.50E−35 |
| 1456 | CGPG8853 | DUF1635 | 1 | 218 | 517 | 2.10E−152 |
| 1457 | CGPG8873 | p450 | 72 | 518 | 236.2 | 6.90E−68 |
| 1458 | CGPG8877 | Exo_endo_phos | 33 | 310 | 121.7 | 2.10E−33 |
| 1459 | CGPG8878 | Pkinase | 79 | 337 | 343.8 | 2.80E−100 |
| 1459 | CGPG8878 | efhand | 400 | 428 | 24.9 | 0.00028 |
| 1459 | CGPG8878 | efhand | 434 | 462 | 34.5 | 3.60E−07 |
| 1460 | CGPG8881 | DUF1677 | 3 | 107 | 192.2 | 1.30E−54 |
| 1461 | CGPG8895 | RNA_polI_A14 | 1 | 137 | 277.8 | 2.20E−80 |
| 1462 | CGPG8906 | MCM | 272 | 635 | 641.9 | 5.40E−190 |
| 1463 | CGPG8917 | Pkinase | 363 | 697 | 244 | 3.20E−70 |
| 1464 | CGPG8919 | Usp | 11 | 141 | 43.4 | 8.00E−10 |
| 1464 | CGPG8919 | Pkinase_Tyr | 405 | 676 | 88.6 | 1.90E−23 |
| 1464 | CGPG8919 | Pkinase | 405 | 676 | 138.8 | 1.50E−38 |
| 1465 | CGPG8925 | DUF617 | 82 | 260 | 262.9 | 6.60E−76 |
| 1466 | CGPG8930 | Lectin_legB | 26 | 261 | 232.7 | 8.20E−67 |
| 1466 | CGPG8930 | Pkinase | 347 | 617 | 166.9 | 5.30E−47 |
| 1466 | CGPG8930 | Pkinase_Tyr | 347 | 617 | 115.3 | 1.80E−31 |
| 1467 | CGPG8937 | LRR_1 | 440 | 461 | 13.9 | 0.57 |
| 1467 | CGPG8937 | LRR_1 | 463 | 485 | 18.7 | 0.022 |
| 1467 | CGPG8937 | LRR_1 | 487 | 510 | 14.6 | 0.36 |
| 1467 | CGPG8937 | Pkinase | 602 | 873 | 111.2 | 3.00E−30 |
| 1467 | CGPG8937 | Pkinase_Tyr | 603 | 873 | 110.1 | 6.30E−30 |
| 1468 | CGPG8942 | RRM_1 | 23 | 94 | 105.3 | 1.80E−28 |
| 1469 | CGPG8946 | Pkinase | 516 | 786 | 150.8 | 3.60E−42 |
| 1469 | CGPG8946 | Pkinase_Tyr | 516 | 786 | 129.6 | 8.70E−36 |
| 1470 | CGPG8990 | V-SNARE | 71 | 221 | 154.1 | 3.70E−43 |
| 1472 | CGPG9008 | TPK_catalytic | 40 | 180 | 114.5 | 3.00E−31 |
| 1472 | CGPG9008 | TPK_B1_binding | 191 | 259 | 94.4 | 3.40E−25 |
| 1473 | CGPG9016 | ETC_C1_NDUFA4 | 54 | 156 | 176.6 | 6.20E−50 |
| 1474 | CGPG9036 | MSP | 93 | 329 | 549 | 4.70E−162 |
| 1475 | CGPG9060 | LSM | 22 | 101 | 66.3 | 1.00E−16 |
| 1477 | CGPG908 | PPR | 62 | 96 | 9.9 | 0.5 |
| 1477 | CGPG908 | PPR | 125 | 158 | 20.9 | 0.0047 |
| 1477 | CGPG908 | PPR | 187 | 221 | 27 | 6.50E−05 |
| 1477 | CGPG908 | PPR | 250 | 284 | 50.4 | 6.20E−12 |
| 1477 | CGPG908 | PPR | 351 | 385 | 53.9 | 5.30E−13 |
| 1477 | CGPG908 | PPR | 386 | 419 | 2.2 | 4 |
| 1477 | CGPG908 | PPR | 422 | 456 | 17.9 | 0.035 |
| 1477 | CGPG908 | PPR | 488 | 522 | 3.4 | 3 |

TABLE 18-continued

| PEP SEQ ID | Construct ID | Pfam domain name | begin | start | score | E-value |
|---|---|---|---|---|---|---|
| 1478 | CGPG9093 | AWPM-19 | 15 | 156 | 325.5 | 9.00E−95 |
| 1479 | CGPG9096 | OTU | 11 | 121 | 104.8 | 2.50E−28 |
| 1482 | CGPG9111 | TB2_DP1_HVA22 | 4 | 101 | 157 | 5.10E−44 |
| 1483 | CGPG9112 | DUF778 | 10 | 177 | 350.3 | 3.20E−102 |
| 1484 | CGPG9123 | DUF833 | 1 | 264 | 236.7 | 4.90E−68 |
| 1485 | CGPG9124 | Exo_endo_phos | 20 | 427 | 39.2 | 1.40E−08 |
| 1485 | CGPG9124 | efhand | 337 | 365 | 31.2 | 3.70E−06 |
| 1486 | CGPG9138 | ThiC | 165 | 588 | 1118.5 | 0 |
| 1488 | CGPG9150 | Pkinase | 56 | 326 | 144.9 | 2.20E−40 |
| 1488 | CGPG9150 | Pkinase_Tyr | 56 | 326 | 129.9 | 6.90E−36 |
| 1489 | CGPG9152 | eIF2A | 217 | 410 | 382.7 | 5.60E−112 |
| 1490 | CGPG9162 | AAA_5 | 211 | 346 | 6.5 | 0.00057 |
| 1490 | CGPG9162 | AAA | 211 | 398 | 309.1 | 8.00E−90 |
| 1491 | CGPG9165 | GATase | 11 | 201 | 185.4 | 1.40E−52 |
| 1491 | CGPG9165 | GMP_synt_C | 432 | 524 | 210.5 | 3.80E−60 |
| 1492 | CGPG9166 | GATase | 28 | 210 | 194.9 | 1.90E−55 |
| 1492 | CGPG9166 | GMP_synt_C | 447 | 539 | 211.2 | 2.30E−60 |
| 1493 | CGPG9171 | Zip | 5 | 266 | 60.5 | 5.40E−15 |
| 1494 | CGPG9177 | Complex1_30kDa | 113 | 181 | 146.8 | 5.60E−41 |
| 1494 | CGPG9177 | Complex1_49kDa | 329 | 600 | 639.1 | 3.70E−189 |
| 1495 | CGPG9178 | PRA-CH | 54 | 129 | 201 | 2.90E−57 |
| 1495 | CGPG9178 | PRA-PH | 142 | 230 | 175.7 | 1.20E−49 |
| 1496 | CGPG9179 | Pkinase | 4 | 283 | 341.9 | 1.10E−99 |
| 1496 | CGPG9179 | Pkinase_Tyr | 4 | 283 | 96.5 | 7.90E−26 |
| 1497 | CGPG9181 | P21-Arc | 17 | 187 | 370.6 | 2.40E−108 |
| 1499 | CGPG9189 | SAC3_GANP | 19 | 164 | 152.8 | 9.30E−43 |
| 1500 | CGPG9201 | TPT | 201 | 350 | 168.8 | 1.40E−47 |
| 1501 | CGPG9222 | YjeF_N | 34 | 199 | 271.5 | 1.70E−78 |
| 1501 | CGPG9222 | Carb_kinase | 257 | 496 | 426.9 | 2.70E−125 |
| 1502 | CGPG9234 | DUF393 | 65 | 183 | 109.6 | 9.00E−30 |
| 1503 | CGPG9237 | Tim17 | 18 | 146 | 112.4 | 1.30E−30 |
| 1504 | CGPG9244 | TOM20_plant | 9 | 200 | 435.3 | 8.30E−128 |
| 1506 | CGPG9249 | Pkinase | 46 | 330 | 137.7 | 3.20E−38 |
| 1506 | CGPG9249 | Pkinase_Tyr | 46 | 330 | 94.3 | 3.60E−25 |
| 1507 | CGPG9251 | Cyclin_N | 54 | 186 | 115.8 | 1.30E−31 |
| 1507 | CGPG9251 | Cyclin_C | 188 | 314 | 23.7 | 0.00055 |
| 1508 | CGPG9280 | DUF1000 | 53 | 168 | 192 | 1.40E−54 |
| 1510 | CGPG9302 | Diphthamide_syn | 30 | 398 | 118.1 | 2.50E−32 |
| 1511 | CGPG931 | Pkinase | 114 | 398 | 303.3 | 4.30E−88 |
| 1512 | CGPG9313 | CN_hydrolase | 5 | 200 | 75.3 | 2.00E−19 |
| 1512 | CGPG9313 | NAD_synthase | 338 | 652 | −11.3 | 1.20E−11 |
| 1514 | CGPG9327 | OPT | 74 | 729 | 779.8 | 1.60E−231 |
| 1515 | CGPG933 | WD40 | 46 | 84 | 23.2 | 0.00093 |
| 1515 | CGPG933 | WD40 | 134 | 173 | 22.9 | 0.0012 |
| 1515 | CGPG933 | WD40 | 177 | 215 | 33.6 | 7.00E−07 |
| 1515 | CGPG933 | WD40 | 222 | 260 | 42.8 | 1.10E−09 |
| 1515 | CGPG933 | WD40 | 314 | 353 | 21.7 | 0.0026 |
| 1515 | CGPG933 | WD40 | 524 | 562 | 31.5 | 3.00E−06 |
| 1515 | CGPG933 | WD40 | 568 | 605 | 23.3 | 0.00085 |
| 1516 | CGPG9334 | Sugar_tr | 7 | 720 | 205.2 | 1.50E−58 |
| 1516 | CGPG9334 | MFS_1 | 11 | 679 | 116.5 | 7.90E−32 |
| 1517 | CGPG967 | BTB | 38 | 135 | 7.2 | 0.00091 |
| 1517 | CGPG967 | NPH3 | 218 | 460 | 370.2 | 3.20E−108 |
| 1518 | CGPG988 | Cystatin | 36 | 124 | 86.1 | 1.10E−22 |

TABLE 19

| Pfam domain name | accession number | gathering cutoff | domain description |
|---|---|---|---|
| 14-3-3 | PF00244.10 | 25 | 14-3-3 protein |
| 2-oxoacid_dh | PF00198.13 | −112 | 2-oxoacid dehydrogenases acyltransferase (catalytic domain) |
| 2OG-FeII_Oxy | PF03171.10 | 11.5 | 2OG-Fe(II) oxygenase superfamily |
| 60KD_IMP | PF02096.11 | −95 | 60 Kd inner membrane protein |
| AAA | PF00004.19 | 12.3 | ATPase family associated with various cellular activities (AAA) |
| AAA_5 | PF07728.4 | 4 | ATPase family associated with various cellular activities (AAA) |
| AA_permease | PF00324.11 | −120.8 | Amino acid permease |
| ABC1 | PF03109.7 | −27.6 | ABC1 family |
| ABC2_membrane | PF01061.14 | −17.9 | ABC-2 type transporter |
| ABC_tran | PF00005.17 | 9.5 | ABC transporter |
| ACT | PF01842.15 | 0 | ACT domain |
| ADH_N | PF08240.2 | −14.5 | Alcohol dehydrogenase GroES-like domain |
| ADH_zinc_N | PF00107.16 | 23.8 | Zinc-binding dehydrogenase |
| AHSA1 | PF08327.1 | 16.3 | Activator of Hsp90 ATPase homolog 1-like protein |

TABLE 19-continued

| Pfam domain name | accession number | gathering cutoff | domain description |
|---|---|---|---|
| AMP-binding | PF00501.18 | 0 | AMP-binding enzyme |
| AOX | PF01786.8 | 25 | Alternative oxidase |
| AP2 | PF00847.10 | 0 | AP2 domain |
| ARM_1 | PF04683.4 | 25 | Adhesion regulating molecule conserved region |
| ATP_synt_H | PF05493.3 | 25 | ATP synthase subunit H |
| AWPM-19 | PF05512.2 | 25 | AWPM-19-like family |
| Aa_trans | PF01490.8 | −128.4 | Transmembrane amino acid transporter protein |
| Abhydrolase_1 | PF00561.10 | 10.3 | alpha/beta hydrolase fold |
| Abhydrolase_3 | PF07859.3 | 25.8 | alpha/beta hydrolase fold |
| Actin | PF00022.9 | −144 | Actin |
| Acyltransferase | PF01553.11 | −0.4 | Acyltransferase |
| Aha1_N | PF09229.1 | −19.7 | Activator of Hsp90 ATPase, N-terminal |
| AlaDh_PNT_C | PF01262.12 | −43.4 | Alanine dehydrogenase/PNT, C-terminal domain |
| AlaDh_PNT_N | PF05222.5 | 25 | Alanine dehydrogenase/PNT, N-terminal domain |
| Aldedh | PF00171.12 | −209.3 | Aldehyde dehydrogenase family |
| Aldose_epim | PF01263.10 | −70.5 | Aldose 1-epimerase |
| Alpha-amylase | PF00128.14 | −92.6 | Alpha amylase, catalytic domain |
| Amidohydro_2 | PF04909.4 | −1.7 | Amidohydrolase |
| Amino_oxidase | PF01593.14 | −11.4 | Flavin containing amine oxidoreductase |
| Aminotran_1_2 | PF00155.11 | −57.5 | Aminotransferase class I and II |
| Aminotran_3 | PF00202.11 | −206.1 | Aminotransferase class-III |
| Aminotran_4 | PF01063.9 | −50 | Aminotransferase class IV |
| Aminotran_5 | PF00266.9 | −164.4 | Aminotransferase class-V |
| Ank | PF00023.20 | 0 | Ankyrin repeat |
| Arf | PF00025.11 | 40 | ADP-ribosylation factor family |
| ArfGap | PF01412.9 | −17 | Putative GTPase activating protein for Arf |
| Arm | PF00514.13 | 17 | Armadillo/beta-catenin-like repeat |
| Asn_synthase | PF00733.11 | −52.8 | Asparagine synthase |
| AstE_AspA | PF04952.5 | −36.8 | Succinylglutamate desuccinylase/Aspartoacylase family |
| B3_4 | PF03483.7 | 10 | B3/4 domain |
| B5 | PF03484.5 | 25 | tRNA synthetase B5 domain |
| B56 | PF01603.10 | −210 | Protein phosphatase 2A regulatory B subunit (B56 family) |
| BCNT | PF07572.3 | 25 | Bucentaur or craniofacial development |
| BNR | PF02012.10 | 0.7 | BNR/Asp-box repeat |
| BRCT | PF00533.16 | 27.8 | BRCA1 C Terminus (BRCT) domain |
| BTB | PF00651.21 | 6.2 | BTB/POZ domain |
| Band_7 | PF01145.15 | −5 | SPFH domain/Band 7 family |
| Barwin | PF00967.8 | 25 | Barwin family |
| Bet_v_I | PF00407.9 | −33 | Pathogenesis-related protein Bet v I family |
| Biotin_lipoyl | PF00364.12 | −2.3 | Biotin-requiring enzyme |
| Brix | PF04427.8 | 11.4 | Brix domain |
| Bystin | PF05291.2 | 25 | Bystin |
| C2 | PF00168.20 | 3.7 | C2 domain |
| CAF1 | PF04857.10 | −100.5 | CAF1 family ribonuclease |
| CBS | PF00571.18 | 17.5 | CBS domain pair |
| CCT | PF06203.4 | 25 | CCT motif |
| CN_hydrolase | PF00795.12 | −13.9 | Carbon-nitrogen hydrolase |
| CPDase | PF07823.2 | −14.5 | Cyclic phosphodiesterase-like protein |
| CPSase_L_D2 | PF02786.7 | −48.9 | Carbamoyl-phosphate synthase L chain, ATP binding domain |
| CPSase_L_D3 | PF02787.9 | −56 | Carbamoyl-phosphate synthetase large chain, oligomerisation domain |
| CPSase_L_chain | PF00289.12 | 14 | Carbamoyl-phosphate synthase L chain, N-terminal domain |
| CRAL_TRIO | PF00650.10 | −26 | CRAL/TRIO domain |
| CRAL_TRIO_N | PF03765.5 | 16 | CRAL/TRIO, N-terminus |
| CS | PF04969.6 | 8.6 | CS domain |
| CTP_transf_1 | PF01148.10 | −38.5 | Cytidylyltransferase family |
| Carb_kinase | PF01256.8 | −66.3 | Carbohydrate kinase |
| Chitin_bind_1 | PF00187.9 | 25.1 | Chitin recognition protein |
| Citrate_synt | PF00285.11 | −101.5 | Citrate synthase |
| Complex1_30 kDa | PF00329.9 | −3 | Respiratory-chain NADH dehydrogenase, 30 Kd subunit |
| Complex1_49 kDa | PF00346.9 | −108 | Respiratory-chain NADH dehydrogenase, 49 Kd subunit |
| Copine | PF07002.6 | −36.5 | Copine |
| CorA | PF01544.9 | −61.3 | CorA-like Mg2+ transporter protein |
| Cornichon | PF03311.4 | 25 | Cornichon protein |
| Cpn60_TCP1 | PF00118.14 | −223.4 | TCP-1/cpn60 chaperonin family |
| Cullin | PF00888.12 | −33.3 | Cullin family |
| Cyclin | PF08613.1 | −34.2 | Cyclin |
| Cyclin_C | PF02984.9 | −13 | Cyclin, C-terminal domain |
| Cyclin_N | PF00134.13 | −14.7 | Cyclin, N-terminal domain |
| Cys_Met_Meta_PP | PF01053.10 | −278.4 | Cys/Met metabolism PLP-dependent enzyme |
| Cystatin | PF00031.11 | 17.5 | Cystatin domain |
| Cyt-b5 | PF00173.18 | 4 | Cytochrome b5-like Heme/Steroid binding domain |
| Cytochrom_C | PF00034.11 | 11.7 | Cytochrome c |
| DAGK_cat | PF00781.14 | −5.7 | Diacylglycerol kinase catalytic domain (presumed) |
| DAO | PF01266.14 | −35 | FAD dependent oxidoreductase |
| DEAD | PF00270.19 | 7.2 | DEAD/DEAH box helicase |
| DHDPS | PF00701.12 | −90 | Dihydrodipicolinate synthetase family |

TABLE 19-continued

| Pfam domain name | accession number | gathering cutoff | domain description |
|---|---|---|---|
| DHquinase_I | PF01487.6 | 25 | Type I 3-dehydroquinase |
| DJ-1_PfpI | PF01965.14 | −7 | DJ-1/PfpI family |
| DREPP | PF05558.3 | 25 | DREPP plasma membrane polypeptide |
| DSHCT | PF08148.2 | −86.9 | DSHCT (NUC185) domain |
| DUF1000 | PF06201.4 | −20.8 | Domain of Unknown Function (DUF1000) |
| DUF1001 | PF06206.2 | −63.3 | Protein of unknown function (DUF1001) |
| DUF1005 | PF06219.3 | 25 | Protein of unknown function (DUF1005) |
| DUF1350 | PF07082.2 | −145.7 | Protein of unknown function (DUF1350) |
| DUF1635 | PF07795.2 | −27.2 | Protein of unknown function (DUF1635) |
| DUF1639 | PF07797.4 | 25 | Protein of unknown function (DUF1639) |
| DUF1644 | PF07800.3 | 25 | Protein of unknown function (DUF1644) |
| DUF1645 | PF07816.2 | −35.3 | Protein of unknown function (DUF1645) |
| DUF1677 | PF07911.4 | 25 | Protein of unknown function (DUF1677) |
| DUF1749 | PF08538.1 | −181.1 | Protein of unknown function (DUF1749) |
| DUF1984 | PF09328.1 | 12.8 | Domain of unknown function (DUF1984) |
| DUF21 | PF01595.10 | −28.2 | Domain of unknown function DUF21 |
| DUF212 | PF02681.5 | −30 | Divergent PAP2 family |
| DUF23 | PF01697.17 | −18.5 | Domain of unknown function |
| DUF231 | PF03005.6 | −58 | *Arabidopsis* proteins of unknown function |
| DUF239 | PF03080.5 | 25 | *Arabidopsis* proteins of unknown function |
| DUF246 | PF03138.5 | −15 | Plant protein family |
| DUF26 | PF01657.8 | 0 | Domain of unknown function DUF26 |
| DUF260 | PF03195.5 | 0.8 | Protein of unknown function DUF260 |
| DUF300 | PF03619.7 | 25 | Domain of unknown function |
| DUF313 | PF03754.4 | 25 | Domain of unknown function (DUF313) |
| DUF383 | PF04063.4 | 25 | Domain of unknown function (DUF383) |
| DUF384 | PF04064.4 | 25 | Domain of unknown function (DUF384) |
| DUF393 | PF04134.3 | 25 | Protein of unknown function, DUF393 |
| DUF506 | PF04720.3 | 25 | Protein of unknown function (DUF506) |
| DUF525 | PF04379.5 | 25 | Protein of unknown function (DUF525) |
| DUF538 | PF04398.3 | 25 | Protein of unknown function, DUF538 |
| DUF581 | PF04570.5 | −3.1 | Protein of unknown function (DUF581) |
| DUF59 | PF01883.9 | −7.9 | Domain of unknown function DUF59 |
| DUF6 | PF00892.11 | 20.8 | Integral membrane protein DUF6 |
| DUF617 | PF04759.4 | 25 | Protein of unknown function, DUF617 |
| DUF623 | PF04844.4 | 25 | Protein of unknown function, DUF623 |
| DUF640 | PF04852.3 | 2.4 | Protein of unknown function (DUF640) |
| DUF676 | PF05057.5 | −60.7 | Putative serine esterase (DUF676) |
| DUF740 | PF05340.3 | 25 | Protein of unknown function (DUF740) |
| DUF778 | PF05608.2 | 25 | Protein of unknown function (DUF778) |
| DUF783 | PF05615.3 | 25 | Protein of unknown function (DUF783) |
| DUF788 | PF05620.2 | 25 | Protein of unknown function (DUF788) |
| DUF791 | PF05631.4 | −136.8 | Protein of unknown function (DUF791) |
| DUF793 | PF05633.2 | 25 | Protein of unknown function (DUF793) |
| DUF827 | PF05701.2 | 25 | Plant protein of unknown function (DUF827) |
| DUF833 | PF05742.2 | −63.1 | Protein of unknown function (DUF833) |
| DUF860 | PF05898.4 | 25 | Plant specific of unknown function (DUF860) |
| DUF862 | PF05903.5 | −21.4 | PPPDE putative peptidase domain |
| DUF914 | PF06027.3 | −193 | Eukaryotic protein of unknown function (DUF914) |
| DUF926 | PF06047.2 | 25 | Domain of Unknown Function (DUF926) |
| DZC | PF08381.1 | 15.3 | Disease resistance/zinc finger/chromosome condensation-like region |
| Dehydrin | PF00257.10 | −4.4 | Dehydrin |
| Di19 | PF05605.3 | 25 | Drought induced 19 protein (Di19) |
| Diphthamide_syn | PF01866.8 | 25 | Putative diphthamide synthesis protein |
| Dirigent | PF03018.5 | 25 | Dirigent-like protein |
| DnaJ | PF00226.21 | −8 | DnaJ domain |
| DnaJ_C | PF01556.9 | −24 | DnaJ C terminal region |
| DnaJ_CXXCXGXG | PF00684.9 | 1 | DnaJ central domain (4 repeats) |
| E1_dh | PF00676.10 | −90 | Dehydrogenase E1 component |
| E3_binding | PF02817.7 | 10 | e3 binding domain |
| EFG_C | PF00679.14 | 6 | Elongation factor G C-terminus |
| ELFV_dehydrog | PF00208.11 | −27 | Glutamate/Leucine/Phenylalanine/Valine dehydrogenase |
| ELFV_dehydrog_N | PF02812.8 | 31.8 | Glu/Leu/Phe/Val dehydrogenase, dimerisation domain |
| ETC_C1_NDUFA4 | PF04800.3 | 25 | ETC complex I subunit conserved region |
| Enolase_C | PF00113.12 | −71.2 | Enolase, C-terminal TIM barrel domain |
| Enolase_N | PF03952.6 | 11.3 | Enolase, N-terminal domain |
| Exo_endo_phos | PF03372.13 | 11 | Endonuclease/Exonuclease/phosphatase family |
| F-box | PF00646.23 | 13.9 | F-box domain |
| FAD_binding_2 | PF00890.14 | −124.8 | FAD binding domain |
| FAD_binding_4 | PF01565.13 | −8.1 | FAD binding domain |
| FAD_binding_8 | PF08022.2 | −10.4 | FAD-binding domain |
| FA_desaturase | PF00487.14 | −46 | Fatty acid desaturase |
| FBA_1 | PF07734.3 | −39.4 | F-box associated |
| FBA_3 | PF08268.2 | −17.1 | F-box associated |
| FBD | PF08387.1 | 25 | FBD |
| FBPase | PF00316.10 | −170.3 | Fructose-1-6-bisphosphatase |

TABLE 19-continued

| Pfam domain name | accession number | gathering cutoff | domain description |
|---|---|---|---|
| FHA | PF00498.16 | 25 | FHA domain |
| FKBP_C | PF00254.18 | −7.6 | FKBP-type peptidyl-prolyl cis-trans isomerase |
| FTHFS | PF01268.9 | −167 | Formate--tetrahydrofolate ligase |
| Fer2_BFD | PF04324.5 | 25 | BFD-like [2Fe—2S] binding domain |
| Fer4 | PF00037.17 | 9.3 | 4Fe—4S binding domain |
| Ferric_reduct | PF01794.9 | −7 | Ferric reductase like transmembrane component |
| Fibrillarin | PF01269.8 | −86.6 | Fibrillarin |
| GAF | PF01590.16 | 23 | GAF domain |
| GATase | PF00117.18 | −38.1 | Glutamine amidotransferase class-I |
| GATase_2 | PF00310.11 | −95.1 | Glutamine amidotransferases class-II |
| GDE_C | PF06202.4 | −218.8 | Amylo-alpha-1,6-glucosidase |
| GHMP_kinases_C | PF08544.3 | 20.8 | GHMP kinases C terminal |
| GHMP_kinases_N | PF00288.16 | 17.1 | GHMP kinases N terminal domain |
| GIDA | PF01134.12 | −226.7 | Glucose inhibited division protein A |
| GILT | PF03227.6 | 25 | Gamma interferon inducible lysosomal thiol reductase (GILT) |
| GMP_synt_C | PF00958.12 | 25 | GMP synthase C terminal domain |
| GRAM | PF02893.10 | 24.4 | GRAM domain |
| GRP | PF07172.2 | 16.8 | Glycine rich protein family |
| GTP_EFTU | PF00009.17 | 8 | Elongation factor Tu GTP binding domain |
| GTP_EFTU_D2 | PF03144.15 | 25 | Elongation factor Tu domain 2 |
| Gal-bind_lectin | PF00337.12 | −30 | Galactoside-binding lectin |
| Galactosyl_T | PF01762.12 | −46 | Galactosyltransferase |
| Gar1 | PF04410.5 | 25 | Gar1 protein RNA binding region |
| Gln-synt_C | PF00120.14 | −124 | Glutamine synthetase, catalytic domain |
| Gln-synt_N | PF03951.9 | 9 | Glutamine synthetase, beta-Grasp domain |
| Globin | PF00042.12 | −8.8 | Globin |
| Glucokinase | PF02685.6 | −157.6 | Glucokinase |
| Glutaminase | PF04960.6 | −143.6 | Glutaminase |
| Glutaredoxin | PF00462.14 | 17.2 | Glutaredoxin |
| Glyco_hydro_1 | PF00232.9 | −301.8 | Glycosyl hydrolase family 1 |
| Glyco_hydro_17 | PF00332.9 | −152.3 | Glycosyl hydrolases family 17 |
| Glyco_tran_28_C | PF04101.6 | −10.4 | Glycosyltransferase family 28 C-terminal domain |
| Glyco_transf_8 | PF01501.10 | −43.2 | Glycosyl transferase family 8 |
| Glycolytic | PF00274.9 | −174.5 | Fructose-bisphosphate aldolase class-I |
| Gp_dh_C | PF02800.10 | −64.1 | Glyceraldehyde 3-phosphate dehydrogenase, C-terminal domain |
| Gp_dh_N | PF00044.14 | −74.2 | Glyceraldehyde 3-phosphate dehydrogenase, NAD binding domain |
| HATPase_c | PF02518.16 | 22.4 | Histidine kinase-, DNA gyrase B-, and HSP90-like ATPase |
| HD | PF01966.12 | 15.3 | HD domain |
| HEAT | PF02985.12 | 11.5 | HEAT repeat |
| HIT | PF01230.13 | −4.5 | HIT domain |
| HLH | PF00010.16 | 8.3 | Helix-loop-helix DNA-binding domain |
| HMA | PF00403.16 | 19.5 | Heavy-metal-associated domain |
| HMG-CoA_red | PF00368.9 | −242 | Hydroxymethylglutaryl-coenzyme A reductase |
| H_PPase | PF03030.7 | −377 | Inorganic H+ pyrophosphatase |
| Helicase_C | PF00271.21 | 2.1 | Helicase conserved C-terminal domain |
| Hexapep | PF00132.14 | 0.3 | Bacterial transferase hexapeptide (three repeats) |
| Hin1 | PF07320.4 | 25 | Harpin-induced protein 1 (Hin1) |
| HisKA | PF00512.15 | 10.3 | His Kinase A (phosphoacceptor) domain |
| Histone | PF00125.14 | 17.4 | Core histone H2A/H2B/H3/H4 |
| Hydrolase | PF00702.16 | 13.6 | haloacid dehalogenase-like hydrolase |
| IGPD | PF00475.9 | 25 | Imidazoleglycerol-phosphate dehydratase |
| IPK | PF03770.7 | 25 | Inositol polyphosphate kinase |
| IQ | PF00612.17 | 11.9 | IQ calmodulin-binding motif |
| Invertase_neut | PF04853.3 | −233.6 | Plant neutral invertase |
| Iso_dh | PF00180.10 | −97 | Isocitrate/isopropylmalate dehydrogenase |
| Isoamylase_N | PF02922.8 | −6.5 | Isoamylase N-terminal domain |
| Isy1 | PF06246.3 | 25 | Isy1-like splicing family |
| K-box | PF01486.8 | 0 | K-box region |
| KR | PF08659.1 | −74.3 | KR domain |
| KTI12 | PF08433.1 | −109.1 | Chromatin associated protein KTI12 |
| Kelch_1 | PF01344.15 | 7.8 | Kelch motif |
| Kelch_2 | PF07646.5 | 14 | Kelch motif |
| LRRNT_2 | PF08263.3 | 18.6 | Leucine rich repeat N-terminal domain |
| LRR_1 | PF00560.23 | 7.7 | Leucine Rich Repeat |
| LRR_2 | PF07723.3 | 6 | Leucine Rich Repeat |
| LSM | PF01423.12 | 13.7 | LSM domain |
| Lectin_legB | PF00139.10 | −110.1 | Legume lectin domain |
| Lipoxygenase | PF00305.9 | −211 | Lipoxygenase |
| Lung_7-TM_R | PF06814.3 | 25 | Lung seven transmembrane receptor |
| LysM | PF01476.10 | 20 | LysM domain |
| MATH | PF00917.16 | 0.5 | MATH domain |
| MBD | PF01429.10 | 12.9 | Methyl-CpG binding domain |
| MCM | PF00493.13 | 25 | MCM2/3/5 family |
| MFS_1 | PF07690.6 | 23.5 | Major Facilitator Superfamily |
| MGDG_synth | PF06925.2 | 25 | Monogalactosyldiacylglycerol (MGDG) synthase |

TABLE 19-continued

| Pfam domain name | accession number | gathering cutoff | domain description |
|---|---|---|---|
| MGS | PF02142.12 | 3 | MGS-like domain |
| MIP | PF00230.10 | −62 | Major intrinsic protein |
| MMR_HSR1 | PF01926.13 | 31.2 | GTPase of unknown function |
| MSF1 | PF04707.4 | 25 | MSF1-like conserved region |
| MSP | PF01716.9 | −71 | Manganese-stabilising protein/photosystem II polypeptide |
| Maf | PF02545.5 | −42 | Maf-like protein |
| Mago-bind | PF09282.1 | 25 | Mago binding |
| Malic_M | PF03949.5 | −143.9 | Malic enzyme, NAD binding domain |
| Metalloenzyme | PF01676.8 | −14.4 | Metalloenzyme superfamily |
| Metallophos | PF00149.18 | 22 | Calcineurin-like phosphoesterase |
| Metallothio_PEC | PF02068.6 | 25 | Plant PEC family metallothionein |
| Methyltransf_11 | PF08241.2 | 20.9 | Methyltransferase domain |
| Methyltransf_12 | PF08242.2 | 23 | Methyltransferase domain |
| Miro | PF08477.3 | 10.8 | Miro-like protein |
| Mito_carr | PF00153.17 | 0 | Mitochondrial carrier protein |
| Mo25 | PF08569.1 | −73.5 | Mo25-like |
| Molybdop_Fe4S4 | PF04879.6 | 13.6 | Molybdopterin oxidoreductase Fe4S4 domain |
| Molybdopterin | PF00384.12 | −50 | Molybdopterin oxidoreductase |
| Molydop_binding | PF01568.11 | 1.1 | Molydopterin dinucleotide binding domain |
| Mov34 | PF01398.11 | −4 | Mov34/MPN/PAD-1 family |
| MtN3_slv | PF03083.6 | 9.7 | MtN3/saliva family |
| Myb_DNA-binding | PF00249.21 | 14 | Myb-like DNA-binding domain |
| NADPH_Ox | PF08414.1 | 25 | Respiratory burst NADPH oxidase |
| NAD_binding_6 | PF08030.2 | −23.6 | Ferric reductase NAD binding domain |
| NAD_synthase | PF02540.7 | −93.3 | NAD synthase |
| NAF | PF03822.5 | 4.5 | NAF domain |
| NDK | PF00334.9 | −59.9 | Nucleoside diphosphate kinase |
| NDUF_B7 | PF05676.3 | −25.7 | NADH-ubiquinone oxidoreductase B18 subunit (NDUFB7) |
| NIF | PF03031.8 | −77.9 | NLI interacting factor-like phosphatase |
| NIR_SIR | PF01077.12 | −19.6 | Nitrite and sulphite reductase 4Fe—4S domain |
| NIR_SIR_ferr | PF03460.7 | 2.4 | Nitrite/Sulfite reductase ferredoxin-like half domain |
| NLE | PF08154.2 | 14 | NLE (NUC135) domain |
| NOI | PF05627.2 | 0.3 | Nitrate-induced NOI protein |
| NOT2_3_5 | PF04153.8 | 25 | NOT2/NOT3/NOT5 family |
| NPH3 | PF03000.5 | 25 | NPH3 family |
| NTP_transferase | PF00483.13 | −90.5 | Nucleotidyl transferase |
| NUDIX | PF00293.18 | 0.2 | NUDIX domain |
| NicO | PF03824.6 | −17 | High-affinity nickel-transport protein |
| Nol1_Nop2_Fmu | PF01189.6 | −68.2 | NOL1/NOP2/sun family |
| Not3 | PF04065.5 | 25 | Not1 N-terminal domain, CCR4-Not complex component |
| Nramp | PF01566.9 | −217 | Natural resistance-associated macrophage protein |
| Nuc_sug_transp | PF04142.6 | −158.6 | Nucleotide-sugar transporter |
| OPT | PF03169.6 | −238.6 | OPT oligopeptide transporter protein |
| OUT | PF02338.9 | 10 | OTU-like cysteine protease |
| Orn_Arg_deC_N | PF02784.7 | −76 | Pyridoxal-dependent decarboxylase, pyridoxal binding domain |
| Orn_DAP_Arg_deC | PF00278.12 | 6.7 | Pyridoxal-dependent decarboxylase, C-terminal sheet domain |
| OstA | PF03968.5 | −12.1 | OstA-like protein |
| P21-Arc | PF04062.5 | −74.5 | P21-ARC (ARP2/3 complex 21 kDa subunit) |
| PADR1 | PF08063.2 | 25 | PADR1 (NUC008) domain |
| PAP2 | PF01569.12 | 8.3 | PAP2 superfamily |
| PARP | PF00644.10 | −55.5 | Poly(ADP-ribose) polymerase catalytic domain |
| PARP_reg | PF02877.5 | 52.8 | Poly(ADP-ribose) polymerase, regulatory domain |
| PAS_2 | PF08446.1 | −2.1 | PAS fold |
| PB1 | PF00564.15 | 12.3 | PB1 domain |
| PBD | PF00786.18 | 12.2 | P21-Rho-binding domain |
| PBP | PF01161.10 | −20.6 | Phosphatidylethanolamine-binding protein |
| PCI | PF01399.17 | 25 | PCI domain |
| PC_rep | PF01851.12 | 0 | Proteasome/cyclosome repeat |
| PDR_assoc | PF08370.2 | 25 | Plant PDR ABC transporter associated |
| PEARLI-4 | PF05278.3 | 25 | *Arabidopsis* phospholipase-like protein (PEARLI 4) |
| PEP-utilizers | PF00391.13 | 0.6 | PEP-utilising enzyme, mobile domain |
| PEP-utilizers_C | PF02896.8 | −173 | PEP-utilising enzyme, TIM barrel domain |
| PFK | PF00365.10 | −132 | Phosphofructokinase |
| PGAM | PF00300.12 | −3 | Phosphoglycerate mutase family |
| PGI | PF00342.9 | −168.9 | Phosphoglucose isomerase |
| PGK | PF00162.9 | −39.9 | Phosphoglycerate kinase |
| PGM_PMM_I | PF02878.6 | −37.5 | Phosphoglucomutase/phosphomannomutase, alpha/beta/alpha domain I |
| PGM_PMM_II | PF02879.6 | −20 | Phosphoglucomutase/phosphomannomutase, alpha/beta/alpha domain II |
| PGM_PMM_III | PF02880.6 | −7.1 | Phosphoglucomutase/phosphomannomutase, alpha/beta/alpha domain III |
| PGM_PMM_IV | PF00408.10 | 7.4 | Phosphoglucomutase/phosphomannomutase, C-terminal domain |
| PI-PLC-X | PF00388.9 | 18.8 | Phosphatidylinositol-specific phospholipase C, X domain |
| PI-PLC-Y | PF00387.9 | −11 | Phosphatidylinositol-specific phospholipase C, Y domain |
| PI3_PI4_kinase | PF00454.17 | 14.8 | Phosphatidylinositol 3- and 4-kinase |
| PLAT | PF01477.13 | 36.3 | PLAT/LH2 domain |

TABLE 19-continued

| Pfam domain name | accession number | gathering cutoff | domain description |
|---|---|---|---|
| PP2C | PF00481.12 | −44 | Protein phosphatase 2C |
| PPAK | PF02818.5 | 0 | PPAK motif |
| PPDK_N | PF01326.9 | −150.2 | Pyruvate phosphate dikinase, PEP/pyruvate binding domain |
| PPR | PF01535.11 | 0 | PPR repeat |
| PRA-CH | PF01502.9 | 25 | Phosphoribosyl-AMP cyclohydrolase |
| PRA-PH | PF01503.8 | −18.3 | Phosphoribosyl-ATP pyrophosphohydrolase |
| PSI_PsaH | PF03244.4 | 25 | Photosystem I reaction centre subunit VI |
| PTR2 | PF00854.12 | −50 | POT family |
| PWP2 | PF04047.4 | 25 | Periodic tryptophan protein 2 WD repeat associated presumed domain |
| Peptidase_C26 | PF07722.3 | 25 | Peptidase C26 |
| Peptidase_C54 | PF03416.9 | −153.2 | Peptidase family C54 |
| Peptidase_M22 | PF00814.15 | −53 | Glycoprotease family |
| PetM | PF08041.2 | 25 | PetM family of cytochrome b6f complex subunit 7 |
| PfkB | PF00294.14 | −67.8 | pfkB family carbohydrate kinase |
| Phi_1 | PF04674.3 | 25 | Phosphate-induced protein 1 conserved region |
| Phosphoesterase | PF04185.5 | −71.5 | Phosphoesterase family |
| Phytochelatin | PF05023.5 | 25 | Phytochelatin synthase |
| Phytochrome | PF00360.10 | 13 | Phytochrome region |
| Pkinase | PF00069.15 | −70.3 | Protein kinase domain |
| Pkinase_Tyr | PF07714.7 | 65 | Protein tyrosine kinase |
| Polyketide_cyc | PF03364.10 | 20.6 | Polyketide cyclase/dehydrase and lipid transport |
| Pre-SET | PF05033.6 | 3.9 | Pre-SET motif |
| Prefoldin | PF02996.8 | 9.3 | Prefoldin subunit |
| Pribosyltran | PF00156.17 | 2 | Phosphoribosyl transferase domain |
| Pro_CA | PF00484.9 | −45 | Carbonic anhydrase |
| Pro_dh | PF01619.8 | −120.5 | Proline dehydrogenase |
| Pro_isomerase | PF00160.11 | −37 | Cyclophilin type peptidyl-prolyl cis-trans isomerase/CLD |
| PseudoU_synth_1 | PF01416.10 | 11 | tRNA pseudouridine synthase |
| Pyr_redox | PF00070.17 | 5 | Pyridine nucleotide-disulphide oxidoreductase |
| Pyr_redox_2 | PF07992.4 | −20 | Pyridine nucleotide-disulphide oxidoreductase |
| Pyr_redox_dim | PF02852.12 | −13 | Pyridine nucleotide-disulphide oxidoreductase, dimerisation domain |
| Pyridoxal_deC | PF00282.9 | −158.6 | Pyridoxal-dependent decarboxylase conserved domain |
| RNA_polI_A14 | PF08203.2 | 25 | Yeast RNA polymerase I subunit RPA14 |
| RNA_pol_A_bac | PF01000.16 | 10 | RNA polymerase Rpb3/RpoA insert domain |
| RNA_pol_I_A49 | PF06870.3 | 25 | A49-like RNA polymerase I associated factor |
| RNA_pol_L | PF01193.14 | 16.9 | RNA polymerase Rpb3/Rpb11 dimerisation domain |
| RRM_1 | PF00076.12 | 17.7 | RNA recognition motif. (a.k.a. RRM, RBD, or RNP domain) |
| RWD | PF05773.12 | 18.4 | RWD domain |
| Radical_SAM | PF04055.11 | 8.5 | Radical SAM superfamily |
| Ras | PF00071.12 | −69.9 | Ras family |
| RelA_SpoT | PF04607.7 | −6.7 | Region found in RelA/SpoT proteins |
| Response_reg | PF00072.14 | 4 | Response regulator receiver domain |
| Reticulon | PF02453.8 | −40 | Reticulon |
| Rho_GDI | PF02115.7 | −55 | RHO protein GDP dissociation inhibitor |
| Rib_5-P_isom_A | PF06026.5 | −84.5 | Ribose 5-phosphate isomerase A (phosphoriboisomerase A) |
| Ribonuc_L-PSP | PF01042.11 | −25 | Endoribonuclease L-PSP |
| Ribosomal_L19 | PF01245.10 | −31 | Ribosomal protein L19 |
| Ribosomal_L37 | PF08561.1 | 25 | Mitochondrial ribosomal protein L37 |
| Ribosomal_S8 | PF00410.9 | −27 | Ribosomal protein S8 |
| SAC3_GANP | PF03399.6 | −15.2 | SAC3/GANP/Nin1/mts/eIF-3 p25 family |
| SET | PF00856.18 | 23.5 | SET domain |
| SH3_1 | PF00018.18 | −8 | SH3 domain |
| SH3_2 | PF07653.7 | 0 | Variant SH3 domain |
| SIR2 | PF02146.8 | −95 | Sir2 family |
| SIS | PF01380.12 | 0 | SIS domain |
| SKI | PF01202.12 | −9.2 | Shikimate kinase |
| SNARE | PF05739.9 | 23.8 | SNARE domain |
| SNARE_assoc | PF09335.1 | −12.1 | SNARE associated Golgi protein |
| SOR_SNZ | PF01680.7 | 25 | SOR/SNZ family |
| SPOC | PF07744.3 | 12.3 | SPOC domain |
| SPT2 | PF08243.2 | 25 | SPT2 chromatin protein |
| SRF-TF | PF00319.9 | 11 | SRF-type transcription factor (DNA-binding and dimerisation domain) |
| Saccharop_dh | PF03435.8 | −77.9 | Saccharopine dehydrogenase |
| Saccharop_dh_N | PF04455.3 | 25 | LOR/SDH bifunctional enzyme conserved region |
| SapB_1 | PF05184.5 | 3 | Saposin-like type B, region 1 |
| SapB_2 | PF03489.7 | 10.8 | Saposin-like type B, region 2 |
| ScpA_ScpB | PF02616.5 | −39 | ScpA/B protein |
| Sel1 | PF08238.2 | 6.2 | Sel1 repeat |
| Self-incomp_S1 | PF05938.2 | −12.7 | Plant self-incompatibility protein S1 |
| Senescence | PF06911.3 | −53.5 | Senescence-associated protein |
| Shikimate_DH | PF01488.10 | −4.4 | Shikimate/quinate 5-dehydrogenase |
| Shikimate_dh_N | PF08501.1 | −12.2 | Shikimate dehydrogenase substrate binding domain |
| Sina | PF03145.7 | −48.4 | Seven in absentia protein family |
| Skp1 | PF01466.9 | −2 | Skp1 family, dimerisation domain |

TABLE 19-continued

| Pfam domain name | accession number | gathering cutoff | domain description |
|---|---|---|---|
| Skp1_POZ | PF03931.5 | 14.9 | Skp1 family, tetramerisation domain |
| Snf7 | PF03357.11 | −22.9 | Snf7 |
| Spermine_synth | PF01564.7 | −93.8 | Spermine/spermidine synthase |
| SpoIIE | PF07228.3 | −13.7 | Stage II sporulation protein E (SpoIIE) |
| Sterol_desat | PF01598.8 | −13 | Sterol desaturase |
| Stig1 | PF04885.4 | 25 | Stigma-specific protein, Stig1 |
| Str_synth | PF03088.7 | 4.7 | Strictosidine synthase |
| Sugar_tr | PF00083.14 | −85 | Sugar (and other) transporter |
| Sulfotransfer_1 | PF00685.17 | −53.1 | Sulfotransferase domain |
| TB2_DP1_HVA22 | PF03134.9 | −25.1 | TB2/DP1, HVA22 family |
| TFIIF_alpha | PF05793.3 | 25 | Transcription initiation factor IIF, alpha subunit (TFIIF-alpha) |
| TFIIS | PF08711.1 | 3 | Transcription elongation factor S-II protein N terminal |
| TFIIS_C | PF01096.9 | 15 | Transcription factor S-II (TFIIS) |
| TFIIS_M | PF07500.4 | 7.4 | Transcription factor S-II (TFIIS), central domain |
| TIM | PF00121.9 | −97 | Triosephosphate isomerase |
| TLD | PF07534.6 | 25 | TLD |
| TMEM14 | PF03647.4 | −1 | Transmembrane proteins 14C |
| TOM20_plant | PF06552.5 | 25 | Plant specific mitochondrial import receptor subunit TOM20 |
| TPK_B1_binding | PF04265.5 | 25 | Thiamin pyrophosphokinase, vitamin B1 binding domain |
| TPK_catalytic | PF04263.7 | −23.8 | Thiamin pyrophosphokinase, catalytic domain |
| TPR_2 | PF07719.7 | 20.1 | Tetratricopeptide repeat |
| TPT | PF03151.7 | −15.3 | Triose-phosphate Transporter family |
| TP_methylase | PF00590.10 | −38 | Tetrapyrrole (Corrin/Porphyrin) Methylases |
| Tcp11 | PF05794.4 | 25 | T-complex protein 11 |
| Tetraspannin | PF00335.10 | −15.4 | Tetraspanin family |
| ThiC | PF01964.9 | 25 | ThiC family |
| ThiF | PF00899.11 | −38.4 | ThiF family |
| ThiG | PF05690.4 | −186.9 | Thiazole biosynthesis protein ThiG |
| Thioredoxin | PF00085.10 | −25.7 | Thioredoxin |
| Tim17 | PF02466.9 | 2.7 | Tim17/Tim22/Tim23 family |
| Transaldolase | PF00923.9 | −49 | Transaldolase |
| Transket_pyr | PF02779.14 | −49 | Transketolase, pyrimidine binding domain |
| Transketolase_C | PF02780.10 | −15.5 | Transketolase, C-terminal domain |
| Transketolase_N | PF00456.11 | −98 | Transketolase, thiamine diphosphate binding domain |
| Transthyretin | PF00576.11 | 25 | Transthyretin precursor (formerly prealbumin) |
| Trehalose_PPase | PF02358.7 | −49.4 | Trehalose-phosphatase |
| Tryp_alpha_amyl | PF00234.12 | −4 | Protease inhibitor/seed storage/LTP family |
| UAA | PF08449.2 | −146.2 | UAA transporter family |
| UBA | PF00627.21 | 20.7 | UBA/TS-N domain |
| UBX | PF00789.11 | 10 | UBX domain |
| UCH | PF00443.19 | −8.6 | Ubiquitin carboxyl-terminal hydrolase |
| UDPGT | PF00201.9 | −151 | UDP-glucoronosyl and UDP-glucosyl transferase |
| UFD1 | PF03152.5 | 25 | Ubiquitin fusion degradation protein UFD1 |
| UQ_con | PF00179.16 | −30 | Ubiquitin-conjugating enzyme |
| Uricase | PF01014.9 | −10.6 | Uricase |
| Usp | PF00582.16 | 21.6 | Universal stress protein family |
| Utp13 | PF08625.1 | −12.4 | Utp13 specific WD40 associated domain |
| V-SNARE | PF05008.5 | −16 | Vesicle transport v-SNARE protein |
| Voltage_CLC | PF00654.10 | −148 | Voltage gated chloride channel |
| WD40 | PF00400.22 | 21.5 | WD domain, G-beta repeat |
| WGR | PF05406.5 | 5.8 | WGR domain |
| WRKY | PF03106.6 | 25 | WRKY DNA-binding domain |
| XG_FTase | PF03254.4 | 25 | Xyloglucan fucosyltransferase |
| XPC-binding | PF09280.1 | 27.6 | XPC-binding domain |
| Xan_ur_permease | PF00860.11 | −151.2 | Permease family |
| YDG_SRA | PF02182.8 | 25 | YDG/SRA domain |
| Y_phosphatase2 | PF03162.4 | −47.6 | Tyrosine phosphatase family |
| YjeF_N | PF03853.5 | 25 | YjeF-related protein N-terminus |
| Zip | PF02535.12 | −25.6 | ZIP Zinc transporter |
| adh_short | PF00106.15 | −40.2 | short chain dehydrogenase |
| cobW | PF02492.9 | −10 | CobW/HypB/UreG, nucleotide-binding domain |
| eIF-1a | PF01176.9 | 20 | Translation initiation factor 1A/IF-1 |
| eIF2A | PF08662.1 | 0 | Eukaryotic translation initiation factor eIF2A |
| efhand | PF00036.22 | 21.7 | EF hand |
| efhand_like | PF09279.1 | 17.8 | Phosphoinositide-specific phospholipase C, efhand-like |
| iPGM_N | PF06415.4 | −263.4 | BPG-independent PGAM N-terminus (iPGM_N) |
| mTERF | PF02536.5 | −60 | mTERF |
| malic | PF00390.9 | 25 | Malic enzyme, N-terminal domain |
| p450 | PF00067.12 | −105 | Cytochrome P450 |
| polyprenyl_synt | PF00348.8 | −43 | Polyprenyl synthetase |
| tRNA-synt_1g | PF09334.1 | −272.5 | tRNA synthetases class I (M) |
| ubiquitin | PF00240.13 | 19.4 | Ubiquitin family |
| zf-C3HC4 | PF00097.15 | 16 | Zinc finger, C3HC4 type (RING finger) |
| zf-CCHC | PF00098.13 | 17.9 | Zinc knuckle |
| zf-CW | PF07496.5 | 25 | CW-type Zinc Finger |
| zf-LSD1 | PF06943.3 | 25 | LSD1 zinc finger |
| zf-MYND | PF01753.9 | 11 | MYND finger |

TABLE 19-continued

| Pfam domain name | accession number | gathering cutoff | domain description |
|---|---|---|---|
| zf-PARP | PF00645.8 | 25 | Poly(ADP-ribose) polymerase and DNA-Ligase Zn-finger region |
| zf-Tim10_DDP | PF02953.6 | −5 | Tim10/DDP family zinc finger |
| zf-UBR | PF02207.10 | 25 | Putative zinc finger in N-recognin (UBR box) |

Example 5

Plasmid Contruction for Transferring Recombinant DNA

This example illustrates the construction of plasmids for transferring recombinant DNA into the nucleus of a plant cell which can be regenerated into a transgenic crop plant of this invention. Primers for PCR amplification of protein coding nucleotides of recombinant DNA are designed at or near the start and stop codons of the coding sequence, in order to eliminate most of the 5' and 3' untranslated regions. DNA of interest, i.e. each DNA identified in Table 2 and the DNA for the identified homologous genes, are cloned and amplified by PCR prior to insertion into the insertion site the base vector.

A. Plant Expression Constructs for Corn Transformation

Elements of an exemplary common expression vector, pMON93039 are illustrated in Table 20. The exemplary base vector which is especially useful for corn transformation is illustrated in FIG. 1 and assembled using technology known in the art.

TABLE 20 pMON93039

| function | name | annotation | Coordinates of SEQ ID NO: 67779 |
|---|---|---|---|
| *Agrobacterium* T-DNA trabsfer | B-AGRtu.right border | Agro right border sequence, essential for transfer of T-DNA. | 11364-11720 |
| Gene of interest expression cassette | E-Os.Act1 | upstream promoter region of the rice actin 1 gene | 19-775 |
| | E-CaMV.35S.2xA1-B3 | duplicated35S A1-B3 domain without TATA box | 788-1120 |
| | P-Os.Act1 | promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | first intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | first exon of the rice actin 1 gene | 3671-3750 |
| | I-Os.Act1 | first intron and flanking UTR exon sequences from the rice actin 1 gene | 3751-4228 |
| | TS-At.ShkG-CTP2 | Transit peptide region of *Arabidopsis* EPSPS | 4238-4465 |
| | CR-AGRtu.aroA-CP4.nat | coding region for bacterial strain CP4 native arogA gene | 4466-5833 |
| | T-AGRtu.nos | A 3' non-translated region of the nopaline synthase gene of *Agrobacterium tumefaciens* Ti plasmid which functions to direct polyadenylation of the mRNA. | 5849-6101 |
| *Agrobacterium* T-DNA transfer | B-AGRtu.left border | Agro left border sequence, essential for transfer of T-DNA. | 6168-6609 |

TABLE 20-continued pMON93039

| function | name | annotation | Coordinates of SEQ ID NO: 67779 |
|---|---|---|---|
| Maintenance in E. coli | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the E. coli plasmid ColE1. | 9220-9808 |
| | P-Ec.aadA-SPC/STR | romoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of E. coli. | 11170-11227 |

B. Plant Expression Constructs for Soybean or Canola Transformation

Figure 2:
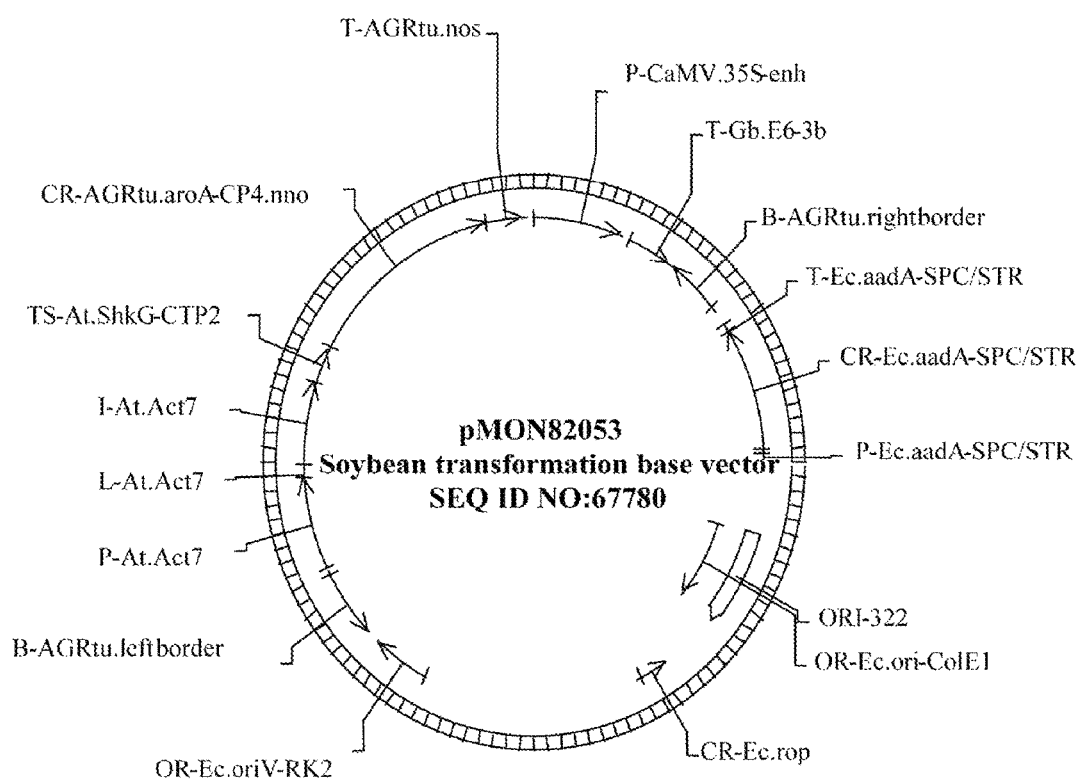

Plasmids for use in transformation of soybean are also prepared. Elements of an exemplary common expression vector plasmid pMON82053 are shown in Table 21 below. This exemplary soybean transformation base vector illustrated in FIG. 2 is assembled using the technology known in the art. DNA of interest, i.e. each DNA identified in Table 2 and the DNA for the identified homologous genes, is cloned and amplified by PCR prior to insertion into the insertion site the base vector at the insertion site between the enhanced 35S CaMV promoter and the termination sequence of cotton E6 gene.

TABLE 21 pMON82053

| function | name | annotation | Coordinates of SEQ ID NO: 67780 |
|---|---|---|---|
| Agrobacterium T-DNA transfer | B-AGRtu.left border | Agro left border sequence, essential for transfer of T-DNA. | 6144-6585 |
| Plant selectable marker expression cassette | P-At.Act7 | Promoter from the arabidopsis actin 7 gene | 6624-7861 |
| | L-At.Act7 | 5'UTR of Arabidopsis Act7 gene | |
| | I-At.Act7 | Intron from the Arabidopsis actin7 gene | |
| | TS-At.ShkG-CTP2 | Transit peptide region of Arabidopsis EPSPS | 7864-8091 |
| | CR-AGRtu.aroA-CP4.nno__At | Synthetic CP4 coding region with dicot preferred codon usage. | 8092-9459 |
| | T-AGRtu.nos | A 3' non-translated region of the nopaline synthase gene of Agrobacterium tumefaciens Ti plasmid which functions to direct polyadenylation of the mRNA. | 9466-9718 |
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton; | 688-1002 |
| Agrobaterium T-DNA transfer | B-AGRtu.right border | Agro right border sequence, essential for transfer of T-DNA. | 1033-1389 |

TABLE 21-continued pMON82053

| function | name | annotation | Coordinates of SEQ ID NO: 67780 |
|---|---|---|---|
| Maintenance in E. coli | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the E. coli plasmid ColE1. | 2945-3533 |
| | P-Ec.aadA-SPC/STR | romoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of E. coli. | 1526-1583 |

C. Plant Expression Constructs for Cotton Transformation

Figure 3:
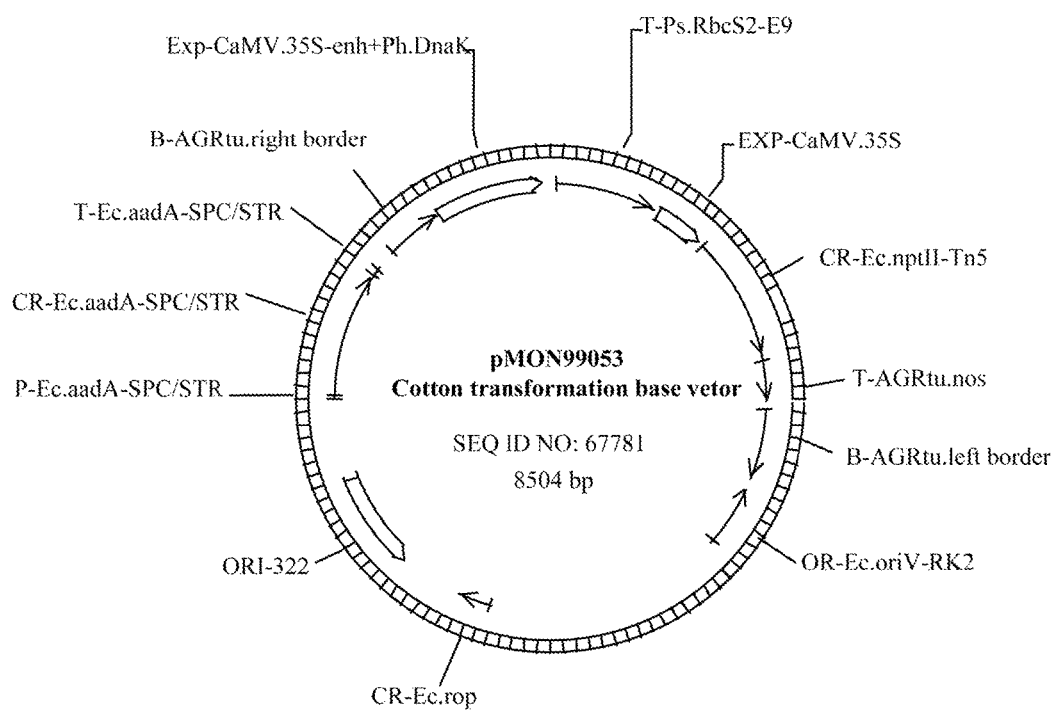

Plasmids for use in transformation of cotton are also prepared. Elements of an exemplary common expression vector plasmid pMON99053 are shown in Table 22 below and FIG. 3. Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 2 is amplified by PCR prior to insertion into the insertion site within the gene of interest expression cassette of one of the base.

TABLE 22 pMON99053

| function | name | annotation | Coordinates of SEQ ID NO: 67781 |
|---|---|---|---|
| Agrobacterium T-DNA transfer | B-AGRtu.right border | Agro right border sequence, essential for transfer of T-DNA. | 11364-11720 |
| Gene of interest expression cassette | Exp-CaMV.35S-enh + ph.DnaK | Enhanced version of the 35S RNA promoter from CaMV plus the petunia hsp70 5' untranslated region | 7794-8497 |
| | T-Ps.RbcS2-E9 | The 3' non-translated region of the pea RbcS2 gene which functions to direct polyadenylation of the mRNA. | 67-699 |
| Plant selectable marker expression cassette | Exp-CaMV.35S | Promoter and 5' untranslated region of the 35S RNA from CaMV | 730-1053 |
| | CR-Ec.nptII-Tn5 | Neomycin Phosphotransferase II gene that confers resistance to neomycin and kanamycin | 1087-1881 |
| | T-AGRtu.nos | A 3' non-translated region of the nopaline synthase gene of Agrobacterium tumefaciens Ti plasmid which functions to direct polyadenylation of the mRNA. | 1913-2165 |
| Agrobacterium T-DNA transfer | B-AGRtu.left border | Agro left border sequence, essential for transfer of T-DNA. | 2211-2652 |
| Maintenance in E. coli | OR-Ec.oriV-RK2 | The vegetative origin of replication from plasmid RK2. | 2739-3135 |
| | CR-Ec.rop | Coding region for repressor of primer from the ColE1 plasmid. Expression of this gene product interferes with primer binding at the origin of replication, keeping plasmid copy number low. | 4644-4835 |

TABLE 22-continued pMON99053

| function | name | annotation | Coordinates of SEQ ID NO: 67781 |
|---|---|---|---|
| | OR-Ec.ori-ColE1 | The minimal origin of replication from the *E. coli* plasmid ColE1. | 5263-5851 |
| | P-Ec.aadA-SPC/STR | romoter for Tn7 adenylyltransferase (AAD(3")) | 6382-6423 |
| | CR-Ec.aadA-SPC/STR | Coding region for Tn7 adenylyltransferase (AAD(3")) conferring spectinomycin and streptomycin resistance. | 6424-7212 |
| | T-Ec.aadA-SPC/STR | 3' UTR from the Tn7 adenylyltransferase (AAD(3")) gene of *E. coli*. | 7213-7270 |

Example 6

Corn Plant Tranformation

This example illustrates the production and identification of transgenic corn cells in seed of transgenic corn plants having an enhanced agronomic trait, i.e. enhanced nitrogen use efficiency, increased yield, enhanced water use efficiency, enhanced tolerance to cold and/or enhanced seed compositions as compared to control plants. Transgenic corn cells are prepared with recombinant DNA expressing each of the protein encoding DNAs listed in Table 2 by *Agrobacterium*-mediated transformation using the corn transformation constructs as disclosed in Example 5.

Corn transformation is effected using methods disclosed in U.S. Patent Application Publication 2004/0344075 A1 where corn embryos are inoculated and co-cultured with the *Agrobacterium tumefaciens* strain ABI and the corn transformation vector. To regenerate transgenic corn plants the transgenic callus resulting from transformation is placed on media to initiate shoot development in plantlets which are transferred to potting soil for initial growth in a growth chamber followed by a mist bench before transplanting to pots where plants are grown to maturity. The plants are self fertilized and seed is harvested for screening as seed, seedlings or progeny R2 plants or hybrids, e.g., for yield trials in the screens indicated above.

Many transgenic events which survive to fertile transgenic plants that produce seeds and progeny plants do not exhibit an enhanced agronomic trait. The transgenic plants and seeds having the transgenic cells of this invention which have recombinant DNA imparting the enhanced agronomic traits are identified by screening for nitrogen use efficiency, yield, water use efficiency, cold tolerance and enhanced seed composition.

Example 7

Soybean Plant Transformation

This example illustrates the production and identification of transgenic soybean cells in seed of transgenic soybean plants having an enhanced agronomic trait, i.e. enhanced nitrogen use efficiency, increased yield, enhanced water use efficiency, enhanced tolerance to cold and/or enhanced seed compositions as compared to control plants. Transgenic soybean cells are prepared with recombinant DNA expressing each of the protein encoding DNAs listed in Table 1 by *Agrobacterium*-mediated transformation using the soybean transformation constructs disclosed in Example 5. Soybean transformation is effected using methods disclosed in U.S. Pat. No. 6,384,301 where soybean meristem explants are wounded then inoculated and co-cultured with the soybean transformation vector, then transferred to selection media for 6-8 weeks to allow selection and growth of transgenic shoots.

The transformation is repeated for each of the protein encoding DNAs identified in Table 2.

Transgenic shoots producing roots are transferred to the greenhouse and potted in soil. Many transgenic events which survive to fertile transgenic plants that produce seeds and progeny plants do not exhibit an enhanced agronomic trait. The transgenic plants and seeds having the transgenic cells of this invention which have recombinant DNA imparting the enhanced agronomic traits are identified by screening for nitrogen use efficiency, yield, water use efficiency, cold tolerance and enhanced seed composition.

Example 8

Selection of Transgenic Plants with Enhanced Agronomic Trait(s)

This example illustrates identification of plant cells of the invention by screening derived plants and seeds for enhanced trait. Transgenic seed and plants in corn, soybean, cotton or canola with recombinant DNA identified in Table 2 are prepared by plant cells transformed with DNA that is stably integrated into the genome of the corn cell. Transgenic corn plant cells are transformed with recombinant DNA from each of the genes identified in Table 2. Progeny transgenic plants and seed of the transformed plant cells are screened for enhanced water usciefficiency, enhanced cold tolerance, increased yield, enhanced nitrogen use efficiency, enhanced seed protein and enhanced seed oil as compared to control plants A. Selection for Enhanced Nitrogen Use Efficiency Transgenic corn seeds provided by the present invention are planted in fields with three levels of nitrogen (N) fertilizer being applied, i.e. low level (0 N), medium level (80 lb/ac) and high level (180 lb/ac). A variety of physiological traits are monitored. Plants with enhanced NUE provide higher yield as compared to control plants.

B. Selection for Increased Yield

Effective selection of enhanced yielding transgenic plants uses hybrid progeny of the transgenic plants for corn, cotton, and canola, or inbred progeny of transgenic plants for soybeanplants plant such as corn, cotton, canola, or inbred plant such as soy, canola and cottoncotton over multiple locations with plants grown under optimal production management practices, and maximum pest control. A useful target for improved yield is a 5% to 10% increase in yield as compared to yield produced by plants grown from seed for a control plant. Selection methods may he applied in multiple and diverse geographic locations, for example up to 16 or more locations, over one or more planting seasons, for example at least two planting seasons, to statistically distinguish yield improvement from natural environmental effects C. Selection for Enhanced Water Use Efficiency (WUE)

The selection process imposes a water withholding period to induce stressdrought followed by watering. For for example, for corn, a useful selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

D. Selection for Growth Under Cold Stress (1) Cold germination assay—Trays of transgenic and control seeds are placed in a growth chamber at 9.7° C. for 24 days (no light). Seeds having higher germination rates as compared to the control are identified.

(2) Cold field efficacy trial—A cold field efficacy trial is used to identify gene constructs that confer enhanced cold vigor at germination and early seedling growth under early spring planting field conditions in conventional-till and simulated no-till environments. Seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions with 3 repetitions per treatment. Two temperature monitors are set up at each location to monitor both air and soil temperature daily.

Seed emergence is defined as the point when the growing shoot breaks the soil surface. The number of emerged seedlings in each plot is counted everyday from the day the earliest plot begins to emerge until no significant changes in emergence occur. In addition, for each planting date, the latest date when emergence is 0 in all plots is also recorded. Seedling vigor is also rated at V3-V4 stage before the average of corn plant height reaches 10 inches, with 1=excellent early growth, 5=Average growth and 9=poor growth. Days to 50% emergence, maximum percent emergence and seedling vigor are used to determine plants with enhanced cold tolerance.

E. Screens for Transgenic Plant Seeds with Increased Protein and/or Oil Levels

This example sets forth a high-throughput selection for identifying plant seeds with improvement in seed composition using the Infratec 1200 series Grain Analyzer, which is a near-infrared transmittance spectrometer used to determine the composition of a bulk seed sample (Table 23). Near infrared analysis is a non-destructive, high-throughput method that can analyze multiple traits in a single sample scan. An NIR calibration for the analytes of interest is used to predict the values of an unknown sample. The NIR spectrum is obtained for the sample and compared to the calibration using a complex chemometric software package that provides predicted values as well as information on how well the sample fits in the calibration.

Infratec Model 1221, 1225, or 1227 with transport module by Foss North America is used with cuvette, item #1000-4033, Foss North America or for small samples with small cell cuvette, Foss standard cuvette modified by Leon Girard Co. Corn and soy check samples of varying composition maintained in check cell cuvettes are supplied by Leon Girard Co. NIT collection software is provided by Maximum Consulting Inc.Software. Calculations are performed automatically by the software. Seed samples are received in packets or containers with barcode labels from the customer. The seed is poured into the cuvettes and analyzed as received.

TABLE 23

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc |
| | Soybean typical: 50 cc; minimum 5 cc |
| Typical analytical range: | Determined in part by the specific calibration. |
| | Corn - moisture 5-15%, oil 5-20%, protein 5-30%, starch 50-75%, and density 1.0-1.3%. |
| | Soybean - moisture 5-15%, oil 15-25%, and protein 35-50%. |

Example 9

Cotton Transgenic Plants with Enhanced Agronomic Traits

Cotton transformation is performed as generally described in WO0036911 and in U.S. Pat. No. 5,846,797. Transgenic cotton plants containing each of the recombinant DNA having a sequence of SEQ ID NO: 1 through SEQ ID NO: 759 are obtained by transforming with recombinant DNA from each of the genes identified in Table 1. Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest to control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

The transgenic cotton plants of this invention are identified from among the transgenic cotton plants by agronomic trait screening as having increased yield and enhanced water use efficiency.

Example 10

Canola Plants with Enhanced Agrominic Traits

This example illustrates plant transformation useful in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with a suspension of overnight grown *Agrobacterium* containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterization are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 2. Transgenic progeny plants and seed of the transformed plant cells are screened for enhanced water use efficiency, enhanced cold tolerance, increased is yield, enhanced nitrogen use efficiency, enhanced seed protein and enhanced seed oil.

Example 11

Selection of Transgenic Plants with Enhanced Agronomic Trait(s)

This example illustrates the preparation and identification by selection of transgenic seeds and plants derived from transgenic plant cells of this invention where the plants and seed are identified by screening for a transgenic plant having an enhanced agronomic trait imparted by expression or suppression of a protein selected from the group including the homologous proteins identified in Example 2. Transgenic plant cells of corn, soybean, cotton, canola, alfalfa, wheat and rice are transformed with recombinant DNA for expressing or suppressing each of the homologs identified in Example 2. Plants are regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. Plants are identified exhibiting enhanced traits imparted by expression or suppression of the homologous proteins.

Example 12

Monocot and Dicot Plant Transformation for the Suppression of Endogeneous Protein This example illustrates monocot and dicot plant transformation to produce nuclei of this invention in cells.of a transgenic plant by transformation where the recombinant DNA suppresses the expression of an endogenous protein identified in Table 24.

Corn, soybean, cotton, or canola tissue are transformed as described in Examples 2-5 using recombinant DNA in the nucleus with DNA that is transcribed into RNA that forms double-stranded RNA targeted to an endogenous gene with DNA encoding the protein. The genes for which the double-stranded RNAs are targeted are the native gene in corn, soybean, cotton or canola that are homologs of the genes encoding the protein that has the function of the protein in *Arabidopsis* as identified in table 24.

Populations of transgenic plants prepared in Examples 6, 7, 9, 10 or 11 with DNA for suppressing a gene identified in Table 2 as providing an enhanced trait by gene suppression are screened to identify an event from those plants with a nucleus of the invention by selecting the trait identified in this specification.

TABLE 24

| PEP SEQ ID | Gene_id | Construct ID | Traits | |
|---|---|---|---|---|
| 760 | CGPG1022.pep | RRM_1 | DS | |
| 761 | CGPG1035.pep | Peptidase_C54 | SS | |
| 763 | CGPG105.pep | AP2 | HS | PEG |
| 764 | CGPG1060.pep | DUF788 | LN | |
| 771 | CGPG1136.pep | RRM_1 | DS | |
| 774 | CGPG1145.pep | LNDIX | LN | |
| 776 | CGPG1173.pep | adh_short | LN | |
| 779 | CGPG122.pep | PTR2 | LN | |
| 781 | CGPG1262.pep | Gar1 | CK | |
| 782 | CGPG128.pep | Response_reg | LN | |

TABLE 24-continued

| PEP SEQ ID | Gene_id | Construct ID | Traits | | | | |
|---|---|---|---|---|---|---|---|
| 784 | CGPG1291.pep | DUF862 | DS | | | | |
| 794 | CGPG1398.pep | Glycolytic | LN | | | | |
| 795 | CGPG1399.pep | Metallophos | LN | | | | |
| 799 | CGPG146.pep | p450 | CS | PP | SS | | |
| 801 | CGPG1528.pep | ATP_synt_H | LN | | | | |
| 803 | CGPG1535.pep | SPT2 | LN | | | | |
| 804 | CGPG1546.pep | CTP_transf_1 | LN | | | | |
| 805 | CGPG1567.pep | Ribosomal_L19 | LN | | | | |
| 807 | CGPG1575.pep | DUF740 | DS | | | | |
| 810 | CGPG1641.pep | Di19 | SP | | | | |
| 812 | CGPG1656.pep | Cyt-b5::FA_desaturase | CS | | | | |
| 813 | CGPG1668.pep | DUF791::MFS_1 | SS | | | | |
| 817 | CGPG1785.pep | PB1::Pkinase_Tyr | CK | | | | |
| 829 | CGPG1938.pep | F-box::LRR_2 | CS | | | | |
| 835 | CGPG2005.pep | NADPH_Ox::Ferric_reduct::FAD_binding_8::NAD_binding_6 | CS | PP | HS | SS | PEG |
| 838 | CGPG2059.pep | LNc_sug_transp | SS | | | | |
| 842 | CGPG2074.pep | HMA::HMA | CK | | | | |
| 845 | CGPG2142.pep | MATH::MATH | DS | | | | |
| 850 | CGPG2213.pep | RNA_pol_I_A49 | CK | PEG | | | |
| 851 | CGPG2247.pep | DUF23 | CK | | | | |
| 852 | CGPG228.pep | p450 | SP | | | | |
| 858 | CGPG2354.pep | ABC1 | PP | | | | |
| 863 | CGPG240.pep | Hydrolase | DS | | | | |
| 869 | CGPG2472.pep | Band_7 | LN | | | | |
| 877 | CGPG274.pep | WD40::WD40::WD40 | PP | LL | | | |
| 879 | CGPG277.pep | IGPD | LN | | | | |
| 893 | CGPG309.pep | Cyclin_N | LN | | | | |
| 911 | CGPG337.pep | Glyco_transt_8 | LN | | | | |
| 917 | CGPG347.pep | DREPP | LN | | | | |
| 931 | CGPG372.pep | SET | LN | | | | |
| 941 | CGPG394.pep | DUF6::TPT | LN | | | | |
| 943 | CGPG397.pep | SOR_SNZ::ThiG | CK | | | | |
| 957 | CGPG421.pep | Pkinase::efhand::efhand::ethand::efhand | LN | | | | |
| 958 | CGPG422.pep | Pkinase | IN | | | | |
| 968 | CGPG430.pep | Pkinase | DS | | | | |
| 996 | CGPG468.pep | Fer4::Fer4 | LN | | | | |
| 1031 | CGPG510.pep | Rho_GDI | SS | | | | |
| 1040 | CGPG519.pep | Abhydrolase_1 | PEG | | | | |
| 1058 | CGPG532.pep | Transket_pyr::Transketolase_C | LN | | | | |
| 1078 | CGPG557.pep | Chitin_bind_1::Barwin | LN | | | | |
| 1083 | CGPG561.pep | XG_FTase | PP | | | | |
| 1091 | CGPG568.pep | FTHFS | LN | | | | |
| 1108 | CGPG580.pep | MGDG_synth::Glyco_tran_28_C | LN | | | | |
| 1134 | CGPG604.pep | PSI_PsaH | LN | | | | |
| 1144 | CGPG614.pep | cobW | LN | | | | |
| 1150 | CGPG620.pep | tRNA-synt_1g | DS | | | | |
| 1212 | CGPG663.pep | Pro_CA | LN | | | | |
| 1232 | CGPG686.pep | RRM_1::zf-CCHC | LN | | | | |
| 1258 | CGPG713.pep | Cyclin_N | LN | | | | |
| 1267 | CGPG72.pep | Amino_oxidase | LN | | | | |
| 1328 | CGPG773.pep | H_PPase | PP | | | | |
| 1357 | CGPG801.pep | Cyt-b5 | LN | | | | |
| 1406 | CGPG841.pep | ArfGap | LN | | | | |
| 1452 | CGPG879.pep | ABC_tran::ABC2_membrane::PDR_assoc::ABC_tran::ABC2_membrane | LN | | | | |
| 1477 | CGPG908.pep | PPR::PPR::PPR::PPR::PPR::PPR::PPR | LN | | | | |
| 1515 | CGPG933.pep | WD40::WD40::WD40::WD40::WD40::WD40::WD40 | SP | | | | |
| 1517 | CGPG967.pep | BTB::NPH3 | CS | | | | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10167482B2). An electronic copy of the "Sequence Listing" will also be available from the USPTO upon request and payment of the fee set forth in 37 CFR 1.19(b)(3).

What is claimed is:

1. A plant cell nucleus comprising a stably integrated recombinant DNA construct wherein said recombinant DNA comprises a heterologous promoter that is functional in said plant cell and that is operably linked to a protein coding DNA encoding at least one protein having an amino acid sequence comprising at least 95% amino acid sequence identity to SEQ ID NO:936 and having the function of SEQ ID NO:936 and wherein said recombinant DNA construct is stably integrated into a chromosome in a plant cell nucleus which is selected by screening a population of transgenic plants that have said recombinant DNA and an enhanced trait as compared to control plants that do not have said recombinant DNA in their nuclei; and wherein said enhanced trait is selected from group of enhanced traits consisting of increased yield and enhanced nitrogen use efficiency.

2. The plant cell nucleus comprising a recombinant DNA construct of claim 1 wherein said protein coding DNA comprises a nucleotide sequence having at least 99% nucleic acid sequence identity to SEQ ID NO:177.

3. The plant cell nucleus comprising a recombinant DNA construct of claim 1 further comprising DNA expressing a protein that provides tolerance from exposure to an herbicide applied at levels that are lethal to a wild type of said plant cell.

4. The plant cell nucleus of claim 3 wherein the agent of said herbicide is a glyphosate, dicamba, or glufosinate compound.

5. A transgenic plant cell or plant comprising a plurality of plant cells with the plant cell nucleus of claim 1.

6. The transgenic plant cell or plant of claim 5 which is homozygous for said recombinant DNA.

7. A transgenic plant cell or plant comprising a plurality of plant cells with the plant cell nucleus of claim 1.

8. The transgenic seed of claim 7 from a corn, soybean, cotton, canola, alfalfa, wheat or rice plant.

9. A transgenic pollen grain comprising a haploid gamete of a plant cell nucleus comprising a recombinant DNA construct of claim 1.

10. A method for manufacturing non-natural, transgenic seed that can be used to produce a crop of transgenic plants with an enhanced trait resulting from expression of recombinant DNA in the plant cell nucleus of claim 1, wherein said method for manufacturing said transgenic seed comprising:

(a) screening a population of plants for said enhanced trait and said recombinant DNA, wherein individual plants in said population can exhibit said trait at a level less than, essentially the same as or greater than the level that said trait is exhibited in control plants which do not contain the recombinant DNA, wherein said enhanced trait is selected from the group of enhanced traits consisting of increased yield and enhanced nitrogen use efficiency, (b) selecting from said population one or more plants that exhibit said trait at a level greater than the level that said trait is exhibited in control plants, and (c) collecting seeds from selected plant selected from step b.

11. The method of claim 10 wherein said method for manufacturing said transgenic seed further comprising (a) verifying that said recombinant DNA is stably integrated in said selected plants, and (b) analyzing tissue of said selected plant to determine the expression or suppression of a protein having the function of a protein having SEQ ID NO:936.

12. The method of claim 10 herein said seed is corn, soybean, cotton, alafalfa, canola wheat or rice seed.

13. A method of producing hybrid corn seed comprising:

(a) acquiring hybrid corn seed from a herbicide tolerant corn plant which also has the plant cell nucleus of claim 1;

(b) producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA, (c) selecting corn plants which are homozygous and hemizygous for said recombinant DNA by treating with an herbicide;

(d) collecting seed from herbicide-treated-surviving corn plants and planting said seed to produce further progeny corn plants;

(e) repeating steps (c) and (d) at least once to produce an inbred corn line; and (f) crossing said inbred corn line with a second corn line to produce hybrid seed.

* * * * *